(12) United States Patent
Pearse et al.

(10) Patent No.: US 10,882,915 B2
(45) Date of Patent: Jan. 5, 2021

(54) COMPOSITIONS AND METHODS FOR THE DEPLETION OF CD117+ CELLS

(71) Applicant: Magenta Therapeutics, Inc., Cambridge, MA (US)

(72) Inventors: Bradley R. Pearse, Watertown, MA (US); Anthony Boitano, Newton, MA (US); Rahul Palchaudhuri, Somerville, MA (US); Sean McDonough, Littleton, MA (US); Rajiv Panwar, Acton, MA (US); Jonathan Philip Belk, Grantham, NH (US); Matthew Duncan Smith, Canton, MI (US)

(73) Assignee: Magenta Therapeutics, Inc., Cambridge, MA (US)

( * ) Notice: Subject to any disclaimer, the term of this patent is extended or adjusted under 35 U.S.C. 154(b) by 223 days.

(21) Appl. No.: 16/168,816

(22) Filed: Oct. 23, 2018

(65) Prior Publication Data
US 2019/0144558 A1 May 16, 2019

Related U.S. Application Data

(60) Provisional application No. 62/576,571, filed on Oct. 24, 2017, provisional application No. 62/576,593, (Continued)

(51) Int. Cl.
*C07K 16/28* (2006.01)
*A61K 35/545* (2015.01)
(Continued)

(52) U.S. Cl.
CPC ........ *C07K 16/2896* (2013.01); *A61K 35/545* (2013.01); *A61K 47/6817* (2017.08);
(Continued)

(58) Field of Classification Search
None
See application file for complete search history.

(56) References Cited

U.S. PATENT DOCUMENTS

| | | |
|---|---|---|
| 5,808,002 A | 9/1998 | Buhring et al. |
| 7,915,391 B2 | 3/2011 | Ng et al. |

(Continued)

FOREIGN PATENT DOCUMENTS

| | | |
|---|---|---|
| EP | 1859811 B1 | 8/2011 |
| WO | 2007127317 A2 | 11/2007 |

(Continued)

OTHER PUBLICATIONS

Palchaudhuri et al., "Non-genotoxic conditioning for hematopoietic stem cell transplantation using a hematopoielic-cell-specific internalizing immunotoxin," Nat Biotechnol. 34(7):738-45 (22 pages) (2016).

(Continued)

*Primary Examiner* — Karl J Puttlitz
(74) *Attorney, Agent, or Firm* — Womble Bond Dickinson (US) LLP; Cristin H. Cowles; Kevin A. Fiala

(57) ABSTRACT

The invention provides compositions and methods useful for the depletion of CD117+ cells and for the treatment of various hematopoietic diseases, metabolic disorders, cancers, and autoimmune diseases, among others. Described herein are antibodies, antigen-binding fragments, and conjugates thereof that can be applied to effect the treatment of these conditions, for instance, by depleting a population of CD117+ cells in a patient, such as a human. The compositions and methods described herein can be used to treat a disorder directly, for instance, by depleting a population of CD117+ cancer cells or autoimmune cells. The compositions and methods described herein can also be used to prepare a patient for hematopoietic stem cell transplant therapy and to improve the engraftment of hematopoietic (Continued)

stem cell transplants by selectively depleting endogenous hematopoietic stem cells prior to the transplant procedure.

27 Claims, 33 Drawing Sheets

Specification includes a Sequence Listing.

Related U.S. Application Data filed on Oct. 24, 2017, provisional application No. 62/576,625, filed on Oct. 24, 2017, provisional application No. 62/576,628, filed on Oct. 24, 2017, provisional application No. 62/576,629, filed on Oct. 24, 2017, provisional application No. 62/576,626, filed on Oct. 24, 2017, provisional application No. 62/576,588, filed on Oct. 24, 2017, provisional application No. 62/576,590, filed on Oct. 24, 2017, provisional application No. 62/576,597, filed on Oct. 24, 2017, provisional application No. 62/576,605, filed on Oct. 24, 2017, provisional application No. 62/638,051, filed on Mar. 2, 2018, provisional application No. 62/638,049, filed on Mar. 2, 2018.

(51) Int. Cl.

| | | |
|---|---|---|
| *C07K 7/64* | (2006.01) | |
| *A61P 37/06* | (2006.01) | |
| *A61P 35/00* | (2006.01) | |
| *A61K 47/68* | (2017.01) | |
| *A61K 38/00* | (2006.01) | |
| *A61K 35/12* | (2015.01) | |
| *A61K 39/00* | (2006.01) | |

(52) U.S. Cl.
CPC ...... *A61K 47/6831* (2017.08); *A61K 47/6849* (2017.08); *A61P 35/00* (2018.01); *A61P 37/06* (2018.01); *C07K 7/64* (2013.01); *C07K 16/2803* (2013.01); *A61K 38/00* (2013.01); *A61K 2035/124* (2013.01); *A61K 2039/505* (2013.01); *C07K 2317/21* (2013.01); *C07K 2317/33* (2013.01); *C07K 2317/52* (2013.01); *C07K 2317/73* (2013.01); *C07K 2317/76* (2013.01); *C07K 2317/77* (2013.01); *C07K 2317/92* (2013.01); *C07K 2317/94* (2013.01)

(56) References Cited

U.S. PATENT DOCUMENTS

| | | |
|---|---|---|
| 8,119,130 B2 | 2/2012 | Barry et al. |
| 10,111,966 B2 | 10/2018 | Nixon et al. |
| 10,280,225 B2 | 5/2019 | Scadden et al. |
| 10,570,207 B2 | 2/2020 | Scadden et al. |
| 2002/0127606 A1 | 9/2002 | Fritz et al. |
| 2003/0022345 A1 | 1/2003 | Olsen et al. |
| 2004/0067532 A1 | 4/2004 | Zhu et al. |
| 2008/0213251 A1 | 9/2008 | Sexton et al. |
| 2009/0318297 A1 | 12/2009 | Cappucilli et al. |
| 2010/0119516 A1 | 5/2010 | Wu et al. |
| 2010/0226927 A1 | 9/2010 | Weissman |
| 2012/0288506 A1 | 11/2012 | Amatulli et al. |
| 2013/0004500 A1 | 1/2013 | Tanaka et al. |
| 2014/0193899 A1 | 7/2014 | Kim et al. |
| 2016/0151515 A1 | 6/2016 | Joubert et al. |
| 2016/0177390 A1 | 6/2016 | Feng et al. |
| 2016/0264651 A1 | 9/2016 | Freimoser-Grundschober et al. |
| 2017/0073414 A1 | 3/2017 | Weiskopf et al. |
| 2017/0114141 A1 | 4/2017 | Amann et al. |
| 2017/0121409 A1 | 5/2017 | Verona et al. |
| 2018/0127497 A1 | 5/2018 | Malik et al. |
| 2018/0193475 A1 | 7/2018 | Abrams et al. |
| 2019/0153114 A1 | 5/2019 | Pearse et al. |
| 2020/0148776 A1 | 5/2020 | Scadden et al. |

FOREIGN PATENT DOCUMENTS

| | | | |
|---|---|---|---|
| WO | 2017191579 A1 | | 11/2007 |
| WO | 2010115629 A3 | | 4/2010 |
| WO | 2012041504 A1 | | 4/2012 |
| WO | 2012119787 A1 | | 9/2012 |
| WO | 2014135282 A1 | | 9/2014 |
| WO | 2015057942 A1 | | 4/2015 |
| WO | 2016071856 A1 | | 5/2016 |
| WO | 2016142049 A1 | | 9/2016 |
| WO | 2016164502 | | 10/2016 |
| WO | 2016164637 A1 | | 10/2016 |
| WO | 2016164745 A1 | | 10/2016 |
| WO | 2017046658 A1 | | 3/2017 |
| WO | 2017134197 A1 | | 8/2017 |
| WO | 2017219029 A8 | | 12/2017 |
| WO | 2018183613 A1 | | 10/2018 |
| WO | 2019084057 | * | 5/2019 |
| WO | 2019084067 | * | 5/2019 |

OTHER PUBLICATIONS

Hamblett et al., Clinical Cancer Research, 2004, vol. 10, pp. 7063-7070.

Holliger and Hudson, Nature Biotechnology, 2005, vol. 23. pp. 1126-1136.

Abstract of Reis et al., Blood, 2015, vol. 126, No. 23, p. 2580.

Abrams et al., "Preclinical Antitumor Activity of a Novel Anti—c-Kit Antibody—Drug Conjugate against Mutant and Wild-type c-Kit—Positive Solid Tumors." Clin Cancer Res. vol. 24(17) p. 4297-4308 (2018).

LeFranc, MP. "Immunoglobulin and T cell receptor genes: IMGT® and the birth and rise of immunoinformatics." Frontiers in immunology, 2014 vol. 5, No. 22.

* cited by examiner

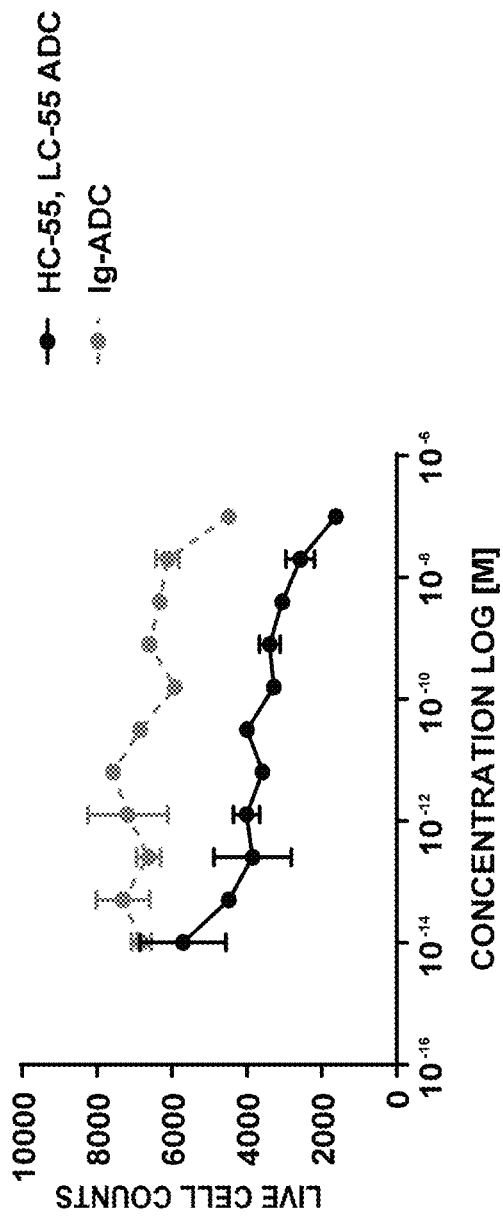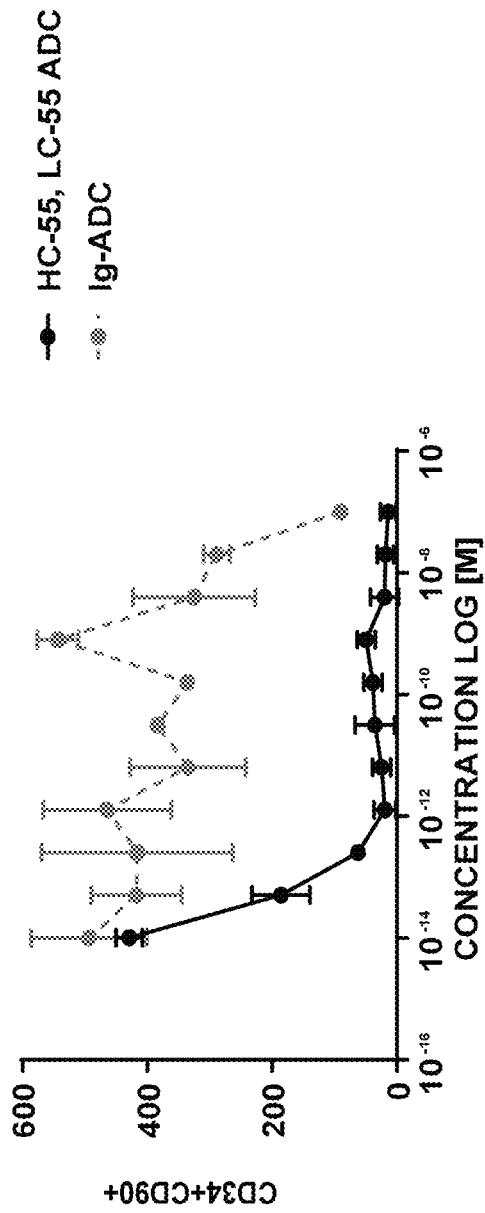
FIG. 6A
FIG. 6B

FIG. 21A

CDR-H1, CDR-H2 indicated above sequences.

```
VH-54  1 QVQLVQSGAEVKKPGSSVKVSCKASGGTFSSYAISWVRQAPGQGLEWMGGIIPIFGTANY
VH-55  1 QVQLVQSGAEVKKPGSSVKVSCKASGGTFRYYAISWVRQAPGQGLEWMGGIIPDFGVANY
VH-56  1 QVQLVQSGAEVKKPGSSVKVSCKASGGTFSLYAISWVRQAPGQGLEWMGGIIPAFGTANY
VH-57  1 QVQLVQSGAEVKKPGSSVKVSCKASGGTFSLYAISWVRQAPGQGLEWMGGIIPHFGLANY
```

CDR-H2 (cont.), CDR-H3

```
VH-54 61 AQKFQGRVTITADESTSTAYMELSSLRSEDTAVYYCARGGLDTDEFDLWGRGTLVTVS
VH-55 61 AQKFQGRVTITADESTSTAYMELSSLRSEDTAVYYCARGGLDTDEFDLWGRGTLVTVS
VH-56 61 AQKFQGRVTITADESTSTAYMELSSLRSEDTAVYYCARGGLDTDEFDLWGRGTLVTVS
VH-57 61 AQKFQGRVTITADESTSTAYMELSSLRSEDTAVYYCARGGLDTDEFDLWGRGTLVTVS
```

FIG. 21B

CDR-L1, CDR-L2

```
VL-54  1 DIQMTQSPSSLSASVGDRVTITCRASQSINSYLNWYQQKPGKAPKLLIYAASSLQSGVPS
VL-55  1 DIQMTQSPSSLSASVGDRVTITCRASQSINSYLNWYQQKPGKAPKLLIYAASSLQSGVPS
VL-56  1 DIQMTQSPSSLSASVGDRVTITCRASQSINSYLNWYQQKPGKAPKLLIYAASSLQSGVPS
VL-57  1 DIQMTQSPSSLSASVGDRVTITCRASQSINSYLNWYQQKPGKAPKLLIYAASSLQSGVPS
```

CDR-L3

```
VL-54 61 RFSGSGSGTDFTLTISSLQPEDFATYYCQQGVSDITFGGGTKVEIK
VL-55 61 RFSGSGSGTDFTLTISSLQPEDFATYYCQQGVSDITFGGGTKVEIK
VL-56 61 RFSGSGSGTDFTLTISSLQPEDFATYYCQQGVSDITFGGGTKVEIK
VL-57 61 RFSGSGSGTDFTLTISSLQPEDFATYYCQQGVSDITFGGGTKVEIK
```

```
VH-58    1 EVQLLESGGGLVQPGGSLRLSCAASGFTFSNYAMSWVRQAPGKGLEWVSAISGSGGSTYY
VH-61    1 EVQLLESGGGLVQPGGSLRLSCAASGFTFSSYVMIWVRQAPGKGLEWVSSISGDSVTYY
                                CDR-H1                      CDR-H2

VH-58   61 ADSVKGRFTISRDNSKNTLYLQMNSLRAEDTAVYYCAKGPPTYHTNYYYMDVWGKGTTVT
VH-61   61 ADSVKGRFTISRDNSKNTLYLQMNSLRAEDTAVYYCAKGPPTYHTNYYYMDVWGKGTTVT
             CDR-H2(cont.)                           CDR-H3

VH-58  121 VSS
VH-61  121 VSS
```

FIG. 22A

```
VL-58    1 DIQMTQSPSSVSASVGDRVTITCRASQGISSWLAWYQQKPGKAPKLLIYAASSLQSGVPS
VL-61    1 DIQMTQSPSSVSASVGDRVTITCRASQGISSWLAWYQQKPGKAPKLLIYAASSLQSGVPS
                            CDR-L1                            CDR-L2

VL-58   61 RFSGSGSGTDFTLTISSLQPEDFATYYCQQTNSFPYTFGGGTKVEIK
VL-61   61 RFSGSGSGTDFTLTISSLQPEDFATYYCQQTNSFPYTFGGGTKVEIK
                                        CDR-L3
```

FIG. 22B

|  |  | CDR-H1 | CDR-H2 |
|---|---|---|---|
| VH-66 | 1 | EVQLVESGGGLVQPGGSLRLSCAASGFTFSDH | YMDWVRQAPGKGLEWVGRTRNKASSYTT |
| VH-67 | 1 | EVQLVESGGGLVQPGGSLRLSCAASGFTFSDA | DMDWVRQAPGKGLEWVGRTRNKAGSYTT |
| VH-68 | 1 | EVQLVESGGGLVQPGRSLRLSCAASGFTFSDHDMN | WVRQAPGKGLEWVGRTRNAAGSYTT |
| VH-69 | 1 | EVQLVESGGGLVQPGGSLRLSCTASGFTFVDHDMDWVRQAPGKGLEWVGRTRNKLGSYTT |

|  |  | CDR-H2 (cont.) | CDR-H3 |
|---|---|---|---|
| VH-66 | 61 | EYAASVKGRFTISRDDSKNSLYLQMNSLKTEDTAVYYCAREPKYWIDFDLWGRGTLVTVSS |
| VH-67 | 61 | EYAASVKGRFTISRDDSKNSLYLQMNSLKTEDTAVYYCAREPKYWIDFDLWGRGTLVTVSS |
| VH-68 | 61 | EYAASVKGRFTISRDDSKNSLYLQMNSLKTEDTAVYYCAREPKYWIDFDLWGRGTLVTVSS |
| VH-69 | 61 | EYAASVKGRFTISRDDSKNSLYLQMNSLKTEDTAVYYCAREPKYWIDFDLWGRGTLVTVSS |

FIG. 23A

|  |  | CDR-L1 | CDR-L2 |
|---|---|---|---|
| VL-66 | 1 | DIQMTQSPSSLSASVGDRVTITCRASQSISSYLNWYQQKPGKAPK |
| VL-67 | 1 | DIQMTQSPSSLSASVGDRVTITCRASQSISSYLNWYQQKPGKAPK |
| VL-68 | 1 | DIQMTQSPSSLSASVGDRVTITCRASQSISSYLNWYQQKPGKAPK |
| VL-69 | 1 | DIQMTQSPSSLSASVGDRVTITCRASQSISSYLNWYQQKPGKAPK |

|  |  | CDR-L3 |
|---|---|---|
| VL-66 | 61 | RFSGSGSGTDFTLTISSLQPEDFATYYCQQSYIAPYTFGGGTKVEI |
| VL-67 | 61 | RFSGSGSGTDFTLTISSLQPEDFATYYCQQSYIAPYTFGGGTKVEI |
| VL-68 | 61 | RFSGSGSGTDFTLTISSLQPEDFATYYCQQSYIAPYTFGGGTKVEI |
| VL-69 | 61 | RFSGSGSGTDFTLTISSLQPEDFATYYCQQSYIAPYTFGGGTKVEI |

FIG. 23B

```
                        SEQUENCE LISTING

<160> NUMBER OF SEQ ID NOS: 146

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Tyr Trp Ile Gly
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile Ile Tyr Pro Gly Asp Ser Asp Thr Arg Tyr Ser Pro Ser Phe Gln
1               5                   10                  15

Gly

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

His Gly Arg Gly Tyr Asn Gly Tyr Glu Gly Ala Phe Asp Ile
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Ser Gln Gly Ile Ser Ser Ala Leu Ala
1               5                   10

<210> SEQ ID NO 5
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 5

Asp Ala Ser Ser Leu Glu Ser
1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Gln Gln Phe Asn Ser Tyr Pro Leu Thr
1               5                   10

<210> SEQ ID NO 7
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ala Val Ile Ser Glu Asn Gly Ser Asp Thr Tyr Tyr Ala Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Gly Ala Val Ser Tyr Phe Asp Val Trp Gly Gln
            100                 105                 110

Gly Thr Leu Val Thr Val Ser Ser
        115                 120

<210> SEQ ID NO 8
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
```

```
                 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Leu Pro Tyr
                 85                  90                  95

Thr Phe Gly Gln Gly Thr Lys Val Glu Ile Lys Arg Thr
            100                 105
```

<210> SEQ ID NO 9
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Ala
             20                  25                  30

Asp Met Asp Trp Val Arg Gln Ala Pro Gly Lys Gly Leu Glu Trp Val
         35                  40                  45

Gly Arg Thr Arg Asn Lys Ala Gly Ser Tyr Thr Thr Glu Tyr Ala Ala
     50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Ala Arg Glu Pro Lys Tyr Trp Ile Asp Phe Asp Leu Trp Gly
            100                 105                 110

Arg Gly Thr Leu Val Thr Val Ser Ser
        115                 120
```

<210> SEQ ID NO 10
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ile Ala Pro Tyr
                 85                  90                  95

Thr Phe Gly Gly Gly Thr Lys Val Glu Ile Lys
            100                 105
```

```
<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Phe Thr Phe Ser Asp Ala Asp Met Asp
1               5

<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Thr Arg Asn Lys Ala Gly Ser Tyr Thr Thr Glu Tyr Ala Ala Ser
1               5                   10                  15

Val Lys Gly

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Arg Glu Pro Lys Tyr Trp Ile Asp Phe Asp Leu
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Ala Ser Gln Ser Ile Ser Ser Tyr Leu Asn
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Ala Ser Ser Leu Gln Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 16

Gln Gln Ser Tyr Ile Ala Pro Tyr Thr
1               5

<210> SEQ ID NO 17
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
gaggtgcagc tggtggagtc tgggggaggc ttggtccagc ctggagggtc cctgagactc    60
tcctgtgcag cctctggatt caccttcagt gacgccgaca tggactgggt ccgccaggct   120
ccagggaagg gctggagtg gttggccgt actagaaaca aagcaggaag ttacaccaca    180
gaatacgccg cgtctgtgaa aggcagattc accatctcaa gagatgattc aaagaactca   240
ctgtatctgc aaatgaacag cctgaaaacc gaggacacgg cggtgtacta ctgcgccaga   300
gagcctaaat actggatcga cttcgaccta tggggagag gtaccttggt caccgtctcc    360
tca                                                                 363
```

<210> SEQ ID NO 18
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcaa agctacatcg ccccttacac ttttggcgga   300
gggaccaagg ttgagatcaa a                                             321
```

<210> SEQ ID NO 19
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Ile Tyr
            20                  25                  30

Ala Ile Ser Trp Val Arg Gln Ala Pro Gly Gln Gly Leu Glu Trp Met
        35                  40                  45

Gly Gly Ile Ile Pro Asp Phe Gly Val Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Leu Asp Thr Asp Glu Phe Asp Leu Trp Gly Arg Gly
            100                 105                 110

Thr Leu Val Thr Val Ser Ser
        115

<210> SEQ ID NO 20
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Asp Ile Thr
                85                  90                  95

Phe Gly Gly Gly Thr Lys Val Glu Ile Lys
            100                 105

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Thr Phe Arg Ile Tyr Ala Ile Ser
1               5

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Ile Ile Pro Asp Phe Gly Val Ala Asn Tyr Ala Gln Lys Phe Gln
1               5                   10                  15

Gly

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic

```
peptide

<400> SEQUENCE: 23

Ala Arg Gly Gly Leu Asp Thr Asp Glu Phe Asp Leu
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Ala Ser Gln Ser Ile Asn Ser Tyr Leu Asn
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Ala Ser Ser Leu Gln Ser
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Gln Gly Val Ser Asp Ile Thr
1               5

<210> SEQ ID NO 27
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
caggtgcagc tggtgcagtc tggggctgag gtgaagaagc ctgggtcctc ggtgaaggtc      60
tcctgcaagg cttctggagg caccttccga atctatgcta tcagctgggt gcgacaggcc     120
cctggacaag gcttgagtg gatgggaggg atcatccctg acttcggtgt agcaaactac     180
gcacagaagt tccagggcag agtcacgatt accgcggacg aatccacgag cacagcctac     240
atggagctga gcagcctgag atctgaggac acggcggtgt actactgcgc cagaggtgga     300
ttggacacag acgagttcga cctatggggg agaggtacct tggtcaccgt ctcctca       357

<210> SEQ ID NO 28
<211> LENGTH: 318
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 28

```
gacatccaga tgacccagtc tccatcctcc ctgtctgcat ctgtaggaga cagagtcacc      60
atcacttgcc gggcaagtca gagcattaac agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcaa ggagtcagtg acatcacttt tggcggaggg     300
accaaggttg agatcaaa                                                   318
```

<210> SEQ ID NO 29
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Leu Asp Thr Asp Glu Phe Asp Leu Trp Gly Arg Gly
            100                 105                 110

Thr Leu Val Thr Val Ser Ser
        115

<210> SEQ ID NO 30
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Asp Ile Thr
                85                  90                  95

```
Phe Gly Gly Gly Thr Lys Val Glu Ile Lys
            100                 105

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Thr Phe Ser Ser Tyr Ala Ile Ser
1               5

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Ile Ile Pro Ile Phe Gly Thr Ala Asn Tyr Ala Gln Lys Phe Gln
1               5                   10                  15

Gly

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Arg Gly Gly Leu Asp Thr Asp Glu Phe Asp Leu
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Ala Ser Gln Ser Ile Asn Ser Tyr Leu Asn
1               5                   10

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Ala Ser Ser Leu Gln Ser
1               5

<210> SEQ ID NO 36
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Gln Gly Val Ser Asp Ile Thr
1               5

<210> SEQ ID NO 37
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggcggtgt actactgcgc cagaggtgga     300
ttggacacag acgagttcga cctatggggg agaggtacct tggtcaccgt ctcctca       357

<210> SEQ ID NO 38
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
gacatccaga tgacccagtc tccatcctcc ctgtctgcat ctgtaggaga cagagtcacc      60
atcacttgcc gggcaagtca gagcattaac agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcaa ggagtcagtg acatcacttt tggcggaggg     300
accaaggttg agatcaaa                                                   318

<210> SEQ ID NO 39
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Leu Tyr
            20                  25                  30

Ala Ile Ser Trp Val Arg Gln Ala Pro Gly Gln Gly Leu Glu Trp Met
        35                  40                  45

Gly Gly Ile Ile Pro Ala Phe Gly Thr Ala Asn Tyr Ala Gln Lys Phe
    50                  55                  60
```

```
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Leu Asp Thr Asp Glu Phe Asp Leu Trp Gly Arg Gly
            100                 105                 110

Thr Leu Val Thr Val Ser Ser
        115

<210> SEQ ID NO 40
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Asn Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Val Ser Asp Ile Thr
                 85                  90                  95

Phe Gly Gly Gly Thr Lys Val Glu Ile Lys
            100                 105

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Thr Phe Ser Leu Tyr Ala Ile Ser
 1               5

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Ile Ile Pro Ala Phe Gly Thr Ala Asn Tyr Ala Gln Lys Phe Gln
 1               5                  10                  15

Gly

<210> SEQ ID NO 43
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 43

Ala Arg Gly Gly Leu Asp Thr Asp Glu Phe Asp Leu
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Ala Ser Gln Ser Ile Asn Ser Tyr Leu Asn
1               5                   10

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Ala Ser Ser Leu Gln Ser
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Gln Gly Val Ser Asp Ile Thr
1               5

<210> SEQ ID NO 47
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
caggtgcagc tggtgcagtc tggggctgag gtgaagaagc ctgggtcctc ggtgaaggtc      60
tcctgcaagg cttctggagg caccttcagc ctctatgcta tctcctgggt gcgacaggcc     120
cctggacaag ggcttgagtg gatgggaggg atcatccctg ccttcggtac cgcaaactac     180
gcacagaagt tccagggcag agtcacgatt accgcggacg aatccacgag cacagcctac     240
atggagctga gcagcctgag atctgaggac acggcggtgt actactgcgc cagaggtgga     300
ttggacacag acgagttcga cctatggggg agaggtacct tggtcaccgt ctcctca        357

<210> SEQ ID NO 48
<211> LENGTH: 318
<212> TYPE: DNA
```

```
<213> ORGANISM: Artificial Sequence
<220> FEATURE:
<223> OTHER INFORMATION: Description of Artificial Sequence: Synthetic
      polynucleotide

<400> SEQUENCE: 48
gacatccaga tgacccagtc tccatcctcc ctgtctgcat ctgtaggaga cagagtcacc    60
atcacttgcc gggcaagtca gagcattaac agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcaa ggagtcagtg acatcacttt tggcggaggg   300
accaaggttg agatcaaa                                                  318

<210> SEQ ID NO 49
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Leu Tyr
                20                  25                  30

Ala Ile Ser Trp Val Arg Gln Ala Pro Gly Gln Gly Leu Glu Trp Met
            35                  40                  45

Gly Gly Ile Ile Pro His Phe Gly Leu Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Leu Asp Thr Asp Glu Phe Asp Leu Trp Gly Arg Gly
            100                 105                 110

Thr Leu Val Thr Val Ser Ser
        115

<210> SEQ ID NO 50
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Gly Val Ser Asp Ile Thr
            85                  90                  95

Phe Gly Gly Gly Thr Lys Val Glu Ile Lys
            100                 105

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Thr Phe Ser Leu Tyr Ala Ile Ser
1               5

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Ile Ile Pro His Phe Gly Leu Ala Asn Tyr Ala Gln Lys Phe Gln
1               5                   10                  15

Gly

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Arg Gly Gly Leu Asp Thr Asp Glu Phe Asp Leu
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Ala Ser Gln Ser Ile Asn Ser Tyr Leu Asn
1               5                   10

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Ala Ser Ser Leu Gln Ser
1               5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Gln Gly Val Ser Asp Ile Thr
1               5

<210> SEQ ID NO 57
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
caggtgcagc tggtgcagtc tggggctgag gtgaagaagc ctgggtcctc ggtgaaggtc      60
tcctgcaagg cttctggagg caccttctcc ctctatgcta tcagctgggt gcgacaggcc     120
cctggacaag ggcttgagtg gatgggaggg atcatccctc acttcggtct cgcaaactac     180
gcacagaagt tccagggcag agtcacgatt accgcggacg aatccacgag cacagcctac     240
atggagctga gcagcctgag atctgaggac acggcggtgt actactgcgc cagaggtgga     300
ttggacacag acgagttcga cctatggggg agaggtacct tggtcaccgt ctcctca        357

<210> SEQ ID NO 58
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
gacatccaga tgacccagtc tccatcctcc ctgtctgcat ctgtaggaga cagagtcacc      60
atcacttgcc gggcaagtca gagcattaac agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcaa ggagtcagtg acatcacttt tggcggaggg     300
accaaggttg agatcaaa                                                    318

<210> SEQ ID NO 59
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Gly Pro Pro Thr Tyr His Thr Asn Tyr Tyr Met Asp Val
            100                 105                 110

Trp Gly Lys Gly Thr Thr Val Thr Val Ser Ser
            115                 120

<210> SEQ ID NO 60
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Asn Ser Phe Pro Tyr
                85                  90                  95

Thr Phe Gly Gly Gly Thr Lys Val Glu Ile Lys
            100                 105

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Phe Thr Phe Ser Asn Tyr Ala Met Ser
 1               5

<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ala Ile Ser Gly Ser Gly Gly Ser Thr Tyr Tyr Ala Asp Ser Val Lys
 1               5                  10                  15

Gly

```
<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ala Lys Gly Pro Pro Thr Tyr His Thr Asn Tyr Tyr Tyr Met Asp Val
1               5                   10                  15

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Ala Ser Gln Gly Ile Ser Ser Trp Leu Ala
1               5                   10

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Ala Ser Ser Leu Gln Ser
1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Gln Thr Asn Ser Phe Pro Tyr Thr
1               5

<210> SEQ ID NO 67
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
gaggtgcagc tgttggagtc tgggggaggc ttggtacagc ctggggggtc cctgagactc      60
tcctgtgcag cctctggatt cacctttagc aattatgcca tgagctgggt ccgccaggct     120
ccagggaagg gctggagtg gtctcagct attagtggta gtggtggtag cacatactac      180
gcagactccg tgaagggccg gttcaccatc tccagagaca attccaagaa cacgctgtat     240
ctgcaaatga acagcctgag agccgaggac acggcggtgt actactgcgc caagggccct     300
cctacatacc acacaaacta ctactacatg gacgtatggg gcaagggtac aactgtcacc     360
gtctcctca                                                              369
```

<210> SEQ ID NO 68
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68

```
gacatccaga tgacccagtc tccatcttcc gtgtctgcat ctgtaggaga cagagtcacc    60
atcacttgtc gggcgagtca gggtattagc agctggttag cctggtatca gcagaaacca   120
gggaaagccc ctaagctcct gatctatgct gcatccagtt tgcaaagtgg ggtcccatca   180
aggttcagcg gcagtggatc tgggacagat ttcactctca ccatcagcag cctgcagcct   240
gaagattttg caacttatta ctgtcagcaa acaaatagtt tcccttacac ttttggcgga   300
gggaccaagg ttgagatcaa a                                             321
```

<210> SEQ ID NO 69
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met Ile Trp Val Arg Gln Ala Pro Gly Lys Gly Leu Glu Trp Val
        35                  40                  45

Ser Ser Ile Ser Gly Asp Ser Val Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Pro Thr Tyr His Thr Asn Tyr Tyr Tyr Met Asp Val
            100                 105                 110

Trp Gly Lys Gly Thr Thr Val Thr Val Ser Ser
        115                 120
```

<210> SEQ ID NO 70
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45
```

-continued

```
Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Asn Ser Phe Pro Tyr
                 85                  90                  95

Thr Phe Gly Gly Gly Thr Lys Val Glu Ile Lys
            100                 105

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Phe Thr Phe Ser Ser Tyr Val Met Ile
1               5

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ser Ile Ser Gly Asp Ser Val Thr Thr Tyr Tyr Ala Asp Ser Val Lys
1               5                   10                  15

Gly

<210> SEQ ID NO 73
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ala Lys Gly Pro Pro Thr Tyr His Thr Asn Tyr Tyr Tyr Met Asp Val
1               5                   10                  15

<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Ala Ser Gln Gly Ile Ser Ser Trp Leu Ala
1               5                   10

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 75

Ala Ala Ser Ser Leu Gln Ser
1               5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gln Gln Thr Asn Ser Phe Pro Tyr Thr
1               5

<210> SEQ ID NO 77
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
gaggtgcagc tgttggagtc tgggggaggc ttggtacagc ctgggggtc cctgagactc      60 tcctgtgcag cctctggatt cacctttagc agctatgtca tgatctgggt ccgccaggct    120
ccagggaagg gctggagtg gtctcaagc attagtggtg acagcgtaac aacatactac     180
gcagactccg tgaagggccg gttcaccatc tccagagaca attccaagaa cacgctgtat    240
ctgcaaatga acagcctgag agccgaggac acggcggtgt actactgcgc caagggccct    300
cctacatacc acacaaacta ctactacatg gacgtatggg gcaagggtac aactgtcacc    360
gtctcctca                                                           369

<210> SEQ ID NO 78
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
gacatccaga tgacccagtc tccatcttcc gtgtctgcat ctgtaggaga cagagtcacc     60
atcacttgtc gggcgagtca gggtattagc agctggttag cctggtatca gcagaaacca    120
gggaaagccc ctaagctcct gatctatgct gcatccagtt tgcaaagtgg ggtcccatca    180
aggttcagcg gcagtggatc tgggacagat ttcactctca ccatcagcag cctgcagcct    240
gaagattttg caacttatta ctgtcagcaa acaaatagtt tcccttacac ttttggcgga    300
gggaccaagg ttgagatcaa a                                              321

<210> SEQ ID NO 79
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Val Gln Leu Val Glu Ser Gly Gly Gly Leu Val Gln Pro Gly Gly
```

```
                1               5                   10                  15
            Ser Leu Arg Leu Ser Cys Ala Ala Ser Gly Phe Thr Phe Ser Asp His
                            20                  25                  30

Tyr Met Asp Trp Val Arg Gln Ala Pro Gly Lys Gly Leu Glu Trp Val
                            35                  40                  45

Gly Arg Thr Arg Asn Lys Ala Ser Ser Tyr Thr Thr Glu Tyr Ala Ala
                            50                  55                  60

Ser Val Lys Gly Arg Phe Thr Ile Ser Arg Asp Asp Ser Lys Asn Ser
             65                 70                  75                  80

Leu Tyr Leu Gln Met Asn Ser Leu Lys Thr Glu Asp Thr Ala Val Tyr
                            85                  90                  95

Tyr Cys Ala Arg Glu Pro Lys Tyr Trp Ile Asp Phe Asp Leu Trp Gly
                            100                 105                 110

Arg Gly Thr Leu Val Thr Val Ser Ser
                            115                 120

<210> SEQ ID NO 80
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
                35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ile Ala Pro Tyr
                85                  90                  95

Thr Phe Gly Gly Gly Thr Lys Val Glu Ile Lys
                100                 105

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Phe Thr Phe Ser Asp His Tyr Met Asp
1               5

<210> SEQ ID NO 82
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82
```

Arg Thr Arg Asn Lys Ala Ser Ser Tyr Thr Thr Glu Tyr Ala Ala Ser
1               5                   10                  15

Val Lys Gly

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ala Arg Glu Pro Lys Tyr Trp Ile Asp Phe Asp Leu
1               5                   10

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Arg Ala Ser Gln Ser Ile Ser Ser Tyr Leu Asn
1               5                   10

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Ala Ser Ser Leu Gln Ser
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln Gln Ser Tyr Ile Ala Pro Tyr Thr
1               5

<210> SEQ ID NO 87
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
gaggtgcagc tggtggagtc tgggggaggc ttggtccagc ctggagggtc cctgagactc        60
tcctgtgcag cctctggatt caccttcagt gaccactaca tggactgggt ccgccaggct       120
ccagggaagg ggctggagtg ggttggccgt actagaaaca agctagtag ttacaccaca         180

```
gaatacgccg cgtctgtgaa aggcagattc accatctcaa gagatgattc aaagaactca    240
ctgtatctgc aaatgaacag cctgaaaacc gaggacacgg cggtgtacta ctgcgccaga    300
gagcctaaat actggatcga cttcgaccta tggggagag gtaccttggt caccgtctcc    360
tca                                                                 363
```

<210> SEQ ID NO 88
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88

```
gacatccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcagcaa agctacatcg cccttacac ttttggcgga    300 gggaccaagg ttgagatcaa a                                             321
```

<210> SEQ ID NO 89
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Ser Asp His
            20                  25                  30

Asp Met Asn Trp Val Arg Gln Ala Pro Gly Lys Gly Leu Glu Trp Val
        35                  40                  45

Gly Arg Thr Arg Asn Ala Ala Gly Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Glu Pro Lys Tyr Trp Ile Asp Phe Asp Leu Trp Gly
            100                 105                 110

Arg Gly Thr Leu Val Thr Val Ser Ser
        115                 120

<210> SEQ ID NO 90
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ile Ala Pro Tyr
                85                  90                  95

Thr Phe Gly Gly Gly Thr Lys Val Glu Ile Lys
            100                 105

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Phe Thr Phe Ser Asp His Asp Met Asn
1               5

<210> SEQ ID NO 92
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Arg Thr Arg Asn Ala Ala Gly Ser Tyr Thr Thr Glu Tyr Ala Ala Ser
1               5                   10                  15

Val Lys Gly

<210> SEQ ID NO 93
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ala Arg Glu Pro Lys Tyr Trp Ile Asp Phe Asp Leu
1               5                   10

<210> SEQ ID NO 94
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Arg Ala Ser Gln Ser Ile Ser Ser Tyr Leu Asn
1               5                   10

<210> SEQ ID NO 95
```

<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ala Ala Ser Ser Leu Gln Ser
1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gln Gln Ser Tyr Ile Ala Pro Tyr Thr
1               5

<210> SEQ ID NO 97
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
gaggtgcagc tggtggagtc tgggggaggc ttggtacagc cagggcggtc cctgagactc    60
tcctgtacag cttctggatt caccttcagt gaccacgaca tgaactgggt ccgccaggct   120
ccagggaagg ggctggagtg ggttggccgt actagaaacg ccgctggaag ttacaccaca   180
gaatacgccg cgtctgtgaa aggcagattc accatctcaa gagatgattc aaagaactca   240
ctgtatctgc aaatgaacag cctgaaaacc gaggacacgg cggtgtacta ctgcgccaga   300
gagcctaaat actggatcga cttcgaccta tggggagag gtaccttggt caccgtctcc   360
tca                                                                363

<210> SEQ ID NO 98
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcaa agctacatcg ccccttacac ttttggcgga   300
gggaccaagg ttgagatcaa a                                            321

<210> SEQ ID NO 99
<211> LENGTH: 121
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 99

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Val Asp His
            20                  25                  30

Asp Met Asp Trp Val Arg Gln Ala Pro Gly Lys Gly Leu Glu Trp Val
        35                  40                  45

Gly Arg Thr Arg Asn Lys Leu Gly Ser Tyr Thr Thr Glu Tyr Ala Ala
50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Glu Pro Lys Tyr Trp Ile Asp Phe Asp Leu Trp Gly
            100                 105                 110

Arg Gly Thr Leu Val Thr Val Ser Ser
        115                 120

<210> SEQ ID NO 100
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ile Ala Pro Tyr
                85                  90                  95

Thr Phe Gly Gly Gly Thr Lys Val Glu Ile Lys
            100                 105

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Phe Thr Phe Val Asp His Asp Met Asp
1               5

<210> SEQ ID NO 102
<211> LENGTH: 19
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Arg Thr Arg Asn Lys Leu Gly Ser Tyr Thr Thr Glu Tyr Ala Ala Ser
1               5                   10                  15
Val Lys Gly

<210> SEQ ID NO 103
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ala Arg Glu Pro Lys Tyr Trp Ile Asp Phe Asp Leu
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Arg Ala Ser Gln Ser Ile Ser Ser Tyr Leu Asn
1               5                   10

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ala Ala Ser Ser Leu Gln Ser
1               5

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gln Gln Ser Tyr Ile Ala Pro Tyr Thr
1               5

<210> SEQ ID NO 107
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107
```

```
gaggtgcagc tggtggagtc tgggggaggc ttggtccagc ctggagggtc cctgagactc    60
tcctgtgcag cctctggatt caccttcgta gaccacgaca tggactgggt ccgccaggct   120
ccagggaagg gctggagtg gttggccgt actagaaaca aactaggaag ttacaccaca    180
```
```
gaatacgccg cgtctgtgaa aggcagattc accatctcaa gagatgattc aaagaactca   240
ctgtatctgc aaatgaacag cctgaaaacc gaggacacgg cggtgtacta ctgcgccaga   300
gagcctaaat actggatcga cttcgaccta tggggagag gtaccttggt caccgtctcc   360
tca                                                                363
```

<210> SEQ ID NO 108
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcaa agctacatcg ccccttacac ttttggcgga   300
gggaccaagg ttgagatcaa a                                              321
```

<210> SEQ ID NO 109
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ile Ala Pro Tyr
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 110
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Asp Met Asp Trp Val Arg Gln Ala Pro Gly Lys Gly Leu Glu Trp Val
        35                  40                  45

Gly Arg Thr Arg Asn Lys Ala Gly Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Glu Pro Lys Tyr Trp Ile Asp Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300
```

```
Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Asp Glu Leu Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly Lys
    450

<210> SEQ ID NO 111
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Asp Met Asp Trp Val Arg Gln Ala Pro Gly Lys Gly Leu Glu Trp Val
        35                  40                  45

Gly Arg Thr Arg Asn Lys Ala Gly Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Glu Pro Lys Tyr Trp Ile Asp Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
```

```
                195                 200                 205
Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Cys Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 112
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Asp Met Asp Trp Val Arg Gln Ala Pro Gly Lys Gly Leu Glu Trp Val
        35                  40                  45

Gly Arg Thr Arg Asn Lys Ala Gly Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95
```

Tyr Cys Ala Arg Glu Pro Lys Tyr Trp Ile Asp Phe Asp Leu Trp Gly
            100                 105                 110
Arg Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
210                 215                 220
Asp Lys Thr His Thr Cys Pro Pro Cys Pro Ala Pro Glu Ala Ala Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Cys Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 113
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Asp Met Asp Trp Val Arg Gln Ala Pro Gly Lys Gly Leu Glu Trp Val
        35                  40                  45

Gly Arg Thr Arg Asn Lys Ala Gly Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Glu Pro Lys Tyr Trp Ile Asp Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Cys Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

```
Asp Lys Ser Arg Trp Gln Gln Gly Asn Val Phe Ser Cys Ser Val Met
            420                 425                 430

His Glu Ala Leu His Asn Ala Tyr Thr Gln Lys Ser Leu Ser Leu Ser
        435                 440                 445

Pro Gly Lys
    450

<210> SEQ ID NO 114
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Asp Met Asp Trp Val Arg Gln Ala Pro Gly Lys Gly Leu Glu Trp Val
        35                  40                  45

Gly Arg Thr Arg Asn Lys Ala Gly Ser Tyr Thr Thr Glu Tyr Ala Ala
50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Glu Pro Lys Tyr Trp Ile Asp Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Cys Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320
```

```
Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn Ala Tyr Thr Gln Lys Ser Leu Ser Leu Ser
        435                 440                 445

Pro Gly Lys
    450

<210> SEQ ID NO 115
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Asp Ile Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
```

<210> SEQ ID NO 116
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 116

Gln Val Gln Leu Val Gln Ser Gly Ala Glu Val Lys Pro Gly Ser
1               5                   10                  15

Ser Val Lys Val Ser Cys Lys Ala Ser Gly Gly Thr Phe Arg Ile Tyr
            20                  25                  30

Ala Ile Ser Trp Val Arg Gln Ala Pro Gly Gln Gly Leu Glu Trp Met
        35                  40                  45

Gly Gly Ile Ile Pro Asp Phe Gly Val Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Leu Asp Thr Asp Glu Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

```
Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 117
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Ile Tyr
            20                  25                  30

Ala Ile Ser Trp Val Arg Gln Ala Pro Gly Gln Gly Leu Glu Trp Met
        35                  40                  45

Gly Gly Ile Ile Pro Asp Phe Gly Val Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Leu Asp Thr Asp Glu Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255
```

```
Arg Thr Pro Glu Val Thr Cys Val Val Cys Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys

<210> SEQ ID NO 118
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Arg Ile Tyr
            20                  25                  30
Ala Ile Ser Trp Val Arg Gln Ala Pro Gly Gln Gly Leu Glu Trp Met
        35                  40                  45
Gly Gly Ile Ile Pro Asp Phe Gly Val Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Gly Gly Leu Asp Thr Asp Glu Phe Asp Leu Trp Gly Arg Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
```

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Cys Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Asp Glu Leu Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 119
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Ile Tyr
            20                  25                  30

Ala Ile Ser Trp Val Arg Gln Ala Pro Gly Gln Gly Leu Glu Trp Met
        35                  40                  45

Gly Gly Ile Ile Pro Asp Phe Gly Val Ala Asn Tyr Ala Gln Lys Phe
    50                  55                  60

```
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Leu Asp Thr Asp Glu Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Cys Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn Ala Tyr Thr Gln Lys Ser Leu Ser Leu Ser Pro Gly
        435                 440                 445

Lys

<210> SEQ ID NO 120
<211> LENGTH: 449
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 120

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Ile Tyr
            20                  25                  30

Ala Ile Ser Trp Val Arg Gln Ala Pro Gly Gln Gly Leu Glu Trp Met
        35                  40                  45

Gly Gly Ile Ile Pro Asp Phe Gly Val Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Leu Asp Thr Asp Glu Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Cys Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
```

```
                385                 390                 395                 400
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn Ala Tyr Thr Gln Lys Ser Leu Ser Leu Ser Pro Gly
                435                 440                 445

Lys

<210> SEQ ID NO 121
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 122
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125
```

```
Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 123
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Cys Val Ser His Glu Asp Pro Glu Val Lys Phe Asn Trp
```

```
                145                 150                 155                 160
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 124
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Ala Ala Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Cys Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 125
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Cys Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn Ala Tyr Thr
305                 310                 315                 320

Gln Lys Ser Leu Ser Leu Ser Pro Gly Lys
                325                 330

<210> SEQ ID NO 126
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Cys Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
```

```
                225                 230                 235                 240
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn Ala Tyr Thr
305                 310                 315                 320

Gln Lys Ser Leu Ser Leu Ser Pro Gly Lys
                325                 330

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ser or Arg
<220> FEATURE:
<221> NAME/KEY: MOD_RES
<222> LOCATION: (5)..(5)
<223> OTHER INFORMATION: Ser, Ile, or Leu

<400> SEQUENCE: 127

Gly Thr Phe Xaa Xaa Tyr Ala Ile Ser
1               5

<210> SEQ ID NO 128
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ile, Asp, Ala, or His
<220> FEATURE:
<221> NAME/KEY: MOD_RES
<222> LOCATION: (8)..(8)
<223> OTHER INFORMATION: Thr, Val, or Leu

<400> SEQUENCE: 128

Gly Ile Ile Pro Xaa Phe Gly Xaa Ala Asn Tyr Ala Gln Lys Phe Gln
1               5                   10                  15

Gly

<210> SEQ ID NO 129
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ala Arg Gly Gly Leu Asp Thr Asp Glu Phe Asp Leu
1               5                   10
```

```
<210> SEQ ID NO 130
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Arg Ala Ser Gln Ser Ile Asn Ser Tyr Leu Asn
1               5                   10

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ala Ala Ser Ser Leu Gln Ser
1               5

<210> SEQ ID NO 132
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gln Gln Gly Val Ser Asp Ile Thr
1               5

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Asn or Ser
<220> FEATURE:
<221> NAME/KEY: MOD_RES
<222> LOCATION: (7)..(7)
<223> OTHER INFORMATION: Ala or Val
<220> FEATURE:
<221> NAME/KEY: MOD_RES
<222> LOCATION: (9)..(9)
<223> OTHER INFORMATION: Ser or Ile

<400> SEQUENCE: 133

Phe Thr Phe Ser Xaa Tyr Xaa Met Xaa
1               5

<210> SEQ ID NO 134
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Ala or Ser
<220> FEATURE:
<221> NAME/KEY: MOD_RES
<222> LOCATION: (5)..(5)
<223> OTHER INFORMATION: Ser or Asp
<220> FEATURE:
<221> NAME/KEY: MOD_RES
<222> LOCATION: (6)..(6)
<223> OTHER INFORMATION: Gly or Ser
<220> FEATURE:
<221> NAME/KEY: MOD_RES
<222> LOCATION: (7)..(7)
<223> OTHER INFORMATION: Gly or Val
<220> FEATURE:
<221> NAME/KEY: MOD_RES
<222> LOCATION: (8)..(8)
<223> OTHER INFORMATION: Ser or Thr

<400> SEQUENCE: 134

Xaa Ile Ser Gly Xaa Xaa Xaa Xaa Thr Tyr Tyr Ala Asp Ser Val Lys
1               5                   10                  15

Gly

<210> SEQ ID NO 135
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ala Lys Gly Pro Pro Thr Tyr His Thr Asn Tyr Tyr Met Asp Val
1               5                   10                  15

<210> SEQ ID NO 136
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Arg Ala Ser Gln Gly Ile Ser Ser Trp Leu Ala
1               5                   10

<210> SEQ ID NO 137
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ala Ala Ser Ser Leu Gln Ser
1               5

<210> SEQ ID NO 138
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138
```

```
Gln Gln Thr Asn Ser Phe Pro Tyr Thr
1               5

<210> SEQ ID NO 139
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ser or Val
<220> FEATURE:
<221> NAME/KEY: MOD_RES
<222> LOCATION: (6)..(6)
<223> OTHER INFORMATION: His or Ala
<220> FEATURE:
<221> NAME/KEY: MOD_RES
<222> LOCATION: (7)..(7)
<223> OTHER INFORMATION: Tyr or Asp
<220> FEATURE:
<221> NAME/KEY: MOD_RES
<222> LOCATION: (9)..(9)
<223> OTHER INFORMATION: Asp or Asn

<400> SEQUENCE: 139

Phe Thr Phe Xaa Asp Xaa Xaa Met Xaa
1               5

<210> SEQ ID NO 140
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Lys or Ala
<220> FEATURE:
<221> NAME/KEY: MOD_RES
<222> LOCATION: (6)..(6)
<223> OTHER INFORMATION: Ala or Leu
<220> FEATURE:
<221> NAME/KEY: MOD_RES
<222> LOCATION: (7)..(7)
<223> OTHER INFORMATION: Ser or Gly

<400> SEQUENCE: 140

Arg Thr Arg Asn Xaa Xaa Xaa Ser Tyr Thr Thr Glu Tyr Ala Ala Ser
1               5                   10                  15

Val Lys Gly

<210> SEQ ID NO 141
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Ala Arg Glu Pro Lys Tyr Trp Ile Asp Phe Asp Leu
1               5                   10

<210> SEQ ID NO 142
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 142

Arg Ala Ser Gln Ser Ile Ser Ser Tyr Leu Asn
1               5                   10

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ala Ala Ser Ser Leu Gln Ser
1               5

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gln Gln Ser Tyr Ile Ala Pro Tyr Thr
1               5

<210> SEQ ID NO 145
<211> LENGTH: 976
<212> TYPE: PRT
<213> ORGANISM: Homo sapiens

<400> SEQUENCE: 145

Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
                20                  25                  30

Glu Pro Ser Pro Pro Ser Ile His Pro Gly Lys Ser Asp Leu Ile Val
            35                  40                  45

Arg Val Gly Asp Glu Ile Arg Leu Leu Cys Thr Asp Pro Gly Phe Val
        50                  55                  60

Lys Trp Thr Phe Glu Ile Leu Asp Glu Thr Asn Glu Asn Lys Gln Asn
65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
        115                 120                 125

Asp Asn Asp Thr Leu Val Arg Cys Pro Leu Thr Asp Pro Glu Val Thr
    130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175
```

```
Arg Ala Tyr His Arg Leu Cys Leu His Cys Ser Val Asp Gln Glu Gly
            180                 185                 190
Lys Ser Val Leu Ser Glu Lys Phe Ile Leu Lys Val Arg Pro Ala Phe
        195                 200                 205
Lys Ala Val Pro Val Ser Val Ser Lys Ala Ser Tyr Leu Leu Arg
    210                 215                 220
Glu Gly Glu Glu Phe Thr Val Thr Cys Thr Ile Lys Asp Val Ser Ser
225                 230                 235                 240
Ser Val Tyr Ser Thr Trp Lys Arg Glu Asn Ser Gln Thr Lys Leu Gln
                245                 250                 255
Glu Lys Tyr Asn Ser Trp His His Gly Asp Phe Asn Tyr Glu Arg Gln
            260                 265                 270
Ala Thr Leu Thr Ile Ser Ser Ala Arg Val Asn Asp Ser Gly Val Phe
        275                 280                 285
Met Cys Tyr Ala Asn Asn Thr Phe Gly Ser Ala Asn Val Thr Thr Thr
    290                 295                 300
Leu Glu Val Val Asp Lys Gly Phe Ile Asn Ile Phe Pro Met Ile Asn
305                 310                 315                 320
Thr Thr Val Phe Val Asn Asp Gly Glu Asn Val Asp Leu Ile Val Glu
                325                 330                 335
Tyr Glu Ala Phe Pro Lys Pro Glu His Gln Gln Trp Ile Tyr Met Asn
            340                 345                 350
Arg Thr Phe Thr Asp Lys Trp Glu Asp Tyr Pro Lys Ser Glu Asn Glu
        355                 360                 365
Ser Asn Ile Arg Tyr Val Ser Glu Leu His Leu Thr Arg Leu Lys Gly
    370                 375                 380
Thr Glu Gly Gly Thr Tyr Thr Phe Leu Val Ser Asn Ser Asp Val Asn
385                 390                 395                 400
Ala Ala Ile Ala Phe Asn Val Tyr Val Asn Thr Lys Pro Glu Ile Leu
                405                 410                 415
Thr Tyr Asp Arg Leu Val Asn Gly Met Leu Gln Cys Val Ala Ala Gly
            420                 425                 430
Phe Pro Glu Pro Thr Ile Asp Trp Tyr Phe Cys Pro Gly Thr Glu Gln
        435                 440                 445
Arg Cys Ser Ala Ser Val Leu Pro Val Asp Val Gln Thr Leu Asn Ser
    450                 455                 460
Ser Gly Pro Pro Phe Gly Lys Leu Val Val Gln Ser Ser Ile Asp Ser
465                 470                 475                 480
Ser Ala Phe Lys His Asn Gly Thr Val Glu Cys Lys Ala Tyr Asn Asp
                485                 490                 495
Val Gly Lys Thr Ser Ala Tyr Phe Asn Phe Ala Phe Lys Gly Asn Asn
            500                 505                 510
Lys Glu Gln Ile His Pro His Thr Leu Phe Thr Pro Leu Leu Ile Gly
        515                 520                 525
Phe Val Ile Val Ala Gly Met Met Cys Ile Ile Val Met Ile Leu Thr
    530                 535                 540
Tyr Lys Tyr Leu Gln Lys Pro Met Tyr Glu Val Gln Trp Lys Val Val
545                 550                 555                 560
Glu Glu Ile Asn Gly Asn Asn Tyr Val Tyr Ile Asp Pro Thr Gln Leu
                565                 570                 575
Pro Tyr Asp His Lys Trp Glu Phe Pro Arg Asn Arg Leu Ser Phe Gly
            580                 585                 590
Lys Thr Leu Gly Ala Gly Ala Phe Gly Lys Val Val Glu Ala Thr Ala
```

|  |  |  |  |  | 595 |  |  |  |  | 600 |  |  |  |  | 605 |  |
|---|---|---|---|---|---|---|---|---|---|---|---|---|---|---|---|---|

Tyr Gly Leu Ile Lys Ser Asp Ala Ala Met Thr Val Ala Val Lys Met
610                615                620

Leu Lys Pro Ser Ala His Leu Thr Glu Arg Glu Ala Leu Met Ser Glu
625                630                635                640

Leu Lys Val Leu Ser Tyr Leu Gly Asn His Met Asn Ile Val Asn Leu
              645                650                655

Leu Gly Ala Cys Thr Ile Gly Gly Pro Thr Leu Val Ile Thr Glu Tyr
              660                665                670

Cys Cys Tyr Gly Asp Leu Leu Asn Phe Leu Arg Arg Lys Arg Asp Ser
              675                680                685

Phe Ile Cys Ser Lys Gln Glu Asp His Ala Glu Ala Ala Leu Tyr Lys
              690                695                700

Asn Leu Leu His Ser Lys Glu Ser Ser Cys Ser Asp Ser Thr Asn Glu
705                710                715                720

Tyr Met Asp Met Lys Pro Gly Val Ser Tyr Val Val Pro Thr Lys Ala
              725                730                735

Asp Lys Arg Arg Ser Val Arg Ile Gly Ser Tyr Ile Glu Arg Asp Val
              740                745                750

Thr Pro Ala Ile Met Glu Asp Glu Leu Ala Leu Asp Leu Glu Asp
              755                760                765

Leu Leu Ser Phe Ser Tyr Gln Val Ala Lys Gly Met Ala Phe Leu Ala
770                775                780

Ser Lys Asn Cys Ile His Arg Asp Leu Ala Ala Arg Asn Ile Leu Leu
785                790                795                800

Thr His Gly Arg Ile Thr Lys Ile Cys Asp Phe Gly Leu Ala Arg Asp
              805                810                815

Ile Lys Asn Asp Ser Asn Tyr Val Val Lys Gly Asn Ala Arg Leu Pro
              820                825                830

Val Lys Trp Met Ala Pro Glu Ser Ile Phe Asn Cys Val Tyr Thr Phe
              835                840                845

Glu Ser Asp Val Trp Ser Tyr Gly Ile Phe Leu Trp Glu Leu Phe Ser
              850                855                860

Leu Gly Ser Ser Pro Tyr Pro Gly Met Pro Val Asp Ser Lys Phe Tyr
865                870                875                880

Lys Met Ile Lys Glu Gly Phe Arg Met Leu Ser Pro Glu His Ala Pro
              885                890                895

Ala Glu Met Tyr Asp Ile Met Lys Thr Cys Trp Asp Ala Asp Pro Leu
              900                905                910

Lys Arg Pro Thr Phe Lys Gln Ile Val Gln Leu Ile Glu Lys Gln Ile
              915                920                925

Ser Glu Ser Thr Asn His Ile Tyr Ser Asn Leu Ala Asn Cys Ser Pro
              930                935                940

Asn Arg Gln Lys Pro Val Val Asp His Ser Val Arg Ile Asn Ser Val
945                950                955                960

Gly Ser Thr Ala Ser Ser Ser Gln Pro Leu Leu Val His Asp Asp Val
              965                970                975

<210> SEQ ID NO 146
<211> LENGTH: 972
<212> TYPE: PRT
<213> ORGANISM: Homo sapiens

<400> SEQUENCE: 146

-continued

```
Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
            20                  25                  30

Glu Pro Ser Pro Ser Ile His Pro Gly Lys Ser Asp Leu Ile Val
        35                  40                  45

Arg Val Gly Asp Glu Ile Arg Leu Leu Cys Thr Asp Pro Gly Phe Val
    50                  55                  60

Lys Trp Thr Phe Glu Ile Leu Asp Glu Thr Asn Glu Asn Lys Gln Asn
65                      70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
        115                 120                 125

Asp Asn Asp Thr Leu Val Arg Cys Pro Leu Thr Asp Pro Glu Val Thr
130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
            180                 185                 190

Lys Ser Val Leu Ser Glu Lys Phe Ile Leu Lys Val Arg Pro Ala Phe
        195                 200                 205

Lys Ala Val Pro Val Val Ser Val Ser Lys Ala Ser Tyr Leu Leu Arg
    210                 215                 220

Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
                245                 250                 255

Glu Lys Tyr Asn Ser Trp His His Gly Asp Phe Asn Tyr Glu Arg Gln
            260                 265                 270

Ala Thr Leu Thr Ile Ser Ser Ala Arg Val Asn Asp Ser Gly Val Phe
        275                 280                 285

Met Cys Tyr Ala Asn Asn Thr Phe Gly Ser Ala Asn Val Thr Thr Thr
    290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
                325                 330                 335

Tyr Glu Ala Phe Pro Lys Pro Glu His Gln Gln Trp Ile Tyr Met Asn
            340                 345                 350

Arg Thr Phe Thr Asp Lys Trp Glu Asp Tyr Pro Lys Ser Glu Asn Glu
        355                 360                 365

Ser Asn Ile Arg Tyr Val Ser Glu Leu His Leu Thr Arg Leu Lys Gly
    370                 375                 380

Thr Glu Gly Gly Thr Tyr Thr Phe Leu Val Ser Asn Ser Asp Val Asn
385                 390                 395                 400

Ala Ala Ile Ala Phe Asn Val Tyr Val Asn Thr Lys Pro Glu Ile Leu
                405                 410                 415

Thr Tyr Asp Arg Leu Val Asn Gly Met Leu Gln Cys Val Ala Ala Gly
```

-continued

```
                420                 425                 430
Phe Pro Glu Pro Thr Ile Asp Trp Tyr Phe Cys Pro Gly Thr Glu Gln
            435                 440                 445
Arg Cys Ser Ala Ser Val Leu Pro Val Asp Val Gln Thr Leu Asn Ser
450                 455                 460
Ser Gly Pro Pro Phe Gly Lys Leu Val Val Gln Ser Ser Ile Asp Ser
465                 470                 475                 480
Ser Ala Phe Lys His Asn Gly Thr Val Glu Cys Lys Ala Tyr Asn Asp
                485                 490                 495
Val Gly Lys Thr Ser Ala Tyr Phe Asn Phe Ala Phe Lys Glu Gln Ile
            500                 505                 510
His Pro His Thr Leu Phe Thr Pro Leu Leu Ile Gly Phe Val Ile Val
            515                 520                 525
Ala Gly Met Met Cys Ile Ile Val Met Ile Leu Thr Tyr Lys Tyr Leu
            530                 535                 540
Gln Lys Pro Met Tyr Glu Val Gln Trp Lys Val Val Glu Glu Ile Asn
545                 550                 555                 560
Gly Asn Asn Tyr Val Tyr Ile Asp Pro Thr Gln Leu Pro Tyr Asp His
                565                 570                 575
Lys Trp Glu Phe Pro Arg Asn Arg Leu Ser Phe Gly Lys Thr Leu Gly
            580                 585                 590
Ala Gly Ala Phe Gly Lys Val Val Glu Ala Thr Ala Tyr Gly Leu Ile
            595                 600                 605
Lys Ser Asp Ala Ala Met Thr Val Ala Val Lys Met Leu Lys Pro Ser
            610                 615                 620
Ala His Leu Thr Glu Arg Glu Ala Leu Met Ser Glu Leu Lys Val Leu
625                 630                 635                 640
Ser Tyr Leu Gly Asn His Met Asn Ile Val Asn Leu Leu Gly Ala Cys
                645                 650                 655
Thr Ile Gly Gly Pro Thr Leu Val Ile Thr Glu Tyr Cys Cys Tyr Gly
            660                 665                 670
Asp Leu Leu Asn Phe Leu Arg Arg Lys Arg Asp Ser Phe Ile Cys Ser
            675                 680                 685
Lys Gln Glu Asp His Ala Glu Ala Leu Tyr Lys Asn Leu Leu His
            690                 695                 700
Ser Lys Glu Ser Ser Cys Ser Asp Ser Thr Asn Glu Tyr Met Asp Met
705                 710                 715                 720
Lys Pro Gly Val Ser Tyr Val Val Pro Thr Lys Ala Asp Lys Arg Arg
                725                 730                 735
Ser Val Arg Ile Gly Ser Tyr Ile Glu Arg Asp Val Thr Pro Ala Ile
            740                 745                 750
Met Glu Asp Asp Glu Leu Ala Leu Asp Leu Glu Asp Leu Leu Ser Phe
            755                 760                 765
Ser Tyr Gln Val Ala Lys Gly Met Ala Phe Leu Ala Ser Lys Asn Cys
            770                 775                 780
Ile His Arg Asp Leu Ala Ala Arg Asn Ile Leu Leu Thr His Gly Arg
785                 790                 795                 800
Ile Thr Lys Ile Cys Asp Phe Gly Leu Ala Arg Asp Ile Lys Asn Asp
                805                 810                 815
Ser Asn Tyr Val Val Lys Gly Asn Ala Arg Leu Pro Val Lys Trp Met
            820                 825                 830
Ala Pro Glu Ser Ile Phe Asn Cys Val Tyr Thr Phe Glu Ser Asp Val
            835                 840                 845
```

```
Trp Ser Tyr Gly Ile Phe Leu Trp Glu Leu Phe Ser Leu Gly Ser Ser
    850             855             860

Pro Tyr Pro Gly Met Pro Val Asp Ser Lys Phe Tyr Lys Met Ile Lys
865             870             875             880

Glu Gly Phe Arg Met Leu Ser Pro Glu His Ala Pro Ala Glu Met Tyr
            885             890             895

Asp Ile Met Lys Thr Cys Trp Asp Ala Asp Pro Leu Lys Arg Pro Thr
        900             905             910

Phe Lys Gln Ile Val Gln Leu Ile Glu Lys Gln Ile Ser Glu Ser Thr
    915             920             925

Asn His Ile Tyr Ser Asn Leu Ala Asn Cys Ser Pro Asn Arg Gln Lys
    930             935             940

Pro Val Val Asp His Ser Val Arg Ile Asn Ser Val Gly Ser Thr Ala
945             950             955             960

Ser Ser Ser Gln Pro Leu Leu Val His Asp Val
            965             970
```

COMPOSITIONS AND METHODS FOR THE DEPLETION OF CD117+ CELLS

RELATED APPLICATIONS

This application claims priority to U.S. Provisional Application No. 62/576,571, filed on Oct. 24, 2017; U.S. Provisional Application No. 62/576,593, filed on Oct. 24, 2017; U.S. Provisional Application No. 62/576,625, filed on Oct. 24, 2017; U.S. Provisional Application No. 62/576,628, filed on Oct. 24, 2017; U.S. Provisional Application No. 62/638,049, filed on Mar. 2, 2018; U.S. Provisional Application No. 62/576,629, filed on Oct. 24, 2017; U.S. Provisional Application No. 62/576,626, filed on Oct. 24, 2017; U.S. Provisional Application No. 62/576,588, filed on Oct. 24, 2017; U.S. Provisional Application No. 62/576,590, filed on Oct. 24, 2017; U.S. Provisional Application No. 62/638,051, filed on Mar. 2, 2018; U.S. Provisional Application No. 62/576,597, filed on Oct. 24, 2017; and U.S. Provisional Application No. 62/576,605, filed on Oct. 24, 2017. The contents of each of the priority applications is incorporated by reference herein.

SEQUENCE LISTING

The instant application contains a Sequence Listing which has been submitted electronically in ASCII format and is hereby incorporated by reference in its entirety. Said ASCII copy, created on Oct. 23, 2018, is named 2018-10-23_Sequence_Listing_M103034_1280US.txt and is 136,396 bytes in size.

FIELD OF THE INVENTION

The invention relates to anti-CD117 antibodies and antibody drug conjugates (ADCs) thereof, as well as the treatment of patients suffering from various pathologies, such as blood diseases, metabolic disorders, cancers, and autoimmune diseases, among others, by administration of an antibody or ADC capable of binding CD117 expressed by a hematopoietic cell, such as a hematopoietic stem cell.

BACKGROUND OF THE INVENTION

Despite advances in the medicinal arts, there remains a demand for treating pathologies of the hematopoietic system, such as diseases of a particular blood cell, metabolic disorders, cancers, and autoimmune conditions, among others. While hematopoietic stem cells have significant therapeutic potential, a limitation that has hindered their use in the clinic has been the difficulty associated with ensuring engraftment of hematopoietic stem cell transplants in a host.

There is currently a need for compositions that target specific endogenous stem cells that can be used as conditioning agents to promote the engraftment of exogenous hematopoietic stem cell grafts such that the multi-potency and hematopoietic functionality of these cells is preserved in the patient following transplantation.

CD117 (also referred to as c-kit or Stem Cell Factor Receptor (SCRF)) is a single transmembrane, receptor tyrosine kinase that binds the ligand Stem Cell Factor (SCF). SCF induces homodimerization of cKIT which activates its tyrosine kinase activity and signals through both the PI3-AKT and MAPK pathways (Kindblom et al., Am J. Path. 1998 152(5):1259).

CD117 was initially discovered as an oncogene and has been studied in the field of oncology (see, for example, Stankov et al. (2014) Curr Pharm Des. 20(17):2849-80). An antibody drug conjugate (KTN0158) directed to CD117 is currently under investigation for the treatment of refractory gastrointestinal stromal tumors (GIST) (e.g., "KTN0158, a humanized anti-KIT monoclonal antibody, demonstrates biologic activity against both normal and malignant canine mast cells" London et al. (2016) Clin Cancer Res DOI: 10.1158/1078-0432.CCR-16-2152).

CD117 is highly expressed on hematopoietic stem cells (HSCs). This expression pattern makes CD117 a potential target for conditioning across a broad range of diseases. There remains, however, a need for anti-CD117 based therapy that is effective for conditioning a patient for transplantation, such as a bone marrow transplantation.

SUMMARY OF THE INVENTION

Described herein are antibodies, and antigen binding portions thereof, that specifically bind human CD117 (also known as c-kit), as well as compositions and methods of using said antibodies. In particular, the antibodies and fragments described herein can be used in anti-CD117 antibody drug conjugates (ADCs).

In one embodiment, an anti-CD117 antibody, or antigen-binding portion thereof, comprises a light chain variable region comprising the amino acid sequence set forth in SEQ ID NO: 10, and a heavy chain variable region comprising the amino acid sequence set forth in SEQ ID NO: 9.

In one embodiment, an anti-CD117 antibody, or antigen-binding portion thereof, comprises a light chain variable region comprising a CDR1 domain as set forth in SEQ ID NO: 14, a CDR2 domain as set forth in SEQ ID NO: 15, and a CDR3 domain as set forth in SEQ ID NO: 16, and comprises a heavy chain variable region comprising a CDR1 domain as set forth in SEQ ID NO: 11, a CDR2 domain as set forth in SEQ ID NO: 12, and a CDR3 domain as set forth in SEQ ID NO: 13.

In one embodiment, an anti-CD117 antibody, or antigen-binding portion thereof, comprises a heavy chain variable region comprising a CDR1 domain comprising the amino acid sequence as set forth in SEQ ID NO: 31, a CDR2 domain comprising the amino acid sequence as set forth in SEQ ID NO:32, and a CDR3 domain comprising the amino acid sequence as set forth in SEQ ID NO: 33; and comprising a light chain variable region comprising a CDR1 domain comprising the amino acid sequence as set forth in SEQ ID NO: 34, a CDR2 domain comprising the amino acid sequence as set forth in SEQ ID NO:35, and a CDR3 domain comprising the amino acid sequence as set forth in SEQ ID NO: 36.

In one embodiment, an anti-CD117 antibody, or antigen-binding portion thereof, comprises a heavy chain variable region comprising a CDR1 domain comprising the amino acid sequence as set forth in SEQ ID NO: 21, a CDR2 domain comprising the amino acid sequence as set forth in SEQ ID NO:22, and a CDR3 domain comprising the amino acid sequence as set forth in SEQ ID NO: 23; and comprising a light chain variable region comprising a CDR1 domain comprising the amino acid sequence as set forth in SEQ ID NO: 24, a CDR2 domain comprising the amino acid sequence as set forth in SEQ ID NO:25, and a CDR3 domain comprising the amino acid sequence as set forth in SEQ ID NO: 26.

In one embodiment, an anti-CD117 antibody, or antigen-binding portion thereof, comprises a heavy chain variable region comprising a CDR1 domain comprising the amino acid sequence as set forth in SEQ ID NO: 41, a CDR2 domain comprising the amino acid sequence as set forth in SEQ ID NO:42, and a CDR3 domain comprising the amino acid sequence as set forth in SEQ ID NO: 43; and comprising a light chain variable region comprising a CDR1 domain comprising the amino acid sequence as set forth in SEQ ID NO: 44, a CDR2 domain comprising the amino acid sequence as set forth in SEQ ID NO:45, and a CDR3 domain comprising the amino acid sequence as set forth in SEQ ID NO: 46.

In one embodiment, an anti-CD117 antibody, or antigen-binding portion thereof, comprises a heavy chain variable region comprising a CDR1 domain comprising the amino acid sequence as set forth in SEQ ID NO: 51, a CDR2 domain comprising the amino acid sequence as set forth in SEQ ID NO:52, and a CDR3 domain comprising the amino acid sequence as set forth in SEQ ID NO: 53; and comprising a light chain variable region comprising a CDR1 domain comprising the amino acid sequence as set forth in SEQ ID NO: 54, a CDR2 domain comprising the amino acid sequence as set forth in SEQ ID NO:55, and a CDR3 domain comprising the amino acid sequence as set forth in SEQ ID NO: 56.

In one embodiment, an anti-CD117 antibody, or antigen-binding portion thereof, comprises a heavy chain variable region comprising a CDR1 domain comprising the amino acid sequence as set forth in SEQ ID NO: 61, a CDR2 domain comprising the amino acid sequence as set forth in SEQ ID NO:62, and a CDR3 domain comprising the amino acid sequence as set forth in SEQ ID NO: 63; and comprising a light chain variable region comprising a CDR1 domain comprising the amino acid sequence as set forth in SEQ ID NO: 64, a CDR2 domain comprising the amino acid sequence as set forth in SEQ ID NO:65, and a CDR3 domain comprising the amino acid sequence as set forth in SEQ ID NO: 66.

In one embodiment, an anti-CD117 antibody, or antigen-binding portion thereof, comprises a heavy chain variable region comprising a CDR1 domain comprising the amino acid sequence as set forth in SEQ ID NO: 71, a CDR2 domain comprising the amino acid sequence as set forth in SEQ ID NO:72, and a CDR3 domain comprising the amino acid sequence as set forth in SEQ ID NO: 73; and comprising a light chain variable region comprising a CDR1 domain comprising the amino acid sequence as set forth in SEQ ID NO: 74, a CDR2 domain comprising the amino acid sequence as set forth in SEQ ID NO:75, and a CDR3 domain comprising the amino acid sequence as set forth in SEQ ID NO: 76.

In one embodiment, an anti-CD117 antibody, or antigen-binding portion thereof, comprises a heavy chain variable region comprising a CDR1 domain comprising the amino acid sequence as set forth in SEQ ID NO: 81, a CDR2 domain comprising the amino acid sequence as set forth in SEQ ID NO:82, and a CDR3 domain comprising the amino acid sequence as set forth in SEQ ID NO: 83; and comprising a light chain variable region comprising a CDR1 domain comprising the amino acid sequence as set forth in SEQ ID NO: 84, a CDR2 domain comprising the amino acid sequence as set forth in SEQ ID NO:85, and a CDR3 domain comprising the amino acid sequence as set forth in SEQ ID NO: 86.

In one embodiment, an anti-CD117 antibody, or antigen-binding portion thereof, comprises a heavy chain variable region comprising a CDR1 domain comprising the amino acid sequence as set forth in SEQ ID NO: 11, a CDR2 domain comprising the amino acid sequence as set forth in SEQ ID NO:12, and a CDR3 domain comprising the amino acid sequence as set forth in SEQ ID NO: 13; and comprising a light chain variable region comprising a CDR1 domain comprising the amino acid sequence as set forth in SEQ ID NO: 14, a CDR2 domain comprising the amino acid sequence as set forth in SEQ ID NO:15, and a CDR3 domain comprising the amino acid sequence as set forth in SEQ ID NO: 16.

In one embodiment, an anti-CD117 antibody, or antigen-binding portion thereof, comprises a heavy chain variable region comprising a CDR1 domain comprising the amino acid sequence as set forth in SEQ ID NO: 91, a CDR2 domain comprising the amino acid sequence as set forth in SEQ ID NO:92, and a CDR3 domain comprising the amino acid sequence as set forth in SEQ ID NO: 93; and comprising a light chain variable region comprising a CDR1 domain comprising the amino acid sequence as set forth in SEQ ID NO: 94, a CDR2 domain comprising the amino acid sequence as set forth in SEQ ID NO:95, and a CDR3 domain comprising the amino acid sequence as set forth in SEQ ID NO: 96.

In one embodiment, an anti-CD117 antibody, or antigen-binding portion thereof, comprises a heavy chain variable region comprising a CDR1 domain comprising the amino acid sequence as set forth in SEQ ID NO: 101, a CDR2 domain comprising the amino acid sequence as set forth in SEQ ID NO:102, and a CDR3 domain comprising the amino acid sequence as set forth in SEQ ID NO: 103; and comprising a light chain variable region comprising a CDR1 domain comprising the amino acid sequence as set forth in SEQ ID NO: 104, a CDR2 domain comprising the amino acid sequence as set forth in SEQ ID NO:105, and a CDR3 domain comprising the amino acid sequence as set forth in SEQ ID NO: 106.

In one embodiment, an anti-CD117 antibody, or antigen-binding portion thereof, comprises a heavy chain variable region comprising a CDR1 domain comprising the amino acid sequence as set forth in SEQ ID NO: 127, a CDR2 domain comprising the amino acid sequence as set forth in SEQ ID NO:128, and a CDR3 domain comprising the amino acid sequence as set forth in SEQ ID NO: 129; and comprising a light chain variable region comprising a CDR1 domain comprising the amino acid sequence as set forth in SEQ ID NO: 130, a CDR2 domain comprising the amino acid sequence as set forth in SEQ ID NO:131, and a CDR3 domain comprising the amino acid sequence as set forth in SEQ ID NO: 132.

In one embodiment, an anti-CD117 antibody, or antigen-binding portion thereof, comprises a heavy chain variable region comprising a CDR1 domain comprising the amino acid sequence as set forth in SEQ ID NO: 133, a CDR2 domain comprising the amino acid sequence as set forth in SEQ ID NO:134, and a CDR3 domain comprising the amino acid sequence as set forth in SEQ ID NO: 135; and comprising a light chain variable region comprising a CDR1 domain comprising the amino acid sequence as set forth in SEQ ID NO: 136, a CDR2 domain comprising the amino acid sequence as set forth in SEQ ID NO:137, and a CDR3 domain comprising the amino acid sequence as set forth in SEQ ID NO: 138.

In one embodiment, an anti-CD117 antibody, or antigen-binding portion thereof, comprises a heavy chain variable region comprising a CDR1 domain comprising the amino acid sequence as set forth in SEQ ID NO: 139, a CDR2 domain comprising the amino acid sequence as set forth in SEQ ID NO:140, and a CDR3 domain comprising the amino acid sequence as set forth in SEQ ID NO: 141; and comprising a light chain variable region comprising a CDR1 domain comprising the amino acid sequence as set forth in SEQ ID NO: 142, a CDR2 domain comprising the amino acid sequence as set forth in SEQ ID NO:143, and a CDR3 domain comprising the amino acid sequence as set forth in SEQ ID NO: 144.

In one embodiment, an anti-CD117 antibody, or antigen-binding portion thereof, comprises a heavy chain variable region comprising the amino acid sequence as set forth in SEQ ID NO: 29, and a light chain variable region comprising the amino acid sequence as set forth in SEQ ID NO: 30.

In one embodiment, an anti-CD117 antibody, or antigen-binding portion thereof, comprises a heavy chain variable region comprising the amino acid sequence as set forth in SEQ ID NO: 19, and a light chain variable region comprising the amino acid sequence as set forth in SEQ ID NO: 20.

In one embodiment, an anti-CD117 antibody, or antigen-binding portion thereof, comprises a heavy chain variable region comprising the amino acid sequence as set forth in SEQ ID NO: 39, and a light chain variable region comprising the amino acid sequence as set forth in SEQ ID NO: 40.

In one embodiment, an anti-CD117 antibody, or antigen-binding portion thereof, comprises a heavy chain variable region comprising the amino acid sequence as set forth in SEQ ID NO: 49, and a light chain variable region comprising the amino acid sequence as set forth in SEQ ID NO: 50.

In one embodiment, an anti-CD117 antibody, or antigen-binding portion thereof, comprises a heavy chain variable region comprising the amino acid sequence as set forth in SEQ ID NO: 59, and a light chain variable region comprising the amino acid sequence as set forth in SEQ ID NO: 60.

In one embodiment, an anti-CD117 antibody, or antigen-binding portion thereof, comprises a heavy chain variable region comprising the amino acid sequence as set forth in SEQ ID NO: 69, and a light chain variable region comprising the amino acid sequence as set forth in SEQ ID NO: 70.

In one embodiment, an anti-CD117 antibody, or antigen-binding portion thereof, comprises a heavy chain variable region comprising the amino acid sequence as set forth in SEQ ID NO: 79, and a light chain variable region comprising the amino acid sequence as set forth in SEQ ID NO: 80.

In one embodiment, an anti-CD117 antibody, or antigen-binding portion thereof, comprises a heavy chain variable region comprising the amino acid sequence as set forth in SEQ ID NO: 9, and a light chain variable region comprising the amino acid sequence as set forth in SEQ ID NO: 10.

In one embodiment, an anti-CD117 antibody, or antigen-binding portion thereof, comprises a heavy chain variable region comprising the amino acid sequence as set forth in SEQ ID NO: 89, and a light chain variable region comprising the amino acid sequence as set forth in SEQ ID NO: 90.

In one embodiment, an anti-CD117 antibody, or antigen-binding portion thereof, comprises a heavy chain variable region comprising the amino acid sequence as set forth in SEQ ID NO: 99, and a light chain variable region comprising the amino acid sequence as set forth in SEQ ID NO: 100.

In some embodiments, an anti-CD117 antibody or antigen-binding fragment thereof comprises an Fc region comprising amino acid substitution D265C (numbering according to EU index).

In some embodiments, an anti-CD117 antibody or antigen-binding fragment thereof comprises an Fc region comprising amino acid substitutions D265C, L234A, and L2345A (numbering according to EU index).

In some embodiments, an anti-CD117 antibody or antigen-binding fragment thereof comprises an Fc region comprising amino acid substitutions D265C and H435A (numbering according to EU index).

In some embodiments, the anti-CD117 antibody or antigen-binding fragment thereof comprises an Fc region comprising amino acid substitutions D265C, L234A, L2345A, and H435A (numbering according to EU index).

In some embodiments, an anti-CD117 antibody or antigen-binding fragment thereof comprises a (i) light chain constant region comprising the amino acid sequence as set forth in SEQ ID NO: 121, and (ii) a heavy chain constant region comprising the amino acid sequence as set forth in SEQ ID NO: 122.

In some embodiments, the anti-CD117 antibody or antigen-binding fragment thereof comprises (i) a light chain constant region comprising the amino acid sequence as set forth in SEQ ID NO: 121, and (ii) a heavy chain constant region comprising the amino acid sequence as set forth in SEQ ID NO: 123.

In some embodiments, the anti-CD117 antibody or antigen-binding fragment thereof comprises (i) a light chain constant region comprising the amino acid sequence as set forth in SEQ ID NO: 121, and (ii) a heavy chain constant region comprising the amino acid sequence as set forth in SEQ ID NO: 124.

In some embodiments, the anti-CD117 antibody or antigen-binding fragment thereof comprises (i) a light chain constant region comprising the amino acid sequence as set forth in SEQ ID NO: 121, and (ii) a heavy chain constant region comprising the amino acid sequence as set forth in SEQ ID NO: 125.

In some embodiments, the anti-CD117 antibody or antigen-binding fragment thereof comprises (i) a light chain constant region comprising the amino acid sequence as set forth in SEQ ID NO: 121, and (ii) a heavy chain constant region comprising the amino acid sequence as set forth in SEQ ID NO: 126.

In one embodiment, the anti-CD117 antibody or antigen-binding fragment thereof is internalized by a CD117+ cell.

In another embodiment, the anti-CD117 antibody or antigen-binding fragment thereof binds CD117 with a $K_d$ of about 0.1 µM to about 1 µM as determined by BLI. In one embodiment, the antibody or antigen binding fragment thereof binds CD117 with a $K_D$ of about 100 nM or less, about 90 nM or less, about 80 nM or less, about 70 nM or less, about 60 nM or less, about 50 nM or less, about 40 nM or less, about 30 nM or less, about 20 nM or less, about 10 nM or less, about 8 nM or less, about 6 nM or less, about 4 nM or less, about 2 nM or less, about 1 nM or less as determined by a Bio-Layer Interferometry (BLI) assay. In yet another embodiment, the antibody or antigen-binding fragment thereof binds CD117 with a $k_{OFF}$ of about $1\times10^{-3}$ $s^{-1}$ to about $1\times10^{6}$ $s^{-1}$ as determined by BLI. In still another embodiment, the antibody or antigen-binding fragment thereof binds CD117 with a $k_{OFF}$ of $1\times10^{-2}$ to $1\times10^{-3}$, $1\times10^{-3}$ to $1\times10^{-4}$, $1\times10^{-5}$ to $1\times10^{-6}$, $1\times10^{-6}$ to $1\times10^{-7}$ or $1\times10^{-7}$ to $1\times10^{-8}$ as measured by bio-layer interferometry (BLI).

In certain embodiments, the anti-CD117 antibody, or antigen-binding fragment thereof, is human.

In certain embodiments, the anti-CD117 antibody is an intact antibody.

In certain embodiments, the anti-CD117 antibody, or antigen-binding fragment thereof, is an IgG, e.g., an IgG1 or an IgG4.

In certain embodiments, the anti-CD117 antibody, or antigen-binding fragment thereof, is the antibody or antigen-binding fragment thereof is a monoclonal antibody.

In certain embodiments, the anti-CD117 antibody, or antigen-binding fragment thereof, comprises a heavy chain constant region having an amino acid sequence as set forth as SEQ ID NO: 122. and/or a light chain constant region comprising an amino acid sequence as set forth in SEQ ID NO: 121.

In certain embodiments, the anti-CD117 antibody, or antigen-binding fragment thereof, comprises a light chain comprising an amino acid sequence as set forth in SEQ ID NO: 109, and a heavy chain comprising an amino acid sequence selected from the group consisting of SEQ ID NO 110, SEQ ID NO: 111, SEQ ID NO: 112, SEQ ID NO: 113, and SEQ ID NO: 114.

The antibodies, fragments, and ADCs described herein, including Antibody 54 (Ab54), Antibody 55 (Ab55), Antibody 56 (Ab56), Antibody 57 (Ab57), Antibody 58 (Ab58), Antibody 61 (Ab61), Antibody 66 (Ab66), Antibody 67 (Ab67), Antibody 68 (Ab68), or Antibody 69 (Ab69) may be used in compositions and methods for the treatment of various disorders of the hematopoietic system, metabolic disorders, cancers, and autoimmune diseases, among others. The invention additionally features methods for conditioning a patient, such as a human patient, prior to receiving hematopoietic stem cell transplant therapy so as to promote the engraftment of hematopoietic stem cell grafts. The patient may be one that is suffering from one or more blood disorders, such as a hemoglobinopathy or other hematopoietic pathology, and is thus in need of hematopoietic stem cell transplantation. As described herein, hematopoietic stem cells are capable of differentiating into a multitude of cell types in the hematopoietic lineage, and can be administered to a patient in order to populate or re-populate a cell type that is deficient in the patient.

The invention features methods of treating a patient with antibodies and ADCs capable of binding proteins expressed by hematopoietic cells, such as CD117 (including, for example, GNNK+ CD117), so as to (i) directly treat a disease such as a blood disorder, metabolic disease, cancer, or autoimmune disease, among others described herein, by selectively depleting a population of cells that express CD117, such as an aberrant blood cell, cancer cell, or autoimmune cell, and/or (ii) deplete a population of endogenous hematopoietic stem cells within the patient. The former activity enables the direct treatment of a wide range of disorders associated with a cell of the hematopoietic lineage, as CD117 may be expressed by a cancerous cell, such as a leukemic cell, an autoimmune lymphocyte, such as a T-cell that expresses a T-cell receptor that cross-reacts with a self-antigen, among other cell types. The latter activity, the selective depletion of hematopoietic stem cells, in turn creates a vacancy that can subsequently be filled by transplantation of an exogenous (for instance, an autologous, allogeneic, or syngeneic) hematopoietic stem cell graft. The invention thus provides methods of treating a variety of hematopoietic conditions, such as sickle cell anemia, thalassemia, Fanconi anemia, Wiskott-Aldrich syndrome, adenosine deaminase deficiency-severe combined immunodeficiency, metachromatic leukodystrophy, Diamond-Blackfan anemia and Schwachman-Diamond syndrome, human immunodeficiency virus infection, and acquired immune deficiency syndrome, as well as cancers and autoimmune diseases, among others.

In a first aspect, the invention provides a method of depleting a population of CD117+ cells in a human patient by administering an effective amount of an antibody or antigen-binding fragment thereof capable of binding CD117, wherein the antibody or antigen-binding fragment is conjugated to a cytotoxin.

In another aspect, the invention provides a method of depleting a population of CD117+ cells in a human patient in need of a hematopoietic stem cell transplant by administering, prior to the patient receiving a transplant including hematopoietic stem cells, an effective amount of an antibody or antigen-binding fragment thereof capable of binding CD117, wherein the antibody or antigen-binding fragment is conjugated to a cytotoxin.

In another aspect, the invention features a method, for example, of treating a human patient in need of a hematopoietic stem cell transplant, including administering to a human patient a transplant including hematopoietic stem cells, wherein the patient has been previously administered an antibody or antigen-binding fragment thereof capable of binding CD117, wherein the antibody or antigen-binding fragment is conjugated to a cytotoxin and was administered in an amount sufficient to deplete a population of CD117+ cells in the patient.

In an additional aspect, the invention features a method, for example, of treating a human patient in need of a hematopoietic stem cell transplant, including: administering to a human patient an antibody or antigen-binding fragment thereof capable of binding CD117, wherein the antibody or antigen-binding fragment is conjugated to a cytotoxin and administered in an amount sufficient to deplete a population of CD117+ cells in the patient, and subsequently administering to the patient a transplant including hematopoietic stem cells.

In some embodiments of any of the foregoing aspects of the invention, the antibody or antigen-binding fragment thereof is conjugated to a cytotoxin.

In one embodiment, an anti-CD117 conjugate is represented by the formula Ab-Z-L-Am, wherein Ab is an antibody or antigen-binding fragment thereof that specifically binds to CD117, L is a linker, Z is a chemical moiety, and Am is an amatoxin, wherein the antibody, or antigen-binding fragment thereof, is a neutral antibody that internalizes when bound to a CD117 expressing cell, and has a human CD117 dissociation rate ($K_{OFF}$) of $1 \times 10^{-3}$ to $1 \times 10^{-6}$ s$^{-1}$ as determined by biolayer interferometry (BLI).

In any of the above aspects, the cytotoxin may be, for example, *pseudomonas* exotoxin A, deBouganin, diphtheria toxin, an amatoxin, such as α-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, or an indolinobenzodiazepine dimer, or a variant thereof.

In some embodiments of any of the above aspects, the CD117 is GNNK+ CD117.

In another aspect, the invention provides a method of depleting a population of CD117+ cells in a human patient in need of a hematopoietic stem cell transplant by administering, prior to the patient receiving a transplant including hematopoietic stem cells, an effective amount of an antibody or fragment thereof capable of binding CD117.

In another aspect, the invention features a method, for example, of treating a human patient in need of a hematopoietic stem cell transplant, including administering to a human patient a transplant including hematopoietic stem cells, wherein the patient has been previously administered an antibody or fragment thereof capable of binding CD117 in an amount sufficient to deplete a population of CD117+ cells in the patient.

In an additional aspect, the invention features a method, for example, of treating a human patient in need of a hematopoietic stem cell transplant, including: administering to a human patient an antibody or fragment thereof capable of binding CD117 in an amount sufficient to deplete a population of CD117+ cells in the patient, and subsequently administering to the patient a transplant including hematopoietic stem cells.

In some embodiments of any of the preceding aspects, the antibody or fragment thereof that binds CD117 (e.g., GNNK+ CD117) is covalently bound to an Fc domain, such as a dimeric Fc domain isolated from a human antibody (for example, isolated from an IgG1, IgG2, IgG3, or IgG4 isotype human antibody). In some embodiments, the Fc domain is a monomeric Fc domain containing a single polypeptide strand. In some embodiments, the N-terminus of the antibody or fragment thereof is bound to the Fc domain. In some embodiments, the C-terminus of the antibody or fragment thereof is bound to the Fc domain. The Fc domain may be conjugated to one or more copies of the antibody or fragment thereof. For instance, conjugates that may be used with the methods described herein include dimeric Fc domains in which each polypeptide strand of the Fc domain is conjugated to the antibody or fragment thereof. The Fc domain may in turn be conjugated to a cytotoxin, such as a cytotoxin described herein (for example, *pseudomonas* exotoxin A, deBouganin, diphtheria toxin, an amatoxin, such as α-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer, or a variant thereof).

In some embodiments of the preceding aspects, the antibody or fragment thereof is covalently bound to a cytotoxin (forming an ADC), such as a cytotoxin described herein (for example, *pseudomonas* exotoxin A, deBouganin, diphtheria toxin, an amatoxin, such as α-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer, or a variant thereof). In some embodiments, the N-terminus of the antibody or fragment thereof is bound to the cytotoxin. In some embodiments, the C-terminus of the antibody or fragment thereof is bound to the cytotoxin. The cytotoxin may in turn be conjugated to an Fc domain of the anti-CD117 antibody.

In some embodiments, the antibody or fragment thereof is covalently bound to the cytotoxin at one site on the antibody or fragment thereof (for example, the N- or C-terminus of the antibody or fragment thereof) and is covalently bound to an Fc domain at another site on the antibody or fragment thereof (for example, the opposite terminus of the antibody or fragment thereof).

In some embodiments, the Fc domain is a human IgG1 isotype Fc domain. In some embodiments, the Fc domain is a human IgG2 isotype Fc domain. In some embodiments, the Fc domain is a human IgG3 isotype Fc domain. In some embodiments, the Fc domain is a human IgG4 isotype Fc domain.

In some embodiments of any of the above aspects, the cytotoxin is an amatoxin or derivative thereof, such as α-amanitin, β-amanitin, γ-amanitin, ε-amanitin, amanin, amaninamide, amanullin, amanullinic acid, and proamanullin. In some embodiments of any of the above aspects, the cytotoxin is an amatoxin, and the antibody, or antigen-binding fragment thereof, conjugated to the cytotoxin is represented by the formula Ab-Z-L-Am, wherein Ab is the antibody, or antigen-binding fragment thereof, L is a linker, Z is a chemical moiety, and Am is the amatoxin. In some embodiments, the amatoxin is conjugated to a linker. In some embodiments, Am-L-Z is represented by formula (I)

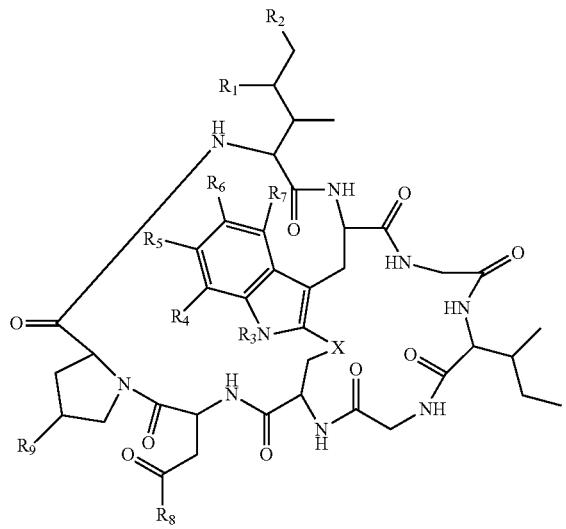

(I)

wherein $R_1$ is H, OH, $OR_A$, or $OR_C$;

$R_2$ is H, OH, $OR_B$, or $OR_C$;

$R_A$ and $R_B$, when present, together with the oxygen atoms to which they are bound, combine to form an optionally substituted 5-membered heterocycloalkyl group;

$R_3$ is H, $R_C$, or $R_D$;

$R_4$ is H, OH, $OR_C$, $OR_D$, $R_C$, or $R_D$;

$R_5$ is H, OH, $OR_C$, $OR_D$, $R_C$, or $R_D$;

$R_6$ is H, OH, $OR_C$, $OR_D$, $R_C$, or $R_D$;

$R_7$ is H, OH, $OR_C$, $OR_D$, $R_C$, or $R_D$;

$R_8$ is OH, $NH_2$, $OR_C$, $OR_D$, $NHR_C$, or $NR_CR_D$;

$R_9$ is H, OH, $OR_C$, or $OR_D$;

X is —S—, —S(O)—, or —$SO_2$—;

$R_C$ is -L-Z;

$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, optionally substituted heteroaryl;

L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, optionally substituted heteroarylene, a peptide, a dipeptide, —(C=O)—, or a combination thereof; and Z is a chemical moiety formed from a coupling reaction between a reactive substituent present on L and a reactive substituent present within an antibody, or antigen-binding fragment thereof, that binds CD117 (such as GNNK+ CD117).

In some embodiments, Am contains exactly one $R_C$ substituent.

In some embodiments, the linker L and the chemical moiety Z, taken together as L-Z, is In some embodiments, Am-L-Z-Ab is

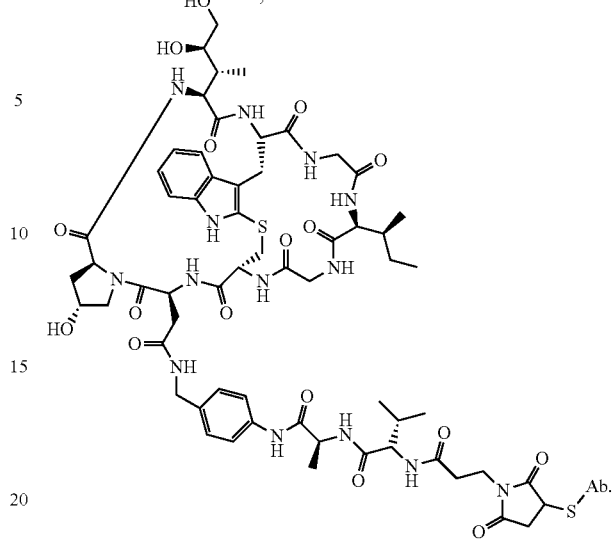

In some embodiments, Am-L-Z-Ab is

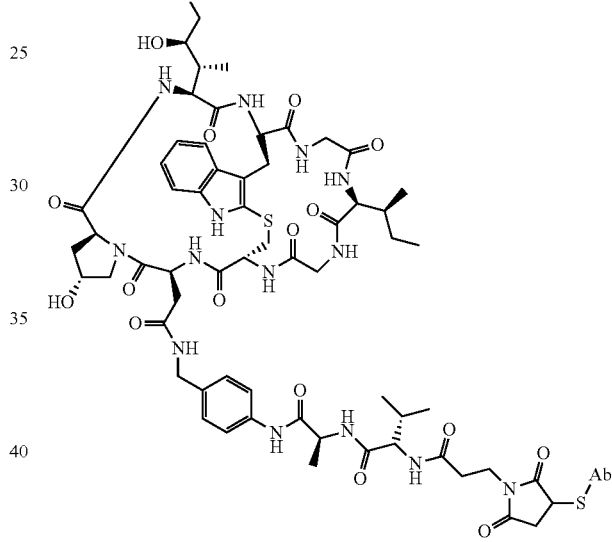

In some embodiments, Am-L-Z is represented by formula (IA)

(IA)

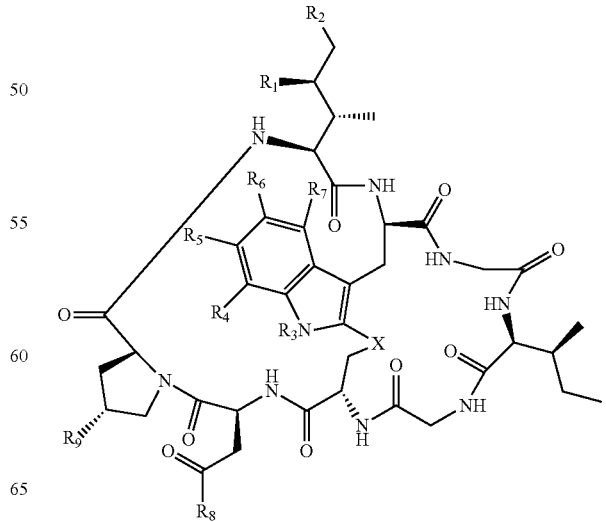

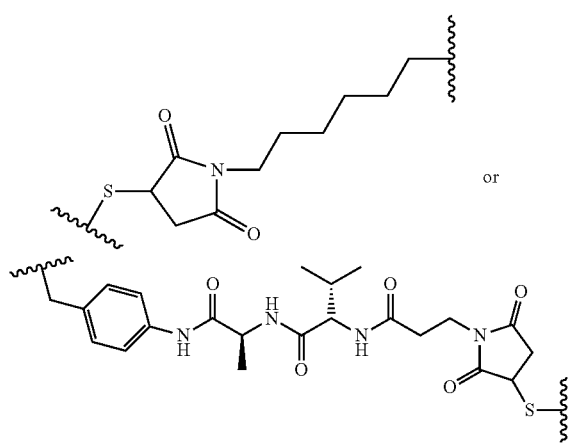

where S is a a sulfur atom which represents the reactive substituent present within an antibody, or antigen-binding fragment thereof, that binds CD117 (e.g., from the —SH group of a cysteine residue).

In some embodiments, L-Z is

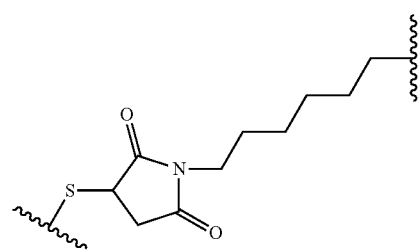 [SMILES: *CCCCCCN1C(=O)CC(S*)C1=O]

In some embodiments, L-Z is

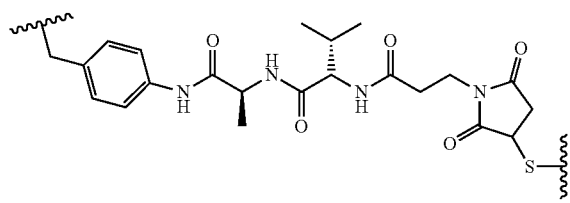

In some embodiments, Am-L-Z-Ab is

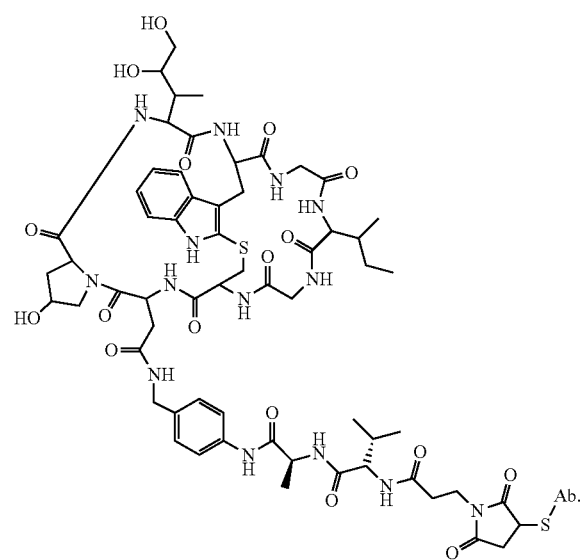

wherein $R_1$ is H, OH, $OR_A$, or $OR_C$;
$R_2$ is H, OH, $O_{RB}$, or $OR_C$;
$R_A$ and $R_B$, when present, together with the oxygen atoms to which they are bound, combine to form an optionally substituted 5-membered heterocycloalkyl group;
$R_3$ is H, $R_C$, or $R_D$;
$R_4$ is H, OH, $OR_C$, $OR_D$, $R_C$, or $R_D$;
$R_5$ is H, OH, $OR_C$, $OR_D$, $R_C$, or $R_D$;
$R_6$ is H, OH, $OR_C$, $OR_D$, $R_C$, or $R_D$;
$R_7$ is H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —$SO_2$—;
$R_C$ is -L-Z;
$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;

L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, optionally substituted heteroarylene, a peptide, a dipeptide, —(C=O)—, or a combination thereof;

Z is a chemical moiety formed from a coupling reaction between a reactive substituent present on L and a reactive substituent present within an antibody, or antigen-binding fragment thereof, that binds CD117 (such as GNNK+ CD117); and wherein Am contains exactly one $R_C$ substituent.

In some embodiments, L-Z is

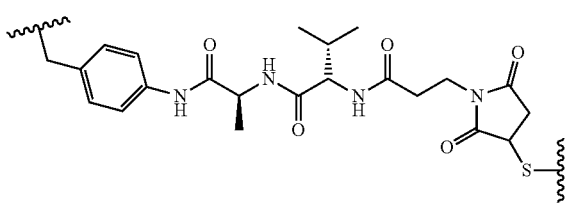

In some embodiments, L-Z is

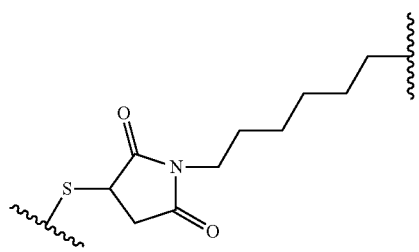 [SMILES: *CCCCCCN1C(=O)CC(S*)C1=O]

In some embodiments, Am-L-Z is represented by formula (IB)

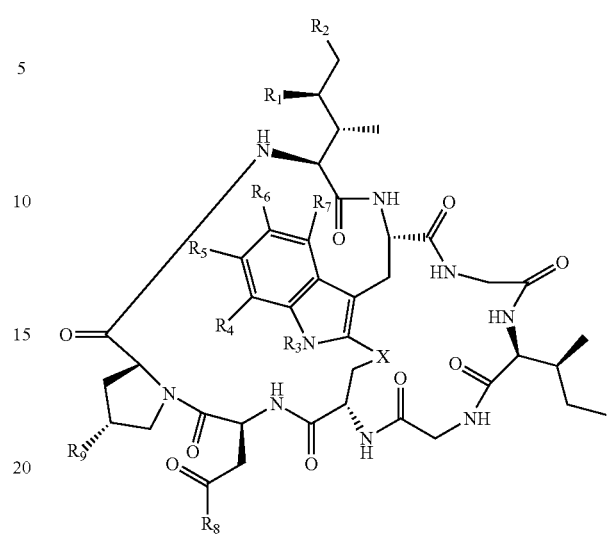

wherein $R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form an optionally substituted 5-membered heterocycloalkyl group;
$R_3$ is H, $R_C$, or $R_D$;
$R_4$ is H, OH, $OR_C$, $OR_D$, $R_C$, or $R_D$;
$R_5$ is H, OH, $OR_C$, $OR_D$, $R_C$, or $R_D$;
$R_6$ is H, OH, $OR_C$, $OR_D$, $R_C$, or $R_D$;
$R_7$ is H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —$SO_2$—;
$R_C$ is -L-Z;
$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;

L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, optionally substituted heteroarylene, a peptide, a dipeptide, —(C=O)—, or a combination thereof;

Z is a chemical moiety formed from a coupling reaction between a reactive substituent present on L and a reactive substituent present within an antibody, or antigen-binding fragment thereof, that binds CD117 (such as GNNK+ CD117); and wherein Am contains exactly one $R_C$ substituent.

In some embodiments, $R_A$ and $R_B$, together with the oxygen atoms to which they are bound, combine to form a 5-membered heterocycloalkyl group of formula:

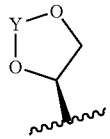

wherein Y is —(C=O)—, —(C=S)—, —(C=NR$_E$)—, or —(CR$_E$R$_{E'}$)—; and

R$_E$ and R$_{E'}$ are each independently optionally substituted C$_1$-C$_6$ alkylene-R$_C$, optionally substituted C$_1$-C$_6$ heteroalkylene-R$_C$, optionally substituted C$_2$-C$_6$ alkenylene-R$_C$, optionally substituted C$_2$-C$_6$ heteroalkenylene-R$_C$, optionally substituted C$_2$-C$_6$ alkynylene-R$_C$, optionally substituted C$_2$-C$_6$ heteroalkynylene-R$_C$, optionally substituted cycloalkylene-R$_C$, optionally substituted heterocycloalkylene-R$_C$, optionally substituted arylene-R$_C$, or optionally substituted heteroarylene-R$_C$.

In some embodiments, Am-L-Z is represented by formula (IA) or formula (IB), wherein R$_1$ is H, OH, OR$_A$, or OR$_C$;
R$_2$ is H, OH, OR$_B$, or OR$_C$;
R$_A$ and R$_B$, when present, together with the oxygen atoms to which they are bound, combine to form:

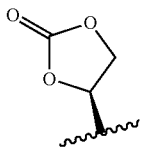

R$_3$ is H or R$_C$;
R$_4$ is H, OH, OR$_C$, OR$_D$, R$_C$, or R$_D$;
R$_5$ is H, OH, OR$_C$, OR$_D$, R$_C$, or R$_D$;
R$_6$ is H, OH, OR$_C$, OR$_D$, R$_C$, or R$_D$;
R$_7$ is H, OH, OR$_C$, OR$_D$, R$_C$, or R$_D$;
R$_8$ is OH, NH$_2$, OR$_C$, or NHR$_C$;
R$_9$ is H or OH; and
wherein R$_C$ and R$_D$ are each as defined above.

In some embodiments, Am is represented by formula (IA) or formula (IB),
wherein R$_1$ is H, OH, OR$_A$, or OR$_C$;
R$_2$ is H, OH, OR$_B$, or OR$_C$;
R$_A$ and R$_B$, when present, together with the oxygen atoms to which they are bound, combine to form:

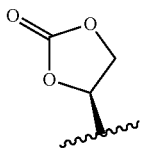

R$_3$ is H or R$_C$;
R$_4$ and R$_5$ are each independently H, OH, OR$_C$, R$_C$, or OR$_D$;
R$_6$ and R$_7$ are each H;
R$_5$ is OH, NH$_2$, OR$_C$, or NHR$_C$;
R$_9$ is H or OH; and
wherein R$_C$ is as defined above.

In some embodiments, Am-L-Z is represented by formula (IA) or formula (IB),
wherein R$_1$ is H, OH, or OR$_A$;
R$_2$ is H, OH, or OR$_B$;
R$_A$ and R$_B$, when present, together with the oxygen atoms to which they are bound, combine to form:

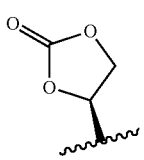

R$_3$, R$_4$, R$_6$, and R$_7$ are each H;
R$_5$ is OR$_C$;
R$_8$ is OH or NH$_2$;
R$_9$ is H or OH; and
wherein R$_C$ is as defined above.

In some embodiments, Am-L-Z is represented by formula (IA) or formula (IB),
wherein R$_1$ and R$_2$ are each independently H or OH;
R$_3$ is R$_C$;
R$_4$, R$_6$, and R$_7$ are each H;
R$_5$ is H, OH, or OC$_1$-C$_6$ alkyl;
R$_8$ is OH or NH$_2$;
R$_9$ is H or OH; and
wherein R$_C$ is as defined above.

In some embodiments, Am-L-Z is represented by formula (IA) or formula (IB),
wherein R$_1$ and R$_2$ are each independently H or OH;
R$_3$, R$_6$, and R$_7$ are each H;
R$_4$ and R$_5$ are each independently H, OH, OR$_C$, or R$_C$;
R$_8$ is OH or NH$_2$;
R$_9$ is H or OH; and
wherein R$_C$ is as defined above.

In some embodiments, Am-L-Z is represented by formula (IA) or formula (IB),
wherein R$_1$ and R$_2$ are each independently H or OH;
R$_3$, R$_6$, and R$_7$ are each H;
R$_4$ and R$_5$ are each independently H or OH;
R$_5$ is OH, NH$_2$, OR$_C$, or NHR$_C$;
R$_9$ is H or OH; and
wherein R$_C$ is as defined above.

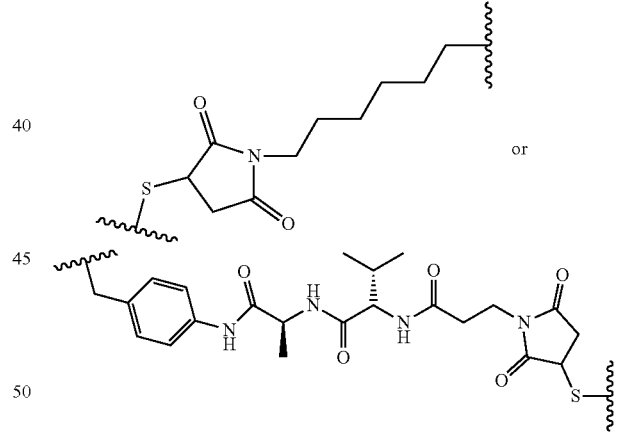

In some embodiments, the linker L and the chemical moiety Z, taken together as L-Z, is In some embodiments, L-Z is

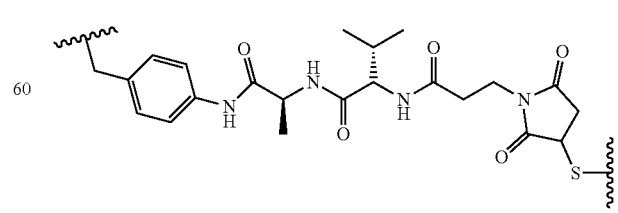

In some embodiments, Am-L-Z is represented by formula (II), formula (IIA), or formula (IIB)

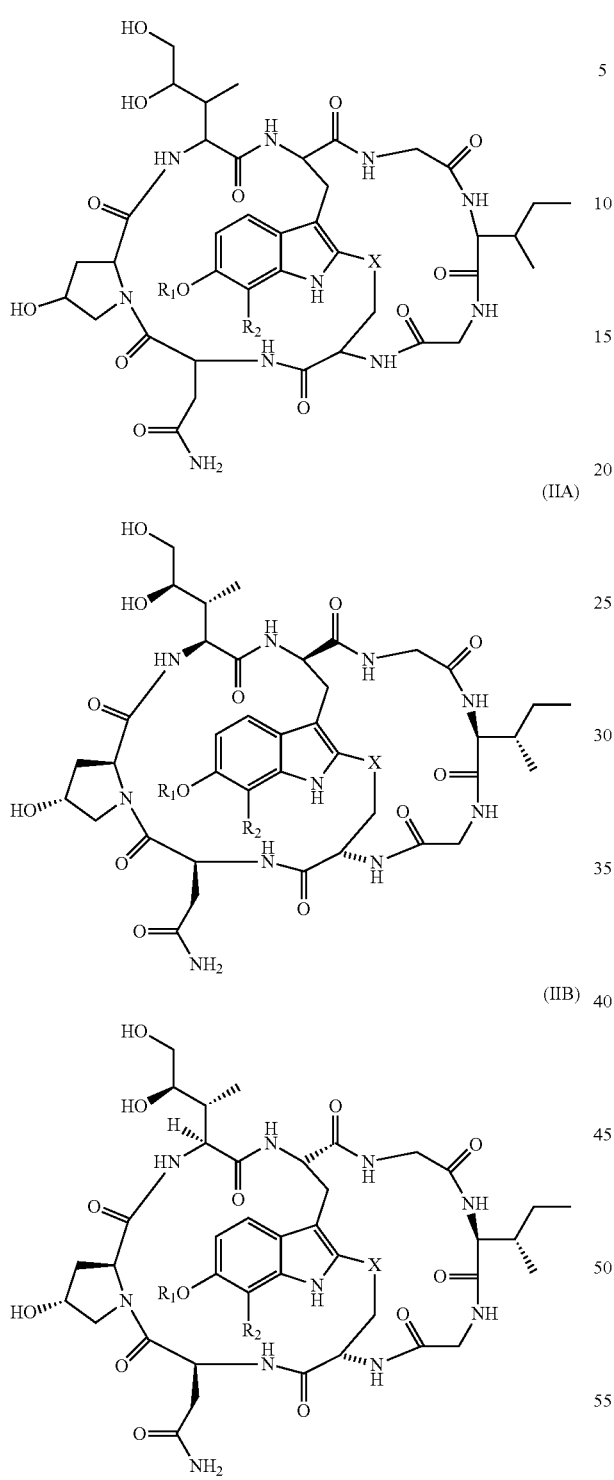

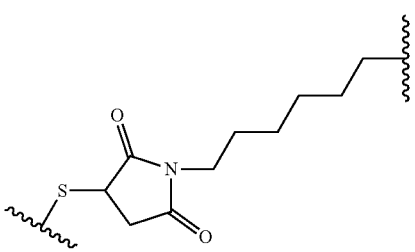

wherein X is S, SO, or SO$_2$; R$_1$ is H or a linker covalently bound to the antibody or antigen-binding fragment thereof through a chemical moiety Z, formed from a coupling reaction between a reactive substituent present on the linker and a reactive substituent present within an antibody, or antigen-binding fragment thereof; and R$_2$ is H or a linker covalently bound to the antibody or antigen-binding fragment thereof through a chemical moiety Z, formed from a coupling reaction between a reactive substituent present on the linker and a reactive substituent present within an antibody, or antigen-binding fragment thereof; wherein when R$_1$ is H, R$_2$ is the linker, and when R$_2$ is H, R$_1$ is the linker. In one embodiment, X is SO, R$_1$ is the linker, and R$_2$ is H.

In some embodiments, R$_1$ is the linker and R$_2$ is H, and the linker and chemical moiety, together as L-Z, is

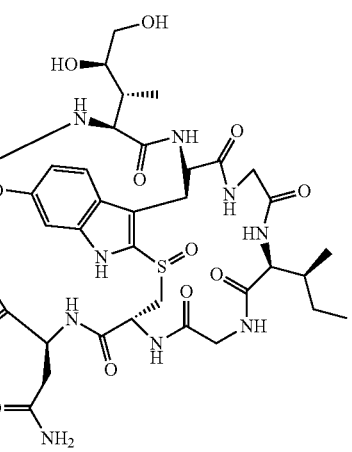

In some embodiments, Am-L-Z-Ab is:

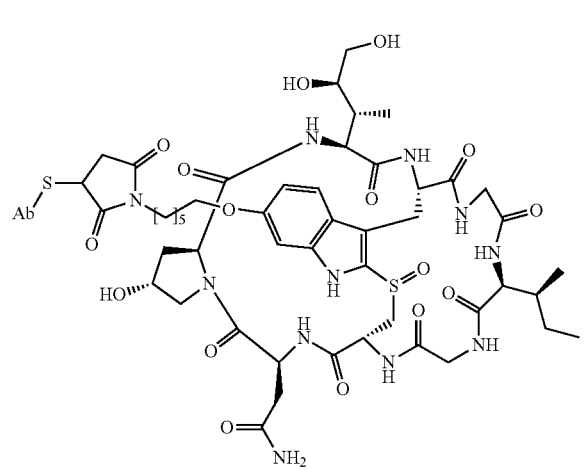

In some embodiments, Am-L-Z-Ab is:

In some embodiments, the conjugate is represented by formula (IV). In some embodiments, the conjugate is represented by formula (IVA). In some embodiments, the conjugate is represented by formula (IVB).

In some embodiments, the Am-L-Z precursor is
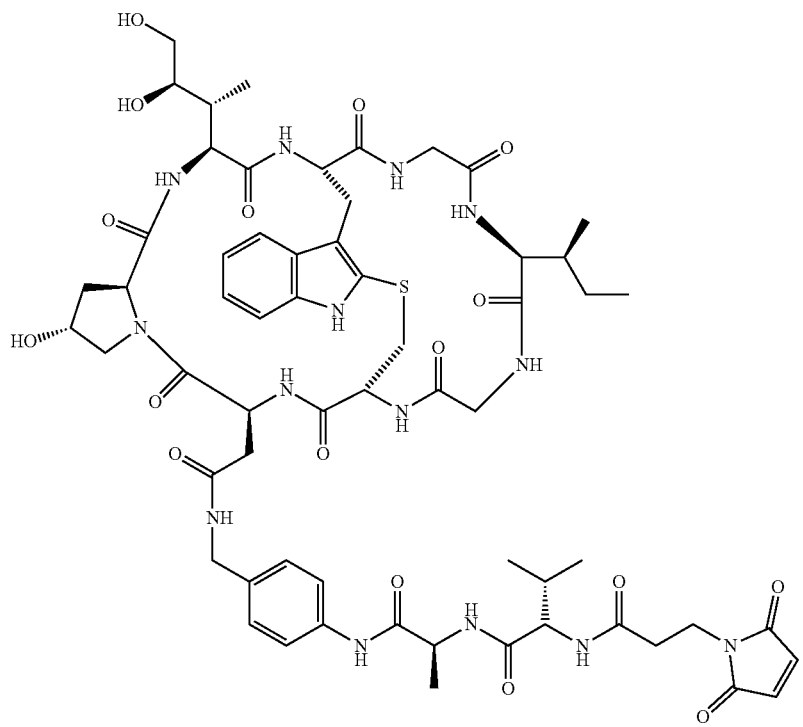
wherein the maleimide reacts with a thiol group found on a cysteine in the antibody.
In some embodiments, the Am-L-Z precursor is
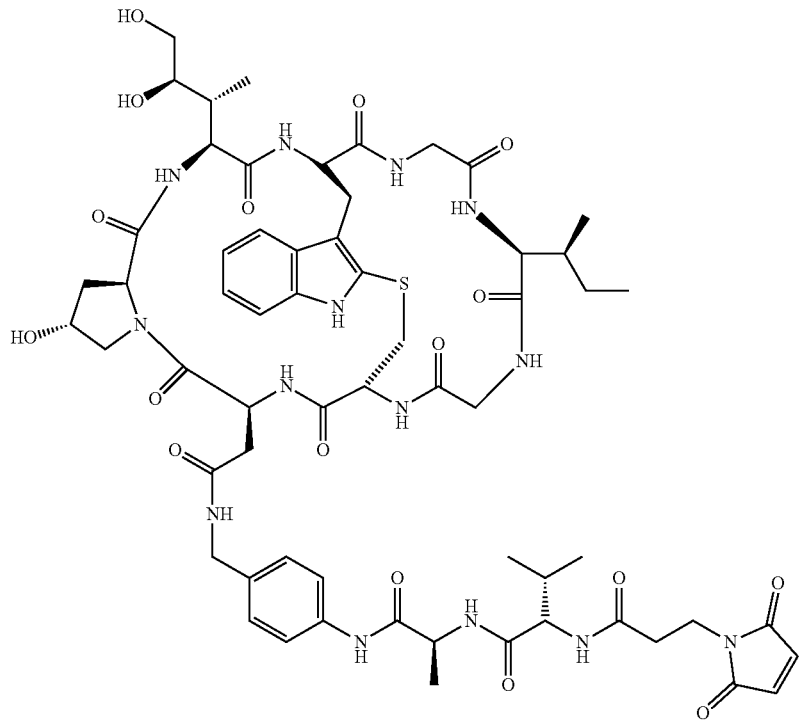
wherein the maleimide reacts with a thiol group found on a cysteine in the antibody.
In some embodiments of any of the above aspects, the cytotoxin is a maytansinoid selected from the group consisting of DM1 and DM4. In some embodiments, the cytotoxin is an auristatin selected from the group consisting of monomethyl auristatin E and monomethyl auristatin F. In some embodiments, the cytotoxin is an anthracycline selected from the group consisting of daunorubicin, doxorubicin, epirubicin, and idarubicin.

In another aspect, the invention features a method of depleting a population of CD117+ cells in a human patient by administering an effective amount of an antibody, or antigen-binding fragment thereof, or ADC capable of binding GNNK+ CD117.

In an additional, the invention features a method of depleting a population of CD117+ cells in a human patient in need of a hematopoietic stem cell transplant by administering, prior to the patient receiving a transplant containing hematopoietic stem cells, an effective amount of an antibody, or antigen-binding fragment thereof, or ADC capable of binding GNNK+ CD117.

In another aspect, the invention features a method, for example, of treating a human patient in need of a hematopoietic stem cell transplant, including administering to a human patient a transplant containing hematopoietic stem cells, wherein the patient has been previously administered an antibody, or antigen-binding fragment thereof, or ADC capable of binding GNNK+ CD117 in an amount sufficient to deplete a population of CD117+ cells in the patient.

In an additional aspect, the invention features a method, for example, of treating a human patient in need of a hematopoietic stem cell transplant, including: administering to a human patient an antibody, or antigen-binding fragment thereof, or ADC capable of binding GNNK+ CD117 in an amount sufficient to deplete a population of CD117+ cells in the patient, and subsequently administering to the patient a transplant including hematopoietic stem cells.

In some embodiments of any of the above aspects, the antibody or antigen-binding fragment thereof is selected from the group consisting of a monoclonal antibody or antigen-binding fragment thereof, a polyclonal antibody or antigen-binding fragment thereof, a humanized antibody or antigen-binding fragment thereof, a bispecific antibody or antigen-binding fragment thereof, a dual-variable immunoglobulin domain, a single-chain Fv molecule (scFv), a diabody, a triabody, a nanobody, an antibody-like protein scaffold, a Fv fragment, a Fab fragment, a F(ab')$_2$ molecule, and a tandem di-scFv. In some embodiments, the antibody has an isotype selected from the group consisting of IgG, IgA, IgM, IgD, and IgE.

In some embodiments of any of the above aspects, the antibody, or antigen-binding fragment thereof, or ADC is internalized by a hematopoietic cell, such as a hematopoietic stem cell, cancer cell, or autoimmune cell following administration to the patient. For instance, the antibody, or antigen-binding fragment thereof, or ADC may be internalized by hematopoietic stem cells, cancer cells, or autoimmune cells by receptor-mediated endocytosis (e.g., upon binding to cell-surface CD117, such as GNNK+CD117). In some embodiments, a cytotoxin covalently bound to the antibody or antigen-binding fragment thereof may be released intracellularly by chemical cleavage (for instance, by enzymatic or non-specific cleavage of a linker described herein). The cytotoxin may then access its intracellular target (such as the mitotic spindle apparatus, nuclear DNA, ribosomal RNA, or topoisomerases, among others) so as to promote the death of an endogenous hematopoietic cell, such as an endogenous hematopoietic stem cell prior to transplantation therapy, an endogenous cancer cell, or an endogenous autoimmune cell, among others.

In some embodiments of any of the above aspects, the antibody, or antigen-binding fragment thereof, or ADC is capable of promoting necrosis of a hematopoietic cell, such as a hematopoietic stem cell, cancer cell, or autoimmune cell, among others. In some embodiments, the antibody or antigen-binding fragment thereof may promote the death of an endogenous hematopoietic stem cell prior to transplantation therapy, an endogenous cancer cell, or an endogenous autoimmune cell, among others, by recruiting one or more complement proteins, natural killer (NK) cells, macrophages, neutrophils, and/or eosinophils to the cell, such as a hematopoietic stem cell upon administration to the patient.

In some embodiments of any of the above aspects, the transplant containing hematopoietic stem cells is administered to the patient after the concentration of the antibody, or antigen-binding fragment thereof, or ADC has substantially cleared from the blood of the patient.

In some embodiments of any of the above aspects, the hematopoietic stem cells or progeny thereof maintain hematopoietic stem cell functional potential after two or more days (for example, from about 2 to about 5 days, from about 2 to about 7 days, from about 2 to about 20 days, from about 2 to about 30 days, such as 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, or more) following transplantation of the hematopoietic stem cells into the patient.

In some embodiments of any of the above aspects, the hematopoietic stem cells or progeny thereof are capable of localizing to hematopoietic tissue, such as the bone marrow, and/or reestablishing hematopoiesis following transplantation of the hematopoietic stem cells into the patient.

In some embodiments of any of the above aspects, upon transplantation into the patient, the hematopoietic stem cells give rise to recovery of a population of cells selected from the group consisting of megakaryocytes, thrombocytes, platelets, erythrocytes, mast cells, myeloblasts, basophils, neutrophils, eosinophils, microglia, granulocytes, monocytes, osteoclasts, antigen-presenting cells, macrophages, dendritic cells, natural killer cells, T-lymphocytes, and B-lymphocytes.

In some embodiments of any of the above aspects, the method is used to treat one or more disorders, such as by depleting a population of hematopoietic stem cells in a patient prior to hematopoietic stem cell transplant therapy so as to provide a niche to which the transplanted hematopoietic stem cells may home. Following transplantation, the hematopoietic stem cells may establish productive hematopoiesis, so as to replenish a deficient cell type in the patient or a cell type that is being actively killed or has been killed, for instance, by chemotherapeutic methods. For instance, the patient may be one that is suffering from a stem cell disorder. In some embodiments, the patient is suffering from a hemoglobinopathy disorder, such as sickle cell anemia, thalassemia, Fanconi anemia, aplastic anemia, and Wiskott-Aldrich syndrome. The patient may be suffering from an immunodeficiency disorder, such as a congenital immunodeficiency disorder or an acquired immunodeficiency disorder (e.g., human immunodeficiency virus or acquired immune deficiency syndrome). In some embodiments, the patient is suffering from a metabolic disorder, such as glycogen storage diseases, mucopolysaccharidoses, Gaucher's Disease, Hurlers Disease, sphingolipidoses, and metachromatic leukodystrophy. In some embodiments, the patient is suffering from a disorder selected from the group consisting of adenosine deaminase deficiency and severe combined immunodeficiency, hyper immunoglobulin M syndrome, Chediak-Higashi disease, hereditary lymphohistiocytosis, osteopetrosis, osteogenesis imperfecta, storage diseases, thalassemia major, systemic sclerosis, systemic lupus erythematosus, and juvenile rheumatoid arthritis. In some embodiments, the patient is suffering from an autoimmune disease, such as scleroderma, multiple sclerosis, ulcerative colitis, Crohn's disease, ant Type 1 diabetes. In some embodiments, the patient is suffering from cancer or myeloproliferative disease, such as a hematological cancer. In some embodiments, the patient is suffering from acute myeloid leukemia, acute lymphoid leukemia, chronic myeloid leukemia, chronic lymphoid leukemia, multiple myeloma, diffuse large B-cell lymphoma, or non-Hodgkin's lymphoma. In some embodiments, the patient is suffering from a myelodysplastic disease, such as myelodysplastic syndrome.

In some embodiments of any of the above aspects, the method is used to directly treat a cancer, such as a cancer characterized by CD117+ cells (e.g., a leukemia characterized by CD117+ cells), by administration of an antibody, or antigen-binding fragment thereof, that depletes a population of CD117+ cancer cells in the patient and/or by administration of an antibody, or antigen-binding fragment thereof, so as to deplete a population of endogenous hematopoietic stem cells prior to hematopoietic stem cell transplantation. In the latter case, the transplantation may in turn re-constitute, for example, a population of cells depleted during the process of eradicating cancer cells. The cancer may be a hematological cancer, such as acute myeloid leukemia, acute lymphoid leukemia, chronic myeloid leukemia, chronic lymphoid leukemia, multiple myeloma, diffuse large B-cell lymphoma, or non-Hodgkin's lymphoma.

In some embodiments of any of the above aspects, the method is used to treat an autoimmune disease, such as by administration of an antibody, or antigen-binding fragment thereof, or ADC so as to deplete a population of CD117+ autoimmune cells and/or by administration of an antibody, or antigen-binding fragment thereof, so as to deplete a population of endogenous hematopoietic stem cells prior to hematopoietic stem cell transplantation. In the latter case, the transplantation may in turn re-constitute, for example, a population of cells depleted during the process of eradicating autoimmune cells. The autoimmune disease may be, for example, scleroderma, multiple sclerosis (MS), human systemic lupus (SLE), rheumatoid arthritis (RA), inflammatory bowel disease (IBD), treating psoriasis, Type 1 diabetes mellitus (Type 1 diabetes), acute disseminated encephalomyelitis (ADEM), Addison's disease, alopecia universalis, ankylosing spondylitisis, antiphospholipid antibody syndrome (APS), aplastic anemia, autoimmune hemolytic anemia, autoimmune hepatitis, autoimmune inner ear disease (AIED), autoimmune lymphoproliferative syndrome (ALPS), autoimmune oophoritis, Balo disease, Behcet's disease, bullous pemphigoid, cardiomyopathy, Chagas' disease, chronic fatigue immune dysfunction syndrome (CFIDS), chronic inflammatory demyelinating polyneuropathy, Crohn's disease, cicatrical pemphigoid, coeliac sprue-dermatitis herpetiformis, cold agglutinin disease, CREST syndrome, Degos disease, discoid lupus, dysautonomia, endometriosis, essential mixed cryoglobulinemia, fibromyalgia-fibromyositis, Goodpasture's syndrome, Grave's disease, Guillain-Barre syndrome (GBS), Hashimoto's thyroiditis, Hidradenitis suppurativa, idiopathic and/or acute thrombocytopenic purpura, idiopathic pulmonary fibrosis, IgA neuropathy, interstitial cystitis, juvenile arthritis, Kawasaki's disease, lichen planus, Lyme disease, Meniere disease, mixed connective tissue disease (MCTD), myasthenia gravis, neuromyotonia, opsoclonus myoclonus syndrome (OMS), optic neuritis, Ord's thyroiditis, pemphigus vulgaris, pernicious anemia, polychondritis, polymyositis and dermatomyositis, primary biliary cirrhosis, polyarteritis nodosa, polyglandular syndromes, polymyalgia rheumatica, primary agammaglobulinemia, Raynaud phenomenon, Reiter's syndrome, rheumatic fever, sarcoidosis, scleroderma, Sjögren's syndrome, stiff person syndrome, Takayasu's arteritis, temporal arteritis (also known as "giant cell arteritis"), ulcerative colitis, uveitis, vasculitis, vitiligo, vulvodynia ("vulvar vestibulitis"), and Wegener's granulomatosis.

Thus, in some embodiments of any of the above aspects, the invention features a method of treating a hemoglobinopathy disorder, such as sickle cell anemia, thalassemia, Fanconi anemia, aplastic anemia, and Wiskott-Aldrich syndrome. In some embodiments, the invention features a method of treating an immunodeficiency disorder, such as a congenital immunodeficiency disorder or an acquired immunodeficiency disorder (e.g., human immunodeficiency virus or acquired immune deficiency syndrome). In some embodiments, the invention features a method of treating a metabolic disorder, such as glycogen storage diseases, mucopolysaccharidoses, Gaucher's Disease, Hurlers Disease, sphingolipidoses, and metachromatic leukodystrophy. In some embodiments, the invention features a method of treating a disorder selected from the group consisting of adenosine deaminase deficiency and severe combined immunodeficiency, hyper immunoglobulin M syndrome, Chediak-Higashi disease, hereditary lymphohistiocytosis, osteopetrosis, osteogenesis imperfecta, storage diseases, thalassemia major, systemic sclerosis, systemic lupus erythematosus, and juvenile rheumatoid arthritis In some embodiments, the invention features a method of treating an autoimmune disease, such as scleroderma, multiple sclerosis, ulcerative colitis, Crohn's disease, or Type 1 diabetes. In some embodiments, the invention features a method of treating a cancer or myeloproliferative disease, such as a hematological cancer. In some embodiments, the invention features a method of treating acute myeloid leukemia, acute lymphoid leukemia, chronic myeloid leukemia, chronic lymphoid leukemia, multiple myeloma, diffuse large B-cell lymphoma, or non-Hodgkin's lymphoma. In some embodiments, the patient is suffering from a myelodysplastic disease, such as myelodysplastic syndrome. In these embodiments, the method may include the steps of administering an antibody, or antigen-binding fragment thereof, or ADC that binds CD117 (e.g., GNNK+ CD117) and/or a hematopoietic stem cell transplant according to the method of any of the above-described aspects and embodiments of the invention.

Similarly, in some embodiments of any of the above aspects, the invention provides a method of treating cancer directly, such as a cancer characterized by CD117+ cells (e.g., a leukemia characterized by CD117+ cells). In these embodiments, the method includes administering an antibody, or antigen-binding fragment thereof, that binds CD117 (e.g., GNNK+ CD117). The cancer may be a hematological cancer, such as acute myeloid leukemia, acute lymphoid leukemia, chronic myeloid leukemia, chronic lymphoid leukemia, multiple myeloma, diffuse large B-cell lymphoma, or non-Hodgkin's lymphoma.

Additionally, in some embodiments of any of the above aspects, the invention provides a method of treating an autoimmune disease, such as multiple sclerosis (MS), human systemic lupus (SLE), rheumatoid arthritis (RA), inflammatory bowel disease (IBD), treating psoriasis, Type 1 diabetes mellitus (Type 1 diabetes) acute disseminated encephalomyelitis (ADEM), Addison's disease, alopecia universalis, ankylosing spondylitisis, antiphospholipid antibody syndrome (APS), aplastic anemia, autoimmune hemolytic anemia, autoimmune hepatitis, autoimmune inner ear disease (AIED), autoimmune lymphoproliferative syndrome (ALPS), autoimmune oophoritis, Balo disease, Behcet's disease, bullous pemphigoid, cardiomyopathy, Chagas' disease, chronic fatigue immune dysfunction syndrome (CFIDS), chronic inflammatory demyelinating polyneuropathy, Crohn's disease, cicatrical pemphigoid, coeliac sprue-dermatitis herpetiformis, cold agglutinin disease, CREST syndrome, Degos disease, discoid lupus, dysautonomia, endometriosis, essential mixed cryoglobulinemia, fibromyalgia-fibromyositis, Goodpasture's syndrome, Grave's disease, Guillain-Barre syndrome (GBS), Hashimoto's thyroiditis, Hidradenitis suppurativa, idiopathic and/or acute thrombocytopenic purpura, idiopathic pulmonary fibrosis, IgA neuropathy, interstitial cystitis, juvenile arthritis, Kawasaki's disease, lichen planus, Lyme disease, Meniere disease, mixed connective tissue disease (MCTD), myasthenia gravis, neuromyotonia, opsoclonus myoclonus syndrome (OMS), optic neuritis, Ord's thyroiditis, pemphigus vulgaris, pernicious anemia, polychondritis, polymyositis and dermatomyositis, primary biliary cirrhosis, polyarteritis nodosa, polyglandular syndromes, polymyalgia rheumatica, primary agammaglobulinemia, Raynaud phenomenon, Reiter's syndrome, rheumatic fever, sarcoidosis, scleroderma, Sjögren's syndrome, stiff person syndrome, Takayasu's arteritis, temporal arteritis (also known as "giant cell arteritis"), ulcerative colitis, uveitis, vasculitis, vitiligo, vulvodynia ("vulvar vestibulitis"), and Wegener's granulomatosis. In these embodiments, the method includes administering an antibody, or antigen-binding fragment thereof, that binds CD117 (e.g., GNNK+ CD117).

In another aspect, the invention features a method of depleting a population of CD117+(e.g., GNNK+ CD117+) cells by contacting the population with an effective amount of a conjugate (or ADC) represented by the formula Ab-Z-L-Am, wherein Ab is an antibody or antigen-binding fragment thereof that binds CD117, Z is a chemical moiety, L

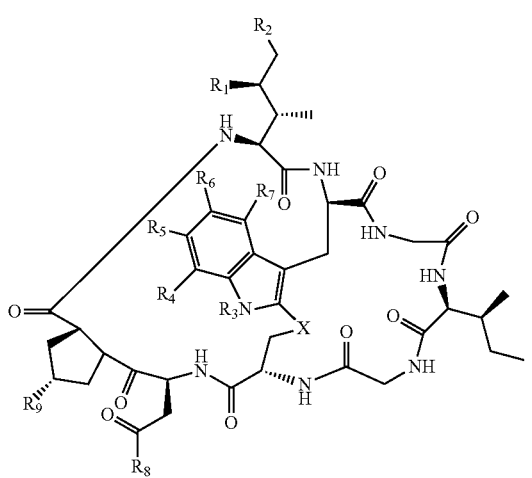

(IA)

is a linker and Am is an amatoxin. Am-L-Z may be represented by formula (IA)

wherein $R_1$ is H, OH, $OR_A$, or $OR_C$;

$R_2$ is H, OH, $OR_B$, or $OR_C$;

$R_A$ and $R_B$, when present, together with the oxygen atoms to which they are bound, combine to form an optionally substituted 5-membered heterocycloalkyl group;

$R_3$ is H, $R_C$, or $R_D$;

$R_4$, $R_5$, $R_6$, and $R_7$ are each independently H, OH, $OR_C$, $OR_D$, $R_C$, or $R_D$;

$R_8$ is OH, $NH_2$, $OR_C$, $OR_D$, $NHR_C$, or $NR_CR_D$;

$R_9$ is H, OH, $OR_C$, or $OR_D$;

X is —S—, —S(O)—, or —$SO_2$—;

$R_C$ is -L-Z;

$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;

L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, optionally substituted heteroarylene, a peptide, a dipeptide, —(C=O)—, or a combination thereof;

and

Z is a chemical moiety formed from a coupling reaction between a reactive substituent present on L and a reactive substituent present within the antibody or antigen-binding fragment thereof, wherein Am contains exactly one $R_C$ substituent.

In some embodiments, the linker L and the chemical moiety Z, taken together as

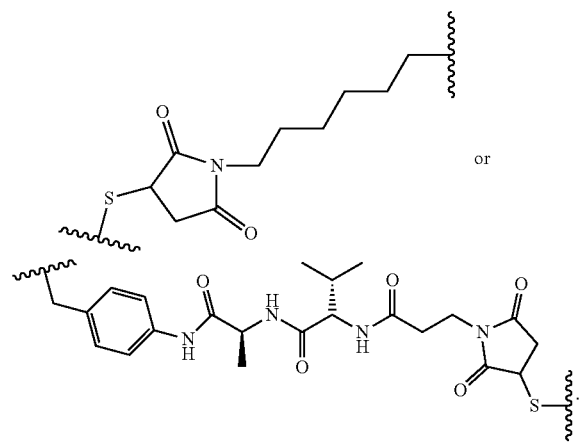

L-Z, is

In some embodiments, L-Z is

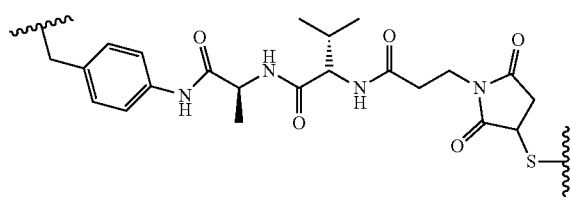

In some embodiments, L-Z is

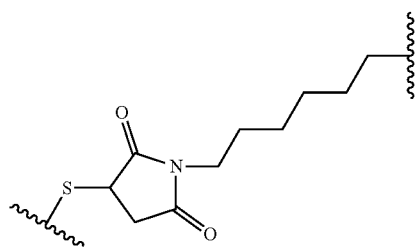 [SMILES: *CCCCCCN1C(=O)CC(S*)C1=O]

In some embodiments, Am-L-Z is represented by formula (IB)

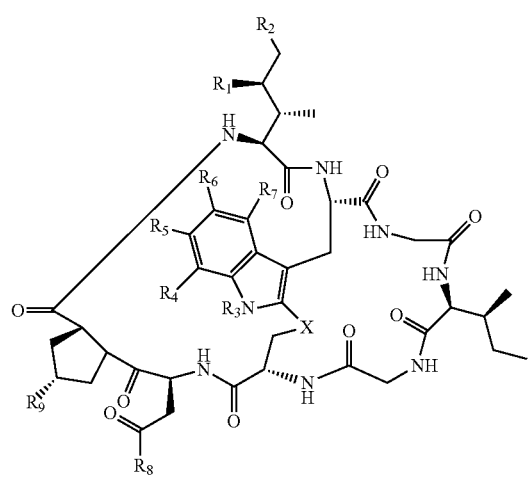

wherein $R_1$ is H, OH, $OR_A$, or $OR_C$;

$R_2$ is H, OH, $OR_B$, or $OR_C$;

$R_A$ and $R_B$, when present, together with the oxygen atoms to which they are bound, combine to form an optionally substituted 5-membered heterocycloalkyl group;

$R_3$ is H, $R_C$, or $R_D$;

$R_4$ is H, OH, $OR_C$, $OR_D$, $R_C$, or $R_D$;

$R_5$ is H, OH, $OR_C$, $OR_D$, $R_C$, or $R_D$;

$R_6$ is H, OH, $OR_C$, $OR_D$, $R_C$, or $R_D$;

$R_7$ is H, OH, $OR_C$, $OR_D$, $R_C$, or $R_D$;

$R_8$ is OH, $NH_2$, $OR_C$, $OR_D$, $NHR_C$, or $NR_CR_D$;

$R_9$ is H, OH, $OR_C$, or $OR_D$;

X is —S—, —S(O)—, or —$SO_2$—;

$R_C$ is -L-Z;

$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;

L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, optionally substituted heteroarylene, a peptide, a dipeptide, —(C=O)—, or a combination thereof;

Z is a chemical moiety formed from a coupling reaction between a reactive substituent present on L and a reactive substituent present within an antibody, or antigen-binding fragment thereof, that binds CD117 (such as GNNK+ CD117); and wherein Am contains exactly one $R_C$ substituent.

In some embodiments, the linker L and the chemical moiety Z, taken together as L-Z, is

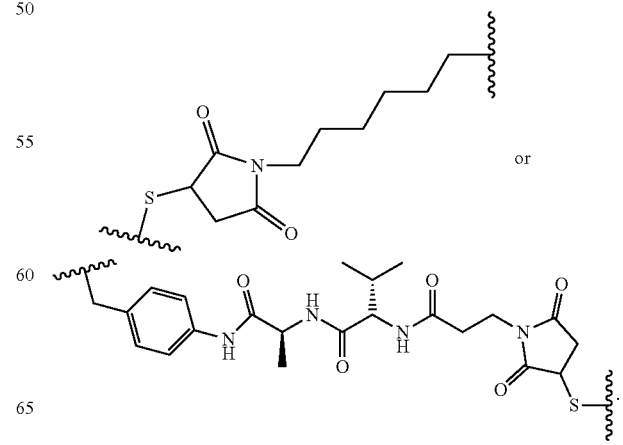

In some embodiments, L-Z is
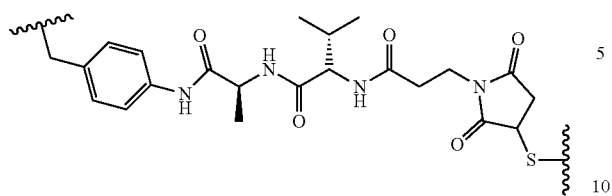
In some embodiments, Am-L-Z-Ab is one of
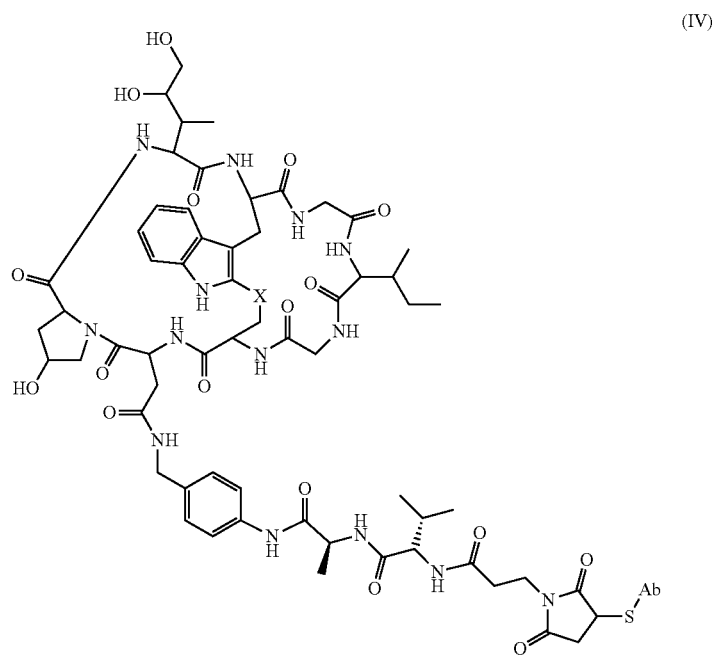
(IV)
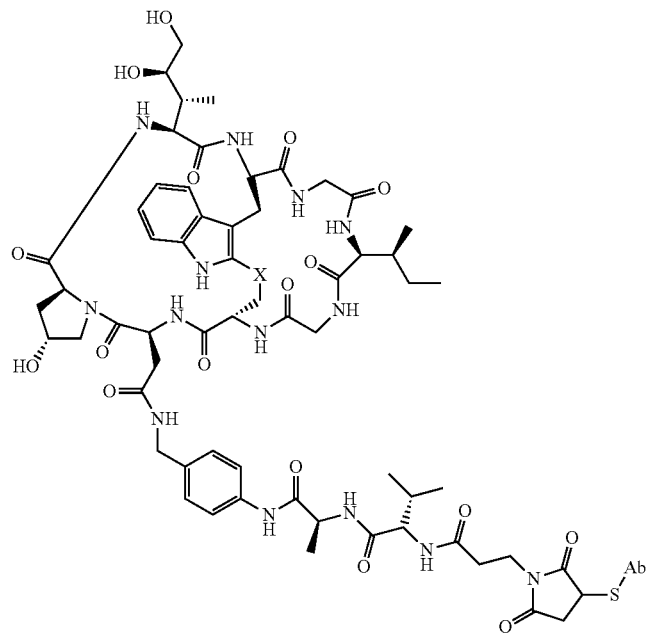
(IVA)

(IVB)

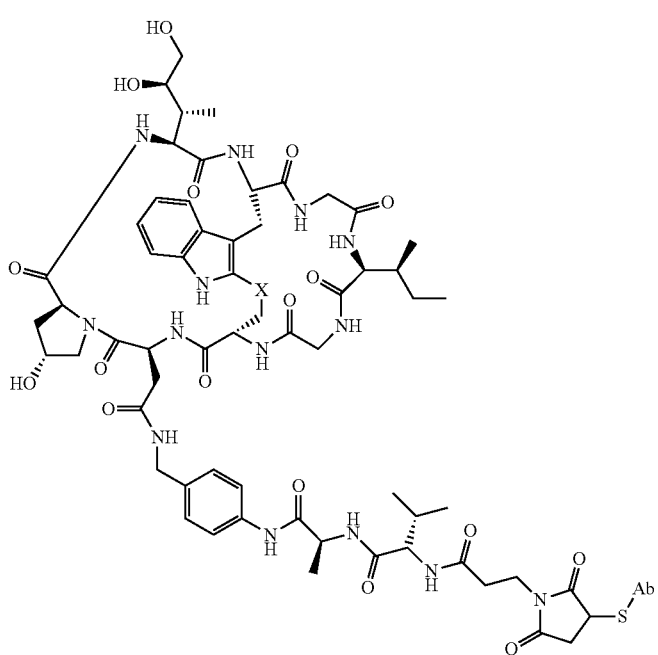

wherein X is S, SO or SO₂.

In some embodiments, the Ab-Z-L-Am is

In some embodiments, the Ab-Z-L-Am is

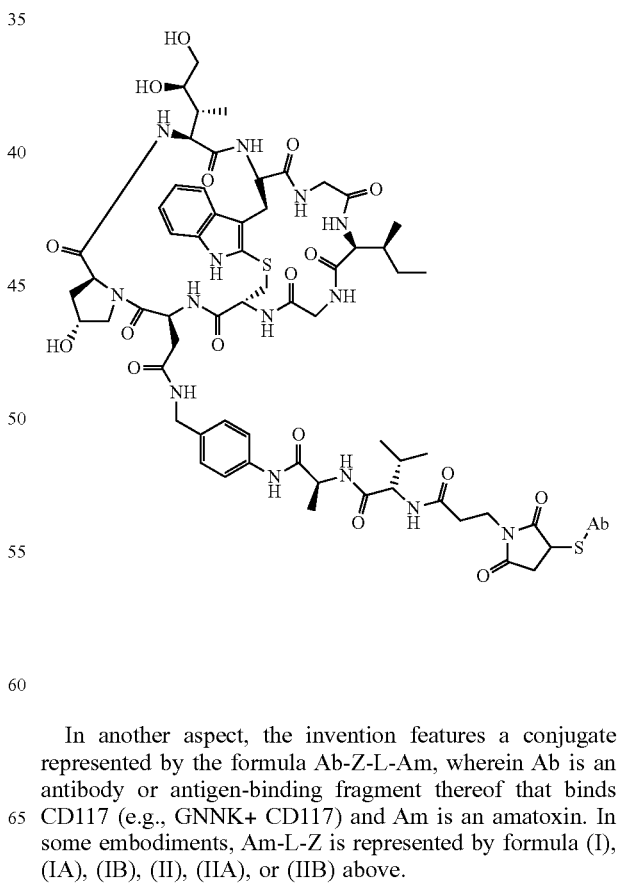

In another aspect, the invention features a conjugate represented by the formula Ab-Z-L-Am, wherein Ab is an antibody or antigen-binding fragment thereof that binds CD117 (e.g., GNNK+ CD117) and Am is an amatoxin. In some embodiments, Am-L-Z is represented by formula (I), (IA), (IB), (II), (IIA), or (IIB) above.

In some embodiments, linker-chemical moiety-amatoxin portion (Am-L-Z) of the conjugate is represented by formula (IA)

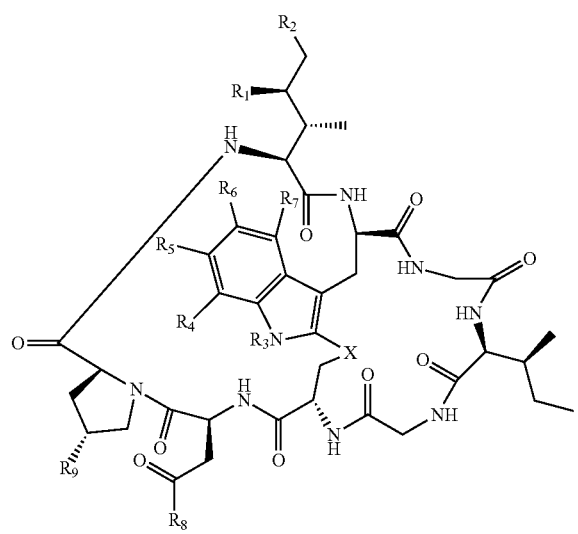

(IA)

wherein $R_1$ is H, OH, $OR_A$, or $OR_C$;

$R_2$ is H, OH, $OR_B$, or $OR_C$;

$R_A$ and $R_B$, when present, together with the oxygen atoms to which they are bound, combine to form an optionally substituted 5-membered heterocycloalkyl group;

$R_3$ is H, $R_C$, or $R_D$;

$R_4$, $R_5$, $R_6$, and $R_7$ are each independently H, OH, $OR_C$, $OR_D$, $R_C$, or $R_D$;

$R_8$ is OH, $NH_2$, $OR_C$, $OR_D$, $NHR_C$, or $NR_CR_D$;

$R_9$ is H, OH, $OR_C$, or $OR_D$;

X is —S—, —S(O)—, or —$SO_2$—;

$R_C$ is -L-Z;

$R_D$ is optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ heteroalkenyl, optionally substituted $C_2$-$C_6$ alkynyl, optionally substituted $C_2$-$C_6$ heteroalkynyl, optionally substituted cycloalkyl, optionally substituted heterocycloalkyl, optionally substituted aryl, or optionally substituted heteroaryl;

L is optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ heteroalkenylene, optionally substituted $C_2$-$C_6$ alkynylene, optionally substituted $C_2$-$C_6$ heteroalkynylene, optionally substituted cycloalkylene, optionally substituted heterocycloalkylene, optionally substituted arylene, optionally substituted heteroarylene, a dipeptide, —(C=O)—, a peptide, or a combination thereof; and Z is a chemical moiety formed from a coupling reaction between a reactive substituent present on L and a reactive substituent present within the antibody or antigen-binding fragment thereof, wherein Am comprises exactly one $R_C$ substituent.

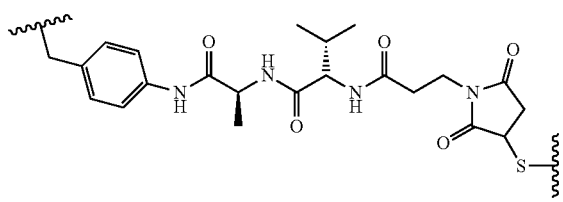

In some embodiments, L-Z is
In some embodiments, L-Z is

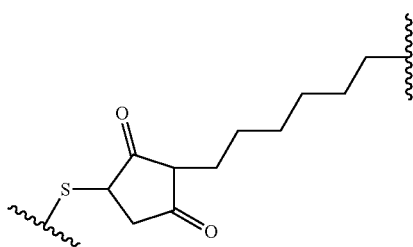 [SMILES: *CCCCCCC1C(=O)CC(S*)C1=O]

In some embodiments, Am-L-Z is represented by formula (IB)

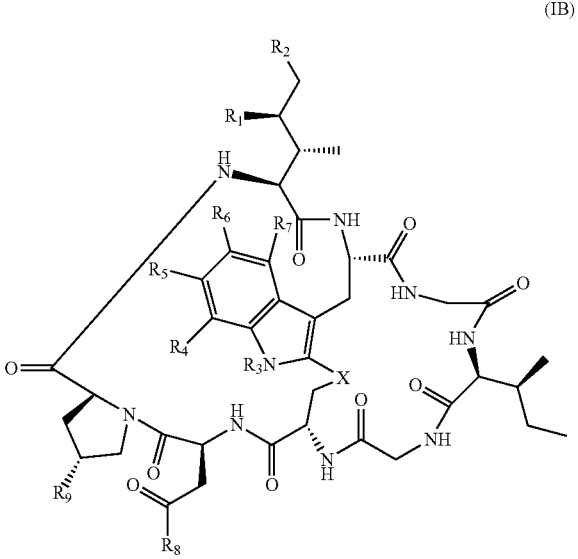

(IB)

wherein $R_1$ is H, OH, $OR_A$, or $OR_C$;

$R_2$ is H, OH, $OR_B$, or $OR_C$;

$R_A$ and $R_B$, when present, together with the oxygen atoms to which they are bound, combine to form an optionally substituted 5-membered heterocycloalkyl group;

$R_3$ is H, $R_C$, or $R_D$;

$R_4$, $R_5$, $R_6$, and $R_7$ are each independently H, OH, $OR_C$, $OR_D$, $R_C$, or $R_D$;

$R_8$ is OH, $NH_2$, $OR_C$, $OR_D$, $NHR_C$, or $NR_CR_D$;

$R_9$ is H, OH, $OR_C$, or $OR_D$;

X is —S—, —S(O)—, or —$SO_2$—;

$R_C$ is -L-Z;

$R_D$ is optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ heteroalkenyl, optionally substituted $C_2$-$C_6$ alkynyl, optionally substituted $C_2$-$C_6$ heteroalkynyl, optionally substituted cycloalkyl, optionally substituted heterocycloalkyl, optionally substituted aryl, or optionally substituted heteroaryl;

L is optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ heteroalkenylene, optionally substituted $C_2$-$C_6$ alkynylene, optionally substituted $C_2$-$C_6$ heteroalkynylene, optionally substituted cycloalkylene, optionally substituted heterocycloalkylene, optionally substituted arylene, optionally substituted heteroarylene, a dipeptide, —(C=O)—, a peptide, or a combination thereof; and Z is a chemical moiety formed from a coupling reaction between a reactive substituent present on L and a reactive substituent present within the antibody or antigen-binding fragment thereof, wherein Am comprises exactly one $R_C$ substituent.

In some embodiments, L-Z is

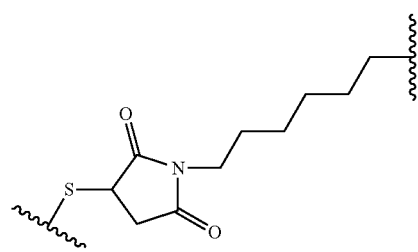 [SMILES: *CCCCCCN1C(=O)CC(S*)C1=O]

In some embodiments, L-Z is

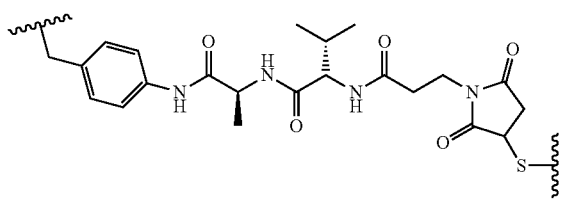

In some embodiments, Am-L-Z is represented by formula (II), formula (IIA), or formula (IIB)

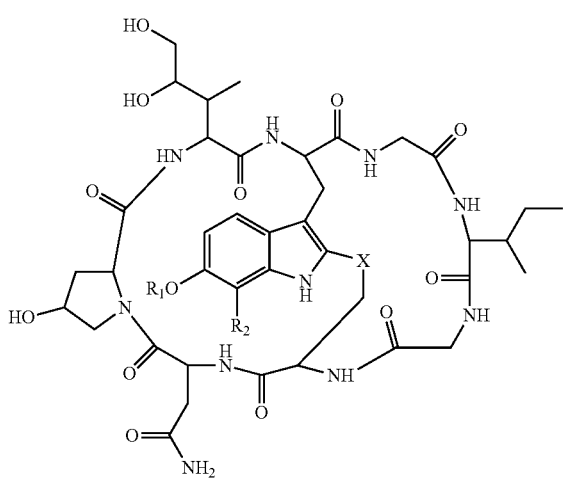

(II)

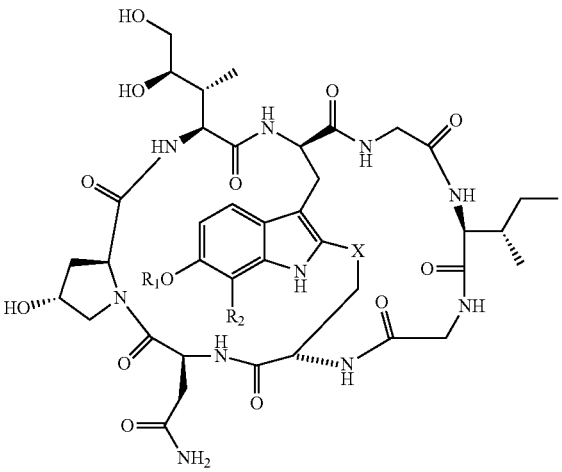

(IIA)

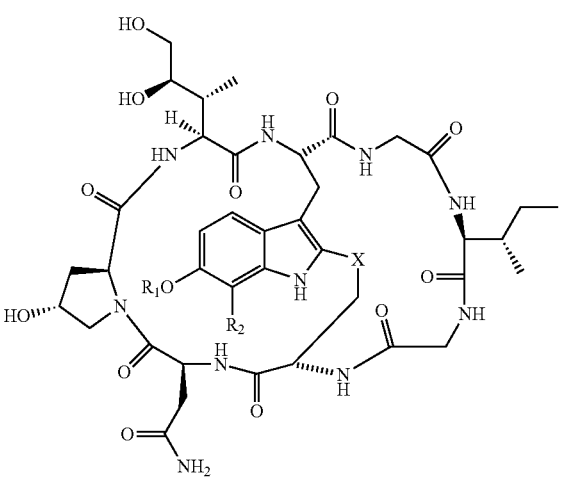

(IIB)

wherein X is S, SO, or $SO_2$;

$R_1$ is H or a linker covalently bound to the antibody or antigen-binding fragment thereof through a chemical moiety Z, formed from a coupling reaction between a reactive substituent present on the linker and a reactive substituent present within an antibody, or antigen-binding fragment thereof; and $R_2$ is H or a linker covalently bound to the antibody or antigen-binding fragment thereof through a chemical moiety Z, formed from a coupling reaction between a reactive substituent present on the linker and a reactive substituent present within an antibody, or antigen-binding fragment thereof;

wherein when $R_1$ is H, $R_2$ is the linker, and when $R_2$ is H, $R_1$ is the linker.

In one embodiment, X is SO, $R_1$ is the linker, and $R_2$ is H.

In some embodiments, L-Z is

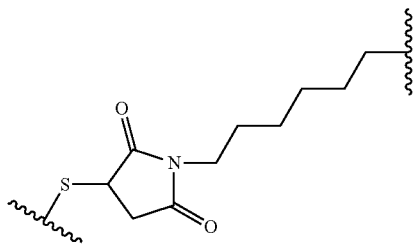 [SMILES: *CCCCCCN1C(=O)CC(S*)C1=O]

In some embodiments of the preceding two aspects, the antibody or antigen-binding fragment thereof is conjugated to the amatoxin by way of a cysteine residue in the Fc domain of the antibody or antigen-binding fragment thereof. In some embodiments, the cysteine residue is introduced by way of a mutation in the Fc domain of the antibody or antigen-binding fragment thereof. For instance, the cysteine residue may be selected from the group consisting of Cys118, Cys239, and Cys265 (e.g., D265C).

In some embodiments of these aspects, the cysteine residue is naturally occurring in the Fc domain of the antibody or antigen-binding fragment thereof. For instance, the Fc domain may be an IgG Fc domain, such as a human IgG1 Fc domain, and the cysteine residue may be selected from the group consisting of Cys261, Cys321, Cys367, and Cys425.

In some embodiments of these aspects, $R_1$ is H, OH, or $OR_A$;

$R_2$ is H, OH, or $OR_B$;

$R_A$ and $R_B$, when present, together with the oxygen atoms to which they are bound, combine to form:

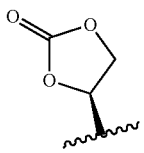

$R_3$, $R_4$, $R_6$, and $R_7$ are each H;
$R_5$ is $OR_C$;
$R_8$ is OH or $NH_2$;
$R_9$ is H or OH; and
X is —S—, —S(O)—, or —SO$_2$—.

In some embodiments, $R_1$ and $R_2$ are each independently H or OH;
$R_3$ is $R_C$;
$R_4$, $R_6$, and $R_7$ are each H;
$R_5$ is H, OH, or $OC_1$-$C_6$ alkyl;
$R_8$ is OH or $NH_2$;
$R_9$ is H or OH; and
X is —S—, —S(O)—, or —SO$_2$—. In some embodiments, $R_1$ and $R_2$ are each independently H or OH;
$R_3$, $R_6$, and $R_7$ are each H;
$R_4$ is $OR_C$, or $R_C$;
$R_5$ is H, OH, or $OC_1$-$C_6$ alkyl;
$R_8$ is OH or $NH_2$;
$R_9$ is H or OH; and
X is —S—, —S(O)—, or —SO$_2$—. In some embodiments, $R_1$ and $R_2$ are each independently H or OH;
$R_3$, $R_6$, and $R_7$ are each H;
$R_4$ and $R_5$ are each independently H or OH;

$R_8$ is $OR_C$ or $NHR_C$;
$R_9$ is H or OH; and
X is —S—, —S(O)—, or —SO$_2$—. In some embodiments of these aspects, the antibody or antigen-binding fragment thereof is internalized by a CD117+ cell.

In some embodiments, Am-L-Z-Ab is:

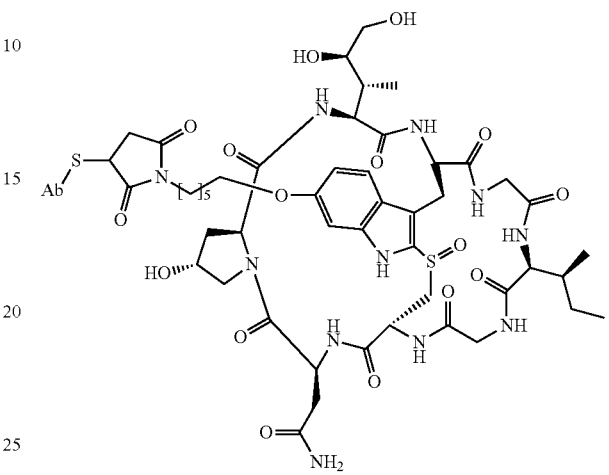

In some embodiments, Am-L-Z-Ab is:

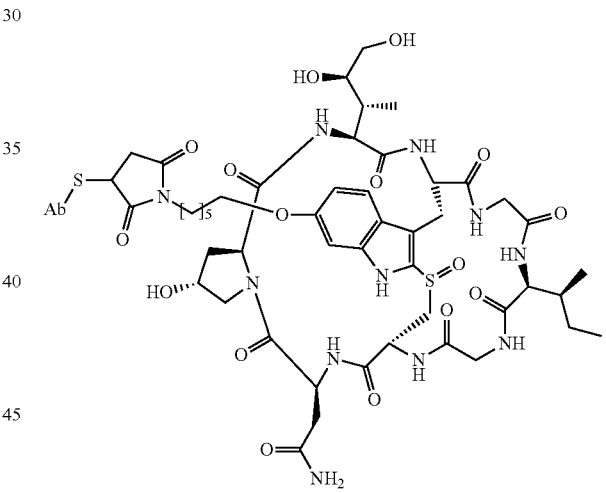

In some embodiments of these aspects, the antibody or antigen-binding fragment thereof binds CD117 with a $K_d$ of less than 1 µM, less than 750 nM, less than 500 nM, less than 250 nM, less than 200 nM, less than 150 nM, less than 100 nM, less than 75 nM, less than 50 nM, less than 10 nM, less than 1 nM, less than 0.1 nM, less than 10 pM, less than 1 pM, or less than 0.1 pM. In some embodiments, the $K_d$ is from about 0.1 pM to about 1 µM.

In some embodiments of these aspects, the antibody or antigen-binding fragment thereof binds CD117 with a $k_{on}$ of from about $9\times10^{-2}$ M$^{-1}$ s$^{-1}$ to about $1\times10^2$ M$^{-1}$s$^{-1}$.

In some embodiments of these aspects, the antibody or antigen-binding fragment thereof competitively inhibits the binding of CD117 to a second antibody or antigen binding fragment thereof, or binds the same epitope as a second antibody, wherein the second antibody or antigen-binding fragment thereof has the following complementarity determining regions (CDRs): a CDR-H1 having the amino acid sequence SYWIG (SEQ ID NO: 1); a CDR-H2 having the amino acid sequence IIYPGDSDTRYSPSFQG (SEQ ID NO: 2); a CDR-H3 having the amino acid sequence HGRGYNGYEGAFDI (SEQ ID NO: 3); a CDR-L1 having the amino acid sequence RASQGISSALA (SEQ ID NO: 4); a CDR-L2 having the amino acid sequence DASSLES (SEQ ID NO: 5); and a CDR-L3 having the amino acid sequence CQQFNSYPLT (SEQ ID NO: 6).

In some embodiments of these aspects, the antibody or antigen-binding fragment thereof competitively inhibits the binding of CD117 to a second antibody or antigen binding fragment thereof, or binds the same epitope as a second antibody, wherein the second antibody or antigen-binding fragment thereof has the following complementarity determining regions (CDRs): a CDR-H1 having the amino acid sequence set forth in SEQ ID NO: 11; a CDR-H2 having the amino acid sequence set forth in SEQ ID NO: 12; a CDR-H3 having the amino acid sequence set forth in SEQ ID NO: 13; a CDR-L1 having the amino acid sequence set forth in SEQ ID NO: 14; a CDR-L2 having the amino acid sequence set forth in SEQ ID NO: 15; and a CDR-L3 having the amino acid sequence set forth in SEQ ID NO: 16.

In one embodiment, the compositions and methods disclosed herein include anti-CD117 antibody Ab67.

In one embodiment, the compositions and methods disclosed herein include anti-CD117 antibody comprising a variable heavy chain amino acid sequence as set forth in SEQ ID NO: 9, and a light chain variable region comprising a light chain amino acid sequence as set forth in SEQ ID NO: 10.

In some embodiments of these aspects, the antibody or antigen-binding fragment thereof is selected from the group consisting of a monoclonal antibody or antigen-binding fragment thereof, a polyclonal antibody or antigen-binding fragment thereof, a humanized antibody or antigen-binding fragment thereof, a bispecific antibody or antigen-binding fragment thereof, a dual-variable immunoglobulin domain, a single-chain Fv molecule (scFv), a diabody, a triabody, a nanobody, an antibody-like protein scaffold, a Fv fragment, a Fab fragment, a F(ab')$_2$ molecule, and a tandem di-scFV.

In another aspect, the invention features a conjugate represented by the formula Ab-Cy, wherein Ab is an antibody or antigen-binding fragment thereof that binds CD117 (e.g., GNNK+ CD117) and Cy is a cytotoxin. In some embodiments of this aspect, the cytotoxin is *pseudomonas* exotoxin A, deBouganin, diphtheria toxin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, or an indolinobenzodiazepine dimer, or a variant of any of the foregoing cytotoxins.

In some embodiments of this aspect, the antibody or antigen-binding fragment thereof is selected from the group consisting of a monoclonal antibody or antigen-binding fragment thereof, a polyclonal antibody or antigen-binding fragment thereof, a humanized antibody or antigen-binding fragment thereof, a bispecific antibody or antigen-binding fragment thereof, a dual-variable immunoglobulin domain, a single-chain Fv molecule (scFv), a diabody, a triabody, a nanobody, an antibody-like protein scaffold, a Fv fragment, a Fab fragment, a F(ab')$_2$ molecule, and a tandem di-scFv. In some embodiments, the antibody has an isotype selected from the group consisting of IgG, IgA, IgM, IgD, and IgE.

In another aspect, the invention features an antibody or fragment thereof that binds CD117 (e.g., GNNK+ CD117) covalently bound to an Fc domain, such as a dimeric Fc domain isolated from a human antibody (for example, isolated from an IgG1, IgG2, IgG3, or IgG4 isotype human antibody). In some embodiments of this aspect, the Fc domain is a monomeric Fc domain containing a single polypeptide strand. In some embodiments of this aspect, the N-terminus of the antibody or fragment thereof is bound to the Fc domain. In some embodiments of this aspect, the C-terminus of the antibody or fragment thereof is bound to the Fc domain. The Fc domain may be conjugated to one or more copies of the antibody or fragment thereof. For instance, conjugates described herein include dimeric Fc domains in which each polypeptide strand of the Fc domain is conjugated to the antibody or fragment thereof. The Fc domain may in turn be conjugated to a cytotoxin, such as a cytotoxin described herein (for example, *pseudomonas* exotoxin A, deBouganin, diphtheria toxin, an amatoxin, such as α-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer, or a variant thereof).

In some embodiments of this aspect, the antibody or fragment thereof is covalently bound to a cytotoxin, such as a cytotoxin described herein (for example, *pseudomonas* exotoxin A, deBouganin, diphtheria toxin, an amatoxin, such as α-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer, or a variant thereof). In some embodiments of this aspect, the N-terminus of the antibody or fragment thereof is bound to the cytotoxin. In some embodiments of this aspect, the C-terminus of the antibody or fragment thereof is bound to the cytotoxin. The cytotoxin may in turn be conjugated to an Fc domain.

In some embodiments of this aspect, the antibody or fragment thereof is covalently bound to the cytotoxin at one site on the antibody or fragment thereof (for example, the N- or C-terminus of the antibody or fragment thereof) and is covalently bound to an Fc domain at another site on the antibody or fragment thereof (for example, the opposite terminus of the antibody or fragment thereof).

In some embodiments of this aspect, the Fc domain is a human IgG1 isotype Fc domain. In some embodiments of this aspect, the Fc domain is a human IgG2 isotype Fc domain. In some embodiments of this aspect, the Fc domain is a human IgG3 isotype Fc domain. In some embodiments of this aspect, the Fc domain is a human IgG4 isotype Fc domain.

In certain embodiments, the foregoing methods and compositions include an anti-CD117 antibody or antigen-binding fragment thereof comprising the CDRs set forth in the heavy and light chain amino acid sequences set forth in Table 10 for any one of Ab54, Ab55, Ab56, Ab57, Ab58, Ab61, Ab66, Ab67, Ab68, or Ab69. In certain embodiments, the foregoing methods and compositions include an anti-CD117 antibody or antigen-binding fragment thereof comprising the variable regions set forth in the heavy and light chain amino acid sequences set forth in Table 10 for any one of Ab54, Ab55, Ab56, Ab57, Ab58, Ab61, Ab66, Ab67, Ab68, or Ab69. In certain embodiments, the foregoing methods and compositions include an IgG1 anti-CD117 antibody or antigen-binding fragment thereof comprising the variable regions set forth in the heavy and light chain amino acid sequences set forth in Table 10 for any one of Ab54, Ab55, Ab56, Ab57, Ab58, Ab61, Ab66, Ab67, Ab68, or Ab69.

BRIEF DESCRIPTION OF THE FIGURES

FIGS. 6A and 6B graphically depict the results of in vitro cell killing assays that show the dose-dependent effect of each indicated ADC on the viability of human CD34+ bone marrow cells. Total live cell counts (FIG. 6A) or viable CD34+CD90+ cell counts (FIG. 6B) (y-axis) in the presence of the HC-55/LC-55 ADC (Ab55 ADC) or control as a function of HC-55/LC-55 ADC (Ab55 ADC) or control concentration (x-axis) are depicted.

FIG. 15A graphically depict the results of in vitro cell killing assays that show Kasumi-1 cell viability as measured in luminescence (RLU) by Celltiter Glo as a function of HC-55/LC-55 ADC (Ab55 ADC), HC-67/LC-67 ADC (Ab67 ADC), or control concentration. FIGS. 15B and 15C graphically depict the results of in vitro cell killing assays that show the dose-dependent effect of each indicated ADC on the viability of human CD34+ bone marrow cells based on total live cell counts (FIG. 15B) or viable CD34+ CD90+ cell counts (FIG. 15C) (y-axis) in the presence of the HC-55/LC-55 ADC (Ab55 ADC), HC-67/LC-67 ADC (Ab67 ADC), or control as a function of antibody concentration (x-axis).

FIG. 16B), or HC-67/LC-67 (Ab67; FIG. 16C) or 15 days (CK6 control (FIG. 16D), HC-55/LC-55 (Ab55; FIG. 16E), or HC-67/LC-67 (Ab67; FIG. 16F) under the indication incubation conditions after analysis by hydrophobic interaction chromatography.

FIGS. 21A and 21B depict multiple sequence alignments of the heavy chain variable regions (VH; FIG. 21A) and the light chain variable regions (LH; FIG. 21B) of antagonist antibodies Ab54, Ab55, Ab66, and Ab67. The CDRs of each variable region are indicated.

FIGS. 22A and 22B depict multiple sequence alignments of the heavy chain variable regions (VH; FIG. 22A) and the light chain variable regions (LH; FIG. 22B) of neutral antibodies Ab58 and Ab61. The CDRs of each variable region are indicated.

FIGS. 23A and 23B depict multiple sequence alignments of the heavy chain variable regions (VH; FIG. 23A) and the light chain variable regions (LH; FIG. 23B) of neutral antibodies Ab66, Ab67, Ab68, and Ab69. The CDRs of each variable region are indicated.

DETAILED DESCRIPTION

Figure 1:
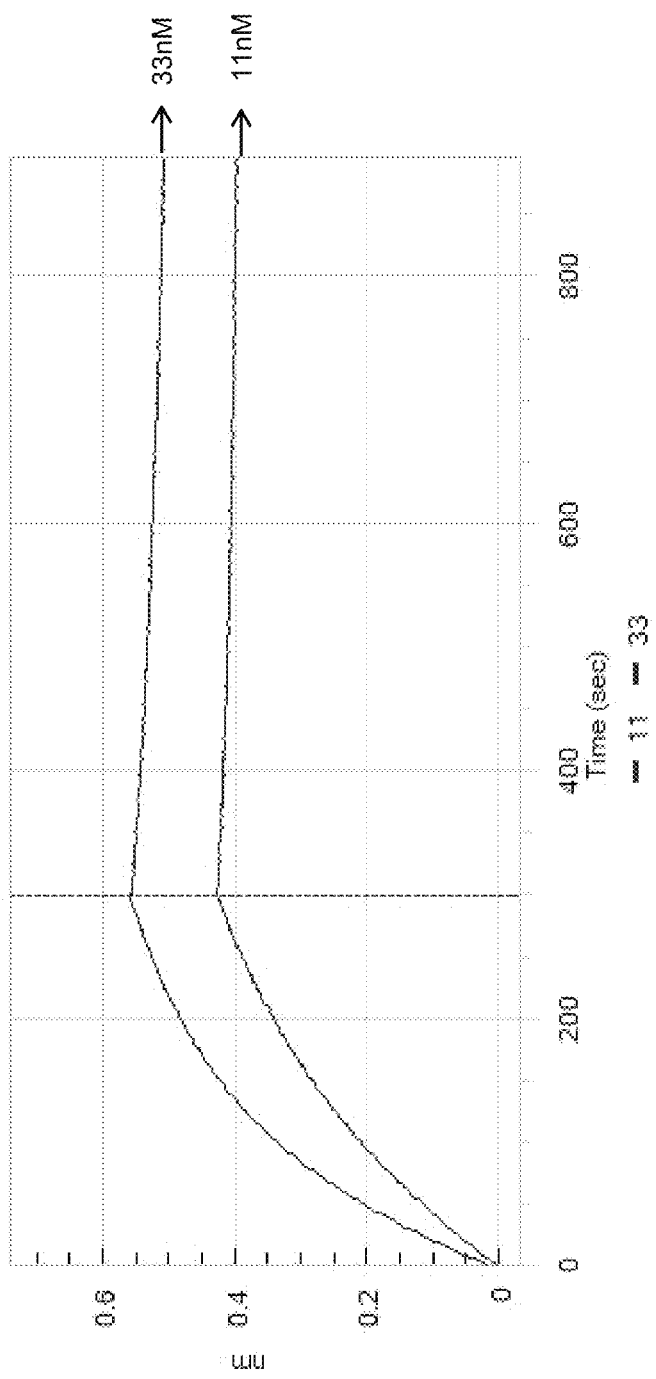
FIG. 1 demonstrates the measurement of binding by Bio-Layer Interferometry (BLI) of the indicated purified IgG (sensor-associated) to purified human CD117 ectodomain (R&D Systems #332-SR) at concentrations of 33.3 nM and 11 nM as a function of time.

Described herein are isolated anti-CD117 human antibodies that bind to human CD117. The antibodies provided herein have many characteristics making them advantageous for therapy, including methods of conditioning human patients for stem cell transplantation. For example, antibodies disclosed herein cross react with rhesus CD117 and are able to internalize. Both of these features also make them advantageous for use in conjugates for delivering cytotoxins to CD117 expressing cells.

The antibodies described herein include both antagonist antibodies and neutral antibodies. Specifically, provided herein are anti-CD117 antibodies Antibody 54 (Ab54), Antibody 55 (Ab55), Antibody 56 (Ab56), Antibody 57 (Ab57), Antibody 58 (Ab58), Antibody 61 (Ab61), Antibody 66 (Ab66), Antibody 67 (Ab67), Antibody 68 (Ab68), and Antibody 69 (Ab69) which are each human anti-CD117 antibodies that specifically bind to the ectodomain of human CD117. The binding regions of Ab54, Ab55, Ab56, Ab57, Ab58, Ab61, Ab66, Ab67, Ab68, and Ab69 are described below, including in Table 10. The anti-CD117 antibodies disclosed herein can be included in anti-CD117 antibody drug conjugates (ADCs; also referred to herein as conjugates).

The anti-CD117 antibodies and conjugates described herein can be used to in methods to treat a variety of disorders, such as diseases of a cell type in the hematopoietic lineage, cancers, autoimmune diseases, metabolic disorders, and stem cell disorders, among others. The compositions and methods described herein may (i) directly deplete a population of cells that give rise to a pathology, such as a population of cancer cells (e.g., leukemia cells) and autoimmune cells (e.g., autoreactive T-cells), and/or (ii) deplete a population of endogenous hematopoietic stem cells so as to promote the engraftment of transplanted hematopoietic stem cells by providing a niche to which the transplanted cells may home. The foregoing activities can be achieved by administration of an ADC, antibody, or antigen-binding fragment thereof, capable of binding an antigen (CD117) expressed by an endogenous disease-causing cell or a hematopoietic stem cell. In the case of direct treatment of a disease, this administration can cause a reduction in the quantity of the cells that give rise to the pathology of interest. In the case of preparing a patient for hematopoietic stem cell transplant therapy, this administration can cause the selective depletion of a population of endogenous hematopoietic stem cells, thereby creating a vacancy in the hematopoietic tissue, such as the bone marrow, that can subsequently be filled by transplanted, exogenous hematopoietic stem cells. This selective depletion is also referred to as conditioning. The invention is based in part on the discovery that ADCs, antibodies, or antigen-binding fragments thereof, capable of binding CD117 (such as GNNK+ D117) can be administered to a patient to effect both of the above activities or as a conditioning agent. ADCs, antibodies, or antigen-binding fragments thereof, that bind CD117 can be administered to a patient suffering from a cancer, such as leukemia, or autoimmune disease to directly deplete a population of cancerous cells or autoimmune cells, and can also be administered to a patient in need of hematopoietic stem cell transplant therapy in order to promote the survival and engraftment potential of transplanted hematopoietic stem cells.

Engraftment of hematopoietic stem cell transplants due to the administration of anti-CD117 antibodies, or antigen-binding fragments thereof, can manifest in a variety of empirical measurements. For instance, engraftment of transplanted hematopoietic stem cells can be evaluated by assessing the quantity of competitive repopulating units (CRU) present within the bone marrow of a patient following administration of an antibody or antigen-binding fragment thereof capable of binding CD117 and subsequent administration of a hematopoietic stem cell transplant. Additionally, one can observe engraftment of a hematopoietic stem cell transplant by incorporating a reporter gene, such as an enzyme that catalyzes a chemical reaction yielding a fluorescent, chromophoric, or luminescent product, into a vector with which the donor hematopoietic stem cells have been transfected and subsequently monitoring the corresponding signal in a tissue into which the hematopoietic stem cells have homed, such as the bone marrow. One can also observe hematopoietic stem cell engraftment by evaluation of the quantity and survival of hematopoietic stem and progenitor cells, for instance, as determined by fluorescence activated cell sorting (FACS) analysis methods known in the art. Engraftment can also be determined by measuring white blood cell counts in peripheral blood during a post-transplant period, and/or by measuring recovery of marrow cells by donor cells in a bone marrow aspirate sample.

The sections that follow provide a description of conjugates, antibodies, or antigen-binding fragments thereof, that can be administered to a patient, such as a patient suffering from a cancer or autoimmune disease, or a patient in need of hematopoietic stem cell transplant therapy in order to promote engraftment of hematopoietic stem cell grafts, as well as methods of administering such therapeutics to a patient (e.g., prior to hematopoietic stem cell transplantation).

Definitions

As used herein, the term "about" refers to a value that is within 10% above or below the value being described. For example, the term "about 5 nM" indicates a range of from 4.5 nM to 5.5 nM.

As used herein, the term "amatoxin" refers to a member of the amatoxin family of peptides produced by *Amanita phalloides* mushrooms, or a variant or derivative thereof, such as a variant or derivative thereof capable of inhibiting RNA polymerase II activity. Amatoxins useful in conjunction with the compositions and methods described herein include compounds according to, but not limited to, formula (III), including α-amanitin, β-amanitin, γ-amanitin, ε-amanitin, amanin, amaninamide, amanullin, amanullinic acid, or proamanullin. As described herein, amatoxins may be conjugated to an antibody, or antigen-binding fragment thereof, for instance, by way of a linker moiety (L) (thus forming a conjugate (i.e., ADC)). Exemplary methods of amatoxin conjugation and linkers useful for such processes are described below. Exemplary linker-containing amatoxins useful for conjugation to an antibody, or antigen-binding fragment, in accordance with the compositions and methods are also described herein.

Formula (III) is as follows:

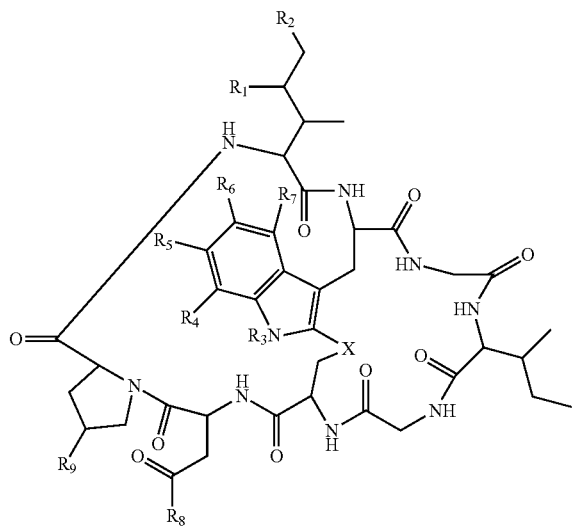

(III)

wherein $R_1$ is H, OH, or $OR_A$;
$R_2$ is H, OH, or $OR_B$;
$R_A$ and $R_B$, when present, together with the oxygen atoms to which they are bound, combine to form an optionally substituted 5-membered heterocycloalkyl group;
$R_3$ is H or $R_D$;
$R_4$ is H, OH, $OR_D$, or $R_D$;
$R_5$ is H, OH, $OR_D$, or $R_D$;
$R_6$ is H, OH, $OR_D$, or $R_D$;
$R_7$ is H, OH, $OR_D$, or $R_D$;
$R_8$ is OH, $NH_2$, or $OR_D$;
$R_9$ is H, OH, or $OR_D$;
X is —S—, —S(O)—, or —SO$_2$—; and $R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl.

For instance, amatoxins useful in conjunction with the compositions and methods described herein include compounds according to formula (IIIA), below:

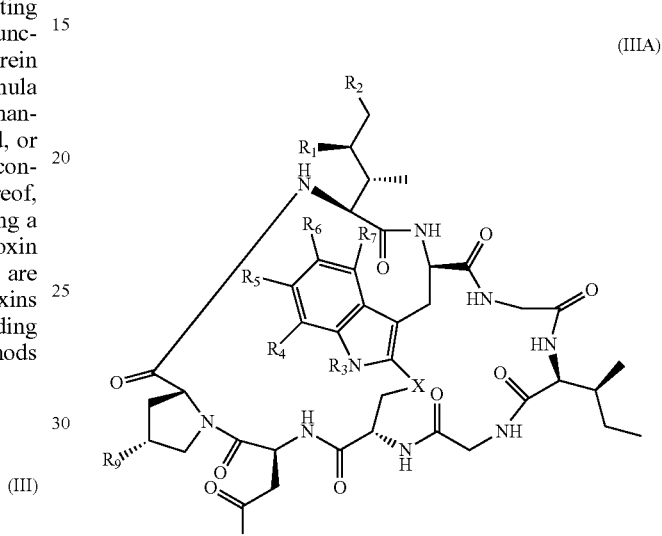

(IIIA)

wherein $R_1$ is H, OH, or $OR_A$;
$R_2$ is H, OH, or $OR_B$;
$R_A$ and $R_B$, when present, together with the oxygen atoms to which they are bound, combine to form an optionally substituted 5-membered heterocycloalkyl group;
$R_3$ is H or $R_D$;
$R_4$ is H, OH, $OR_D$, or $R_D$;
$R_5$ is H, OH, $OR_D$, or $R_D$;
$R_6$ is H, OH, $OR_D$, or $R_D$;
$R_7$ is H, OH, $OR_D$, or $R_D$;
$R_8$ is OH, $NH_2$, or $OR_D$;
$R_9$ is H, OH, or $OR_D$;
X is —S—, —S(O)—, or —SO$_2$—; and $R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl.

Amatoxins useful in conjunction with the compositions and methods described herein also include compounds according to formula (IIIB), below:

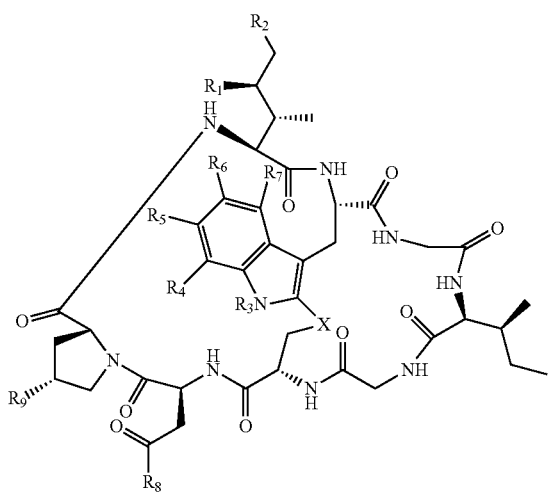

(IIIB)

wherein $R_1$ is H, OH, or $OR_A$;

$R_2$ is H, OH, or $OR_B$;

$R_A$ and $R_B$, when present, together with the oxygen atoms to which they are bound, combine to form an optionally substituted 5-membered heterocycloalkyl group;

$R_3$ is H or $R_D$;

$R_4$ is H, OH, $OR_D$, or $R_D$;

$R_5$ is H, OH, $OR_D$, or $R_D$;

$R_6$ is H, OH, $OR_D$, or $R_D$;

$R_7$ is H, OH, $OR_D$, or $R_D$;

$R_8$ is OH, $NH_2$, or $OR_D$;

$R_9$ is H, OH, or $OR_D$;

X is —S—, —S(O)—, or —$SO_2$—; and $R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl.

As described herein, amatoxins may be conjugated to an antibody, or antigen-binding fragment thereof, for instance, by way of a linker moiety (thus forming a conjugate). Exemplary methods of amatoxin conjugation and linkers useful for such processes are described in the section entitled "Linkers for chemical conjugation," as well as in Table 1, below. Exemplary linker-containing amatoxins useful for conjugation to an antibody, or antigen-binding fragment, in accordance with the compositions and methods described herein are shown in structural formulas (I), (IA), (IB), (II), (IIA), and (IIB) recited herein.

As used herein, the term "antibody" refers to an immunoglobulin molecule that specifically binds to, or is immunologically reactive with, a particular antigen, and includes monoclonal, genetically engineered, and otherwise modified forms of antibodies, including but not limited to chimeric antibodies, humanized antibodies, heteroconjugate antibodies (e.g., bi- tri- and quad-specific antibodies, diabodies, triabodies, and tetrabodies), and antigen binding fragments of antibodies, including, for example, Fab', F(ab')$_2$, Fab, Fv, rIgG, and scFv fragments. Unless otherwise indicated, the term "monoclonal antibody" (mAb) is meant to include both intact molecules, as well as antibody fragments (including, for example, Fab and F(ab')$_2$ fragments) that are capable of specifically binding to a target protein. As used herein, the Fab and F(ab')$_2$ fragments refer to antibody fragments that lack the Fc fragment of an intact antibody. Examples of these antibody fragments are described herein.

The antibodies of the present invention are generally isolated or recombinant. "Isolated," when used herein refers to a polypeptide, e.g., an antibody, that has been identified and separated and/or recovered from a cell or cell culture from which it was expressed. Ordinarily, an isolated antibody will be prepared by at least one purification step. Thus, an "isolated antibody," refers to an antibody which is substantially free of other antibodies having different antigenic specificities. For instance, an isolated antibody that specifically binds to CD117 is substantially free of antibodies that specifically bind antigens other than CD117.

The term "antigen-binding fragment," as used herein, refers to one or more fragments of an antibody that retain the ability to specifically bind to a target antigen. The antigen-binding function of an antibody can be performed by fragments of a full-length antibody. The antibody fragments can be, for example, a Fab, F(ab')$_2$, scFv, diabody, a triabody, an affibody, a nanobody, an aptamer, or a domain antibody. Examples of binding fragments encompassed of the term "antigen-binding fragment" of an antibody include, but are not limited to: (i) a Fab fragment, a monovalent fragment consisting of the $V_L$, $V_H$, $C_L$, and $C_H1$ domains; (ii) a F(ab')$_2$ fragment, a bivalent fragment containing two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb including $V_H$ and $V_L$ domains; (vi) a dAb fragment that consists of a $V_H$ domain (see, e.g., Ward et al., Nature 341:544-546, 1989); (vii) a dAb which consists of a $V_H$ or a $V_L$ domain; (viii) an isolated complementarity determining region (CDR); and (ix) a combination of two or more (e.g., two, three, four, five, or six) isolated CDRs which may optionally be joined by a synthetic linker. Furthermore, although the two domains of the Fv fragment, $V_L$ and $V_H$, are coded for by separate genes, they can be joined, using recombinant methods, by a linker that enables them to be made as a single protein chain in which the $V_L$ and $V_H$ regions pair to form monovalent molecules (known as single chain Fv (scFv); see, for example, Bird et al., Science 242:423-426, 1988 and Huston et al., Proc. Natl. Acad. Sci. USA 85:5879-5883, 1988). These antibody fragments can be obtained using conventional techniques known to those of skill in the art, and the fragments can be screened for utility in the same manner as intact antibodies. Antigen-binding fragments can be produced by recombinant DNA techniques, enzymatic or chemical cleavage of intact immunoglobulins, or, in certain cases, by chemical peptide synthesis procedures known in the art.

As used herein, the term "anti-CD117 antibody" or "an antibody that binds to CD117" refers to an antibody that is capable of binding CD117 with sufficient affinity such that the antibody is useful as a diagnostic and/or therapeutic agent in targeting CD117. The amino acid sequences of the two main isoforms of human CD117 are provided in SEQ ID NO: 145 (isoform 1) and SEQ ID NO: 146 (isoform 2).

As used herein, the term "bispecific antibody" refers to, for example, a monoclonal, often a human or humanized antibody that is capable of binding at least two different antigens. For instance, one of the binding specificities can be directed towards a hematopoietic stem cell surface antigen, CD117 (e.g., GNNK+ CD117), and the other can specifically bind a different hematopoietic stem cell surface antigen or another cell surface protein, such as a receptor or receptor subunit involved in a signal transduction pathway that potentiates cell growth, among others.

As used herein, the term "complementarity determining region" (CDR) refers to a hypervariable region found both in the light chain and the heavy chain variable domains of an antibody. The more highly conserved portions of variable domains are referred to as framework regions (FRs). The amino acid positions that delineate a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The antibodies described herein may contain modifications in these hybrid hypervariable positions. The variable domains of native heavy and light chains each contain four framework regions that primarily adopt a β-sheet configuration, connected by three CDRs, which form loops that connect, and in some cases form part of, the β-sheet structure. The CDRs in each chain are held together in close proximity by the framework regions in the order FR1-CDR1-FR2-CDR2-FR3-CDR3-FR4 and, with the CDRs from the other antibody chains, contribute to the formation of the target binding site of antibodies (see Kabat et al., Sequences of Proteins of Immunological Interest, National Institute of Health, Bethesda, Md., 1987). In certain embodiments, numbering of immunoglobulin amino acid residues is performed according to the immunoglobulin amino acid residue numbering system of Kabat et al., unless otherwise indicated (although any antibody numbering scheme, including, but not limited to IMGT and Chothia, can be utilized).

As used herein, the terms "condition" and "conditioning" refer to processes by which a patient is prepared for receipt of a transplant containing hematopoietic stem cells. Such procedures promote the engraftment of a hematopoietic stem cell transplant (for instance, as inferred from a sustained increase in the quantity of viable hematopoietic stem cells within a blood sample isolated from a patient following a conditioning procedure and subsequent hematopoietic stem cell transplantation. According to the methods described herein, a patient may be conditioned for hematopoietic stem cell transplant therapy by administration to the patient of an ADC, antibody or antigen-binding fragment thereof capable of binding an antigen expressed by hematopoietic stem cells, such as CD117 (e.g., GNNK+ CD117). As described herein, the antibody may be covalently conjugated to a cytotoxin so as to form a drug-antibody conjugate. Administration of an ADC, antibody, antigen-binding fragment thereof, or drug-antibody conjugate capable of binding one or more of the foregoing antigens to a patient in need of hematopoietic stem cell transplant therapy can promote the engraftment of a hematopoietic stem cell graft, for example, by selectively depleting endogenous hematopoietic stem cells, thereby creating a vacancy filled by an exogenous hematopoietic stem cell transplant.

As used herein, the term "conjugate" refers to a compound formed by the chemical bonding of a reactive functional group of one molecule, such as an antibody or antigen-binding fragment thereof, with an appropriately reactive functional group of another molecule, such as a cytotoxin described herein. Conjugates may include a linker between the two molecules bound to one another. Examples of linkers that can be used for the formation of a conjugate include peptide-containing linkers, such as those that contain naturally occurring or non-naturally occurring amino acids, such as D-amino acids. Linkers can be prepared using a variety of strategies described herein and known in the art. Depending on the reactive components therein, a linker may be cleaved, for example, by enzymatic hydrolysis, photolysis, hydrolysis under acidic conditions, hydrolysis under basic conditions, oxidation, disulfide reduction, nucleophilic cleavage, or organometallic cleavage (see, for example, Leriche et al., Bioorg. Med. Chem., 20:571-582, 2012). Notably, the term "conjugate" (when referring to a compound) is also referred to interchangeably herein as a "drug conjugate", "antibody drug conjugate" or "ADC".

As used herein, the term "coupling reaction" refers to a chemical reaction in which two or more substituents suitable for reaction with one another react so as to form a chemical moiety that joins (e.g., covalently) the molecular fragments bound to each substituent. Coupling reactions include those in which a reactive substituent bound to a fragment that is a cytotoxin, such as a cytotoxin known in the art or described herein, reacts with a suitably reactive substituent bound to a fragment that is an antibody, or antigen-binding fragment thereof, such as an antibody, antigen-binding fragment thereof, or specific anti-CD117 antibody that binds CD117 (such as GNNK+ CD117) known in the art or described herein. Examples of suitably reactive substituents include a nucleophile/electrophile pair (e.g., a thiol/haloalkyl pair, an amine/carbonyl pair, or a thiol/α,β-unsaturated carbonyl pair, among others), a diene/dienophile pair (e.g., an azide/alkyne pair, among others), and the like. Coupling reactions include, without limitation, thiol alkylation, hydroxyl alkylation, amine alkylation, amine condensation, amidation, esterification, disulfide formation, cycloaddition (e.g., [4+2] Diels-Alder cycloaddition, [3+2] Huisgen cycloaddition, among others), nucleophilic aromatic substitution, electrophilic aromatic substitution, and other reactive modalities known in the art or described herein.

As used herein, "CRU (competitive repopulating unit)" refers to a unit of measure of long-term engrafting stem cells, which can be detected after in-vivo transplantation.

As used herein, the term "donor" refers to a human or animal from which one or more cells are isolated prior to administration of the cells, or progeny thereof, into a recipient. The one or more cells may be, for example, a population of hematopoietic stem cells.

As used herein, the term "diabody" refers to a bivalent antibody containing two polypeptide chains, in which each polypeptide chain includes $V_H$ and $V_L$ domains joined by a linker that is too short (e.g., a linker composed of five amino acids) to allow for intramolecular association of $V_H$ and $V_L$ domains on the same peptide chain. This configuration forces each domain to pair with a complementary domain on another polypeptide chain so as to form a homodimeric structure. Accordingly, the term "triabody" refers to trivalent antibodies containing three peptide chains, each of which contains one $V_H$ domain and one $V_L$ domain joined by a linker that is exceedingly short (e.g., a linker composed of 1-2 amino acids) to permit intramolecular association of $V_H$ and $V_L$ domains within the same peptide chain. In order to fold into their native structures, peptides configured in this way typically trimerize so as to position the $V_H$ and $V_L$ domains of neighboring peptide chains spatially proximal to one another (see, for example, Holliger et al., Proc. Natl. Acad. Sci. USA 90:6444-48, 1993).

As used herein, "drug-to-antibody ratio" or "DAR" refers to the number of drugs, e.g., amatoxin, attached to the antibody of a conjugate. The DAR of an ADC can range from 1 to 8, although higher loads are also possible depending on the number of linkage sites on an antibody. In certain embodiments, the conjugate has a DAR of 1, 2, 3, 4, 5, 6, 7, or 8.

As used herein, a "dual variable domain immunoglobulin" ("DVD-Ig") refers to an antibody that combines the target-binding variable domains of two monoclonal antibodies via linkers to create a tetravalent, dual-targeting single agent (see, for example, Gu et al., Meth. Enzymol., 502:25-41, 2012).

As used herein, the term "endogenous" describes a substance, such as a molecule, cell, tissue, or organ (e.g., a hematopoietic stem cell or a cell of hematopoietic lineage, such as a megakaryocyte, thrombocyte, platelet, erythrocyte, mast cell, myeloblast, basophil, neutrophil, eosinophil, microglial cell, granulocyte, monocyte, osteoclast, antigen-presenting cell, macrophage, dendritic cell, natural killer cell, T-lymphocyte, or B-lymphocyte) that is found naturally in a particular organism, such as a human patient.

As used herein, the term "engraftment potential" is used to refer to the ability of hematopoietic stem and progenitor cells to repopulate a tissue, whether such cells are naturally circulating or are provided by transplantation. The term encompasses all events surrounding or leading up to engraftment, such as tissue homing of cells and colonization of cells within the tissue of interest. The engraftment efficiency or rate of engraftment can be evaluated or quantified using any clinically acceptable parameter as known to those of skill in the art and can include, for example, assessment of competitive repopulating units (CRU); incorporation or expression of a marker in tissue(s) into which stem cells have homed, colonized, or become engrafted; or by evaluation of the progress of a subject through disease progression, survival of hematopoietic stem and progenitor cells, or survival of a recipient. Engraftment can also be determined by measuring white blood cell counts in peripheral blood during a post-transplant period. Engraftment can also be assessed by measuring recovery of marrow cells by donor cells in a bone marrow aspirate sample.

As used herein, the term "exogenous" describes a substance, such as a molecule, cell, tissue, or organ (e.g., a hematopoietic stem cell or a cell of hematopoietic lineage, such as a megakaryocyte, thrombocyte, platelet, erythrocyte, mast cell, myeloblast, basophil, neutrophil, eosinophil, microglial cell, granulocyte, monocyte, osteoclast, antigen-presenting cell, macrophage, dendritic cell, natural killer cell, T-lymphocyte, or B-lymphocyte) that is not found naturally in a particular organism, such as a human patient. Exogenous substances include those that are provided from an external source to an organism or to cultured matter extracted therefrom.

The terms "Fc", "Fc region," and "Fc domain," as used herein refer to the portion of an IgG antibody that correlates to a crystallizable fragment obtained by papain digestion of an IgG molecule. The Fc region comprises the C-terminal half of two heavy chains of an IgG molecule that are linked by disulfide bonds. It has no antigen binding activity but contains the carbohydrate moiety and binding sites for complement and Fc receptors, including the FcRn receptor. An Fc region contains the second constant domain CH2 (e.g., residues at EU positions 231-340 of IgG1) and the third constant domain CH3 (e.g., residues at EU positions 341-447 of human IgG1). As used herein, the Fc region includes the "lower hinge region" (e.g., residues at EU positions 233-239 of IgG1). Fc can refer to this region in isolation, or this region in the context of an antibody, antibody fragment, or Fc fusion protein. Polymorphisms have been observed at a number of positions in Fc domains, including but not limited to EU positions 270, 272, 312, 315, 356, and 358, and thus slight differences between the sequences presented in the instant application and sequences known in the art can exist. Thus, a "wild type IgG Fc domain" or "WT IgG Fc domain" refers to any naturally occurring IgG Fc region (i.e., any allele). The sequences of the heavy chains of human IgG1, IgG2, IgG3 and IgG4 can be found in a number of sequence databases, for example, at the Uniprot database (www.uniprot.org) under accession numbers P01857 (IGHG1_HUMAN), P01859 (IGHG2_HUMAN), P01860 (IGHG3_HUMAN), and P01861 (IGHG1_HUMAN), respectively. An example of a "WT" Fc region is provided in SEQ ID NO: 122 (which provides a heavy chain constant region containing an Fc region).

The terms "modified Fc region" or "variant Fc region" as used herein refers to an IgG Fc domain comprising one or more amino acid substitutions, deletions, insertions or modifications introduced at any position within the Fc region.

The terms "full length antibody" and "intact antibody" are used herein interchangeably to refer to an antibody in its substantially intact form, and not an antibody fragment as defined herein. Thus, for an IgG antibody, an intact antibody comprises two heavy chains each comprising a variable region, a constant region and an Fc region, and two light chains each comprising a variable region and a constant region. More specifically, an intact IgG comprises two light chains each comprising a light chain variable region (VL) and a light chain constant region (CL), and comprises two heavy chains each comprising a heavy chain variable region (VH) and three heavy chain constant regions (CH1, CH2, and CH3). CH2 and CH3 represent the Fc region of the heavy chain.

As used herein, the term "framework region" or "FW region" includes amino acid residues that are adjacent to the CDRs of an antibody or antigen-binding fragment thereof. FW region residues may be present in, for example, human antibodies, humanized antibodies, monoclonal antibodies, antibody fragments, Fab fragments, single chain antibody fragments, scFv fragments, antibody domains, and bispecific antibodies, among others.

As used herein, the term "hematopoietic stem cells" ("HSCs") refers to immature blood cells having the capacity to self-renew and to differentiate into mature blood cells containing diverse lineages including but not limited to granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells). Such cells may include CD34+ cells. CD34+ cells are immature cells that express the CD34 cell surface marker. In humans, CD34+ cells are believed to include a subpopulation of cells with the stem cell properties defined above, whereas in mice, HSCs are CD34-. In addition, HSCs also refer to long term repopulating HSCs (LT-HSC) and short term repopulating HSCs (ST-HSC). LT-HSCs and ST-HSCs are differentiated, based on functional potential and on cell surface marker expression. For example, human HSCs are CD34+, CD38-, CD45RA-, CD90+, CD49F+, and lin- (negative for mature lineage markers including CD2, CD3, CD4, CD7, CD8, CD10, CD11B, CD19, CD20, CD56, CD235A). In mice, bone marrow LT-HSCs are CD34-, SCA-1+, C-kit+, CD135-, Slamfl/CD150+, CD48-, and lin- (negative for mature lineage markers including Ter119, CD11b, G0, CD3, CD4, CD8, B220, IL7ra), whereas ST-HSCs are CD34+, SCA-1+, C-kit+, CD135−, Slamfl/CD150+, and lin− (negative for mature lineage markers including Ter119, CD11 b, Gr1, CD3, CD4, CD8, B220, IL7ra). In addition, ST-HSCs are less quiescent and more proliferative than LT-HSCs under homeostatic conditions. However, LT-HSC have greater self-renewal potential (i.e., they survive throughout adulthood, and can be serially transplanted through successive recipients), whereas ST-HSCs have limited self-renewal (i.e., they survive for only a limited period of time, and do not possess serial transplantation potential). Any of these HSCs can be used in the methods described herein. ST-HSCs are particularly useful because they are highly proliferative and thus, can more quickly give rise to differentiated progeny.

As used herein, the term "hematopoietic stem cell functional potential" refers to the functional properties of hematopoietic stem cells which include 1) multi-potency (which refers to the ability to differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells), 2) self-renewal (which refers to the ability of hematopoietic stem cells to give rise to daughter cells that have equivalent potential as the mother cell, and further that this ability can repeatedly occur throughout the lifetime of an individual without exhaustion), and 3) the ability of hematopoietic stem cells or progeny thereof to be reintroduced into a transplant recipient whereupon they home to the hematopoietic stem cell niche and re-establish productive and sustained hematopoiesis.

As used herein, the term "human antibody" is intended to include antibodies having variable and constant regions derived from human germline immunoglobulin sequences. A human antibody may include amino acid residues not encoded by human germline immunoglobulin sequences (e.g., mutations introduced by random or site-specific mutagenesis in vitro or during gene rearrangement or by somatic mutation in vivo). However, the term "human antibody", as used herein, is not intended to include antibodies in which CDR sequences derived from the germline of another mammalian species, such as a mouse, have been grafted onto human framework sequences. A human antibody can be produced in a human cell (for example, by recombinant expression) or by a non-human animal or a prokaryotic or eukaryotic cell that is capable of expressing functionally rearranged human immunoglobulin (such as heavy chain and/or light chain) genes. When a human antibody is a single chain antibody, it can include a linker peptide that is not found in native human antibodies. For example, an Fv can contain a linker peptide, such as two to about eight glycine or other amino acid residues, which connects the variable region of the heavy chain and the variable region of the light chain. Such linker peptides are considered to be of human origin. Human antibodies can be made by a variety of methods known in the art including phage display methods using antibody libraries derived from human immunoglobulin sequences. Human antibodies can also be produced using transgenic mice that are incapable of expressing functional endogenous immunoglobulins, but which can express human immunoglobulin genes (see, for example, PCT Publication Nos. WO 1998/24893; WO 1992/01047; WO 1996/34096; WO 1996/33735; U.S. Pat. Nos. 5,413,923; 5,625,126; 5,633,425; 5,569,825; 5,661,016; 5,545,806; 5,814,318; 5,885,793; 5,916,771; and 5,939,598).

A "humanized" antibody refers to an antibody that contains minimal sequences derived from non-human immunoglobulin. Thus, "humanized" forms of non-human (e.g., murine) antibodies are chimeric antibodies that contain minimal sequence derived from the non-human antibody. All or substantially all of the FW regions may also be those of a human immunoglobulin sequence. The humanized antibody can also contain at least a portion of an immunoglobulin constant region (Fc), typically that of a human immunoglobulin consensus sequence. Methods of antibody humanization are known in the art and have been described, for example, in Riechmann et al., Nature 332:323-7, 1988; U.S. Pat. Nos. 5,530,101; 5,585,089; 5,693,761; 5,693,762; and 6,180,370.

As used herein, patients that are "in need of" a hematopoietic stem cell transplant include patients that exhibit a defect or deficiency in one or more blood cell types, as well as patients having a stem cell disorder, autoimmune disease, cancer, or other pathology described herein. Hematopoietic stem cells generally exhibit 1) multi-potency, and can thus differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells), 2) self-renewal, and can thus give rise to daughter cells that have equivalent potential as the mother cell, and 3) the ability to be reintroduced into a transplant recipient whereupon they home to the hematopoietic stem cell niche and re-establish productive and sustained hematopoiesis. Hematopoietic stem cells can thus be administered to a patient defective or deficient in one or more cell types of the hematopoietic lineage in order to re-constitute the defective or deficient population of cells in vivo. For example, the patient may be suffering from cancer, and the deficiency may be caused by administration of a chemotherapeutic agent or other medicament that depletes, either selectively or non-specifically, the cancerous cell population. Additionally or alternatively, the patient may be suffering from a hemoglobinopathy (e.g., a non-malignant hemoglobinopathy), such as sickle cell anemia, thalassemia, Fanconi anemia, aplastic anemia, and Wiskott-Aldrich syndrome. The subject may be one that is suffering from adenosine deaminase severe combined immunodeficiency (ADA SCID), HIV/AIDS, metachromatic leukodystrophy, Diamond-Blackfan anemia, and Schwachman-Diamond syndrome. The subject may have or be affected by an inherited blood disorder (e.g., sickle cell anemia) or an autoimmune disorder. Additionally or alternatively, the subject may have or be affected by a malignancy, such as neuroblastoma or a hematologic cancer. For instance, the subject may have a leukemia, lymphoma, or myeloma. In some embodiments, the subject has acute myeloid leukemia, acute lymphoid leukemia, chronic myeloid leukemia, chronic lymphoid leukemia, multiple myeloma, diffuse large B-cell lymphoma, or non-Hodgkin's lymphoma. In some embodiments, the subject has myelodysplastic syndrome. In some embodiments, the subject has an autoimmune disease, such as scleroderma, multiple sclerosis, ulcerative colitis, Crohn's disease, Type 1 diabetes, or another autoimmune pathology described herein. In some embodiments, the subject is in need of chimeric antigen receptor T-cell (CART) therapy. In some embodiments, the subject has or is otherwise affected by a metabolic storage disorder. The subject may suffer or otherwise be affected by a metabolic disorder selected from the group consisting of glycogen storage diseases, mucopolysaccharidoses, Gaucher's Disease, Hurlers Disease, sphingolipidoses, metachromatic leukodystrophy, or any other diseases or disorders which may benefit from the treatments and therapies disclosed herein and including, without limitation, severe combined immunodeficiency, Wiscott-Aldrich syndrome, hyper immunoglobulin M (IgM) syndrome, Chediak-Higashi disease, hereditary lymphohistiocytosis, osteopetrosis, osteogenesis imperfecta, storage diseases, thalassemia major, sickle cell disease, systemic sclerosis, systemic lupus erythematosus, multiple sclerosis, juvenile rheumatoid arthritis and those diseases, or disorders described in "Bone Marrow Transplantation for Non-Malignant Disease," ASH Education Book, 1:319-338 (2000), the disclosure of which is incorporated herein by reference in its entirety as it pertains to pathologies that may be treated by administration of hematopoietic stem cell transplant therapy. Additionally or alternatively, a patient "in need of" a hematopoietic stem cell transplant may one that is or is not suffering from one of the foregoing pathologies, but nonetheless exhibits a reduced level (e.g., as compared to that of an otherwise healthy subject) of one or more endogenous cell types within the hematopoietic lineage, such as megakaryocytes, thrombocytes, platelets, erythrocytes, mast cells, myeloblasts, basophils, neutrophils, eosinophils, microglia, granulocytes, monocytes, osteoclasts, antigen-presenting cells, macrophages, dendritic cells, natural killer cells, T-lymphocytes, and B-lymphocytes. One of skill in the art can readily determine whether one's level of one or more of the foregoing cell types, or other blood cell type, is reduced with respect to an otherwise healthy subject, for instance, by way of flow cytometry and fluorescence activated cell sorting (FACS) methods, among other procedures, known in the art.

As used herein, the term "monoclonal antibody" refers to an antibody that is derived from a single clone, including any eukaryotic, prokaryotic, or phage clone, and not the method by which it is produced.

As used herein a "neutral antibody" refers to an antibody, or an antigen binding fragment thereof, that is not capable of significantly neutralizing, blocking, inhibiting, abrogating, reducing or interfering with the activities of a particular or specified target (e.g., CD117), including the binding of receptors to ligands or the interactions of enzymes with substrates. In one embodiment, a neutral anti-CD117 antibody, or fragment thereof, is an anti-CD117 antibody that does not substantially inhibit SCF-dependent cell proliferation and does not cross block SCF binding to CD117. An example of a neutral antibody is Ab67 (or an antibody having the binding regions of Ab67). In contrast, an "antagonist" anti-CD117 antibody inhibits SCF-dependent proliferation and is able to cross block SCF binding to CD117. An example of an antagonist antibody is Ab55 (or an antibody having the binding regions of Ab55).

As used herein, the term "recipient" refers to a patient that receives a transplant, such as a transplant containing a population of hematopoietic stem cells. The transplanted cells administered to a recipient may be, e.g., autologous, syngeneic, or allogeneic cells.

As used herein, the term "sample" refers to a specimen (e.g., blood, blood component (e.g., serum or plasma), urine, saliva, amniotic fluid, cerebrospinal fluid, tissue (e.g., placental or dermal), pancreatic fluid, chorionic villus sample, and cells) taken from a subject.

As used herein, the term "scFv" refers to a single chain Fv antibody in which the variable domains of the heavy chain and the light chain from an antibody have been joined to form one chain. scFv fragments contain a single polypeptide chain that includes the variable region of an antibody light chain ($V_L$) (e.g., CDR-L1, CDR-L2, and/or CDR-L3) and the variable region of an antibody heavy chain ($V_H$) (e.g., CDR-H1, CDR-H2, and/or CDR-H3) separated by a linker. The linker that joins the $V_L$ and $V_H$ regions of a scFv fragment can be a peptide linker composed of proteinogenic amino acids. Alternative linkers can be used to so as to increase the resistance of the scFv fragment to proteolytic degradation (for example, linkers containing D-amino acids), in order to enhance the solubility of the scFv fragment (for example, hydrophilic linkers such as polyethylene glycol-containing linkers or polypeptides containing repeating glycine and serine residues), to improve the biophysical stability of the molecule (for example, a linker containing cysteine residues that form intramolecular or intermolecular disulfide bonds), or to attenuate the immunogenicity of the scFv fragment (for example, linkers containing glycosylation sites). It will also be understood by one of ordinary skill in the art that the variable regions of the scFv molecules described herein can be modified such that they vary in amino acid sequence from the antibody molecule from which they were derived. For example, nucleotide or amino acid substitutions leading to conservative substitutions or changes at amino acid residues can be made (e.g., in CDR and/or framework residues) so as to preserve or enhance the ability of the scFv to bind to the antigen recognized by the corresponding antibody.

The terms "specific binding" or "specifically binding", as used herein, refers to the ability of an antibody to recognize and bind to a specific protein structure (epitope) rather than to proteins generally. If an antibody is specific for epitope "A", the presence of a molecule containing epitope A (or free, unlabeled A), in a reaction containing labeled "A" and the antibody, will reduce the amount of labeled A bound to the antibody. By way of example, an antibody "binds specifically" to a target if the antibody, when labeled, can be competed away from its target by the corresponding non-labeled antibody. In one embodiment, an antibody specifically binds to a target, e.g., CD117, if the antibody has a $K_D$ for the target of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, or less (less meaning a number that is less than $10^{-12}$, e.g. $10^{-13}$). In one embodiment, the term "specific binding to CD117" or "specifically binds to CD117," as used herein, refers to an antibody or that binds to CD117 and has a dissociation constant ($K_D$) of $1.0 \times 10^{-7}$ M or less, as determined by surface plasmon resonance. In one embodiment, $K_D$ (M) is determined according to standard bio-layer interferometery (BLI). In one embodiment, $K_{off}$ (1/s) is determined according to standard bio-layer interferometery (BLI). It shall be understood, however, that the antibody may be capable of specifically binding to two or more antigens which are related in sequence. For example, in one embodiment, an antibody can specifically bind to both human and a non-human (e.g., mouse or non-human primate) orthologs of CD117.

As used herein, the terms "subject" and "patient" refer to an organism, such as a human, that receives treatment for a particular disease or condition as described herein. For instance, a patient, such as a human patient, may receive treatment prior to hematopoietic stem cell transplant therapy in order to promote the engraftment of exogenous hematopoietic stem cells.

As used herein, the phrase "substantially cleared from the blood" refers to a point in time following administration of a therapeutic agent (such as an anti-CD117 antibody, or antigen-binding fragment thereof) to a patient when the concentration of the therapeutic agent in a blood sample isolated from the patient is such that the therapeutic agent is not detectable by conventional means (for instance, such that the therapeutic agent is not detectable above the noise threshold of the device or assay used to detect the therapeutic agent). A variety of techniques known in the art can be used to detect antibodies, or antibody fragments, such as ELISA-based detection assays known in the art or described herein. Additional assays that can be used to detect antibodies, or antibody fragments, include immunoprecipitation techniques and immunoblot assays, among others known in the art.

As used herein, the phrase "stem cell disorder" broadly refers to any disease, disorder, or condition that may be treated or cured by conditioning a subject's target tissues, and/or by ablating an endogenous stem cell population in a target tissue (e.g., ablating an endogenous hematopoietic stem or progenitor cell population from a subject's bone marrow tissue) and/or by engrafting or transplanting stem cells in a subject's target tissues. For example, Type I diabetes has been shown to be cured by hematopoietic stem cell transplant and may benefit from conditioning in accordance with the compositions and methods described herein. Additional disorders that can be treated using the compositions and methods described herein include, without limitation, sickle cell anemia, thalassemias, Fanconi anemia, aplastic anemia, Wiskott-Aldrich syndrome, ADA SCID, HIV/AIDS, metachromatic leukodystrophy, Diamond-Blackfan anemia, and Schwachman-Diamond syndrome. Additional diseases that may be treated using the patient conditioning and/or hematopoietic stem cell transplant methods described herein include inherited blood disorders (e.g., sickle cell anemia) and autoimmune disorders, such as scleroderma, multiple sclerosis, ulcerative colitis, and Crohn's disease. Additional diseases that may be treated using the conditioning and/or transplantation methods described herein include a malignancy, such as a neuroblastoma or a hematologic cancer, such as leukemia, lymphoma, and myeloma. For instance, the cancer may be acute myeloid leukemia, acute lymphoid leukemia, chronic myeloid leukemia, chronic lymphoid leukemia, multiple myeloma, diffuse large B-cell lymphoma, or non-Hodgkin's lymphoma. Additional diseases treatable using the conditioning and/or transplantation methods described herein include myelodysplastic syndrome. In some embodiments, the subject has or is otherwise affected by a metabolic storage disorder. For example, the subject may suffer or otherwise be affected by a metabolic disorder selected from the group consisting of glycogen storage diseases, mucopolysaccharidoses, Gaucher's Disease, Hurlers Disease, sphingolipidoses, metachromatic leukodystrophy, or any other diseases or disorders which may benefit from the treatments and therapies disclosed herein and including, without limitation, severe combined immunodeficiency, Wiscott-Aldrich syndrome, hyper immunoglobulin M (IgM) syndrome, Chediak-Higashi disease, hereditary lymphohistiocytosis, osteopetrosis, osteogenesis imperfecta, storage diseases, thalassemia major, sickle cell disease, systemic sclerosis, systemic lupus erythematosus, multiple sclerosis, juvenile rheumatoid arthritis and those diseases, or disorders described in "Bone Marrow Transplantation for Non-Malignant Disease," ASH Education Book, 1:319-338 (2000), the disclosure of which is incorporated herein by reference in its entirety as it pertains to pathologies that may be treated by administration of hematopoietic stem cell transplant therapy.

As used herein, the term "transfection" refers to any of a wide variety of techniques commonly used for the introduction of exogenous DNA into a prokaryotic or eukaryotic host cell, such as electroporation, lipofection, calcium-phosphate precipitation, DEAE-dextran transfection and the like.

As used herein, the terms "treat" or "treatment" refers to reducing the severity and/or frequency of disease symptoms, eliminating disease symptoms and/or the underlying cause of said symptoms, reducing the frequency or likelihood of disease symptoms and/or their underlying cause, and improving or remediating damage caused, directly or indirectly, by disease. Beneficial or desired clinical results include, but are not limited to, promoting the engraftment of exogenous hematopoietic cells in a patient following antibody conditioning therapy as described herein and subsequent hematopoietic stem cell transplant therapy. Additional beneficial results include an increase in the cell count or relative concentration of hematopoietic stem cells in a patient in need of a hematopoietic stem cell transplant following conditioning therapy and subsequent administration of an exogenous hematopoietic stem cell graft to the patient. Beneficial results of therapy described herein may also include an increase in the cell count or relative concentration of one or more cells of hematopoietic lineage, such as a megakaryocyte, thrombocyte, platelet, erythrocyte, mast cell, myeloblast, basophil, neutrophil, eosinophil, microglial cell, granulocyte, monocyte, osteoclast, antigen-presenting cell, macrophage, dendritic cell, natural killer cell, T-lymphocyte, or B-lymphocyte, following conditioning therapy and subsequent hematopoietic stem cell transplant therapy. Additional beneficial results may include the reduction in quantity of a disease-causing cell population, such as a population of cancer cells (e.g., CD117+ leukemic cells) or autoimmune cells (e.g., CD117+ autoimmune lymphocytes, such as a CD117+ T-cell that expresses a T-cell receptor that cross-reacts with a self-antigen). Insofar as the methods of the present invention are directed to preventing disorders, it is understood that the term "prevent" does not require that the disease state be completely thwarted. Rather, as used herein, the term preventing refers to the ability of the skilled artisan to identify a population that is susceptible to disorders, such that administration of the compounds of the present invention may occur prior to onset of a disease. The term does not imply that the disease state is completely avoided.

As used herein, the terms "variant" and "derivative" are used interchangeably and refer to naturally-occurring, synthetic, and semi-synthetic analogues of a compound, peptide, protein, or other substance described herein. A variant or derivative of a compound, peptide, protein, or other substance described herein may retain or improve upon the biological activity of the original material.

As used herein; the term "vector" includes a nucleic acid vector, such as a plasmid, a DNA vector, a plasmid, a RNA vector, virus, or other suitable replicon. Expression vectors described herein may contain a polynucleotide sequence as well as, for example, additional sequence elements used for the expression of proteins and/or the integration of these polynucleotide sequences into the genome of a mammalian cell. Certain vectors that can be used for the expression of antibodies and antibody fragments of the invention include plasmids that contain regulatory sequences, such as promoter and enhancer regions, which direct gene transcription. Other useful vectors for expression of antibodies and antibody fragments contain polynucleotide sequences that enhance the rate of translation of these genes or improve the stability or nuclear export of the mRNA that results from gene transcription. These sequence elements may include, for example, 5' and 3' untranslated regions and a polyadenylation signal site in order to direct efficient transcription of the gene carried on the expression vector. The expression vectors described herein may also contain a polynucleotide encoding a marker for selection of cells that contain such a vector. Examples of a suitable marker include genes that encode resistance to antibiotics, such as ampicillin, chloramphenicol, kanamycin, and nourseothricin.

The term "acyl" as used herein refers to —C(=O)R, wherein R is hydrogen ("aldehyde"), alkyl, alkenyl, alkynyl, carbocyclyl, aryl, heteroaryl, or heterocyclyl, as defined herein. Non-limiting examples include formyl, acetyl, propanoyl, benzoyl, and acryloyl.

As used herein, the term "alkyl" refers to a straight- or branched-chain alkyl group having, for example, from 1 to 20 carbon atoms in the chain. Examples of alkyl groups include methyl, ethyl, n-propyl, isopropyl, butyl, isobutyl, sec-butyl, tert-butyl, pentyl, isopentyl, tert-pentyl, hexyl, isohexyl, and the like.

As used herein, the term "alkylene" refers to a straight- or branched-chain divalent alkyl group. The divalent positions may be on the same or different atoms within the alkyl chain. Examples of alkylene include methylene, ethylene, propylene, isopropylene, and the like.

As used herein, the term "heteroalkyl" refers to a straight or branched-chain alkyl group having, for example, from 1 to 20 carbon atoms in the chain, and further containing one or more heteroatoms (e.g., oxygen, nitrogen, or sulfur, among others) in the chain.

As used herein, the term "heteroalkylene" refers to a straight- or branched-chain divalent heteroalkyl group. The divalent positions may be on the same or different atoms within the heteroalkyl chain. The divalent positions may be one or more heteroatoms.

As used herein, the term "alkenyl" refers to a straight- or branched-chain alkenyl group having, for example, from 2 to 20 carbon atoms in the chain. Examples of alkenyl groups include vinyl, propenyl, isopropenyl, butenyl, tert-butylenyl, hexenyl, and the like.

As used herein, the term "alkenylene" refers to a straight- or branched-chain divalent alkenyl group. The divalent positions may be on the same or different atoms within the alkenyl chain. Examples of alkenylene include ethenylene, propenylene, isopropenylene, butenylene, and the like.

As used herein, the term "heteroalkenyl" refers to a straight- or branched-chain alkenyl group having, for example, from 2 to 20 carbon atoms in the chain, and further containing one or more heteroatoms (e.g., oxygen, nitrogen, or sulfur, among others) in the chain.

As used herein, the term "heteroalkenylene" refers to a straight- or branched-chain divalent heteroalkenyl group. The divalent positions may be on the same or different atoms within the heteroalkenyl chain. The divalent positions may be one or more heteroatoms.

As used herein, the term "alkynyl" refers to a straight- or branched-chain alkynyl group having, for example, from 2 to 20 carbon atoms in the chain. Examples of alkynyl groups include propargyl, butynyl, pentynyl, hexynyl, and the like.

As used herein, the term "alkynylene" refers to a straight- or branched-chain divalent alkynyl group. The divalent positions may be on the same or different atoms within the alkynyl chain.

As used herein, the term "heteroalkynyl" refers to a straight- or branched-chain alkynyl group having, for example, from 2 to 20 carbon atoms in the chain, and further containing one or more heteroatoms (e.g., oxygen, nitrogen, or sulfur, among others) in the chain.

As used herein, the term "heteroalkynylene" refers to a straight- or branched-chain divalent heteroalkynyl group. The divalent positions may be on the same or different atoms within the heteroalkynyl chain. The divalent positions may be one or more heteroatoms.

As used herein, the term "cycloalkyl" refers to a monocyclic, or fused, bridged, or spiro polycyclic ring structure that is saturated and has, for example, from 3 to 12 carbon ring atoms. Examples of cycloalkyl groups include cyclopropyl, cyclobutyl, cyclopentyl, cyclohexyl, cycloheptyl, cyclooctyl, bicyclo[3.1.0]hexane, and the like.

As used herein, the term "cycloalkylene" refers to a divalent cycloalkyl group. The divalent positions may be on the same or different atoms within the ring structure. Examples of cycloalkylene include cyclopropylene, cyclobutylene, cyclopentylene, cyclohexylene, and the like.

As used herein, the term "heterocyloalkyl" refers to a monocyclic, or fused, bridged, or spiro polycyclic ring structure that is saturated and has, for example, from 3 to 12 ring atoms per ring structure selected from carbon atoms and heteroatoms selected from, e.g., nitrogen, oxygen, and sulfur, among others. The ring structure may contain, for example, one or more oxo groups on carbon, nitrogen, or sulfur ring members. Examples of heterocycloalkyls include by way of example and not limitation dihydroypyridyl, tetrahydropyridyl (piperidyl), tetrahydrothiophenyl, piperidinyl, 4-piperidonyl, pyrrolidinyl, 2-pyrrolidonyl, tetrahydrofuranyl, tetrahydropyranyl, bis-tetrahydropyranyl, tetrahydroquinolinyl, tetrahydroisoquinolinyl, decahydroquinolinyl, octahydroisoquinolinyl, piperazinyl, quinuclidinyl, and morpholinyl.

As used herein, the term "heterocycloalkylene" refers to a divalent heterocyclolalkyl group. The divalent positions may be on the same or different atoms within the ring structure.

As used herein, the term "aryl" refers to a monocyclic or multicyclic aromatic ring system containing, for example, from 6 to 19 carbon atoms. Aryl groups include, but are not limited to, phenyl, fluorenyl, naphthyl, and the like. The divalent positions may be one or more heteroatoms.

As used herein, the term "arylene" refers to a divalent aryl group. The divalent positions may be on the same or different atoms.

As used herein, the term "heteroaryl" refers to a monocyclic heteroaromatic, or a bicyclic or a tricyclic fused-ring heteroaromatic group in which one or more ring atoms is a heteroatom, e.g. nitrogen, oxygen, or sulfur. Heteroaryl groups include pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl, benzoquinolyl, and the like.

As used herein, the term "heteroarylene" refers to a divalent heteroaryl group. The divalent positions may be on the same or different atoms. The divalent positions may be one or more heteroatoms.

Unless otherwise constrained by the definition of the individual substituent, the foregoing chemical moieties, such as "alkyl", "alkylene", "heteroalkyl", "heteroalkylene", "alkenyl", "alkenylene", "heteroalkenyl", "heteroalkenylene", "alkynyl", "alkynylene", "heteroalkynyl", "heteroalkynylene", "cycloalkyl", "cycloalkylene", "heterocyclolalkyl", "heterocycloalkylene", "aryl," "arylene", "heteroaryl", and "heteroarylene" groups can optionally be substituted with, for example, from 1 to 5 substituents selected from the group consisting of alkyl, alkenyl, alkynyl, cycloalkyl, heterocycloalkyl, alkyl aryl, alkyl heteroaryl, alkyl cycloalkyl, alkyl heterocycloalkyl, amino, ammonium, acyl, acyloxy, acylamino, aminocarbonyl, alkoxycarbonyl, ureido, carbamate, aryl, heteroaryl, sulfinyl, sulfonyl, alkoxy, sulfanyl, halogen, carboxy, trihalomethyl, cyano, hydroxy, mercapto, nitro, and the like. Typical substituents include, but are not limited to, —X, —R, —OH, —OR, —SH, —SR, NH$_2$, —NHR, —N(R)$_2$, —N$^+$(R)$_3$, —CX$_3$, —CN, —OCN, —SCN, —NCO, —NCS, —NO, —NO$_2$, —N$_3$, —NC(=O)H, —NC(=O)R, —C(=O)H, —C(=O)R, —C(=O)NH$_2$, —C(=O)N(R)$_2$, —SO$_3$—, —SO$_3$H, —S(=O)$_2$R, —OS(=O)$_2$OR, —S(=O)$_2$NH$_2$, —S(=O)$_2$N(R)$_2$, —S(=O)R, —OP(=O)(OH)$_2$, —OP(=O)(OR)$_2$, —P(=O)(OR)$_2$, —PO$_3$, —PO$_3$H$_2$, —C(=O)X, —C(=S)R, —CO$_2$H, —CO$_2$R, —CO$_2$—, —C(=S)OR, —C(=O)SR, —C(=S)SR, —C(=O)NH$_2$, —C(=O)N(R)$_2$, —C(=S)NH$_2$, —C(=S)N(R)$_2$, —C(=NH)NH$_2$, and —C(=NR)N(R)$_2$; wherein each X is independently selected for each occasion from F, Cl, Br, and I; and each R is independently selected for each occasion from alkyl, aryl, heterocycloalkyl or heteroaryl, protecting group and prodrug moiety. Wherever a group is described as "optionally substituted," that group can be substituted with one or more of the above substituents, independently for each occasion.

Wherever a group is described as "optionally substituted," that group can be substituted with one or more of the above substituents, independently for each occasion. The substitution may include situations in which neighboring substituents have undergone ring closure, such as ring closure of vicinal functional substituents, to form, for instance, lactams, lactones, cyclic anhydrides, acetals, hemiacetals, thioacetals, aminals, and hemiaminals, formed by ring closure, for example, to furnish a protecting group.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH$_2$—, —CH$_2$CH$_2$—, —CH$_2$CH(CH$_3$)CH$_2$—, and the like. Other radical naming conventions clearly indicate that the radical is a di-radical such as "alkylene," "alkenylene," "arylene," "heterocycloalkylene," and the like.

Wherever a substituent is depicted as a di-radical (i.e., has two points of attachment to the rest of the molecule), it is to be understood that the substituent can be attached in any directional configuration unless otherwise indicated Anti-CD117 Antibodies The present invention is based in part on the discovery that antibodies, or antigen-binding fragments thereof, capable of binding CD117, such as GNNK+ CD117, can be used as therapeutic agents alone or as conjugates (ADCs) to, for example, (i) treat cancers and autoimmune diseases characterized by CD117+ cells and (ii) promote the engraftment of transplanted hematopoietic stem cells in a patient in need of transplant therapy. These therapeutic activities can be caused, for instance, by the binding of isolated anti-CD117 antibodies, antigen-binding fragments thereof, that bind to CD117 (e.g., GNNK+ CD117) expressed on the surface of a cell, such as a cancer cell, autoimmune cell, or hematopoietic stem cell and subsequently inducing cell death. The depletion of endogenous hematopoietic stem cells can provide a niche toward which transplanted hematopoietic stem cells can home, and subsequently establish productive hematopoiesis. In this way, transplanted hematopoietic stem cells may successfully engraft in a patient, such as human patient suffering from a stem cell disorder described herein.

Antibodies and antigen-binding fragments capable of binding human CD117 (also referred to as c-Kit, mRNA NCBI Reference Sequence: NM_000222.2, Protein NCBI Reference Sequence: NP_000213.1), including those capable of binding GNNK+ CD117, can be used in conjunction with the compositions and methods described herein in order to condition a patient for hematopoietic stem cell transplant therapy. Polymorphisms affecting the coding region or extracellular domain of CD117 in a significant percentage of the population are not currently well-known in non-oncology indications. There are at least four isoforms of CD117 that have been identified, with the potential of additional isoforms expressed in tumor cells. Two of the CD117 isoforms are located on the intracellular domain of the protein, and two are present in the external juxtamembrane region. The two extracellular isoforms, GNNK+ and GNNK−, differ in the presence (GNNK+) or absence (GNNK−) of a 4 amino acid sequence. These isoforms are reported to have the same affinity for the ligand (SCF), but ligand binding to the GNNK− isoform was reported to increase internalization and degradation. The GNNK+ isoform can be used as an immunogen in order to generate antibodies capable of binding CD117, as antibodies generated against this isoform will be inclusive of the GNNK+ and GNNK-proteins. The amino acid sequences of human CD117 isoforms 1 and 2 are described in SEQ ID Nos: 145 and 146, respectively. In certain embodiments, anti-human CD117 (hCD117) antibodies disclosed herein are able to bind to both isoform 1 and isoform 2 of human CD117.

As described below, a yeast library screen of human antibodies was performed to identify novel anti-CD117 antibodies, and fragments thereof, having diagnostic and therapeutic use. Antibody 54 (Ab54), Antibody 55 (Ab55), Antibody 56 (Ab56), Antibody 57 (Ab57), Antibody 58 (Ab58), Antibody 61 (Ab61), Antibody 66 (Ab66), Antibody 67 (Ab67), Antibody 68 (Ab68), and Antibody 69 (Ab69) were human antibodies that were identified in this screen. These antibodies cross react with human CD117 and rhesus CD117. Further, these antibodies disclosed herein are able to bind to both isoforms of human CD117, i.e., isoform 1 (SEQ ID NO: 145) and isoform 2 (SEQ ID NO: 146).

The amino acid sequences for the various binding regions of anti-CD117 antibodies Ab54, Ab55, Ab56, Ab57, Ab58, Ab61, Ab66, Ab67, Ab68, and Ab69 are described in Table 10. Included in the invention are human anti-CD117 antibodies comprising the CDRs as set forth in Table 10, as well as human anti-CD117 antibodies comprising the variable regions set forth in Table 10.

In one embodiment, the invention provides an anti-CD117 antibody, or antigen-binding fragment thereof, comprising binding regions, e.g., CDRs, variable regions, corresponding to those of Antibody 55. The heavy chain variable region (VH) amino acid sequence of Antibody 55 (i.e., Ab55) is set forth in SEQ ID NO: 19 (see Table 10). The VH CDR domain amino acid sequences of Antibody 55 are set forth in SEQ ID NO: 21 (VH CDR1); SEQ ID NO: 22 (VH CDR2), and SEQ ID NO: 23 (VH CDR3). The light chain variable region (VL) amino acid sequence of Antibody 55 is described in SEQ ID NO: 20 (see Table 10). The VL CDR domain amino acid sequences of Antibody 55 are set forth in SEQ ID NO: 24 (VL CDR1); SEQ ID NO: 25 (VL CDR2), and SEQ ID NO: 26 (VL CDR3). The heavy chain constant region of Antibody 55 is set forth in SEQ ID NO: 122. The light chain constant region of Antibody 55 is set forth in SEQ ID NO: 121. Thus, in certain embodiments, an anti-CD117 antibody, or antigen-binding portion thereof, comprises a variable heavy chain CDR set (CDR1, CDR2, and CDR3) as set forth in SEQ ID Nos: 21, 22, and 23, and a light chain variable region CDR set as set forth in SEQ ID Nos: 24, 25, and 26. In other embodiments, an anti-CD117 antibody, or antigen-binding portion thereof, comprises a variable light chain comprising the amino acid residues set forth in SEQ ID NO: 20, and a heavy chain variable region as set forth in SEQ ID NO: 19.

In one embodiment, the invention provides an anti-CD117 antibody, or antigen-binding fragment thereof, comprising binding regions, e.g., CDRs, variable regions, corresponding to those of Antibody 54. The heavy chain variable region (VH) amino acid sequence of Antibody 54 (i.e., Ab54) is set forth in SEQ ID NO: 29 (see Table 10). The VH CDR domain amino acid sequences of Antibody 54 are set forth in SEQ ID NO: 31 (VH CDR1); SEQ ID NO: 32 (VH CDR2), and SEQ ID NO: 33 (VH CDR3). The light chain variable region (VL) amino acid sequence of Antibody 54 is described in SEQ ID NO: 30 (see Table 10). The VL CDR domain amino acid sequences of Antibody 54 are set forth in SEQ ID NO: 34 (VL CDR1); SEQ ID NO: 35 (VL CDR2), and SEQ ID NO: 36 (VL CDR3). The heavy chain constant region of Antibody 54 is set forth in SEQ ID NO: 122. The light chain constant region of Antibody 54 is set forth in SEQ ID NO: 121. Thus, in certain embodiments, an anti-CD117 antibody, or antigen-binding portion thereof, comprises a variable heavy chain CDR set (CDR1, CDR2, and CDR3) as set forth in SEQ ID Nos: 31, 32, and 33, and a light chain variable region CDR set as set forth in SEQ ID Nos: 34, 35, and 36. In other embodiments, an anti-CD117 antibody, or antigen-binding portion thereof, comprises a variable light chain comprising the amino acid residues set forth in SEQ ID NO: 30, and a heavy chain variable region as set forth in SEQ ID NO: 29.

In one embodiment, the invention provides an anti-CD117 antibody, or antigen-binding fragment thereof, comprising binding regions, e.g., CDRs, variable regions, corresponding to those of Antibody 56. The heavy chain variable region (VH) amino acid sequence of Antibody 56 (i.e., Ab56) is set forth in SEQ ID NO: 39 (see Table 10). The VH CDR domain amino acid sequences of Antibody 56 are set forth in SEQ ID NO: 41 (VH CDR1); SEQ ID NO: 42 (VH CDR2), and SEQ ID NO: 43 (VH CDR3). The light chain variable region (VL) amino acid sequence of Antibody 56 is described in SEQ ID NO: 40 (see Table 10). The VL CDR domain amino acid sequences of Antibody 56 are set forth in SEQ ID NO: 44 (VL CDR1); SEQ ID NO: 45 (VL CDR2), and SEQ ID NO: 46 (VL CDR3). The heavy chain constant region of Antibody 56 is set forth in SEQ ID NO: 122. The light chain constant region of Antibody 56 is set forth in SEQ ID NO: 121. Thus, in certain embodiments, an anti-CD117 antibody, or antigen-binding portion thereof, comprises a variable heavy chain CDR set (CDR1, CDR2, and CDR3) as set forth in SEQ ID Nos: 41, 42, and 43, and a light chain variable region CDR set as set forth in SEQ ID Nos: 44, 45, and 46. In other embodiments, an anti-CD117 antibody, or antigen-binding portion thereof, comprises a variable light chain comprising the amino acid residues set forth in SEQ ID NO: 40, and a heavy chain variable region as set forth in SEQ ID NO: 39.

In one embodiment, the invention provides an anti-CD117 antibody, or antigen-binding fragment thereof, comprising binding regions, e.g., CDRs, variable regions, corresponding to those of Antibody 57. The heavy chain variable region (VH) amino acid sequence of Antibody 57 (i.e., Ab57) is set forth in SEQ ID NO: 49 (see Table 10). The VH CDR domain amino acid sequences of Antibody 57 are set forth in SEQ ID NO: 51 (VH CDR1); SEQ ID NO: 52 (VH CDR2), and SEQ ID NO: 53 (VH CDR3). The light chain variable region (VL) amino acid sequence of Antibody 57 is described in SEQ ID NO: 50 (see Table 10). The VL CDR domain amino acid sequences of Antibody 57 are set forth in SEQ ID NO: 54 (VL CDR1); SEQ ID NO: 55 (VL CDR2), and SEQ ID NO: 56 (VL CDR3). The heavy chain constant region of Antibody 57 is set forth in SEQ ID NO: 122. The light chain constant region of Antibody 57 is set forth in SEQ ID NO: 121. Thus, in certain embodiments, an anti-CD117 antibody, or antigen-binding portion thereof, comprises a variable heavy chain CDR set (CDR1, CDR2, and CDR3) as set forth in SEQ ID Nos: 51, 52, and 53, and a light chain variable region CDR set as set forth in SEQ ID Nos: 54, 55, and 56. In other embodiments, an anti-CD117 antibody, or antigen-binding portion thereof, comprises a variable light chain comprising the amino acid residues set forth in SEQ ID NO: 50, and a heavy chain variable region as set forth in SEQ ID NO: 49.

In one embodiment, the invention provides an anti-CD117 antibody, or antigen-binding fragment thereof, comprising binding regions, e.g., CDRs, variable regions, corresponding to those of Antibody 58. The heavy chain variable region (VH) amino acid sequence of Antibody 58 (i.e., Ab58) is set forth in SEQ ID NO: 59 (see Table 10). The VH CDR domain amino acid sequences of Antibody 58 are set forth in SEQ ID NO: 61 (VH CDR1); SEQ ID NO: 62 (VH CDR2), and SEQ ID NO: 63 (VH CDR3). The light chain variable region (VL) amino acid sequence of Antibody 58 is described in SEQ ID NO: 60 (see Table 10). The VL CDR domain amino acid sequences of Antibody 58 are set forth in SEQ ID NO: 64 (VL CDR1); SEQ ID NO: 65 (VL CDR2), and SEQ ID NO: 66 (VL CDR3). The heavy chain constant region of Antibody 58 is set forth in SEQ ID NO: 122. The light chain constant region of Antibody 58 is set forth in SEQ ID NO: 121. Thus, in certain embodiments, an anti-CD117 antibody, or antigen-binding portion thereof, comprises a variable heavy chain CDR set (CDR1, CDR2, and CDR3) as set forth in SEQ ID Nos: 61, 62, and 63, and a light chain variable region CDR set as set forth in SEQ ID Nos: 64, 65, and 66. In other embodiments, an anti-CD117 antibody, or antigen-binding portion thereof, comprises a variable light chain comprising the amino acid residues set forth in SEQ ID NO: 60, and a heavy chain variable region as set forth in SEQ ID NO: 59.

In one embodiment, the invention provides an anti-CD117 antibody, or antigen-binding fragment thereof, comprising binding regions, e.g., CDRs, variable regions, corresponding to those of Antibody 61. The heavy chain variable region (VH) amino acid sequence of Antibody 61 (i.e., Ab61) is set forth in SEQ ID NO: 69 (see Table 10). The VH CDR domain amino acid sequences of Antibody 61 are set forth in SEQ ID NO: 71 (VH CDR1); SEQ ID NO: 72 (VH CDR2), and SEQ ID NO: 73 (VH CDR3). The light chain variable region (VL) amino acid sequence of Antibody 61 is described in SEQ ID NO: 70 (see Table 10). The VL CDR domain amino acid sequences of Antibody 61 are set forth in SEQ ID NO: 74 (VL CDR1); SEQ ID NO: 75 (VL CDR2), and SEQ ID NO: 76 (VL CDR3). The heavy chain constant region of Antibody 61 is set forth in SEQ ID NO: 122. The light chain constant region of Antibody 61 is set forth in SEQ ID NO: 121. Thus, in certain embodiments, an anti-CD117 antibody, or antigen-binding portion thereof, comprises a variable heavy chain CDR set (CDR1, CDR2, and CDR3) as set forth in SEQ ID Nos: 71, 72, and 73, and a light chain variable region CDR set as set forth in SEQ ID Nos: 74, 75, and 76. In other embodiments, an anti-CD117 antibody, or antigen-binding portion thereof, comprises a variable light chain comprising the amino acid residues set forth in SEQ ID NO: 70, and a heavy chain variable region as set forth in SEQ ID NO: 69.

In one embodiment, the invention provides an anti-CD117 antibody, or antigen-binding fragment thereof, comprising binding regions, e.g., CDRs, variable regions, corresponding to those of Antibody 66. The heavy chain variable region (VH) amino acid sequence of Antibody 66 (i.e., Ab66) is set forth in SEQ ID NO: 79 (see Table 10). The VH CDR domain amino acid sequences of Antibody 66 are set forth in SEQ ID NO: 81 (VH CDR1); SEQ ID NO: 82 (VH CDR2), and SEQ ID NO: 83 (VH CDR3). The light chain variable region (VL) amino acid sequence of Antibody 66 is described in SEQ ID NO: 80 (see Table 10). The VL CDR domain amino acid sequences of Antibody 66 are set forth in SEQ ID NO: 84 (VL CDR1); SEQ ID NO: 85 (VL CDR2), and SEQ ID NO: 86 (VL CDR3). The heavy chain constant region of Antibody 66 is set forth in SEQ ID NO: 122. The light chain constant region of Antibody 66 is set forth in SEQ ID NO: 121. Thus, in certain embodiments, an anti-CD117 antibody, or antigen-binding portion thereof, comprises a variable heavy chain CDR set (CDR1, CDR2, and CDR3) as set forth in SEQ ID Nos: 81, 82, and 83, and a light chain variable region CDR set as set forth in SEQ ID Nos: 84, 85, and 86. In other embodiments, an anti-CD117 antibody, or antigen-binding portion thereof, comprises a variable light chain comprising the amino acid residues set forth in SEQ ID NO: 80, and a heavy chain variable region as set forth in SEQ ID NO: 79.

In one embodiment, the invention provides an anti-CD117 antibody, or antigen-binding fragment thereof, comprising binding regions, e.g., CDRs, variable regions, corresponding to those of Antibody 67. The heavy chain variable region (VH) amino acid sequence of Antibody 67 is set forth in SEQ ID NO: 9 (see Table 2). The VH CDR domain amino acid sequences of Antibody 67 are set forth in SEQ ID NO 11 (VH CDR1); SEQ ID NO: 12 (VH CDR2), and SEQ ID NO: 13 (VH CDR3). The light chain variable region (VL) amino acid sequence of Antibody 67 is described in SEQ ID NO: 10 (see Table 2). The VL CDR domain amino acid sequences of Antibody 67 are set forth in SEQ ID NO 14 (VL CDR1); SEQ ID NO: 15 (VL CDR2), and SEQ ID NO: 16 (VL CDR3). The full length heavy chain (HC) of Antibody 67 is set forth in SEQ ID NO: 110, and the full length heavy chain constant region of Antibody 67 is set forth in SEQ ID NO: 122. The light chain (LC) of Antibody 67 is set forth in SEQ ID NO: 109. The light chain constant region of Antibody 67 is set forth in SEQ ID NO: 121. Thus, in certain embodiments, an anti-CD117 antibody, or antigen-binding portion thereof, comprises a variable heavy chain CDR set (CDR1, CDR2, and CDR3) as set forth in SEQ ID Nos: 11, 12, and 13, and a light chain variable region CDR set as set forth in SEQ ID Nos: 14, 15, and 16. In other embodiments, an anti-CD117 antibody, or antigen-binding portion thereof, comprises a variable heavy chain comprising the amino acid residues set forth in SEQ ID NO: 9, and a heavy chain variable region as set forth in SEQ ID NO: 10. In further embodiments, an anti-CD117 antibody comprises a heavy chain comprising SEQ ID NO: 110 and a light chain comprising SEQ ID NO: 109.

In one embodiment, the invention provides an anti-CD117 antibody, or antigen-binding fragment thereof, comprising binding regions, e.g., CDRs, variable regions, corresponding to those of Antibody 68. The heavy chain variable region (VH) amino acid sequence of Antibody 68 (i.e., Ab68) is set forth in SEQ ID NO: 89 (see Table 10). The VH CDR domain amino acid sequences of Antibody 68 are set forth in SEQ ID NO: 91 (VH CDR1); SEQ ID NO: 92 (VH CDR2), and SEQ ID NO: 93 (VH CDR3). The light chain variable region (VL) amino acid sequence of Antibody 68 is described in SEQ ID NO: 90 (see Table 10). The VL CDR domain amino acid sequences of Antibody 68 are set forth in SEQ ID NO: 94 (VL CDR1); SEQ ID NO: 95 (VL CDR2), and SEQ ID NO: 96 (VL CDR3). The heavy chain constant region of Antibody 68 is set forth in SEQ ID NO: 122. The light chain constant region of Antibody 68 is set forth in SEQ ID NO: 121. Thus, in certain embodiments, an anti-CD117 antibody, or antigen-binding portion thereof, comprises a variable heavy chain CDR set (CDR1, CDR2, and CDR3) as set forth in SEQ ID Nos: 91, 92, and 93, and a light chain variable region CDR set as set forth in SEQ ID Nos: 94, 95, and 96. In other embodiments, an anti-CD117 antibody, or antigen-binding portion thereof, comprises a variable light chain comprising the amino acid residues set forth in SEQ ID NO: 90, and a heavy chain variable region as set forth in SEQ ID NO: 89.

In one embodiment, the invention provides an anti-CD117 antibody, or antigen-binding fragment thereof, comprising binding regions, e.g., CDRs, variable regions, corresponding to those of Antibody 69. The heavy chain variable region (VH) amino acid sequence of Antibody 69 (i.e., Ab69) is set forth in SEQ ID NO: 99 (see Table 10). The VH CDR domain amino acid sequences of Antibody 69 are set forth in SEQ ID NO: 101 (VH CDR1); SEQ ID NO: 102 (VH CDR2), and SEQ ID NO: 103 (VH CDR3). The light chain variable region (VL) amino acid sequence of Antibody 69 is described in SEQ ID NO: 100 (see Table 10). The VL CDR domain amino acid sequences of Antibody 69 are set forth in SEQ ID NO: 104 (VL CDR1); SEQ ID NO: 105 (VL CDR2), and SEQ ID NO: 106 (VL CDR3). The heavy chain constant region of Antibody 69 is set forth in SEQ ID NO: 122. The light chain constant region of Antibody 69 is set forth in SEQ ID NO: 121. Thus, in certain embodiments, an anti-CD117 antibody, or antigen-binding portion thereof, comprises a variable heavy chain CDR set (CDR1, CDR2, and CDR3) as set forth in SEQ ID Nos: 101, 102, and 103, and a light chain variable region CDR set as set forth in SEQ ID Nos: 104, 105, and 106. In other embodiments, an anti-CD117 antibody, or antigen-binding portion thereof, comprises a variable light chain comprising the amino acid residues set forth in SEQ ID NO: 100, and a heavy chain variable region as set forth in SEQ ID NO: 99.

Certain of the anti-CD117 antibodies described herein are neutral antibodies, in that the antibodies do not substantially inhibit CD117 activity on a CD117 expressing cell. Neutral antibodies can be identified using, for example, an in in vitro stem cell factor (SCF)-dependent cell proliferation assay (see, e.g., Example 11 described herein). In an SCF dependent cell proliferation assay, a neutral CD117 antibody will not kill CD34+ cells that are dependent on SCF to divide, as a neutral antibody will not block SCF from binding to CD117 such as to inhibit CD117 activity.

Neutral antibodies can be used for diagnostic purposes, given their ability to specifically bind to human CD117, but are also effective for killing CD117 expressing cells when conjugated to a cytotoxin, such as those described herein. Typically, antibodies used in conjugates have agonistic or antagonistic activity that is unique to the antibody. Described herein, however, is a unique approach to conjugates, especially in the context wherein the conjugate is being used as a conditioning agent prior to a stem cell transplantation. While antagonistic antibodies alone or in combination with a cytotoxin as a conjugate can be effective given the killing ability of the antibody alone in addition to the cytotoxin, conditioning with a conjugate comprising a neutral anti-CD117 antibody presents an alternative strategy where the activity of the antibody is secondary to the effect of the cytotoxin, but the internalizing and affinity characteristics, e.g., dissociation rate, of the antibody are important for effective delivery of the cytotoxin.

Examples of neutral anti-CD117 antibodies include Ab58, Ab61, Ab66, Ab67, Ab68, and Ab69. A comparison of the amino acid sequences of the CDRs of neutral, anti-CD117 antibody CDRs reveals consensus sequences among two groups of neutral antibodies identified. A comparison of the heavy and light chain variable regions of Ab58 and Ab61 is described in FIGS. 22a and 22b, respectively. Ab58 and Ab61 share the same light chain CDRs and HC CDR3, with slight variations in the HC CDR1 and HC CDR2. Consensus sequences for the HC CDR1 and CDR2 are described in SEQ ID Nos: 133 and 134. Ab66, Ab67, Ab68, and Ab69 are also neutral antibodies. The heavy and light chain variable regions of these antibodies are described in FIG. 23A and FIG. 23B, respectively. While Ab66, Ab67, Ab68, and Ab69 share the same light chain CDRs and the same HC CDR3, these antibodies have variability within their HC CDR1 and HC CDR2 regions. Consensus sequences for these antibodies in the HC CDR1 and HC CDR2 regions are provided in SEQ ID Nos: 139 and 140, respectively.

Antagonist antibodies are also provided herein, including Ab54, Ab55, Ab56, and Ab57. A comparison of the variable heavy and light chain amino acid sequences for these antibodies is provided in FIGS. 21A and 22B, respectively. While Ab54, Ab55, Ab56, and Ab57 share the same light chain CDRs and the same HC CDR3, these antibodies have variability within their HC CDR1 and HC CDR2 regions. Consensus sequences for these antibodies in the HC CDR1 and HC CDR2 regions are provided in SEQ ID Nos: 127 and 128, respectively.

The anti-CD117 antibodies described herein can be in the form of full-length antibodies, bispecific antibodies, dual variable domain antibodies, multiple chain or single chain antibodies, and/or binding fragments that specifically bind human CD117, including but not limited to Fab, Fab', (Fab')2, Fv), scFv (single chain Fv), surrobodies (including surrogate light chain construct), single domain antibodies, camelized antibodies and the like. They also can be of, or derived from, any isotype, including, for example, IgA (e.g., IgA1 or IgA2), IgD, IgE, IgG (e.g. IgG1, IgG2, IgG3 or IgG4), or IgM. In some embodiments, the anti-CD117 antibody is an IgG (e.g. IgG1, IgG2, IgG3 or IgG4).

Antibodies for use in conjunction with the methods described herein include variants of those antibodies described above, such as antibody fragments that contain or lack an Fc domain, as well as humanized variants of non-human antibodies described herein and antibody-like protein scaffolds (e.g., $^{10}$Fn3 domains) containing one or more, or all, of the CDRs or equivalent regions thereof of an antibody, or antibody fragment, described herein. Exemplary antigen-binding fragments of the foregoing antibodies include a dual-variable immunoglobulin domain, a single-chain Fv molecule (scFv), a diabody, a triabody, a nanobody, an antibody-like protein scaffold, a Fv fragment, a Fab fragment, a F(ab')$_2$ molecule, and a tandem di-scFv, among others.

In one embodiment, anti-CD117 antibodies comprising one or more radiolabeled amino acids are provided. A radiolabeled anti-CD117 antibody may be used for both diagnostic and therapeutic purposes (conjugation to radiolabeled molecules is another possible feature). Nonlimiting examples of labels for polypeptides include, but are not limited to 3H, 14C, 15N, 35S, 90Y, 99Tc, and 125I, 131I, and 186Re. Methods for preparing radiolabeled amino acids and related peptide derivatives are known in the art (see for instance Junghans et al., in Cancer Chemotherapy and Biotherapy 655-686 (2d edition, Chafner and Longo, eds., Lippincott Raven (1996)) and U.S. Pat. Nos. 4,681,581, 4,735,210, 5,101,827, 5,102,990 (U.S. RE35,500), U.S. Pat. Nos. 5,648,471 and 5,697,902. For example, a radioisotope may be conjugated by a chloramine T method.

The anti-CD117 antibodies or binding fragments described herein may also include modifications and/or mutations that alter the properties of the antibodies and/or fragments, such as those that increase half-life, increase or decrease ADCC, etc., as is known in the art.

In one embodiment, the anti-CD117 antibody, or binding fragment thereof, comprises a variant Fc region, wherein said variant Fc region comprises at least one amino acid modification relative to a wild-type Fc region, such that said molecule has an altered affinity for an FcgammaR. Certain amino acid positions within the Fc region are known through crystallography studies to make a direct contact with FcγR. Specifically amino acids 234-239 (hinge region), amino acids 265-269 (B/C loop), amino acids 297-299 (C'/E loop), and amino acids 327-332 (F/G) loop. (see Sondermann et al., 2000 Nature, 406: 267-273). Thus, the anti-CD117 antibodies described herein may comprise variant Fc regions comprising modification of at least one residue that makes a direct contact with an Fcγ R based on structural and crystallographic analysis. In one embodiment, the Fc region of the anti-CD117 antibody (or fragment thereof) comprises an amino acid substitution at amino acid 265 according to the EU index as in Kabat et al., Sequences of Proteins of Immunological Interest, 5th Ed. Public Health Service, NH1, MD (1991), expressly incorporated herein by references. The "EU index as in Kabat" refers to the numbering of the human IgG1 EU antibody. The EU index or EU index as in Kabat or EU numbering scheme refers to the numbering of the EU antibody (Edelman et al., 1969, Proc Natl Acad Sci USA 63:78-85, hereby entirely incorporated by reference.) In one embodiment, the Fc region comprises a D265A mutation. In one embodiment, the Fc region comprises a D265C mutation. In some embodiments, the Fc region of the anti-CD117 antibody (or fragment thereof) comprises an amino acid substitution at amino acid 234 according to the EU index as in Kabat. In one embodiment, the Fc region comprises a L234A mutation. In some embodiments, the Fc region of the anti-CD117 antibody (or fragment thereof) comprises an amino acid substitution at amino acid 235 according to the EU index as in Kabat. In one embodiment, the Fc region comprises a L235A mutation. In yet another embodiment, the Fc region comprises a L234A and L235A mutation. In a further embodiment, the Fc region comprises a D265C, L234A, and L235A mutation.

In certain aspects a variant IgG Fc domain comprises one or more amino acid substitutions resulting in decreased or ablated binding affinity for an Fc.gamma.R and/or C1q as compared to the wild type Fc domain not comprising the one or more amino acid substitutions. Fc binding interactions are essential for a variety of effector functions and downstream signaling events including, but not limited to, antibody dependent cell-mediated cytotoxicity (ADCC) and complement dependent cytotoxicity (CDC). Accordingly, in certain aspects, an antibody comprising a modified Fc region (e.g., comprising a L234A, L235A, and a D265C mutation) has substantially reduced or abolished effector functions.

Affinity to an Fc region can be determined using a variety of techniques known in the art, for example but not limited to, equilibrium methods (e.g., enzyme-linked immunoabsorbent assay (ELISA); KinExA, Rathanaswami et al. Analytical Biochemistry, Vol. 373:52-60, 2008; or radioimmunoassay (RIA)), or by a surface plasmon resonance assay or other mechanism of kinetics-based assay (e.g., BIACORE™. analysis or Octet™ analysis (forteBIO)), and other methods such as indirect binding assays, competitive binding assays fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions. One example of a competitive binding assay is a radioimmunoassay comprising the incubation of labeled antigen with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound in the presence of increasing amounts of an unlabeled second antibody.

The antibodies of the invention may be further engineered to further modulate antibody half-life by introducing additional Fc mutations, such as those described for example in (Dall'Acqua et al. (2006) J Biol Chem 281: 23514-24), (Zalevsky et al. (2010) Nat Biotechnol 28: 157-9), (Hinton et al. (2004) J Biol Chem 279: 6213-6), (Hinton et al. (2006) J Immunol 176: 346-56), (Shields et al. (2001) J Biol Chem 276: 6591-604), (Petkova et al. (2006) Int Immunol 18: 1759-69), (Datta-Mannan et al. (2007) Drug Metab Dispos 35: 86-94), (Vaccaro et al. (2005) Nat Biotechnol 23: 1283-8), (Yeung et al. (2010) Cancer Res 70: 3269-77) and (Kim et al. (1999) Eur J Immunol 29: 2819-25), and include positions 250, 252, 253, 254, 256, 257, 307, 376, 380, 428, 434 and 435. Exemplary mutations that may be made singularly or in combination are T250Q, M252Y, I253A, S254T, T256E, P257I, T307A, D376V, E380A, M428L, H433K, N434S, N434A, N434H, N434F, H435A and H435R mutations.

Thus, in one embodiment, the Fc region comprises a mutation resulting in a decrease in half life. An antibody having a short half life may be advantageous in certain instances where the antibody is expected to function as a short-lived therapeutic, e.g., the conditioning step described herein where the antibody is administered followed by HSCs. Ideally, the antibody would be substantially cleared prior to delivery of the HSCs, which also generally express CD117 but are not the target of the anti-CD117 antibody, unlike the endogenous stem cells. In one embodiment, the Fc regions comprise a mutation at position 435 (EU index according to Kabat). In one embodiment, the mutation is an H435A mutation.

In one embodiment, the anti-CD117 antibody described herein has a half life of equal to or less than 24 hours, a half life of equal to or less than 22 hours, a half life of equal to or less than 20 hours, a half life of equal to or less than 18 hours, a half life of equal to or less than 16 hours, a half life of equal to or less than 14 hours, equal to or less than 13 hours, equal to or less than 12 hours, or equal to or less than 11 hours. In one embodiment, the half life of the antibody is 11 hours to 24 hours; 12 hours to 22 hours; 10 hours to 20 hours; 8 hours to 18 hours; or 14 hours to 24 hours.

In some aspects, the Fc region comprises two or more mutations that confer reduced half-life and greatly diminish or completely abolish an effector function of the antibody. In some embodiments, the Fc region comprises a mutation resulting in a decrease in half-life and a mutation of at least one residue that can make direct contact with an FcγR (e.g., as based on structural and crystallographic analysis). In one embodiment, the Fc region comprises a H435A mutation, a L234A mutation, and a L235A mutation. In one embodiment, the Fc region comprises a H435A mutation and a D265C mutation. In one embodiment, the Fc region comprises a H435A mutation, a L234A mutation, a L235A mutation, and a D265C mutation.

In some embodiments, the antibody or antigen-binding fragment thereof is conjugated to a cytotoxin (e.g., amatoxin) by way of a cysteine residue in the Fc domain of the antibody or antigen-binding fragment thereof. In some embodiments, the cysteine residue is introduced by way of a mutation in the Fc domain of the antibody or antigen-binding fragment thereof. For instance, the cysteine residue may be selected from the group consisting of Cys118, Cys239, and Cys265. In one embodiment, the Fc region of the anti-CD117 antibody (or fragment thereof) comprises an amino acid substitution at amino acid 265 according to the EU index as in Kabat. In one embodiment, the Fc region comprises a D265C mutation. In one embodiment, the Fc region comprises a D265C and H435A mutation. In one embodiment, the Fc region comprises a D265C, a L234A, and a L235A mutation. In one embodiment, the Fc region comprises a D265C, a L234A, a L235A, and a H435A mutation.

In some embodiments of these aspects, the cysteine residue is naturally occurring in the Fc domain of the antibody or antigen-binding fragment thereof. For instance, the Fc domain may be an IgG Fc domain, such as a human IgG1 Fc domain, and the cysteine residue may be selected from the group consisting of Cys261, Cys321, Cys367, and Cys425.

For example, in one embodiment, the Fc region of Antibody 67 is modified to comprise a D265C mutation (e.g., SEQ ID NO: 111). In another embodiment, the Fc region of Antibody 67 is modified to comprise a D265C, L234A, and L235A mutation (e.g., SEQ ID NO: 112). In yet another embodiment, the Fc region of Antibody 67 is modified to comprise a D265C and H435A mutation (e.g., SEQ ID NO: 113). In a further embodiment, the Fc region of Antibody 67 is modified to comprise a D265C, L234A, L235A, and H435A mutation (e.g., SEQ ID NO: 114).

In regard to Antibody 55, in one embodiment, the Fc region of Antibody 55 is modified to comprise a D265C mutation (e.g., SEQ ID NO: 117). In another embodiment, the Fc region of Antibody 55 is modified to comprise a D265C, L234A, and L235A mutation (e.g., SEQ ID NO: 118). In yet another embodiment, the Fc region of Antibody 55 is modified to comprise a D265C and H435A mutation (e.g., SEQ ID NO: 119). In a further embodiment, the Fc region of Antibody 55 is modified to comprise a D265C, L234A, L235A, and H435A mutation (e.g., SEQ ID NO: 120).

The Fc regions of any one of Antibody 54, Antibody 55, Antibody 56, Antibody 57, Antibody 58, Antibody 61, Antibody 66, Antibody 67, Antibody 68, or Antibody 69 can be modified to comprise a D265C mutation (e.g., as in SEQ ID NO: 123); a D265C, L234A, and L235A mutation (e.g., as in SEQ ID NO: 124); a D265C and H435A mutation (e.g., as in SEQ ID NO: 125); or a D265C, L234A, L235A, and H435A mutation (e.g., as in SEQ ID NO: 126).

The variant Fc domains described herein are defined according to the amino acid modifications that compose them. For all amino acid substitutions discussed herein in regard to the Fc region, numbering is always according to the EU index. Thus, for example, D265C is an Fc variant with the aspartic acid (D) at EU position 265 substituted with cysteine (C) relative to the parent Fc domain. Likewise, e.g., D265C/L234A/L235A defines a variant Fc variant with substitutions at EU positions 265 (D to C), 234 (L to A), and 235 (L to A) relative to the parent Fc domain. A variant can also be designated according to its final amino acid composition in the mutated EU amino acid positions. For example, the L234A/L235A mutant can be referred to as LALA. It is noted that the order in which substitutions are provided is arbitrary.

In one embodiment, the anti-CD117 antibody, or antigen binding fragment thereof, comprises variable regions having an amino acid sequence that is at least 95%, 96%, 97% or 99% identical to the SEQ ID Nos disclosed herein. Alternatively, the anti-CD117 antibody, or antigen binding fragment thereof, comprises CDRs comprising the SEQ ID Nos disclosed herein with framework regions of the variable regions described herein having an amino acid sequence that is at least 95%, 96%, 97% or 99% identical to the SEQ ID Nos disclosed herein.

In certain embodiments, an anti-CD117 antibody, or antigen binding fragment thereof, has a certain dissociation rate which is particularly advantageous when used as a part of a conjugate. For example, an anti-CD117 antibody has, in certain embodiments, an off rate constant (Koff) for human CD117 and/or rhesus CD117 of $1\times10^{-2}$ to $1\times10^{-3}$, $1\times10^{-3}$ to $1\times10^{-4}$, $1\times10^{-5}$ to $1\times10^{-6}$, $1\times10^{-6}$ to $1\times10^{-7}$ or $1\times10^{-7}$ to $1\times10^{-8}$, as measured by bio-layer interferometry (BLI). In some embodiments, the antibody or antigen-binding fragment thereof binds CD117 (e.g., human CD117 and/or rhesus CD117) with a $K_D$ of about 100 nM or less, about 90 nM or less, about 80 nM or less, about 70 nM or less, about 60 nM or less, about 50 nM or less, about 40 nM or less, about 30 nM or less, about 20 nM or less, about 10 nM or less, about 8 nM or less, about 6 nM or less, about 4 nM or less, about 2 nM or less, about 1 nM or less as determined by a Bio-Layer Interferometry (BLI) assay.

The antibodies, and binding fragments thereof, disclosed herein can be used in conjugates, as described in more detail below.

Antibodies may be produced using recombinant methods and compositions, e.g., as described in U.S. Pat. No. 4,816,567. In one embodiment, isolated nucleic acid encoding an anti-CD117 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-CLL-1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-CD117 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR− CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

In one embodiment, the anti-CD117 antibody, or antigen binding fragment thereof, comprises variable regions having an amino acid sequence that is at least 95%, 96%, 97% or 99% identical to the SEQ ID Nos disclosed herein. Alternatively, the anti-CD117 antibody, or antigen binding fragment thereof, comprises CDRs comprising the SEQ ID Nos disclosed herein with framework regions of the variable regions described herein having an amino acid sequence that is at least 95%, 96%, 97% or 99% identical to the SEQ ID Nos disclosed herein.

In one embodiment, the anti-CD117 antibody, or antigen binding fragment thereof, comprises a heavy chain variable region and a heavy chain constant region having an amino acid sequence that is disclosed herein. In another embodiment, the anti-CD117 antibody, or antigen binding fragment thereof, comprises a light chain variable region and a light chain constant region having an amino acid sequence that is disclosed herein. In yet another embodiment, the anti-CD117 antibody, or antigen binding fragment thereof, comprises a heavy chain variable region, a light chain variable region, a heavy chain constant region and a light chain constant region having an amino acid sequence that is disclosed herein.

Methods of Identifying Anti-CD117 Antibodies

Provided herein are novel anti-CD117 antibodies that may be used, for example, in conditioning methods for stem cell transplantation. In view of the disclosure herein, other anti-CD117 antibodies, e.g., neutral antibodies, can be identified.

Methods for high throughput screening of antibody, or antibody fragment libraries for molecules capable of binding CD117 (e.g., GNNK+ CD117) can be used to identify and affinity mature antibodies useful for treating cancers, autoimmune diseases, and conditioning a patient (e.g., a human patient) in need of hematopoietic stem cell therapy as described herein. Such methods include in vitro display techniques known in the art, such as phage display, bacterial display, yeast display, mammalian cell display, ribosome display, mRNA display, and cDNA display, among others. The use of phage display to isolate ligands that bind biologically relevant molecules has been reviewed, for example, in Felici et al., Biotechnol. Annual Rev. 1:149-183, 1995; Katz, Annual Rev. Biophys. Biomol. Struct. 26:27-45, 1997; and Hoogenboom et al., Immunotechnology 4:1-20, 1998, the disclosures of each of which are incorporated herein by reference as they pertain to in vitro display techniques. Randomized combinatorial peptide libraries have been constructed to select for polypeptides that bind cell surface antigens as described in Kay, Perspect. Drug Discovery Des. 2:251-268, 1995 and Kay et al., Mol. Divers. 1:139-140, 1996, the disclosures of each of which are incorporated herein by reference as they pertain to the discovery of antigen-binding molecules. Proteins, such as multimeric proteins, have been successfully phage-displayed as functional molecules (see, for example, EP 0349578; EP 4527839; and EP 0589877, as well as Chiswell and McCafferty, Trends Biotechnol. 10:80-84 1992, the disclosures of each of which are incorporated herein by reference as they pertain to the use of in vitro display techniques for the discovery of antigen-binding molecules). In addition, functional antibody fragments, such as Fab and scFv fragments, have been expressed in in vitro display formats (see, for example, McCafferty et al., Nature 348: 552-554, 1990; Barbas et al., Proc. Natl. Acad. Sci. USA 88:7978-7982, 1991; and Clackson et al., Nature 352:624-628, 1991, the disclosures of each of which are incorporated herein by reference as they pertain to in vitro display platforms for the discovery of antigen-binding molecules). These techniques, among others, can be used to identify and improve the affinity of antibodies that bind CD117 (e.g., GNNK+ CD117) that can in turn be used to deplete endogenous hematopoietic stem cells in a patient (e.g., a human patient) in need of hematopoietic stem cell transplant therapy.

In addition to in vitro display techniques, computational modeling techniques can be used to design and identify antibodies, and antibody fragments, in silico that bind CD117 (e.g., GNNK+ CD117). For example, using computational modeling techniques, one of skill in the art can screen libraries of antibodies, and antibody fragments, in silico for molecules capable of binding specific epitopes, such as extracellular epitopes of this antigen. The antibodies, and antigen-binding fragments thereof, identified by these computational techniques can be used in conjunction with the therapeutic methods described herein, such as the cancer and autoimmune disease treatment methods described herein and the patient conditioning procedures described herein.

Additional techniques can be used to identify antibodies, and antigen-binding fragments thereof, that bind CD117 (e.g., GNNK+ CD117) on the surface of a cell (e.g., a cancer cell, autoimmune cell, or hematopoietic stem cell) and that are internalized by the cell, for instance, by receptor-mediated endocytosis. For example, the in vitro display techniques described above can be adapted to screen for antibodies, and antigen-binding fragments thereof, that bind CD117 (e.g., GNNK+ CD117) on the surface of a cancer cell, autoimmune cell, or hematopoietic stem cell and that are subsequently internalized. Phage display represents one such technique that can be used in conjunction with this screening paradigm. To identify antibodies, and fragments thereof, that bind CD117 (e.g., GNNK+ CD117) and are subsequently internalized by cancer cells, autoimmune cells, or hematopoietic stem cells, one of skill in the art can adapt the phage display techniques described, for example, in Williams et al., Leukemia 19:1432-1438, 2005, the disclosure of which is incorporated herein by reference in its entirety. For example, using mutagenesis methods known in the art, recombinant phage libraries can be produced that encode antibodies, antibody fragments, such as scFv fragments, Fab fragments, diabodies, triabodies, and $^{10}$Fn3 domains, among others, or ligands that contain randomized amino acid cassettes (e.g., in one or more, or all, of the CDRs or equivalent regions thereof or an antibody or antibody fragment). The framework regions, hinge, Fc domain, and other regions of the antibodies or antibody fragments may be designed such that they are non-immunogenic in humans, for instance, by virtue of having human germline antibody sequences or sequences that exhibit only minor variations relative to human germline antibodies.

Using phage display techniques described herein or known in the art, phage libraries containing randomized antibodies, or antibody fragments, covalently bound to the phage particles can be incubated with CD117 (e.g., GNNK+ CD117) antigen, for instance, by first incubating the phage library with blocking agents (such as, for instance, milk protein, bovine serum albumin, and/or IgG so as to remove phage encoding antibodies, or fragments thereof, that exhibit non-specific protein binding and phage that encode antibodies or fragments thereof that bind Fc domains, and then incubating the phage library with a population of hematopoietic stem cells. The phage library can be incubated with the target cells, such as cancer cells, autoimmune cells, or hematopoietic stem cells for a time sufficient to allow CD117-specific antibodies, or antigen-binding fragments thereof, (e.g., GNNK+ CD117-specific antibodies, or antigen-binding fragments thereof) to bind cell-surface CD117 (e.g., sell-surface GNNK+ CD117) antigen and to subsequently be internalized by the cancer cells, autoimmune cells, or hematopoietic stem cells (e.g., from 30 minutes to 6 hours at 4° C., such as 1 hour at 4° C.). Phage containing antibodies, or fragments thereof, that do not exhibit sufficient affinity for one or more of these antigens so as to permit binding to, and internalization by, cancer cells, autoimmune cells, or hematopoietic stem cells can subsequently be removed by washing the cells, for instance, with cold (4° C.) 0.1 M glycine buffer at pH 2.8. Phage bound to antibodies, or fragments thereof, that have been internalized by the cancer cells, autoimmune cells, or hematopoietic stem cells can be identified, for instance, by lysing the cells and recovering internalized phage from the cell culture medium. The phage can then be amplified in bacterial cells, for example, by incubating bacterial cells with recovered phage in 2×YT medium using methods known in the art. Phage recovered from this medium can then be characterized, for instance, by determining the nucleic acid sequence of the gene(s) encoding the antibodies, or fragments thereof, inserted within the phage genome. The encoded antibodies, or fragments thereof, can subsequently be prepared de novo by chemical synthesis (for instance, of antibody fragments, such as scFv fragments) or by recombinant expression (for instance, of full-length antibodies).

An exemplary method for in vitro evolution of anti-CD117 (e.g., anti-GNNK+CD117) antibodies for use with the compositions and methods described herein is phage display. Phage display libraries can be created by making a designed series of mutations or variations within a coding sequence for the CDRs of an antibody or the analogous regions of an antibody-like scaffold (e.g., the BC, CD, and DE loops of $^{10}$Fn3 domains). The template antibody-encoding sequence into which these mutations are introduced may be, for example, a naive human germline sequence. These mutations can be performed using standard mutagenesis techniques known in the art. Each mutant sequence thus encodes an antibody corresponding to the template save for one or more amino acid variations. Retroviral and phage display vectors can be engineered using standard vector construction techniques known in the art. P3 phage display vectors along with compatible protein expression vectors can be used to generate phage display vectors for antibody diversification.

The mutated DNA provides sequence diversity, and each transformant phage displays one variant of the initial template amino acid sequence encoded by the DNA, leading to a phage population (library) displaying a vast number of different but structurally related amino acid sequences. Due to the well-defined structure of antibody hypervariable regions, the amino acid variations introduced in a phage display screen are expected to alter the binding properties of the binding peptide or domain without significantly altering its overall molecular structure.

In a typical screen, a phage library may be contacted with and allowed to bind one of the foregoing antigens or an epitope thereof. To facilitate separation of binders and non-binders, it is convenient to immobilize the target on a solid support. Phage bearing a CD117-binding moiety can form a complex with the target on the solid support, whereas non-binding phage remain in solution and can be washed away with excess buffer. Bound phage can then be liberated from the target by changing the buffer to an extreme pH (pH 2 or pH 10), changing the ionic strength of the buffer, adding denaturants, or other known means.

The recovered phage can then be amplified through infection of bacterial cells, and the screening process can be repeated with the new pool that is now depleted in non-binding antibodies and enriched for antibodies that bind CD117 (e.g., GNNK+ CD117). The recovery of even a few binding phage is sufficient to amplify the phage for a subsequent iteration of screening. After a few rounds of selection, the gene sequences encoding the antibodies or antigen-binding fragments thereof derived from selected phage clones in the binding pool are determined by conventional methods, thus revealing the peptide sequence that imparts binding affinity of the phage to the target. During the panning process, the sequence diversity of the population diminishes with each round of selection until desirable peptide-binding antibodies remain. The sequences may converge on a small number of related antibodies or antigen-binding fragments thereof. An increase in the number of phage recovered at each round of selection is an indication that convergence of the library has occurred in a screen.

Another method for identifying anti-CD117 antibodies includes using humanizing non-human antibodies that bind CD117 (e.g., GNNK+ CD117), for instance, according to the following procedure. Consensus human antibody heavy chain and light chain sequences are known in the art (see e.g., the "VBASE" human germline sequence database; Kabat et al. Sequences of Proteins of Immunological Interest, Fifth Edition, U.S. Department of Health and Human Services, NIH Publication No. 91-3242, 1991; Tomlinson et al., J. Mol. Biol. 227:776-798, 1992; and Cox et al. Eur. J. Immunol. 24:827-836, 1994, the disclosures of each of which are incorporated herein by reference as they pertain to consensus human antibody heavy chain and light chain sequences. Using established procedures, one of skill in the art can identify the variable domain framework residues and CDRs of a consensus antibody sequence (e.g., by sequence alignment). One can substitute one or more CDRs of the heavy chain and/or light chain variable domains of consensus human antibody with one or more corresponding CDRs of a non-human antibody that binds CD117 (e.g., GNNK+ CD117) as described herein in order to produce a humanized antibody. This CDR exchange can be performed using gene editing techniques described herein or known in the art.

One example of a consensus human antibody that may be used in the preparation of a humanized antibody comprises a heavy chain variable domain set forth in SEQ ID NO: 7: EVQLVESGGGLVQPGGSLRLSCAASGFTFSDYAMSWVRQAPGKGLEWVAVISENGSD TYYADSVKGRFTISRDDSKNTLYLQMNSLRAEDTAVYYCARDRGGAVSYFDVWGQGTL VTVSS (SEQ ID NO: 7) and a light chain variable domain set forth in SEQ ID NO: 8: DIQMTQSPSSLSASVGDRVTITCRASQDVSSYLAWYQQKPGKAPKLLIYAASSLESGVP SRFSGSGSGTDFTLTISSLQPEDFATYYCQQYNSLPYTFGQGTKVEIKRT (SEQ ID NO: 8), identified in U.S. Pat. No. 6,054,297 (Genentech), the disclosure of which is incorporated herein by reference as it pertains to human antibody consensus sequences. The CDRs in the above sequences are shown in bold.

To produce humanized antibodies, one can recombinantly express a polynucleotide encoding the above consensus sequence in which one or more variable region CDRs have been replaced with one or more variable region CDR sequences of a non-human antibody that binds CD117 (e.g., GNNK+ CD117). As the affinity of the antibody for the hematopoietic stem cell antigen is determined primarily by the CDR sequences, the resulting humanized antibody is expected to exhibit an affinity for the hematopoietic stem cell antigen that is about the same as that of the non-human antibody from which the humanized antibody was derived. Methods of determining the affinity of an antibody for a target antigen include, for instance, ELISA-based techniques described herein and known in the art, as well as surface plasmon resonance, fluorescence anisotropy, and isothermal titration calorimetry, among others.

The internalizing capacity of the anti-CD117 antibodies, or fragments thereof, can be assessed, for instance, using radionuclide internalization assays known in the art. For example, antibodies, or fragments thereof, identified using in vitro display techniques described herein or known in the art can be functionalized by incorporation of a radioactive isotope, such as $^{18}F$, $^{75}Br$, $^{77}Br$, $^{122}I$, $^{123}I$, $^{124}I$, $^{125}I$, $^{129}I$, $^{131}I$, $^{211}At$, $^{67}Ga$, $^{111}In$, $^{99}TC$, $^{169}Yb$, $^{186}Re$, $^{64}Cu$, $^{67}Cu$, $^{177}Lu$, $^{77}As$, $^{72}As$, $^{86}Y$, $^{90}Y$, $^{89}Zr$, $^{212}Bi$, $^{213}Bi$, or $^{225}Ac$. For instance, radioactive halogens, such as $^{18}F$, $^{75}Br$, $^{77}Br$, $^{122}I$, $^{123}I$, $^{124}I$, $^{125}I$, $^{129}I$, $^{131}I$, $^{211}At$, can be incorporated into antibodies, or fragments thereof, using beads, such as polystyrene beads, containing electrophilic halogen reagents (e.g., Iodination Beads, Thermo Fisher Scientific, Inc., Cambridge, Mass.). Radiolabeled antibodies, or fragments thereof, can be incubated with cancer cells, autoimmune cells, or hematopoietic stem cells for a time sufficient to permit internalization (e.g., from 30 minutes to 6 hours at 4° C., such as 1 hour at 4° C.). The cells can then be washed to remove non-internalized antibodies, or fragments thereof, (e.g., using cold (4° C.) 0.1 M glycine buffer at pH 2.8). Internalized antibodies, or fragments thereof, can be identified by detecting the emitted radiation (e.g., γ-radiation) of the resulting cancer cells, autoimmune cells, or hematopoietic stem cells in comparison with the emitted radiation (e.g., γ-radiation) of the recovered wash buffer.

Antibody Drug Conjugates (ADCs)
Cytotoxins

Antibodies and antigen-binding fragments thereof described herein can be conjugated (linked) to a cytotoxin via a linker. In some embodiments, the cytotoxic molecule is conjugated to a cell internalizing antibody, or antigen-binding fragment thereof as disclosed herein such that following the cellular uptake of the antibody, or fragment thereof, the cytotoxin may access its intracellular target and mediate hematopoietic cell death. Any number of cytotoxins can be conjugated to the anti-CD117 antibody, e.g., 1, 2, 3, 4, 5, 6, 7, or 8.

Cytotoxins suitable for use with the compositions and methods described herein include DNA-intercalating agents, (e.g., anthracyclines), agents capable of disrupting the mitotic spindle apparatus (e.g., vinca alkaloids, maytansine, maytansinoids, and derivatives thereof), RNA polymerase inhibitors (e.g., an amatoxin, such as α-amanitin, and derivatives thereof), and agents capable of disrupting protein biosynthesis (e.g., agents that exhibit rRNA N-glycosidase activity, such as saporin and ricin A-chain), among others known in the art.

In some embodiments, the cytotoxin is a microtubule-binding agent (for instance, maytansine or a maytansinoid), an amatoxin, pseudomonas exotoxin A, deBouganin, diphtheria toxin, saporin, an auristatin, an anthracycline, a calicheamicin, irinotecan, SN-38, a duocarmycin, a pyrrolobenzodiazepine (PBD), a pyrrolobenzodiazepine dimer, an indolinobenzodiazepine, an indolinobenzodiazepine dimer, or a variant thereof, or another cytotoxic compound described herein or known in the art.

Antibodies, or antigen-binding fragments thereof, described herein (e.g., antibodies, or antigen-binding fragments, that recognize and bind CD117 (such as GNNK+ CD117)) can be conjugated to a cytotoxin, such as pseudomonas exotoxin A, deBouganin, diphtheria toxin, an amatoxin, such as α-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer, or a variant thereof, or another cytotoxic compound described herein or known in the art, for example, in order to treat a cancer or autoimmune disease described herein or to promote the depletion of endogenous hematopoietic stem cells upon administration to a patient (e.g., a human patient) in need of hematopoietic stem cell transplant therapy. In some embodiments, the cytotoxic molecule is conjugated to an internalizing antibody, or antigen-binding fragment thereof, such that following the cellular uptake of the antibody, or antigen-binding fragment, the cytotoxin may access its intracellular target and mediate endogenous hematopoietic cell death. Cytotoxins suitable for use with the compositions and methods described herein include DNA-intercalating agents, (e.g., anthracyclines), agents capable of disrupting the mitotic spindle apparatus (e.g., vinca alkaloids, maytansine, maytansinoids, and derivatives thereof), RNA polymerase inhibitors (e.g., an amatoxin, such as α-amanitin and derivatives thereof), agents capable of disrupting protein biosynthesis (e.g., agents that exhibit rRNA N-glycosidase activity, such as saporin and ricin A-chain), among others known in the art.

Additional cytotoxins suitable for use with the compositions and methods described herein include, without limitation, 5-ethynyluracil, abiraterone, acylfulvene, adecypenol, adozelesin, aldesleukin, altretamine, ambamustine, amidox, amifostine, aminolevulinic acid, amrubicin, amsacrine, anagrelide, anastrozole, andrographolide, angiogenesis inhibitors, antarelix, anti-dorsalizing morphogenetic protein-1, antiandrogen, prostatic carcinoma, antiestrogen, antineoplaston, antisense oligonucleotides, aphidicolin glycinate, apoptosis gene modulators, apoptosis regulators, apurinic acid, asulacrine, atamestane, atrimustine, axinastatin 1, axinastatin 2, axinastatin 3, axinastatin 4, azasetron, azatoxin, azatyrosine, baccatin III derivatives, balanol, batimastat, BCR/ABL antagonists, benzochlorins, benzoylstaurosporine, beta lactam derivatives, beta-alethine, betaclamycin B, betulinic acid, bFGF inhibitors, bicalutamide, bisantrene, bisaziridinylspermine, bisnafide, bistratene A, bizelesin, breflate, bleomycin A2, bleomycin B2, bropirimine, budotitane, buthionine sulfoximine, calcipotriol, calphostin C, camptothecin derivatives (e.g., 10-hydroxy-camptothecin), capecitabine, carboxamide-amino-triazole, carboxyamido-triazole, carzelesin, casein kinase inhibitors, castanospermine, cecropin B, cetrorelix, chlorins, chloroquinoxaline sulfonamide, cicaprost, cis-porphyrin, cladribine, clomifene and analogues thereof, clotrimazole, collismycin A, collismycin B, combretastatin A4, combretastatin analogues, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, 2'deoxycoformycin (DCF), deslorelin, dexifosfamide, dexrazoxane, dexverapamil, diaziquone, didemnin B, didox, diethylnorspermine, dihydro-5-azacytidine, dihydrotaxol, dioxamycin, diphenyl spiromustine, discodermolide, docosanol, dolasetron, doxifluridine, droloxifene, dronabinol, duocarmycin SA, ebselen, ecomustine, edelfosine, edrecolomab, eflornithine, elemene, emitefur, epothilones, epithilones, epristeride, estramustine and analogues thereof, etoposide, etoposide 4'-phosphate (also referred to as etopofos), exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, ganirelix, gelatinase inhibitors, gemcitabine, glutathione inhibitors, hepsulfam, homoharringtonine (HHT), hypericin, ibandronic acid, idoxifene, idramantone, ilmofosine, ilomastat, imidazoacridones, imiquimod, immunostimulant peptides, iobenguane, iododoxorubicin, ipomeanol, irinotecan, iroplact, irsogladine, isobengazole, jasplakinolide, kahalalide F, lamellarin-N triacetate, lanreotide, leinamycin, lenograstim, lentinan sulfate, leptolstatin, letrozole, lipophilic platinum compounds, lissoclinamide 7, lobaplatin, lometrexol, lonidamine, losoxantrone, loxoribine, lurtotecan, lutetium texaphyrin, lysofylline, masoprocol, maspin, matrix metalloproteinase inhibitors, menogaril, merbarone, meterelin, methioninase, metoclopramide, MIF inhibitor, ifepristone, miltefosine, mirimostim, mithracin, mitoguazone, mitolactol, mitomycin and analogues thereof, mitonafide, mitoxantrone, mofarotene, molgramostim, mycaperoxide B, myriaporone, N-acetyldinaline, N-substituted benzamides, nafarelin, nagrestip, napavin, naphterpin, nartograstim, nedaplatin, nemorubicin, neridronic acid, nilutamide, nisamycin, nitrullyn, octreotide, okicenone, onapristone, ondansetron, oracin, ormaplatin, oxaliplatin, oxaunomycin, paclitaxel and analogues thereof, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, phenazinomycin, picibanil, pirarubicin, piritrexim, podophyllotoxin, porfiromycin, purine nucleoside phosphorylase inhibitors, raltitrexed, rhizoxin, rogletimide, rohitukine, rubiginone B1, ruboxyl, safingol, saintopin, sarcophytol A, sargramostim, sobuzoxane, sonermin, sparfosic acid, spicamycin D, spiromustine, stipiamide, sulfinosine, tallimustine, tegafur, temozolomide, teniposide, thaliblastine, thiocoraline, tirapazamine, topotecan, topsentin, triciribine, trimetrexate, veramine, vinorelbine, vinxaltine, vorozole, zeniplatin, and zilascorb, among others.

Anti-CD117 antibodies, and antigen-binding fragments thereof, described herein can be conjugated to a cytotoxin that is a microtubule binding agent. As used herein, the term "microtubule-binding agent" refers to a compound which acts by disrupting the microtubular network that is essential for mitotic and interphase cellular function in a cell. Examples of microtubule-binding agents include, but are not limited to, maytasine, maytansinoids, and derivatives thereof, such as those described herein or known in the art, vinca alkaloids, such as vinblastine, vinblastine sulfate, vincristine, vincristine sulfate, vindesine, and vinorelbine, taxanes, such as docetaxel and paclitaxel, macrolides, such as discodermolides, cochicine, and epothilones, and derivatives thereof, such as epothilone B or a derivative thereof.

Maytansinoids

In some embodiments, the microtubule binding agent is a maytansine, a maytansinoid or a maytansinoid analog. Maytansinoids are mitototic inhibitors which bind microtubules and act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533. Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Examples of suitable maytansinoids include esters of maytansinol, synthetic maytansinol, and maytansinol analogs and derivatives. Included herein are any cytotoxins that inhibit microtubule formation and that are highly toxic to mammalian cells, as are maytansinoids, maytansinol, and maytansinol analogs, and derivatives.

Examples of suitable maytansinol esters include those having a modified aromatic ring and those having modifications at other positions. Such suitable maytansinoids are disclosed in U.S. Pat. Nos. 4,137,230; 4,151,042; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,362,663; 4,364,866; 4,424,219; 4,450,254; 4,322,348; 4,362,663; 4,371,533; 5,208,020; 5,416,064; 5,475,092; 5,585,499; 5,846,545; 6,333,410; 7,276,497; and 7,473,796, the disclosures of each of which are incorporated herein by reference as they pertain to maytansinoids and derivatives thereof.

In some embodiments, the immunoconjugates of the invention utilize the thiol-containing maytansinoid (DM1), formally termed $N^{2'}$-deacetyl-$N^{2'}$-(3-mercapto-1-oxopropyl)-maytansine, as the cytotoxic agent. DM1 is represented by the structural formula (VII):

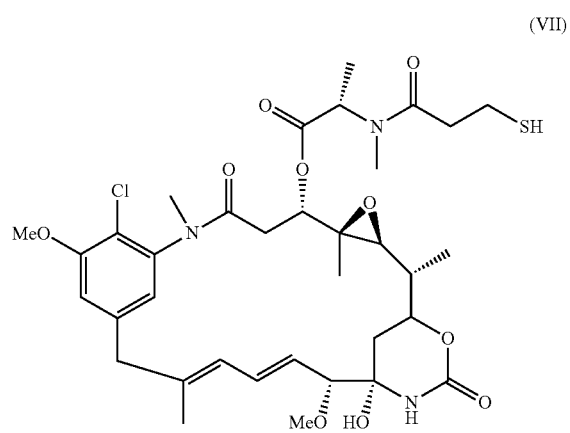 [SMILES: COc1cc2cc(c1Cl)N(C)C(=O)C[C@H](OC(=O)[C@H](C)N(C)C(=O)CCS)[C@]1(C)O[C@H]1[C@H](C)C1C[C@@](O)(NC(=O)O1)[C@H](OC)/C=C/C=C(\C)C2]

(VII)

In another embodiment, the conjugates of the present invention utilize the thiol-containing maytansinoid $N^{2'}$-deacetyl-$N^{2'}$(4-methyl-4-mercapto-1-oxopentyl)-maytansine (e.g., DM4) as the cytotoxic agent. DM4 is represented by the structural formula (V):

(V)

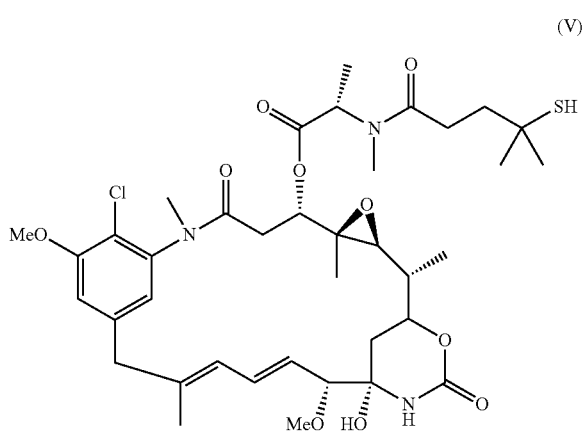 [SMILES: COc1cc2cc(c1Cl)N(C)C(=O)C[C@H](OC(=O)[C@H](C)N(C)C(=O)CCC(C)(C)S)[C@]1(C)O[C@H]1[C@H](C)C1C[C@@](O)(NC(=O)O1)[C@H](OC)/C=C/C=C(\C)C2]

Another maytansinoid comprising a side chain that contains a sterically hindered thiol bond is $N^{2'}$-deacetyl-N-$^{2'}$(4-mercapto-1-oxopentyl)-maytansine (termed DM3), represented by the structural formula (VI):

(VI)

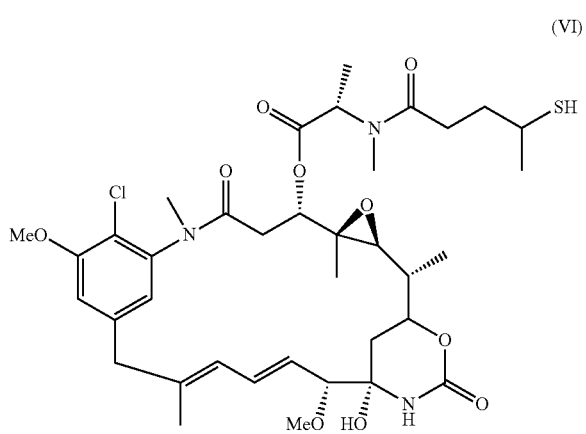 [SMILES: COc1cc2cc(c1Cl)N(C)C(=O)C[C@H](OC(=O)[C@H](C)N(C)C(=O)CCC(C)S)[C@]1(C)O[C@H]1[C@H](C)C1C[C@@](O)(NC(=O)O1)[C@H](OC)/C=C/C=C(\C)C2]

Each of the maytansinoids taught in U.S. Pat. Nos. 5,208,020 and 7,276,497, can also be used in the conjugate of the present invention. In this regard, the entire disclosure of U.S. Pat. Nos. 5,208,020 and 7,276,697 is incorporated herein by reference.

Many positions on maytansinoids can serve as the position to chemically link the linking moiety. For example, the C-3 position having a hydroxyl group, the C-14 position modified with hydroxymethyl, the C-15 position modified with hydroxy and the C-20 position having a hydroxy group are all expected to be useful. In some embodiments, the C-3 position serves as the position to chemically link the linking moiety, and in some particular embodiments, the C-3 position of maytansinol serves as the position to chemically link the linking moiety. There are many linking groups known in the art for making antibody-maytansinoid conjugates, including, for example, those disclosed in U.S. Pat. Nos. 5,208,020, 6,441,163, and EP Patent No. 0425235 B1; Chari et al., Cancer Research 52:127-131 (1992); and U.S. 2005/0169933 A1, the disclosures of which are hereby expressly incorporated by reference. Additional linking groups are described and exemplified herein.

The present disclosure also includes various isomers and mixtures of maytansinoids and conjugates. Certain compounds and conjugates of the present invention may exist in various stereoisomeric, enantiomeric, and diastereomeric forms. Several descriptions for producing such antibody-maytansinoid conjugates are provided in U.S. Pat. Nos. 5,208,020, 5,416,064 6,333,410, 6,441,163, 6,716,821, and 7,368,565, each of which is incorporated herein in its entirety.

A therapeutically effective number of maytansinoid molecules bound per antibody molecule can be determined by measuring spectrophotometrically the ratio of the absorbance at 252 nm and 280 nm. An average of 3 to 4 maytansinoid molecules conjugated per antibody molecule can enhancing cytotoxicity of target cells without negatively affecting the function or solubility of the antibody, although one molecule of toxin/antibody can enhance cytotoxicity over antibody alone. The average number of maytansinoid molecules/antibody or antigen binding fragment thereof can be, for example, 1-10 or 2-5.

Anthracyclines

In other embodiments, the antibodies and antigen-binding fragments thereof described herein can be conjugated to a cytotoxin that is an anthracycline molecule.

Anthracyclines are antibiotic compounds that exhibit cytotoxic activity. Studies have indicated that anthracyclines may operate to kill cells by a number of different mechanisms including: 1) intercalation of the drug molecules into the DNA of the cell thereby inhibiting DNA-dependent nucleic acid synthesis; 2) production by the drug of free radicals which then react with cellular macromolecules to cause damage to the cells or 3) interactions of the drug molecules with the cell membrane [see, e.g., C. Peterson et al., "Transport And Storage Of Anthracycline In Experimental Systems And Human Leukemia" in *Anthracycline Antibiotics In Cancer Therapy*; N. R. Bachur, "Free Radical Damage" id. at pp. 97-102]. Because of their cytotoxic potential anthracyclines have been used in the treatment of numerous cancers such as leukemia, breast carcinoma, lung carcinoma, ovarian adenocarcinoma and sarcomas [see e.g., P. H-Wiernik, in *Anthracycline: Current Status And New Developments* p 11]. Commonly used anthracyclines include doxorubicin, epirubicin, idarubicin and daunomycin.

The anthracycline analog, doxorubicin (ADRIAMYCINO) is thought to interact with DNA by intercalation and inhibition of the progression of the enzyme topoisomerase II, which unwinds DNA for transcription. Doxorubicin stabilizes the topoisomerase II complex after it has broken the DNA chain for replication, preventing the DNA double helix from being resealed and thereby stopping the process of replication. Doxorubicin and daunorubicin (DAUNOMYCIN) are prototype cytotoxic natural product anthracycline chemotherapeutics (Sessa et al., (2007) Cardiovasc. Toxicol. 7:75-79).

Pyrrolobenzodiazepines (PBDs)

In other embodiments, the anti-CD117 antibodies or antigen-binding fragments thereof described herein can be conjugated to a cytotoxin that is a pyrrolobenzodiazepine (PBD) or a cytotoxin that comprises a PBD. PBDs are natural products produced by certain actinomycetes and have been shown to be sequence selective DNA alkylating compounds. PBD cytotoxins include, but are not limited to, anthramycin, dimeric PBDs, and those disclosed in, for example, Hartley, J. A. (2011). "The development of pyrrolobenzodiazepines as antitumour agents." Expert Opin. Inv. Drug, 20(6), 733-744; and Antonow, D.; Thurston, D. E. (2011) "Synthesis of DNA-interactive pyrrolo[2,1-c][1,4]benzodiazepines (PBDs)." Chem. Rev. 111: 2815-2864.

Calicheamicin

In other embodiments, the antibodies and antigen-binding fragments thereof described herein can be conjugated to a cytotoxin that is a calicheamicin molecule. The calicheamicin family of antibiotics are capable of producing double-stranded DNA breaks at sub-picomolar concentrations. For the preparation of conjugates of the calicheamicin family, see U.S. Pat. Nos. 5,712,374; 5,714,586; 5,739,116; 5,767,285; 5,770,701; 5,770,710; 5,773,001; and 5,877,296 (all to American Cyanamid Company). Structural analogues of calicheamicin which may be used include, but are not limited to, those disclosed in, for example, Hinman et al., Cancer Research 53:3336-3342 (1993), Lode et al., Cancer Research 58:2925-2928 (1998), and the aforementioned U.S. patents to American Cyanamid.

Auristatins

Anti-CD117 antibodies, and antigen-binding fragments thereof, described herein can be conjugated to a cytotoxin that is an auristatin (U.S. Pat. Nos. 5,635,483; 5,780,588). Auristatins are anti-mitotic agents that interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). (U.S. Pat. Nos. 5,635,483; 5,780,588). The auristatin drug moiety may be attached to the antibody through the N-(amino) terminus or the C- (carboxyl) terminus of the peptidic drug moiety (WO 02/088172).

Exemplary auristatin embodiments include the N-terminus linked monomethylauristatin drug moieties DE and DF, disclosed in Senter et al, Proceedings of the American Association for Cancer Research, Volume 45, Abstract Number 623, presented Mar. 28, 2004, the disclosure of which is expressly incorporated by reference in its entirety.

An exemplary auristatin embodiment is MMAE, wherein the wavy line indicates the point of covalent attachment to the linker of an antibody-linker conjugate (-L-Z-Ab, as described herein).

thesis, 1996, 719-725; Pettit et al (1996) J. Chem. Soc. Perkin Trans. 15:859-863; and Doronina (2003) Nat. Biotechnol. 21(7):778-784.

Amatoxins

In some embodiments, the cytotoxin of the antibody-drug conjugate is an RNA polymerase inhibitor. In some embodiments, the RNA polymerase inhibitor is an amatoxin or derivative thereof.

In some embodiments, the cytotoxin is an amatoxin or derivative thereof, such as α-amanitin, β-amanitin, γ-amanitin, ε-amanitin, amanin, amaninamide, amanullin, amanullinic acid, and proamanullin. Structures of the various naturally occurring amatoxins are represented by formula II and accompanying Table 1, and are disclosed in, e.g., Zanotti et al., Int. J. Peptide Protein Res. 30, 1987, 450-459.

For instance, the antibodies, and antigen-binding fragments, described herein may be bound to an amatoxin so as to form a conjugate represented by the formula Ab-Z-L-Am, wherein Ab is the antibody, or antigen-binding fragment thereof, L is a linker, Z is a chemical moiety and Am is an amatoxin. Many positions on amatoxins or derivatives thereof can serve as the position to covalently bond the linking moiety L, and, hence the antibodies or antigen-binding fragments thereof. In some embodiments, Am-L-Z is represented by formula (I)

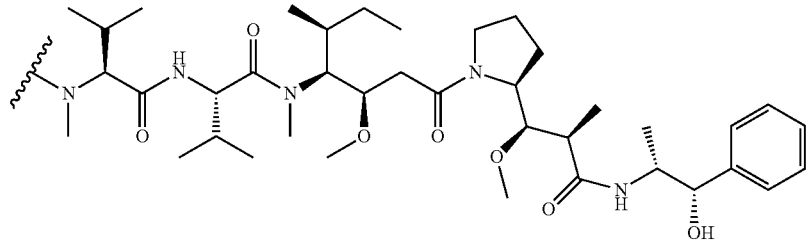 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

Another exemplary auristatin embodiment is MMAF, wherein the wavy line indicates the point of covalent attachment to the linker of an antibody-linker conjugate (-L-Z-Ab, as described herein), as disclosed in US 2005/0238649:

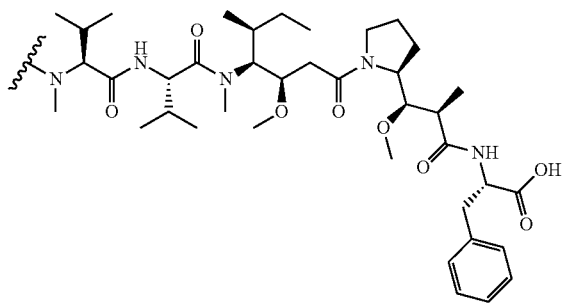 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

Auristatins may be prepared according to the methods of: U.S. Pat. Nos. 5,635,483; 5,780,588; Pettit et al (1989) J. Am. Chem. Soc. 111:5463-5465; Pettit et al (1998) Anti-Cancer Drug Design 13:243-277; Pettit, G. R., et al. Syn- (I)

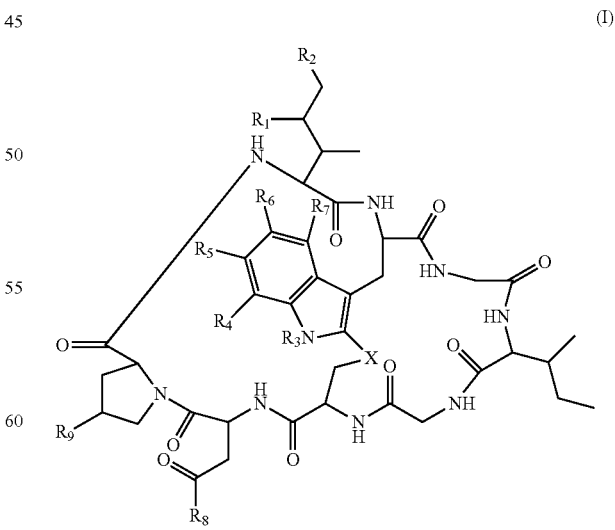

wherein $R_1$ is H, OH, $OR_A$, or $OR_C$;

$R_2$ is H, OH, $OR_B$, or $OR_C$;

$R_A$ and $R_B$, when present, together with the oxygen atoms to which they are bound, combine to form an optionally substituted 5-membered heterocycloalkyl group;

$R_3$ is H, $R_C$, or $R_D$;

$R_4$ is H, OH, $OR_C$, $OR_D$, $R_C$, or $R_D$;

$R_5$ is H, OH, $OR_C$, $OR_D$, $R_C$, or $R_D$;

$R_6$ is H, OH, $OR_C$, $OR_D$, $R_C$, or $R_D$;

$R_7$ is H, OH, $OR_C$, $OR_D$, $R_C$, or $R_D$;

$R_8$ is OH, $NH_2$, $OR_C$, $OR_D$, $NHR_C$, or $NR_CR_D$;

$R_9$ is H, OH, $OR_C$, or $OR_D$;

X is —S—, —S(O)—, or —$SO_2$—;

$R_C$ is -L-Z;

$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;

L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, optionally substituted heteroarylene, a peptide, a dipeptide, —(C=O)—, or a combination thereof;

and

Z is a chemical moiety formed from a coupling reaction between a reactive substituent present on L and a reactive substituent present within an antibody, or antigen-binding fragment thereof, that binds CD117 (such as GNNK+ CD117).

In some embodiments, Am contains exactly one $R_C$ substituent.

In some embodiments, L-Z is

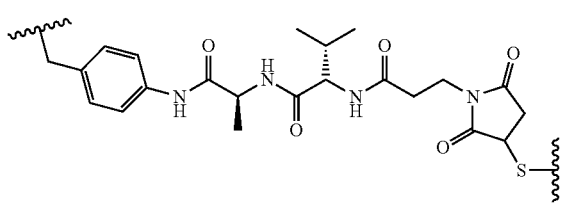

where S is a sulfur atom which represents the reactive substituent present within an antibody, or antigen-binding fragment thereof, that binds CD117 (e.g., from the —SH group of a cysteine residue).

In some embodiments, the conjugate is represented by one of formulas IV, IVA, or IVB:

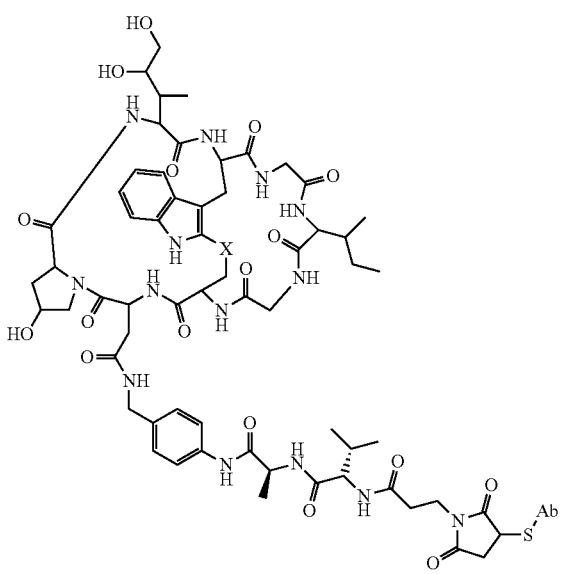

(IV)

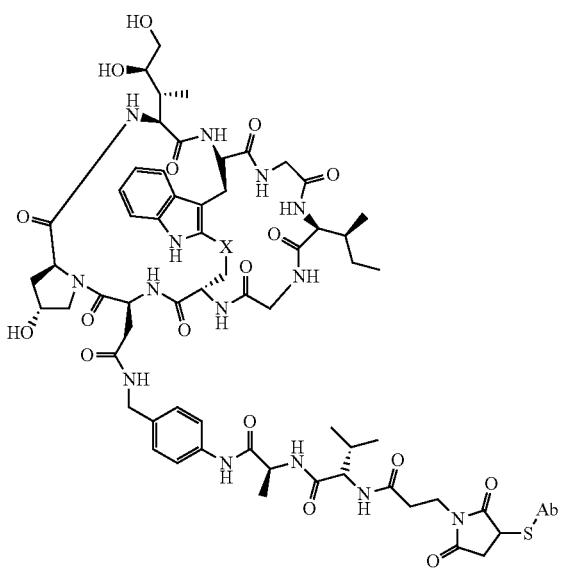

(IVA)

(IVB)
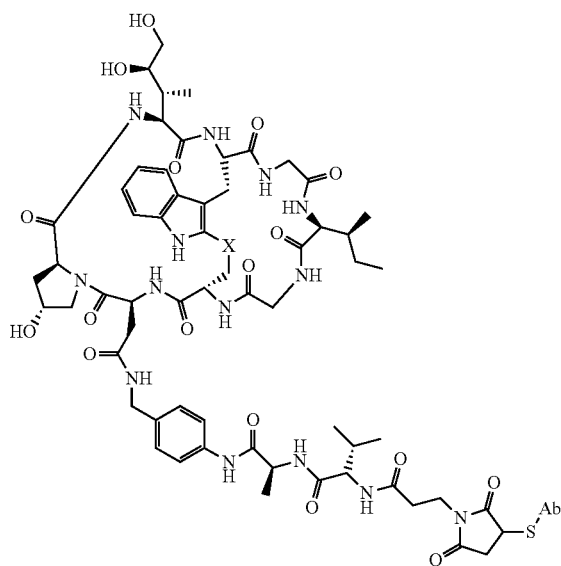
where X is S, SO or SO₂, and the Ab is shown to indicate the point of Ab attachment.
In some embodiments, Am-L-Z is
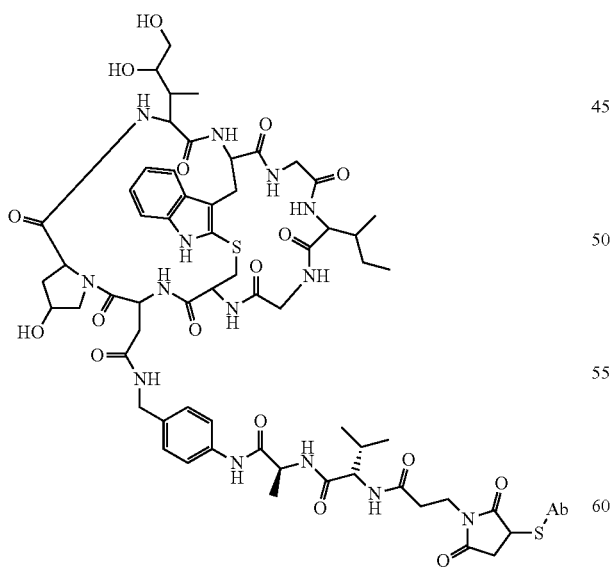
where Ab is shown to indicate the point of Ab attachment.
In some embodiments, Am-L-Z-Ab is
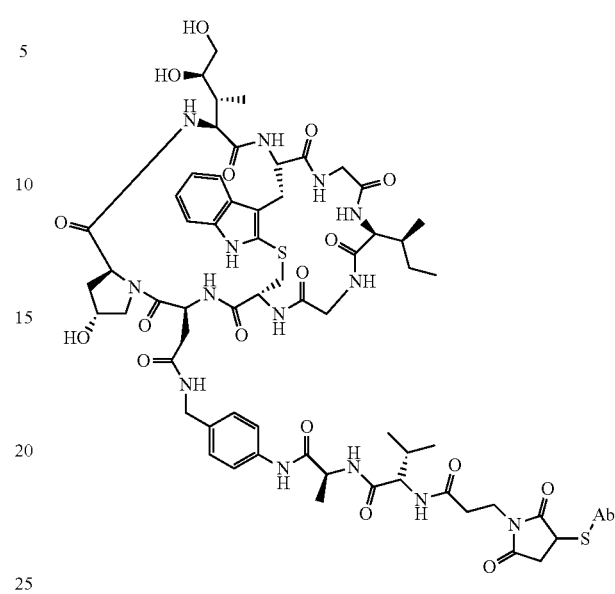
where Ab is shown to indicate the point of Ab attachment.
In some embodiments, Am-L-Z-Ab is
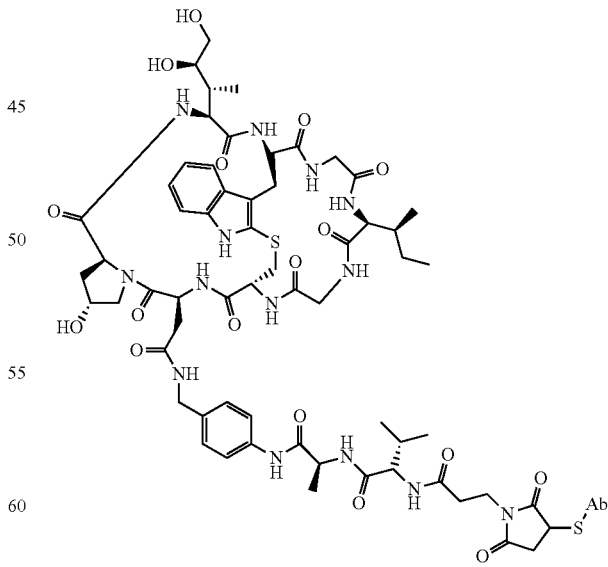
where Ab is shown to indicate the point of Ab attachment.

In some embodiments, the Am-L-Z precursor is
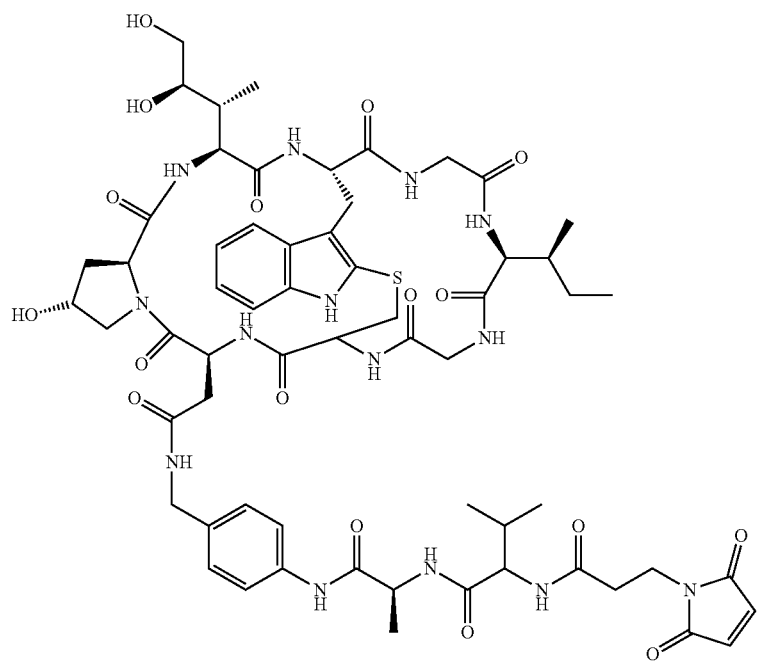
wherein the maleimide reacts with a thiol group found on a cysteine in the antibody.
In some embodiments, the Am-L-Z precursor is
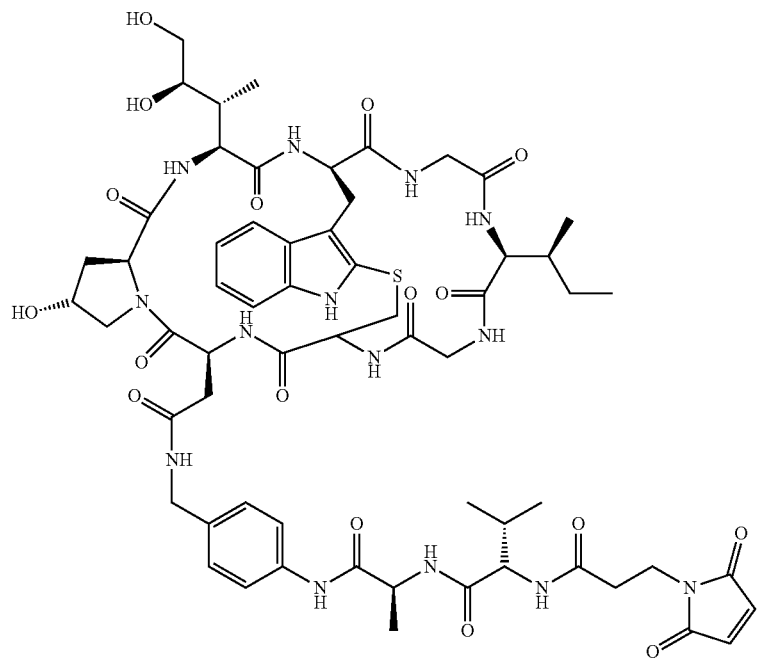
wherein the maleimide reacts with a thiol group found on a cysteine in the antibody.

In some embodiments, Am-L-Z is represented by formula (IA)

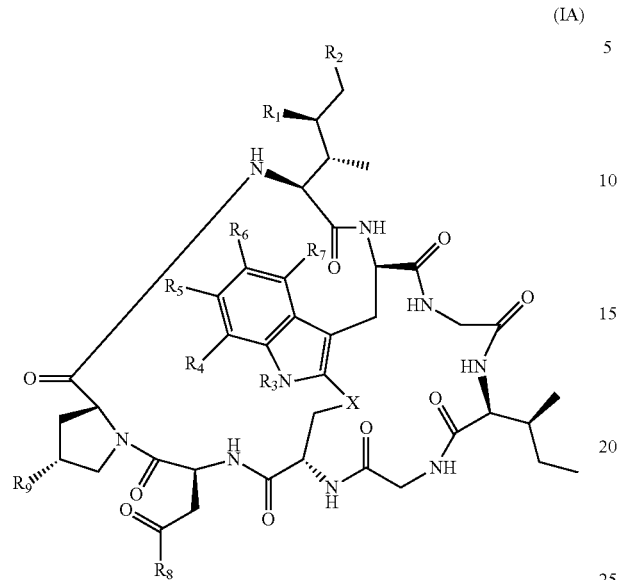

wherein $R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form an optionally substituted 5-membered heterocycloalkyl group;
$R_3$ is H, $R_C$, or $R_D$;
$R_4$ is H, OH, $OR_C$, $OR_D$, $R_C$, or $R_D$;
$R_5$ is H, OH, $OR_C$, $OR_D$, $R_C$, or $R_D$;
$R_6$ is H, OH, $OR_C$, $OR_D$, $R_C$, or $R_D$;
$R_7$ is H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —$SO_2$—;
$R_C$ is -L-Z;
$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;
L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, optionally substituted heteroarylene, a peptide, a dipeptide, —(C=O)—, or a combination thereof;
Z is a chemical moiety formed from a coupling reaction between a reactive substituent present on L and a reactive substituent present within an antibody, or antigen-binding fragment thereof, that binds CD117 (such as GNNK+ CD117); and
wherein Am contains exactly one $R_C$ substituent.

In some embodiments, L-Z is

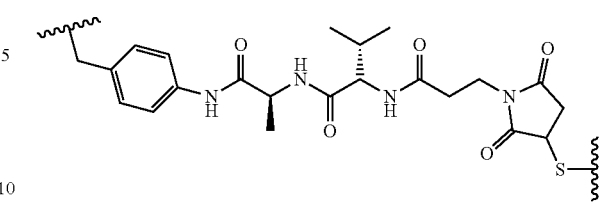

In some embodiments, Am-L-Z is represented by formula (IB)

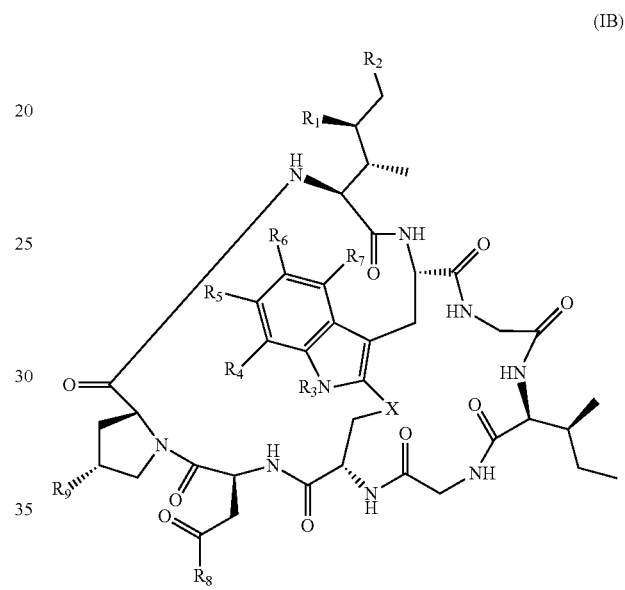

wherein $R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form an optionally substituted 5-membered heterocycloalkyl group;
$R_3$ is H, $R_C$, or $R_D$;
$R_4$ is H, OH, $OR_C$, $OR_D$, $R_C$, or $R_D$;
$R_5$ is H, OH, $OR_C$, $OR_D$, $R_C$, or $R_D$;
$R_6$ is H, OH, $OR_C$, $OR_D$, $R_C$, or $R_D$;
$R_7$ is H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —$SO_2$—;
$R_C$ is -L-Z;
$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;
L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, optionally substituted heteroarylene, a peptide, a dipeptide, —(C═O)—, or a combination thereof;

Z is a chemical moiety formed from a coupling reaction between a reactive substituent present on L and a reactive substituent present within an antibody, or antigen-binding fragment thereof, that binds CD117 (such as GNNK+ CD117); and wherein Am contains exactly one $R_C$ substituent.

In some embodiments, L-Z is

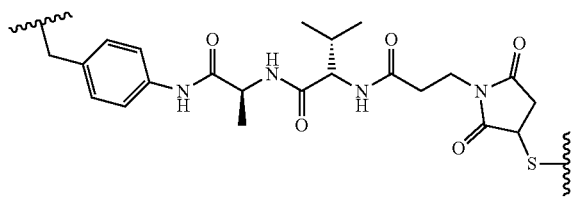

In some embodiments, $R_A$ and $R_B$, when present, together with the oxygen atoms to which they are bound, combine to form a 5-membered heterocycloalkyl group of formula:

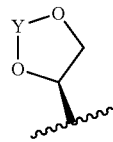

wherein Y is —(C═O)—, —(C═S)—, —(C═NR$_E$)—, or —(CR$_E$R$_{E'}$)—; and $R_E$ and $R_{E'}$ are each independently optionally substituted $C_1$-$C_6$ alkylene-$R_C$, optionally substituted $C_1$-$C_6$ heteroalkylene-$R_C$, optionally substituted $C_2$-$C_6$ alkenylene-$R_C$, optionally substituted $C_2$-$C_6$ heteroalkenylene-$R_C$, optionally substituted $C_2$-$C_6$ alkynylene-$R_C$, optionally substituted $C_2$-$C_6$ heteroalkynylene-$R_C$, optionally substituted cycloalkylene-$R_C$, optionally substituted heterocycloalkylene-$R_C$, optionally substituted arylene-$R_C$, or optionally substituted heteroarylene-$R_C$.

In some embodiments, Am-L-Z is represented by formula (IA) or formula (IB),
wherein $R_1$ is H, OH, OR$_A$, or OR$_C$;
$R_2$ is H, OH, OR$_B$, or OR$_C$;
$R_A$ and $R_B$, when present, together with the oxygen atoms to which they are bound, combine to form:

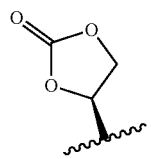 [SMILES: *[C@@H]1COC(=O)O1]

$R_3$ is H or $R_C$;
$R_4$ is H, OH, OR$_C$, OR$_D$, $R_C$, or $R_D$;
$R_5$ is H, OH, OR$_C$, OR$_D$, $R_C$, or $R_D$;
$R_6$ is H, OH, OR$_C$, OR$_D$, $R_C$, or $R_D$;
$R_7$ is H, OH, OR$_C$, OR$_D$, $R_C$, or $R_D$;
$R_8$ is OH, NH$_2$, OR$_C$, or NHR$_C$;
$R_9$ is H or OH;
X is —S—, —S(O)—, or —SO$_2$—; and
wherein $R_C$ and $R_D$ are each as defined above.

In some embodiments, Am-L-Z is represented by formula (IA) or formula (IB),
wherein $R_1$ is H, OH, OR$_A$, or OR$_C$;
$R_2$ is H, OH, OR$_B$, or OR$_C$;
$R_A$ and $R_B$, when present, together with the oxygen atoms to which they are bound, combine to form:

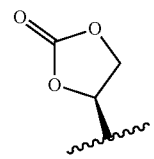 [SMILES: *[C@@H]1COC(=O)O1]

$R_3$ is H or $R_C$;
$R_4$ and $R_5$ are each independently H, OH, OR$_C$, $R_C$, or OR$_D$;
$R_6$ and $R_7$ are each H;
$R_8$ is OH, NH$_2$, OR$_C$, or NHR$_C$;
$R_9$ is H or OH;
X is —S—, —S(O)—, or —SO$_2$—; and
wherein $R_C$ is as defined above.

In some embodiments, Am-L-Z is represented by formula (IA) or formula (IB),
wherein $R_1$ is H, OH, or OR$_A$;
$R_2$ is H, OH, or OR$_B$;
$R_A$ and $R_B$, when present, together with the oxygen atoms to which they are bound, combine to form:

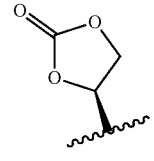 [SMILES: *[C@@H]1COC(=O)O1]

$R_3$, $R_4$, $R_6$, and $R_7$ are each H;
$R_5$ is OR$_C$;
$R_8$ is OH or NH$_2$;
$R_9$ is H or OH;
X is —S—, —S(O)—, or —SO$_2$—; and
wherein $R_C$ is as defined above. Such amatoxin conjugates are described, for example, in US Patent Application Publication No. 2016/0002298, the disclosure of which is incorporated herein by reference in its entirety.

In some embodiments, Am-L-Z is represented by formula (IA) or formula (IB),
wherein $R_1$ and $R_2$ are each independently H or OH;
$R_3$ is $R_C$;
$R_4$, $R_6$, and $R_7$ are each H;
$R_5$ is H, OH, or OC$_1$-C$_6$ alkyl;
$R_8$ is OH or NH$_2$;
$R_9$ is H or OH;
X is —S—, —S(O)—, or —SO$_2$—; and
wherein $R_C$ is as defined above. Such amatoxin conjugates are described, for example, in US Patent Application Publication No. 2014/0294865, the disclosure of which is incorporated herein by reference in its entirety.

In some embodiments, Am-L-Z is represented by formula (IA) or formula (IB), wherein $R_1$ and $R_2$ are each independently H or OH;

$R_3$, $R_6$, and $R_7$ are each H;

$R_4$ and $R_5$ are each independently H, OH, $OR_C$, or $R_C$;

$R_8$ is OH or $NH_2$;

$R_9$ is H or OH;

X is —S—, —S(O)—, or —SO$_2$—; and wherein $R_C$ is as defined above. Such amatoxin conjugates are described, for example, in US Patent Application Publication No. 2015/0218220, the disclosure of which is incorporated herein by reference in its entirety.

In some embodiments, Am-L-Z is represented by formula (IA) or formula (IB), wherein $R_1$ and $R_2$ are each independently H or OH;

$R_3$, $R_6$, and $R_7$ are each H;

$R_4$ and $R_5$ are each independently H or OH;

$R_5$ is OH, $NH_2$, $OR_C$, or $NHR_C$;

$R_9$ is H or OH;

X is —S—, —S(O)—, or —SO$_2$—; and wherein $R_C$ is as defined above. Such amatoxin conjugates are described, for example, in U.S. Pat. Nos. 9,233,173 and 9,399,681, as well as in US 2016/0089450, the disclosures of each of which are incorporated herein by reference in their entirety.

In some embodiments, Am-L-Z is

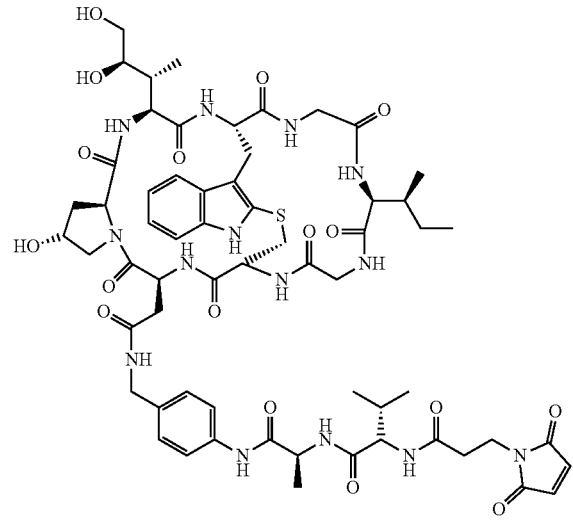

Additional amatoxins that may be used for conjugation to an antibody, or antigen-binding fragment thereof, in accordance with the compositions and methods described herein are described, for example, in WO 2016/142049; WO 2016/071856; WO 2017/149077; WO 2018/115466; and WO 2017/046658, the disclosures of each of which are incorporated herein by reference in their entirety.

In some embodiments, Am-L-Z is represented by formula (II), formula (IIA), or formula (IIB)

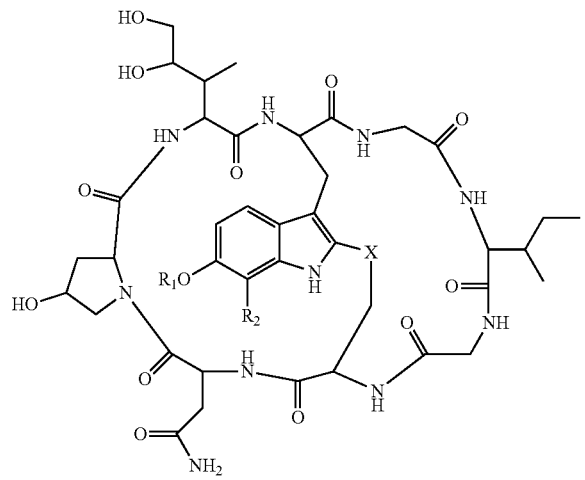

(II)

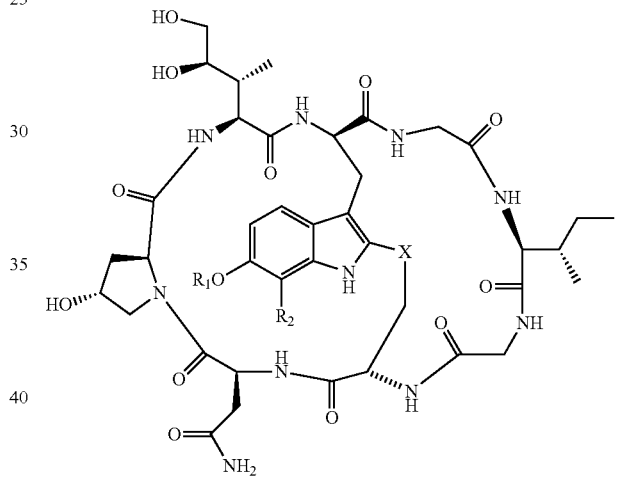

(IIA)

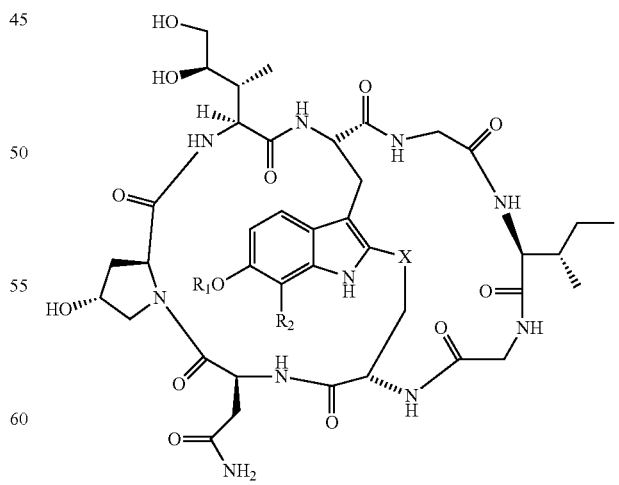

(IIB)

wherein X is S, SO, or SO$_2$; $R_1$ is H or a linker covalently bound to the antibody or antigen-binding fragment thereof through a chemical moiety Z, formed from a coupling reaction between a reactive substituent present on the linker and a reactive substituent present within an antibody, or antigen-binding fragment thereof; and $R_2$ is H or a linker covalently bound to the antibody or antigen-binding fragment thereof through a chemical moeity Z, formed from a coupling reaction between a reactive substituent present on the linker and a reactive substituent present within an antibody, or antigen-binding fragment thereof; wherein when $R_1$ is H, $R_2$ is the linker, and when $R_2$ is H, $R_1$ is the linker. In some embodiments, $R_1$ is the linker and $R_2$ is H, and the linker and chemical moiety, together as L-Z, is

[Chemical structure]

In one embodiment, Am-L-Z-Ab is:

[Chemical structure]

In some embodiments, the cytotoxin is an α-amanitin. In some embodiments, the α-amanitin is a compound of formula III. In some embodiments, the α-amanitin of formula III is attached to an anti-CD117 antibody via a linker L. The linker L may be attached to the α-amanitin of formula III at any one of several possible positions (e.g., any of $R^1$-$R^9$) to provide an α-amanitin-linker conjugate of formula I, IA, IB, II, IIA, or IIB. In some embodiments, the linker is attached at position $R^1$. In some embodiments, the linker is attached at position $R^2$. In some embodiments, the linker is attached at position $R^3$. In some embodiments, the linker is attached at position $R^4$. In some embodiments, the linker is attached at position $R^5$. In some embodiments, the linker is attached at position $R^6$. In some embodiments, the linker is attached at position $R^7$. In some embodiments, the linker is attached at position $R^8$. In some embodiments, the linker is attached at position $R^9$. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$-unit, wherein n is an integer from 1-6.

In some embodiments, the linker includes a —(CH$_2$)$_n$-unit, where n is an integer from 2-6. In some embodiments, the linker is -PAB-Cit-Val-((C=O)(CH$_2$)$_n$—. In some embodiments, the linker is -PAB-Ala-Val-((C=O)(CH$_2$)$_n$—. In some embodiments, the linker L and the chemical moiety Z, taken together as L-Z, is

[Chemical structures] or

In some embodiments, the cytotoxin is a β-amanitin. In some embodiments, the α-amanitin is a compound of formula III. In some embodiments, the β-amanitin of formula III is attached to an anti-CD117 antibody via a linker L. The linker L may be attached to the β-amanitin of formula III at any one of several possible positions (e.g., any of $R^1$-$R^9$) to provide an β-amanitin-linker conjugate of formula I, IA, IB, II, IIA, or IIB. In some embodiments, the linker is attached at position $R^1$. In some embodiments, the linker is attached at position $R^2$. In some embodiments, the linker is attached at position $R^3$. In some embodiments, the linker is attached at position $R^4$. In some embodiments, the linker is attached at position $R^5$. In some embodiments, the linker is attached at position $R^6$. In some embodiments, the linker is attached at position $R^7$. In some embodiments, the linker is attached at position $R^8$. In some embodiments, the linker is attached at position $R^9$. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$-unit, wherein n is an integer from 1-6.

In some embodiments, the linker includes a —(CH$_2$)$_n$-unit, where n is an integer from 2-6. In some embodiments, the linker is -PAB-Cit-Val-((C=O)(CH$_2$)$_n$—. In some embodiments, the linker is -PAB-Ala-Val-((C=O)(CH$_2$)$_n$—. In some embodiments, the linker L and the chemical moiety Z, taken together as L-Z, is

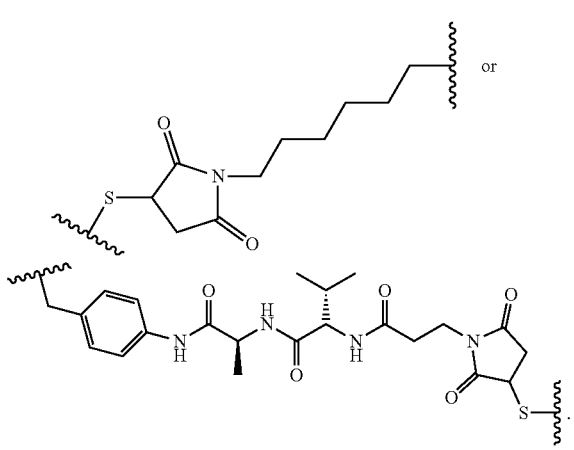

In some embodiments, the cytotoxin is a γ-amanitin. In some embodiments, the γ-amanitin is a compound of formula III. In some embodiments, the γ-amanitin of formula III is attached to an anti-CD117 antibody via a linker L. The linker L may be attached to the γ-amanitin of formula III at any one of several possible positions (e.g., any of $R^1$-$R^9$) to provide an γ-amanitin-linker conjugate of formula I, IA, IB, II, IIA, or IIB. In some embodiments, the linker is attached at position $R^1$. In some embodiments, the linker is attached at position $R^2$. In some embodiments, the linker is attached at position $R^3$. In some embodiments, the linker is attached at position $R^4$. In some embodiments, the linker is attached at position $R^5$. In some embodiments, the linker is attached at position $R^6$. In some embodiments, the linker is attached at position $R^7$. In some embodiments, the linker is attached at position $R^8$. In some embodiments, the linker is attached at position $R^9$. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$-unit, wherein n is an integer from 1-6.

In some embodiments, the linker includes a —(CH$_2$)$_n$-unit, where n is an integer from 2-6. In some embodiments, the linker is -PAB-Cit-Val-((C=O)(CH$_2$)$_n$—. In some embodiments, the linker is -PAB-Ala-Val-((C=O)(CH$_2$)$_n$—. In some embodiments, the linker L and the chemical moiety Z, taken together as L-Z, is

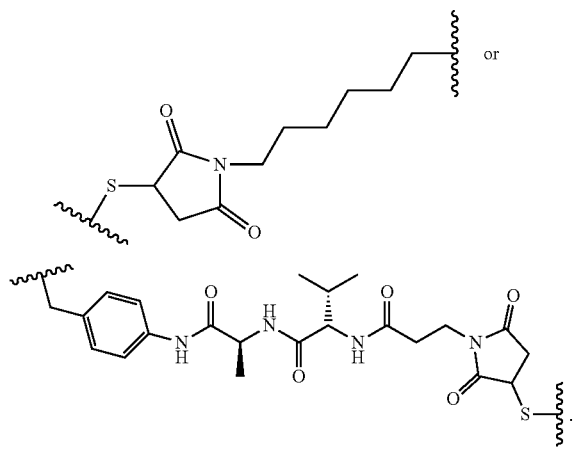

In some embodiments, the cytotoxin is a ε-amanitin. In some embodiments, the ε-amanitin is a compound of formula III. In some embodiments, the ε-amanitin of formula III is attached to an anti-CD117 antibody via a linker L. The linker L may be attached to the ε-amanitin of formula III at any one of several possible positions (e.g., any of $R^1$-$R^9$) to provide an ε-amanitin-linker conjugate of formula I, IA, IB, II, IIA, or IIB. In some embodiments, the linker is attached at position $R^1$. In some embodiments, the linker is attached at position $R^2$. In some embodiments, the linker is attached at position $R^3$. In some embodiments, the linker is attached at position $R^4$. In some embodiments, the linker is attached at position $R^5$. In some embodiments, the linker is attached at position $R^6$. In some embodiments, the linker is attached at position $R^7$. In some embodiments, the linker is attached at position $R^8$. In some embodiments, the linker is attached at position $R^9$. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$-unit, wherein n is an integer from 1-6.

In some embodiments, the linker includes a —(CH$_2$)$_n$-unit, where n is an integer from 2-6. In some embodiments, the linker is -PAB-Cit-Val-((C=O)(CH$_2$)$_n$—. In some embodiments, the linker is -PAB-Ala-Val-((C=O)(CH$_2$)$_n$—. In some embodiments, the linker L and the chemical moiety Z, taken together as L-Z, is

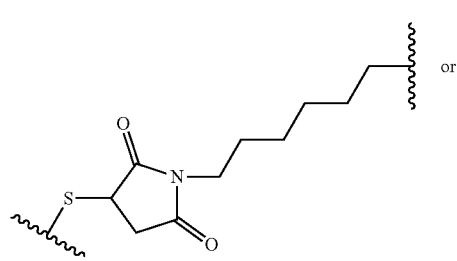

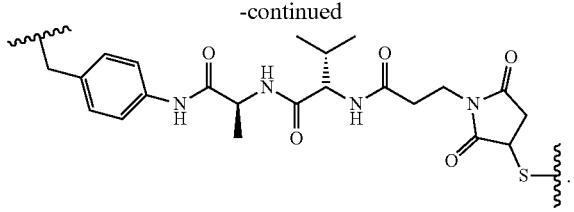

In some embodiments, the cytotoxin is an amanin. In some embodiments, the amanin. is a compound of formula III. In some embodiments, the amanin of formula III is attached to an anti-CD117 antibody via a linker L. The linker L may be attached to the amanin of formula III at any one of several possible positions (e.g., any of $R^1$-$R^9$) to provide an amanin-linker conjugate of formula I, IA, IB, II, IIA, or IIB. In some embodiments, the linker is attached at position $R^1$. In some embodiments, the linker is attached at position $R^2$. In some embodiments, the linker is attached at position $R^3$. In some embodiments, the linker is attached at position $R^4$. In some embodiments, the linker is attached at position $R^5$. In some embodiments, the linker is attached at position $R^6$. In some embodiments, the linker is attached at position $R^7$. In some embodiments, the linker is attached at position $R^8$. In some embodiments, the linker is attached at position $R^9$. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$-unit, wherein n is an integer from 1-6.

In some embodiments, the linker includes a —(CH$_2$)$_n$- unit, where n is an integer from 2-6. In some embodiments, the linker is -PAB-Cit-Val-((C=O)(CH$_2$)$_n$—. In some embodiments, the linker is -PAB-Ala-Val-((C=O)(CH$_2$)$_n$—. In some embodiments, the linker L and the chemical moiety Z, taken together as L-Z, is

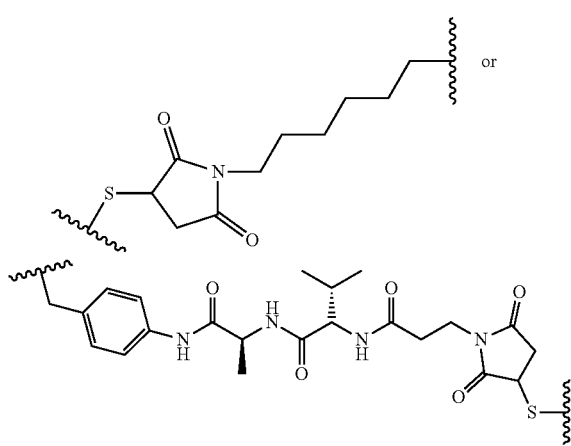

In some embodiments, the cytotoxin is an amaninamide. In some embodiments, the amaninamide is a compound of formula III. In some embodiments, the amaninamide of formula III is attached to an anti-CD117 antibody via a linker L. The linker L may be attached to the amaninamide of formula III at any one of several possible positions (e.g., any of $R^1$-$R^9$) to provide an amaninamide-linker conjugate of formula I, IA, IB, II, IIA, or IIB. In some embodiments, the linker is attached at position $R^1$. In some embodiments, the linker is attached at position $R^2$. In some embodiments, the linker is attached at position $R^3$. In some embodiments, the linker is attached at position $R^4$. In some embodiments, the linker is attached at position $R^5$. In some embodiments, the linker is attached at position $R^6$. In some embodiments, the linker is attached at position $R^7$. In some embodiments, the linker is attached at position $R^8$. In some embodiments, the linker is attached at position $R^9$. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$-unit, wherein n is an integer from 1-6.

In some embodiments, the linker includes a —(CH$_2$)$_n$- unit, where n is an integer from 2-6. In some embodiments, the linker is -PAB-Cit-Val-((C=O)(CH$_2$)$_n$—. In some embodiments, the linker is -PAB-Ala-Val-((C=O)(CH$_2$)$_n$—. In some embodiments, the linker L and the chemical moiety Z, taken together as L-Z, is

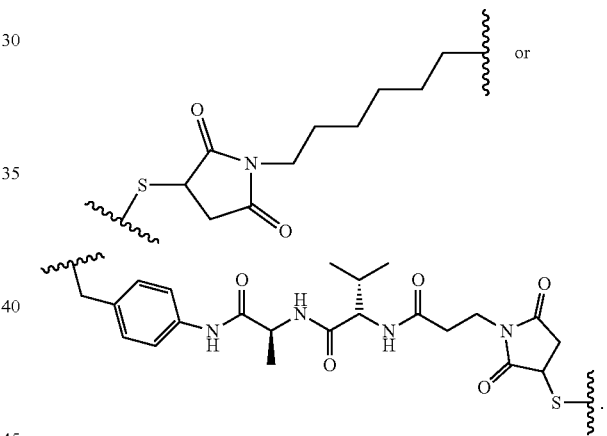

In some embodiments, the cytotoxin is an amanullin. In some embodiments, the amanullin is a compound of formula III. In some embodiments, the amanullin of formula III is attached to an anti-CD117 antibody via a linker L. The linker L may be attached to the amanullin of formula III at any one of several possible positions (e.g., any of $R^1$-$R^9$) to provide an amanullin-linker conjugate of formula I, IA, IB, II, IIA, or IIB. In some embodiments, the linker is attached at position $R^1$. In some embodiments, the linker is attached at position $R^2$. In some embodiments, the linker is attached at position $R^3$. In some embodiments, the linker is attached at position $R^4$. In some embodiments, the linker is attached at position $R^5$. In some embodiments, the linker is attached at position $R^6$. In some embodiments, the linker is attached at position $R^7$. In some embodiments, the linker is attached at position $R^8$. In some embodiments, the linker is attached at position $R^9$. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C═O)(CH$_2$)$_n$-unit, wherein n is an integer from 1-6.

In some embodiments, the linker includes a —(CH$_2$)$_n$-unit, where n is an integer from 2-6. In some embodiments, the linker is -PAB-Cit-Val-((C═O)(CH$_2$)$_n$—. In some embodiments, the linker is -PAB-Ala-Val-((C═O)(CH$_2$)$_n$—. In some embodiments, the linker L and the chemical moiety Z, taken together as L-Z, is

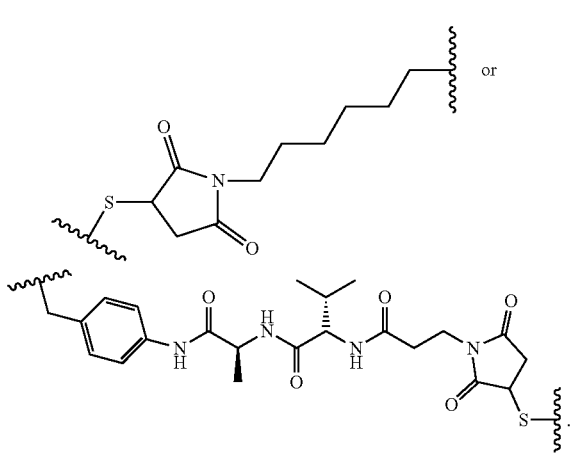

In some embodiments, the cytotoxin is an amanullinic acid. In some embodiments, the amanullinic acid is a compound of formula III. In some embodiments, the amanullinic acid of formula III is attached to an anti-CD117 antibody via a linker L. The linker L may be attached to the amanullinic acid of formula III at any one of several possible positions (e.g., any of R$^1$-R$^9$) to provide an amanullinic acid-linker conjugate of formula I, IA, IB, II, IIA, or IIB. In some embodiments, the linker is attached at position R$^1$. In some embodiments, the linker is attached at position R$^2$. In some embodiments, the linker is attached at position R$^3$. In some embodiments, the linker is attached at position R$^4$. In some embodiments, the linker is attached at position R$^5$. In some embodiments, the linker is attached at position R$^6$. In some embodiments, the linker is attached at position R$^7$. In some embodiments, the linker is attached at position R$^8$. In some embodiments, the linker is attached at position R$^9$. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C═O)(CH$_2$)$_n$-unit, wherein n is an integer from 1-6.

In some embodiments, the linker includes a —(CH$_2$)$_n$-unit, where n is an integer from 2-6. In some embodiments, the linker is -PAB-Cit-Val-((C═O)(CH$_2$)$_n$—. In some embodiments, the linker is -PAB-Ala-Val-((C═O)(CH$_2$)$_n$—. In some embodiments, the linker L and the chemical moiety Z, taken together as L-Z, is

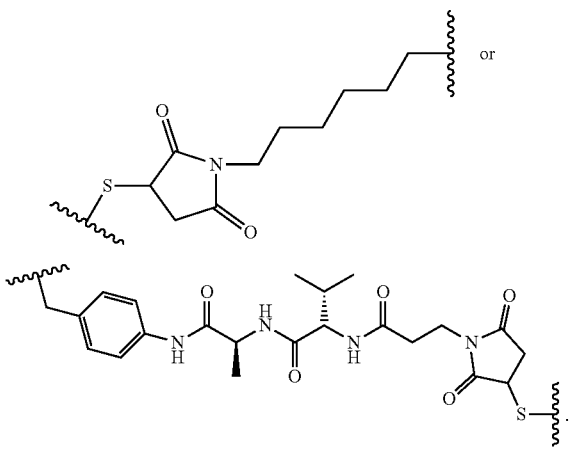

In some embodiments, the cytotoxin is a proamanullin. In some embodiments, the proamanullin is a compound of formula III. In some embodiments, the proamanullin of formula III is attached to an anti-CD117 antibody via a linker L. The linker L may be attached to the proamanullin of formula III at any one of several possible positions (e.g., any of R$^1$-R$^9$) to provide an proamanullin-linker conjugate of formula I, IA, IB, II, IIA, or IIB. In some embodiments, the linker is attached at position R$^1$. In some embodiments, the linker is attached at position R$^2$. In some embodiments, the linker is attached at position R$^3$. In some embodiments, the linker is attached at position R$^4$. In some embodiments, the linker is attached at position R$^5$. In some embodiments, the linker is attached at position R$^6$. In some embodiments, the linker is attached at position R$^7$. In some embodiments, the linker is attached at position R$^8$. In some embodiments, the linker is attached at position R$^9$. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C═O)(CH$_2$)$_n$-unit, wherein n is an integer from 1-6.

In some embodiments, the linker includes a —(CH$_2$)$_n$-unit, where n is an integer from 2-6. In some embodiments, the linker is -PAB-Cit-Val-((C═O)(CH$_2$)$_n$—. In some embodiments, the linker is -PAB-Ala-Val-((C═O)(CH$_2$)$_n$—. In some embodiments, the linker L and the chemical moiety Z, taken together as L-Z, is

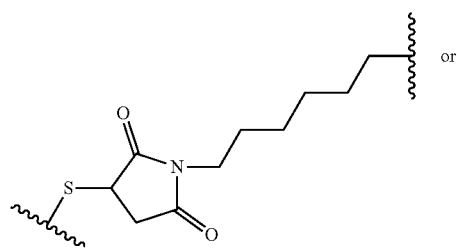

-continued

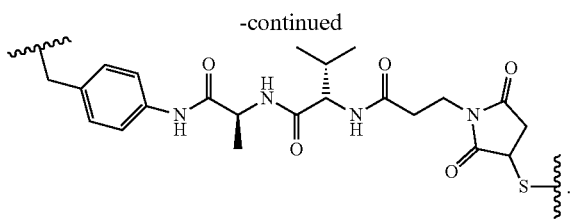
Synthetic methods of making amatoxin are described in U.S. Pat. No. 9,676,702, which is incorporated by reference herein.

Antibodies, and antigen-binding fragments, for use with the compositions and methods described herein can be conjugated to an amatoxin, such as α-amanitin or a variant thereof, using conjugation techniques known in the art or described herein. For instance, antibodies, and antigen-binding fragments thereof, that recognize and bind CD117 (such as GNNK+ CD117) can be conjugated to an amatoxin, such as α-amanitin or a variant thereof, as described in US 2015/0218220, the disclosure of which is incorporated herein by reference as it pertains, for example, to amatoxins, such as α-amanitin and variants thereof, as well as covalent linkers that can be used for covalent conjugation.

Exemplary antibody-drug conjugates useful in conjunction with the methods described herein may be formed by the reaction of an antibody, or antigen-binding fragment thereof, with an amatoxin that is conjugated to a linker containing a substituent suitable for reaction with a reactive residue on the antibody, or antigen-binding fragment thereof. Amatoxins that are conjugated to a linker containing a substituent suitable for reaction with a reactive residue on the antibody, or antigen-binding fragment thereof, described herein include, without limitation, 7'C-(4-(6-(maleimido)hexanoyl)piperazin-1-yl)-amatoxin; 7'C-(4-(6-(maleimido)hexanamido)piperidin-1-yl)-amatoxin; 7'C-(4-(6-(6-(maleimido)hexanamido)hexanoyl)piperazin-1-yl)-amatoxin; 7'C-(4-(4-((maleimido)methyl)cyclohexanecarbonyl)piperazin-1-yl)-amatoxin; 7'C-(4-(6-(4-((maleimido)methyl)cyclohexanecarboxamido)hexanoyl)piperazin-1-yl)-amatoxin; 7'C-(4-(2-(6-(maleimido)hexanamido)ethyl)piperidin-1-yl)-amatoxin; 7'C-(4-(2-(6-(6-(maleimido)hexanamido)hexanamido)ethyl)piperidin-1-yl)-amatoxin; 7'C-(4-(2-(4-((maleimido)methyl)cyclohexanecarboxamido)ethyl)piperidin-1-yl)-amatoxin; 7'C-(4-(2-(6-(4-((maleimido)methyl)cyclohexanecarboxamido)hexanamido)ethyl)piperidin-1-yl)-amatoxin; 7'C-(4-(2-(3-carboxypropanamido)ethyl)piperidin-1-yl)-amatoxin; 7'C-(4-(2-(2-bromoacetamido)ethyl)piperidin-1-yl)-amatoxin; 7'C-(4-(2-(3-(pyridin-2-yldisulfanyl)propanamido)ethyl)piperidin-1-yl)-amatoxin; 7'C-(4-(2-(4-(maleimido)butanamido)ethyl)piperidin-1-yl)-amatoxin; 7'C-(4-(2-(maleimido)acetyl)piperazin-1-yl)-amatoxin; 7'C-(4-(3-(maleimido)propanoyl)piperazin-1-yl)-amatoxin; 7'C-(4-(4-(maleimido)butanoyl)piperazin-1-yl)-amatoxin; 7'C-(4-(2-(6-(4-((maleimido)methyl)cyclohexanecarboxamido)hexanamido)ethyl)piperidin-1-yl)-amatoxin; 7'C-(3-((6-(maleimido)hexanamido)methyl)pyrrolidin-1-yl)-amatoxin; 7'C-(3-((6-(6-(maleimido)hexanamido)hexanamido)methyl)pyrrolidin-1-yl)-amatoxin; 7'C-(3-((4-((maleimido)methyl)cyclohexanecarboxamido)methyl)pyrrolidin-1-yl)-amatoxin; 7'C-(3-((6-((4-(maleimido)methyl)cyclohexanecarboxamido)hexanamido)methyl)pyrrolidin-1-yl)-amatoxin; 7'C-(4-(2-(6-(2-(aminooxy)acetamido)hexanamido)ethyl)piperidin-1-yl)-amatoxin; 7'C-(4-(2-(4-(2-(aminooxy)acetamido)butanamido)ethyl)piperidin-1-yl)-amatoxin; 7'C-(4-(4-(2-(aminooxy)acetamido)butanoyl)piperazin-1-yl)-amatoxin; 7'C-(4-(6-(2-(aminooxy)acetamido)hexanoyl)piperazin-1-yl)-amatoxin; 7'C-((4-(6-(maleimido)hexanamido)piperidin-1-yl)methyl)-amatoxin; 7'C-((4-(2-(6-(maleimido)hexanamido)ethyl)piperidin-1-yl)methyl)-amatoxin; 7'C-((4-(6-(maleimido)hexanoyl)piperazin-1-yl)methyl)-amatoxin; (R)-7'C-((3-((6-(maleimido)hexanamido)methyl)pyrrolidin-1-yl)methyl)-amatoxin; (S)-7'C-((3-((6-(maleimido)hexanamido)methyl)pyrrolidin-1-yl)methyl)-amatoxin; 7'C-((4-(2-(6-(6-(maleimido)hexanamido)hexanamido)ethyl)piperidin-1-yl)methyl)-amatoxin; 7'C-((4-(2-(4-((maleimido)methyl)cyclohexanecarboxamido)ethyl)piperidin-1-yl)methyl)-amatoxin; 7'C-((4-(2-(6-(4-((maleimido)methyl)cyclohexanecarboxamido)hexanamido)ethyl)piperidin-1-yl)methyl)-amatoxin; 7'C-((4-(2-(6-(maleimido)hexanamido)ethyl)piperazin-1-yl)methyl)-amatoxin; 7'C-((4-(2-(6-(6-(maleimido)hexanamido)hexanamido)ethyl)piperazin-1-yl)methyl)-amatoxin; 7'C-((4-(2-(4-((maleimido)methyl)cyclohexanecarboxamido)ethyl)piperazin-1-yl)methyl)-amatoxin; 7'C-((4-(2-(6-(4-((maleimido)methyl)cyclohexanecarboxamido)hexanamido)ethyl)piperazin-1-yl)methyl)-amatoxin; 7'C-((3-((6-(6-(maleimido)hexanamido)hexanamido)-S-methyl)pyrrolidin-1-yl)methyl)-amatoxin; 7'C-((3-((6-(6-(maleimido)hexanamido)hexanamido)-R-methyl)pyrrolidin-1-yl)methyl)-amatoxin; 7'C-((3-((4-((maleimido)methyl)cyclohexanecarboxamido)-S-methyl)pyrrolidin-1-yl)methyl)-amatoxin; 7'C-((3-((4-((maleimido)methyl)cyclohexanecarboxamido)-R-methyl)pyrrolidin-1-yl)methyl)-amatoxin; 7'C-((3-((6-(4-((maleimido)methyl)cyclohexanecarboxamido)hexanamido)methyl)pyrrolidin-1-yl)methyl)-amatoxin; 7'C-((4-(2-(3-carboxypropanamido)ethyl)piperazin-1-yl)methyl)-amatoxin; 7'C-((4-(6-(6-(maleimido)hexanamido)hexanoyl)piperazin-1-yl)methyl)-amatoxin; 7'C-((4-(6-(4-((maleimido)methyl)cyclohexanecarboxamido)hexanoyl)piperazin-1-yl)methyl)-amatoxin; 7'C-((4-(2-(maleimido)acetyl)piperazin-1-yl)methyl)-amatoxin; 7'C-((4-(3-(maleimido)propanoyl)piperazin-1-yl)methyl)-amatoxin; 7'C-((4-(4-(maleimido)butanoyl)piperazin-1-yl)methyl)-amatoxin; 7'C-((4-(2-(2-(maleimido)acetamido)ethyl)piperidin-1-yl)methyl)-amatoxin; 7'C-((4-(2-(4-(maleimido)butanamido)ethyl)piperidin-1-yl)methyl)-amatoxin; 7'C-((4-(2-(6-(4-((maleimido)methyl)cyclohexanecarboxamido)hexanamido)ethyl)piperidin-1-yl)methyl)-amatoxin; 7'C-((3-((6-(maleimido)hexanamido)methyl)azetidin-1-yl)methyl)-amatoxin; 7'C-((3-(2-(6-(maleimido)hexanamido)ethyl)azetidin-1-yl)methyl)-amatoxin; 7'C-((3-((4-((maleimido)methyl)cyclohexanecarboxamido)methyl)azetidin-1-yl)methyl)-amatoxin; 7'C-((3-(2-(4-((maleimido)methyl)cyclohexanecarboxamido)ethyl)azetidin-1yl)methyl)-amatoxin; 7'C-((3-(2-(6-(4-((maleimido)methyl)cyclohexanecarboxamido)hexanamido)ethyl)azetidin-1-yl)methyl)-amatoxin; 7'C-(((2-(6-(maleimido)-N-methylhexanamido)ethyl)(methyl)amino)methyl)-amatoxin; 7'C-(((4-(6-(maleimido)-N-methylhexanamido)butyl(methyl)amino)methyl)-amatoxin; 7'C-((2-(2-(6-(maleimido)hexanamido)ethyl)aziridin-1-yl)methyl)-amatoxin; 7'C-((2-(2-(6-(4-((maleimido)methyl)cyclohexanecarboxamido)hexanamido)ethyl)aziridin-1-yl)methyl)-amatoxin; 7'C-((4-(6-(6-(2-(aminooxy)acetamido)hexanamido)hexanoyl)piperazin-1-yl)methyl)-amatoxin; 7'C-((4-(1-(aminooxy)-2-oxo-6,9,12,15-tetraoxa-3-azaheptadecan-17-oyl)piperazin-1-yl)methyl)-amatoxin; 7'C-((4-(2-(2-(aminooxy)acetamido)acetyl)piperazin-1-yl)methyl)-amatoxin; 7'C-((4-(3-(2-(aminooxy)acetamido)propanoyl)piperazin-1-yl)methyl)-amatoxin; 7'C-((4-(4-(2-(aminooxy)

acetamido)butanoyl)piperazin-1-yl)methyl)-amatoxin; 7'C-((4-(2-(6-(2-(aminooxy)acetamido)hexanamido)ethyl) piperidin-1-yl)methyl)-amatoxin; 7'C-((4-(2-(2-(2-(aminooxy)acetamido)acetamido)ethyl)piperidin-1-yl) methyl)-amatoxin; 7'C-((4-(2-(4-(2-(aminooxy)acetamido) butanamido)ethyl)piperidin-1-yl)methyl)-amatoxin; 7'C-((4-(20-(aminooxy)-4,19-dioxo-6,9,12,15-tetraoxa-3,18-diazaeicosyl)piperidin-1-yl)methyl)-amatoxin; 7'C-(((2-(6-(2-(aminooxy)acetamido)-N-methylhexanamido)ethyl) (methyl)amino)methyl)-amatoxin; 7'C-(((4-(6-(2-(aminooxy)acetamido)-N-methylhexanamido)butyl) (methyl)amino)methyl)-amatoxin; 7'C-((3-((6-(4-((maleimido)methyl)cyclohexanecarboxamido) hexanamido)methyl)pyrrolidin-1-yl)-S-methyl)-amatoxin; 7'C-((3-((6-(4-((maleimido)methyl)cyclohexanecarboxamido)hexanamido)-R-methyl)pyrrolidin-1-yl)methyl)-amatoxin; 7'C-((4-(2-(2-bromoacetamido)ethyl)piperazin-1-yl)methyl)-amatoxin; 7'C-((4-(2-(2-bromoacetamido)ethyl) piperidin-1-yl)methyl)-amatoxin; 7'C-((4-(2-(3-(pyridine-2-yldisulfanyl)propanamido)ethyl)piperidin-1-yl)methyl)-amatoxin; 6'O-(6-(6-(maleimido)hexanamido)hexyl)-amatoxin; 6'O-(5-(4-((maleimido)methyl) cyclohexanecarboxamido)pentyl)-amatoxin; 6'O-(2-((6-(maleimido)hexyl)oxy)-2-oxoethyl)-amatoxin; 6'O-((6-(maleimido)hexyl)carbamoyl)-amatoxin; 6'O-((6-(4-((maleimido)methyl)cyclohexanecarboxamido)hexyl) carbamoyl)-amatoxin; 6'O-(6-(2-bromoacetamido)hexyl)-amatoxin; 7'C-(4-(6-(azido)hexanamido)piperidin-1-yl)-amatoxin; 7'C-(4-(hex-5-ynoylamino)piperidin-1-yl)-amatoxin; 7'C-(4-(2-(6-(maleimido)hexanamido)ethyl) piperazin-1-yl)-amatoxin; 7'C-(4-(2-(6-(6-(maleimido) hexanamido)hexanamido)ethyl)piperazin-1-yl)-amatoxin; 6'O-(6-(6-(11,12-didehydro-5,6-dihydro-dibenz[b,f]azocin-5-yl)-6-oxohexanamido)hexyl)-amatoxin; 6'O-(6-(hex-5-ynoylamino)hexyl)-amatoxin; 6'O-(6-(2-(aminooxy)acetylamido)hexyl)-amatoxin; 6'O-((6-aminooxy)hexyl)-amatoxin; and 6'O-(6-(2-iodoacetamido)hexyl)-amatoxin. The foregoing linkers, among others useful in conjunction with the compositions and methods described herein, are described, for example, in US Patent Application Publication No. 2015/0218220, the disclosure of which is incorporated herein by reference in its entirety.

Additional cytotoxins that can be conjugated to antibodies, or antigen-binding fragments thereof, that recognize and bind CD117 (such as GNNK+ CD117 for use in directly treating a cancer, autommine condition, or for conditioning a patient (e.g., a human patient) in preparation for hematopoietic stem cell transplant therapy include, without limitation, 5-ethynyluracil, abiraterone, acylfulvene, adecypenol, adozelesin, aldesleukin, altretamine, ambamustine, amidox, amifostine, aminolevulinic acid, amrubicin, amsacrine, anagrelide, anastrozole, andrographolide, angiogenesis inhibitors, antarelix, anti-dorsalizing morphogenetic protein-1, antiandrogen, prostatic carcinoma, antiestrogen, antineoplaston, antisense oligonucleotides, aphidicolin glycinate, apoptosis gene modulators, apoptosis regulators, apurinic acid, asulacrine, atamestane, atrimustine, axinastatin 1, axinastatin 2, axinastatin 3, azasetron, azatoxin, azatyrosine, baccatin III derivatives, balanol, batimastat, BCR/ABL antagonists, benzochlorins, benzoylstaurosporine, beta lactam derivatives, beta-alethine, betaclamycin B, betulinic acid, bFGF inhibitors, bicalutamide, bisantrene, bisaziridinylspermine, bisnafide, bistratene A, bizelesin, breflate, bleomycin A2, bleomycin B2, bropirimine, budotitane, buthionine sulfoximine, calcipotriol, calphostin C, camptothecin derivatives (e.g., 10-hydroxy-camptothecin), capecitabine, carboxamide-amino-triazole, carboxyamidotriazole, carzelesin, casein kinase inhibitors, castanospermine, cecropin B, cetrorelix, chlorins, chloroquinoxaline sulfonamide, cicaprost, cis-porphyrin, cladribine, clomifene and analogues thereof, clotrimazole, collismycin A, collismycin B, combretastatin A4, combretastatin analogues, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, 2'deoxycoformycin (DCF), deslorelin, dexifosfamide, dexrazoxane, dexverapamil, diaziquone, didemnin B, didox, diethylnorspermine, dihydro-5-azacytidine, dihydrotaxol, dioxamycin, diphenyl spiromustine, discodermolide, docosanol, dolasetron, doxifluridine, droloxifene, dronabinol, duocarmycin SA, ebselen, ecomustine, edelfosine, edrecolomab, eflornithine, elemene, emitefur, epothilones, epithilones, epristeride, estramustine and analogues thereof, etoposide, etoposide 4'-phosphate (also referred to as etopofos), exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, ganirelix, gelatinase inhibitors, gemcitabine, glutathione inhibitors, hepsulfam, homoharringtonine (HHT), hypericin, ibandronic acid, idoxifene, idramantone, ilmofosine, ilomastat, imidazoacridones, imiquimod, immunostimulant peptides, iobenguane, iododoxorubicin, ipomeanol, irinotecan, iroplact, irsogladine, isobengazole, jasplakinolide, kahalalide F, lamellarin-N triacetate, lanreotide, leinamycin, lenograstim, lentinan sulfate, leptolstatin, letrozole, lipophilic platinum compounds, lissoclinamide 7, lobaplatin, lometrexol, lonidamine, losoxantrone, loxoribine, lurtotecan, lutetium texaphyrin, lysofylline, masoprocol, maspin, matrix metalloproteinase inhibitors, menogaril, rnerbarone, meterelin, methioninase, metoclopramide, MIF inhibitor, ifepristone, miltefosine, mirimostim, mithracin, mitoguazone, mitolactol, mitomycin and analogues thereof, mitonafide, mitoxantrone, mofarotene, molgramostim, mycaperoxide B, myriaporone, N-acetyldinaline, N-substituted benzamides, nafarelin, nagrestip, napavin, naphterpin, nartograstim, nedaplatin, nemorubicin, neridronic acid, nilutamide, nisamycin, nitrullyn, octreotide, okicenone, onapristone, ondansetron, oracin, ormaplatin, oxaliplatin, oxaunomycin, paclitaxel and analogues thereof, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, phenazinomycin, picibanil, pirarubicin, piritrexim, podophyllotoxin, porfiromycin, purine nucleoside phosphorylase inhibitors, raltitrexed, rhizoxin, rogletimide, rohitukine, rubiginone B1, ruboxyl, safingol, saintopin, sarcophytol A, sargramostim, sobuzoxane, sonermin, sparfosic acid, spicamycin D, spiromustine, stipiamide, sulfinosine, tallimustine, tegafur, temozolomide, teniposide, thaliblastine, thiocoraline, tirapazamine, topotecan, topsentin, triciribine, trimetrexate, veramine, vinorelbine, vinxaltine, vorozole, zeniplatin, and zilascorb, among others.

Linkers for Chemical Conjugation

A variety of linkers can be used to conjugate antibodies, or antigen-binding fragments, described herein (e.g., antibodies, or antigen-binding fragments thereof, that recognize and bind CD117 (such as GNNK+ CD117) with a cytotoxic molecule.

The term "Linker" as used herein means a divalent chemical moiety comprising a covalent bond or a chain of atoms that covalently attaches an antibody or fragment thereof (Ab) to a drug moiety (D) to form antibody-drug conjugates of the present disclosure (ADCs; Ab-Z-L-Cytotoxin). Suitable linkers have two reactive termini, one for conjugation to an antibody and the other for conjugation to a cytotoxin. The antibody conjugation reactive terminus of the linker (reactive moiety, Z') is typically a site that is capable of conjugation to the antibody through a cysteine thiol or lysine amine group on the antibody, and so is typically a thiol-reactive group such as a double bond (as in maleimide) or a leaving group such as a chloro, bromo, iodo, or an R-sulfanyl group, or an amine-reactive group such as a carboxyl group; while the antibody conjugation reactive terminus of the linker is typically a site that is capable of conjugation to the cytotoxin through formation of an amide bond with a basic amine or carboxyl group on the cytotoxin, and so is typically a carboxyl or basic amine group. When the term "linker" is used in describing the linker in conjugated form, one or both of the reactive termini will be absent (such as reactive moiety Z, having been converted to chemical moiety Z) or incomplete (such as being only the carbonyl of the carboxylic acid) because of the formation of the bonds between the linker and/or the cytotoxin, and between the linker and/or the antibody or antigen-binding fragment thereof. Such conjugation reactions are described further herein below.

In some embodiments, the linker is cleavable under intracellular conditions, such that cleavage of the linker releases the drug unit from the antibody in the intracellular environment. In yet other embodiments, the linker unit is not cleavable and the drug is released, for example, by antibody degradation. The linkers useful for the present ADCs are preferably stable extracellularly, prevent aggregation of ADC molecules and keep the ADC freely soluble in aqueous media and in a monomeric state. Before transport or delivery into a cell, the ADC is preferably stable and remains intact, i.e. the antibody remains linked to the drug moiety. The linkers are stable outside the target cell and may be cleaved at some efficacious rate inside the cell. An effective linker will: (i) maintain the specific binding properties of the antibody; (ii) allow intracellular delivery of the conjugate or drug moiety; (iii) remain stable and intact, i.e. not cleaved, until the conjugate has been delivered or transported to its targeted site; and (iv) maintain a cytotoxic, cell-killing effect or a cytostatic effect of the cytotoxic moiety. Stability of the ADC may be measured by standard analytical techniques such as mass spectroscopy, HPLC, and the separation/analysis technique LC/MS. Covalent attachment of the antibody and the drug moiety requires the linker to have two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known, and methods have been described their resulting conjugates (Hermanson, G. T. (1996) Bioconjugate Techniques; Academic Press: New York, p. 234-242).

Linkers include those that may be cleaved, for instance, by enzymatic hydrolysis, photolysis, hydrolysis under acidic conditions, hydrolysis under basic conditions, oxidation, disulfide reduction, nucleophilic cleavage, or organometallic cleavage (see, for example, Leriche et al., Bioorg. Med. Chem., 20:571-582, 2012, the disclosure of which is incorporated herein by reference as it pertains to linkers suitable for covalent conjugation).

Linkers hydrolyzable under acidic conditions include, for example, hydrazones, semicarbazones, thiosemicarbazones, cis-aconitic amides, orthoesters, acetals, ketals, or the like. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661, the disclosure of each of which is incorporated herein by reference in its entirety as it pertains to linkers suitable for covalent conjugation. Such linkers are relatively stable under neutral pH conditions, such as those in the blood, but are unstable at below pH 5.5 or 5.0, the approximate pH of the lysosome.

Linkers cleavable under reducing conditions include, for example, a disulfide. A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene), SPDB and SMPT (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935, the disclosure of each of which is incorporated herein by reference in its entirety as it pertains to linkers suitable for covalent conjugation Additional linkers suitable for the synthesis of drug-antibody conjugates as described herein include those capable of releasing a cytotoxin by a 1,6-elimination process (a "self-immolative" group), such as p-aminobenzyl alcohol (PABC), p-aminobenzyl (PAB), 6-maleimidohexanoic acid, pH-sensitive carbonates, and other reagents described in Jain et al., Pharm. Res. 32:3526-3540, 2015, the disclosure of which is incorporated herein by reference in its entirety.

In some embodiments, the linker includes a self-immolative group such as the afore-mentioned PAB or PABC (para-aminobenzyloxycarbonyl), which are disclosed in, for example, Carl et al., J. Med. Chem. (1981) 24:479-480; Chakravarty et al (1983) J. Med. Chem. 26:638-644; U.S. Pat. No. 6,214,345; US20030130189; US20030096743; U.S. Pat. No. 6,759,509; US20040052793; U.S. Pat. Nos. 6,218,519; 6,835,807; 6,268,488; US20040018194; WO98/13059; US20040052793; U.S. Pat. Nos. 6,677,435; 5,621,002; US20040121940; WO2004/032828). Other such chemical moieties capable of this process ("self-immolative linkers") include methylene carbamates and heteroaryl groups such as aminothiazoles, aminoimidazoles, aminopyrimidines, and the like. Linkers containing such heterocyclic self-immolative groups are disclosed in, for example, U.S. Patent Publication Nos. 20160303254 and 20150079114, and U.S. Pat. No. 7,754,681; Hay et al. (1999) Bioorg. Med. Chem. Lett. 9:2237; US 2005/0256030; de Groot et al (2001) J. Org. Chem. 66:8815-8830; and U.S. Pat. No. 7,223,837.

Linkers susceptible to enzymatic hydrolysis can be, e.g., a peptide-containing linker that is cleaved by an intracellular peptidase or protease enzyme, including, but not limited to, a lysosomal or endosomal protease. One advantage of using intracellular proteolytic release of the therapeutic agent is that the agent is typically attenuated when conjugated and the serum stabilities of the conjugates are typically high. In some embodiments, the peptidyl linker is at least two amino acids long or at least three amino acids long. Exemplary amino acid linkers include a dipeptide, a tripeptide, a tetrapeptide or a pentapeptide. Examples of suitable peptides include those containing amino acids such as Valine, Alanine, Citrulline (Cit), Phenylalanine, Lysine, Leucine, and Glycine. Amino acid residues which comprise an amino acid linker component include those occurring naturally, as well as minor amino acids and non-naturally occurring amino acid analogs, such as citrulline. Exemplary dipeptides include valine-citrulline (vc or val-cit) and alanine-phenylalanine (af or ala-phe). Exemplary tripeptides include glycine-valine-citrulline (gly-val-cit) and glycine-glycine-glycine (gly-gly-gly). In some embodiments, the linker includes a dipeptide such as Val-Cit, Ala-Val, or Phe-Lys, Val-Lys, Ala-Lys, Phe-Cit, Leu-Cit, Ile-Cit, Phe-Arg, or Trp-Cit. Linkers containing dipeptides such as Val-Cit or Phe-Lys are disclosed in, for example, U.S. Pat. No. 6,214,345, the disclosure of which is incorporated herein by reference in its entirety as it pertains to linkers suitable for covalent conjugation. In some embodiments, the linker includes a dipeptide selected from Val-Ala and Val-Cit. In some embodiments, a dipeptide is used in combination with a self-immolative linker.

Linkers suitable for use herein further may include one or more groups selected from $C_1$-$C_6$ alkylene, $C_1$-$C_6$ heteroalkylene, $C_2$-$C_6$ alkenylene, $C_2$-$C_6$ heteroalkenylene, $C_2$-$C_6$ alkynylene, $C_2$-$C_6$ heteroalkynylene, $C_3$-$C_6$ cycloalkylene, heterocycloalkylene, arylene, heteroarylene, and combinations thereof, each of which may be optionally substituted. Non-limiting examples of such groups include $(CH_2)_n$, $(CH_2CH_2O)_n$, and —(C=O)$(CH_2)_n$— units, wherein n is an integer from 1-6, independently selected for each occasion.

In some embodiments, the linker may include one or more of a hydrazine, a disulfide, a thioether, a dipeptide, a p-aminobenzyl (PAB) group, a heterocyclic self-immolative group, an optionally substituted $C_1$-$C_6$ alkyl, an optionally substituted $C_1$-$C_6$ heteroalkyl, an optionally substituted $C_2$-$C_6$ alkenyl, an optionally substituted $C_2$-$C_6$ heteroalkenyl, an optionally substituted $C_2$-$C_6$ alkynyl, an optionally substituted $C_2$-$C_6$ heteroalkynyl, an optionally substituted $C_3$-$C_6$ cycloalkyl, an optionally substituted heterocycloalkyl, an optionally substituted aryl, an optionally substituted heteroaryl, a solubility enhancing group, acyl, —(C=O)—, or —$(CH_2CH_2O)_n$— group, wherein n is an integer from 1-6. One of skill in the art will recognize that one or more of the groups listed may be present in the form of a bivalent (diradical) species, e.g., $C_1$-$C_6$ alkylene and the like.

In some embodiments, the linker includes a p-aminobenzyl group (PAB). In one embodiment, the p-aminobenzyl group is disposed between the cytotoxic drug and a protease cleavage site in the linker. In one embodiment, the p-aminobenzyl group is part of a p-aminobenzyloxycarbonyl unit. In one embodiment, the p-aminobenzyl group is part of a p-aminobenzylamido unit.

In some embodiments, the linker comprises PAB, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB.

In some embodiments, the linker comprises a combination of one or more of a peptide, oligosaccharide, —$(CH_2)_n$—, —$(CH_2CH_2O)_n$—, PAB, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB.

In some embodiments, the linker comprises a —(C=O)$(CH_2)_n$— unit, wherein n is an integer from 1-6.

Linkers that can be used to conjugate an antibody, or antigen-binding fragment thereof, to a cytotoxic agent include those that are covalently bound to the cytotoxic agent on one end of the linker and, on the other end of the linker, contain a chemical moiety formed from a coupling reaction between a reactive substituent present on the linker and a reactive substituent present within the antibody, or antigen-binding fragment thereof, that binds CD117 (such as GNNK+ CD117). Reactive substituents that may be present within an antibody, or antigen-binding fragment thereof, that binds CD117 (such as GNNK+ CD117) include, without limitation, hydroxyl moieties of serine, threonine, and tyrosine residues; amino moieties of lysine residues; carboxyl moieties of aspartic acid and glutamic acid residues; and thiol moieties of cysteine residues, as well as propargyl, azido, haloaryl (e.g., fluoroaryl), haloheteroaryl (e.g., fluoroheteroaryl), haloalkyl, and haloheteroalkyl moieties of non-naturally occurring amino acids.

Examples of linkers useful for the synthesis of drug-antibody conjugates include those that contain electrophiles, such as Michael acceptors (e.g., maleimides), activated esters, electron-deficient carbonyl compounds, and aldehydes, among others, suitable for reaction with nucleophilic substituents present within antibodies or antigen-binding fragments, such as amine and thiol moieties. For instance, linkers suitable for the synthesis of drug-antibody conjugates include, without limitation, succinimidyl 4-(N-maleimidomethyl)-cyclohexane-L-carboxylate (SMCC), N-succinimidyl iodoacetate (SIA), sulfo-SMCC, m-maleimidobenzoyl-N-hydroxysuccinimidyl ester (MBS), sulfo-MBS, and succinimidyl iodoacetate, among others described, for instance, Liu et al., 18:690-697, 1979, the disclosure of which is incorporated herein by reference as it pertains to linkers for chemical conjugation. Additional linkers include the non-cleavable maleimidocaproyl linkers, which are particularly useful for the conjugation of microtubule-disrupting agents such as auristatins, are described by Doronina et al., Bioconjugate Chem. 17:14-24, 2006, the disclosure of which is incorporated herein by reference as it pertains to linkers for chemical conjugation.

It will be recognized by one of skill in the art that any one or more of the chemical groups, moieties and features disclosed herein may be combined in multiple ways to form linkers useful for conjugation of the antibodies and cytotoxins as disclosed herein. Further linkers useful in conjunction with the compositions and methods described herein, are described, for example, in U.S. Patent Application Publication No. 2015/0218220, the disclosure of which is incorporated herein by reference in its entirety.

Linkers useful in conjunction with the antibody-drug described herein include, without limitation, linkers containing chemical moieties formed by coupling reactions as depicted in Table 1, below. Curved lines designate points of attachment to the antibody, or antigen-binding fragment, and the cytotoxic molecule, respectively.

TABLE 1

Exemplary chemical moieties formed by coupling reactions in the formation of antibody-drug

| Exemplary Coupling Reactions | Chemical Moiety Z Formed by Coupling Reactions |
|---|---|
| [3 + 2] Cycloaddition | 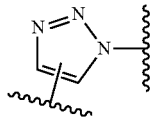 |
| [3 + 2] Cycloaddition | 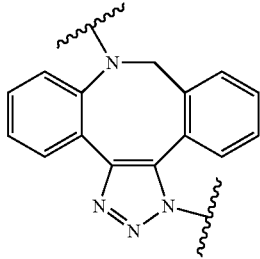 [SMILES: *N1Cc2ccccc2-c2c(nnn2*)-c2ccccc21] |
| [3 + 2] Cycloaddition, Esterification | 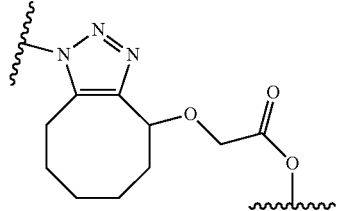 [SMILES: *OC(=O)COC1CCCCCc2c1nnn2*] |
| [3 + 2] Cycloaddition, Esterification | 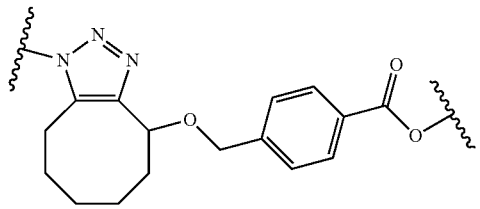 [SMILES: *OC(=O)c1ccc(COC2CCCCCc3c2nnn3*)cc1] |
| [3 + 2] Cycloaddition, Esterification | 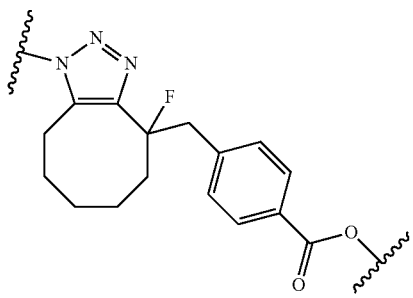 [SMILES: *OC(=O)c1ccc(CC2(F)CCCCCc3c2nnn3*)cc1] |

TABLE 1-continued

Exemplary chemical moieties formed by coupling reactions in the formation of antibody-drug

| Exemplary Coupling Reactions | Chemical Moiety Z Formed by Coupling Reactions |
|---|---|
| [3 + 2] Cycloaddition, Esterification | |
| [3 + 2] Cycloaddition, Esterification | |
| [3 + 2] Cycloaddition, Esterification | |
| [3 + 2] Cycloaddition, Esterification | |
| [3 + 2] Cycloaddition, Esterification | |

TABLE 1-continued
Exemplary chemical moieties formed by coupling reactions in the formation of antibody-drug
| Exemplary Coupling Reactions | Chemical Moiety Z Formed by Coupling Reactions |
|---|---|
| [3 + 2] Cycloaddition, Esterification | 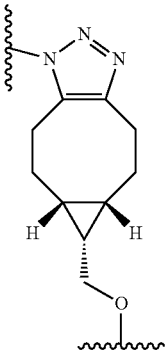 [SMILES: *OC[C@@H]1[C@@H]2CCc3c(nnn3*)CC[C@@H]21] |
| [3 + 2] Cycloaddition, Esterification | 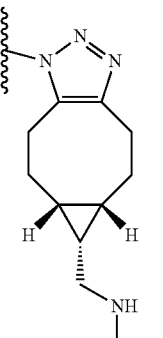 |
| [3 + 2] Cycloaddition, Esterification | 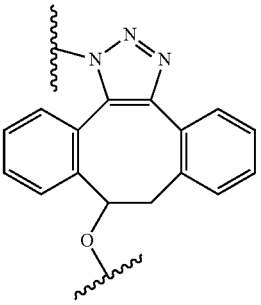 [SMILES: *OC1Cc2ccccc2-c2nnn(*)c2-c2ccccc21] |
| [3 + 2] Cycloaddition, Etherification | 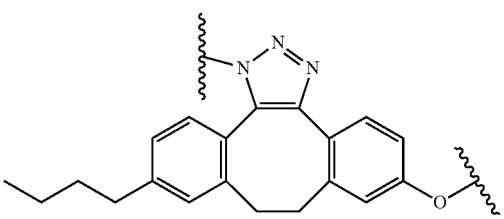 [SMILES: *Oc1ccc2c(c1)CCc1cc(CCCC)ccc1-c1c-2nnn1*] |
| [3 + 2] Cycloaddition | 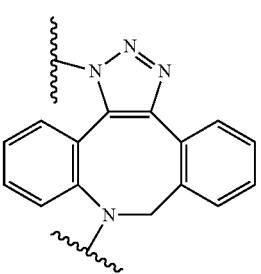 [SMILES: *N1Cc2ccccc2-c2nnn(*)c2-c2ccccc21] |

TABLE 1-continued

Exemplary chemical moieties formed by coupling reactions in the formation of antibody-drug

| Exemplary Coupling Reactions | Chemical Moiety Z Formed by Coupling Reactions |
|---|---|
| Michael addition | [structure] |
| Michael addition | [structure] |
| Imine condensation, Amidation | [structure] |
| Imine condensation | [structure] |
| Disulfide formation | [structure] |
| Thiol alkylation | [structure] |
| Condensation, Michael addition | [structure] |

One of skill in the art will recognize that a reactive substituent Z attached to the linker and a reactive substituent on the antibody or antigen-binding fragment thereof, are engaged in the covalent coupling reaction to produce the chemical moiety Z, and will recognize the reactive substituent Z. Therefore, antibody-drug conjugates useful in conjunction with the methods described herein may be formed by the reaction of an antibody, or antigen-binding fragment thereof, with a linker or cytotoxin-linker conjugate, as described herein, the linker or cytotoxin-linker conjugate including a reactive substituent Z, suitable for reaction with a reactive substituent on the antibody, or antigen-binding fragment thereof, to form the chemical moiety Z.

As depicted in Table 1, examples of suitably reactive substituents on the linker and antibody or antigen-binding fragment thereof include a nucleophile/electrophile pair (e.g., a thiol/haloalkyl pair, an amine/carbonyl pair, or a thiol/α,β-unsaturated carbonyl pair, and the like), a diene/dienophile pair (e.g., an azide/alkyne pair, or a diene/α,β-unsaturated carbonyl pair, among others), and the like. Coupling reactions between the reactive substituents to form the chemical moiety Z include, without limitation, thiol alkylation, hydroxyl alkylation, amine alkylation, amine or hydroxylamine condensation, hydrazine formation, amidation, esterification, disulfide formation, cycloaddition (e.g., [4+2] Diels-Alder cycloaddition, [3+2] Huisgen cycloaddition, among others), nucleophilic aromatic substitution, electrophilic aromatic substitution, and other reactive modalities known in the art or described herein. Preferably, the linker contains an electrophilic functional group for reaction with a nucleophilic functional group on the antibody, or antigen-binding fragment thereof.

Reactive substituents that may be present within an antibody, or antigen-binding fragment thereof, as disclosed herein include, without limitation, nucleophilic groups such as (i)N-terminal amine groups, (ii) side chain amine groups, e.g. lysine, (iii) side chain thiol groups, e.g. cysteine, and (iv) sugar hydroxyl or amino groups where the antibody is glycosylated. Reactive substituents that may be present within an antibody, or antigen-binding fragment thereof, as disclosed herein include, without limitation, hydroxyl moieties of serine, threonine, and tyrosine residues; amino moieties of lysine residues; carboxyl moieties of aspartic acid and glutamic acid residues; and thiol moieties of cysteine residues, as well as propargyl, azido, haloaryl (e.g., fluoroaryl), haloheteroaryl (e.g., fluoroheteroaryl), haloalkyl, and haloheteroalkyl moieties of non-naturally occurring amino acids. In some embodiments, the reactive substituents present within an antibody, or antigen-binding fragment thereof as disclosed herein include, are amine or thiol moieties. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues). U.S. Pat. No. 7,521,541 teaches engineering antibodies by introduction of reactive cysteine amino acids.

In some embodiments, the reactive moiety Z attached to the linker is a nucleophilic group which is reactive with an electrophilic group present on an antibody. Useful electrophilic groups on an antibody include, but are not limited to, aldehyde and ketone carbonyl groups. The heteroatom of a nucleophilic group can react with an electrophilic group on an antibody and form a covalent bond to the antibody. Useful nucleophilic groups include, but are not limited to, hydrazide, oxime, amino, hydroxyl, hydrazine, thiosemicarbazone, hydrazine carboxylate, and arylhydrazide.

In some embodiments, Z is the product of a reaction between reactive nucleophilic substituents present within the antibodies, or antigen-binding fragments thereof, such as amine and thiol moieties, and a reactive electrophilic substituent Z. For instance, Z may be a Michael acceptor (e.g., maleimide), activated ester, electron-deficient carbonyl compound, or an aldehyde, among others.

In some embodiments, the ADC comprises an anti-CD117 antibody conjugated to an amatoxin of any of formulae I, IA, IB, II, IIA, or IIB as disclosed herein via la inker and a chemical moiety Z. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$— unit, wherein n is an integer from 1-6. In some embodiments, the linker is -PAB-Cit-Val-((C=O)(CH$_2$)$_n$ In some embodiments, the linker includes a —(CH$_2$)$_n$— unit, where n is an integer from 2-6. In some embodiments, the linker is -PAB-Cit-Val-((C=O)(CH$_2$)$_n$—. In some embodiments, the linker is -PAB-Ala-Val-((C=O)(CH$_2$)$_n$—. In some embodiments, the linker is —(CH$_2$)$_n$— wherein n is an integer from 2-6. In some embodiments, the linker is —(CH$_2$)$_n$—, wherein n is 6.

In some embodiments, the chemical moiety Z is selected from Table 1. In some embodiments, the chemical moiety Z is

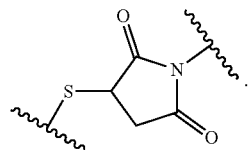

where S is a sulfur atom which represents the reactive substituent present within an antibody, or antigen-binding fragment thereof, that binds CD117 (e.g., from the —SH group of a cysteine residue).

In some embodiments, the linker L and the chemical moiety Z, taken together as

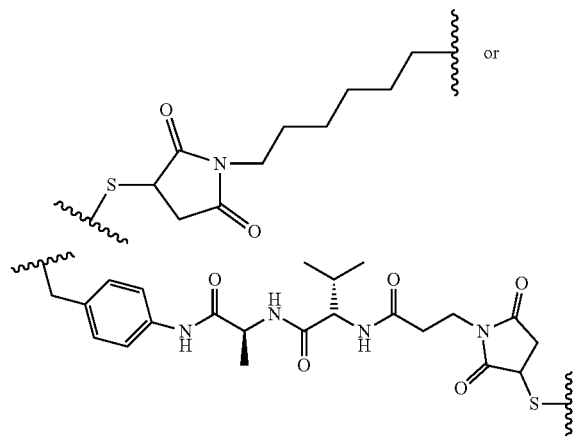

L-Z, is

In some embodiments, L-Z is

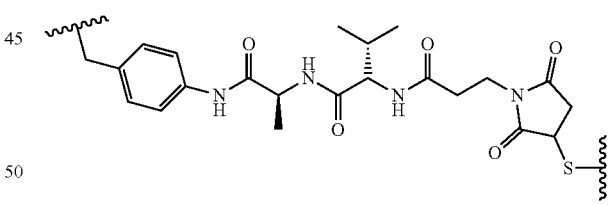

In some embodiments, L-Z is

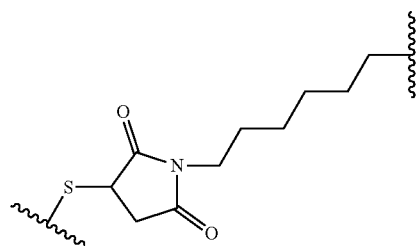 [SMILES: *CCCCCCN1C(=O)CC(S*)C1=O]

One of skill in the art will recognize the linker-reactive substituent group structure, prior to conjugation with the antibody or antigen binding fragment thereof, as including as the group Z a maleimide. The foregoing linker moieties and amatoxin-linker conjugates, among others useful in conjunction with the compositions and methods described herein, are described, for example, in U.S. Patent Application Publication No. 2015/0218220 and Patent Application Publication No. WO2017/149077, the disclosure of each of which is incorporated herein by reference in its entirety.

Preparation of Antibody-Drug Conjugates

In the ADCs of formula I as disclosed herein, an antibody or antigen binding fragment thereof is conjugated to one or more cytotoxic drug moieties (D), e.g. about 1 to about 20 drug moieties per antibody, through a linker L and a chemical moiety Z as disclosed herein. The ADCs of the present disclosure may be prepared by several routes, employing organic chemistry reactions, conditions, and reagents known to those skilled in the art, including: (1) reaction of a reactive substituent of an antibody or antigen binding fragment thereof with a bivalent linker reagent to form Ab-Z-L as described herein above, followed by reaction with a drug moiety D; or (2) reaction of a reactive substituent of a drug moiety with a bivalent linker reagent to form D-L-Z, followed by reaction with a reactive substituent of an antibody or antigen binding fragment thereof as described herein above to form an ADC of formula D-L-Z-Ab, such as Am-Z-L-Ab. Additional methods for preparing ADC are described herein.

In another aspect, the antibody or antigen binding fragment thereof has one or more lysine residues that can be chemically modified to introduce one or more sulfhydryl groups. The ADC is then formed by conjugation through the sulfhydryl group's sulfur atom as described herein above. The reagents that can be used to modify lysine include, but are not limited to, N-succinimidyl S-acetylthioacetate (SATA) and 2-Iminothiolane hydrochloride (Traut's Reagent).

In another aspect, the antibody or antigen binding fragment thereof can have one or more carbohydrate groups that can be chemically modified to have one or more sulfhydryl groups. The ADC is then formed by conjugation through the sulfhydryl group's sulfur atom as described herein above.

In yet another aspect, the antibody can have one or more carbohydrate groups that can be oxidized to provide an aldehyde (—CHO) group (see, for e.g., Laguzza, et al., J. Med. Chem. 1989, 32(3), 548-55). The ADC is then formed by conjugation through the corresponding aldehyde as described herein above. Other protocols for the modification of proteins for the attachment or association of cytotoxins are described in Coligan et al., Current Protocols in Protein Science, vol. 2, John Wiley & Sons (2002), incorporated herein by reference.

Methods for the conjugation of linker-drug moieties to cell-targeted proteins such as antibodies, immunoglobulins or fragments thereof are found, for example, in U.S. Pat. Nos. 5,208,020; 6,441,163; WO2005037992; WO2005081711; and WO2006/034488, all of which are hereby expressly incorporated by reference in their entirety.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

Methods of Treatment

The aforementioned anti-CD117 antibodies or conjugates thereof may be used in the following methods for treatment.

As described herein, hematopoietic stem cell transplant therapy can be administered to a subject in need of treatment so as to populate or re-populate one or more blood cell types. Hematopoietic stem cells generally exhibit multi-potency, and can thus differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells). Hematopoietic stem cells are additionally capable of self-renewal, and can thus give rise to daughter cells that have equivalent potential as the mother cell, and also feature the capacity to be reintroduced into a transplant recipient whereupon they home to the hematopoietic stem cell niche and re-establish productive and sustained hematopoiesis.

Hematopoietic stem cells can thus be administered to a patient defective or deficient in one or more cell types of the hematopoietic lineage in order to re-constitute the defective or deficient population of cells in vivo, thereby treating the pathology associated with the defect or depletion in the endogenous blood cell population. The compositions and methods described herein can thus be used to treat a non-malignant hemoglobinopathy (e.g., a hemoglobinopathy selected from the group consisting of sickle cell anemia, thalassemia, Fanconi anemia, aplastic anemia, and Wiskott-Aldrich syndrome). Additionally or alternatively, the compositions and methods described herein can be used to treat an immunodeficiency, such as a congenital immunodeficiency. Additionally or alternatively, the compositions and methods described herein can be used to treat an acquired immunodeficiency (e.g., an acquired immunodeficiency selected from the group consisting of HIV and AIDS). The compositions and methods described herein can be used to treat a metabolic disorder (e.g., a metabolic disorder selected from the group consisting of glycogen storage diseases, mucopolysaccharidoses, Gaucher's Disease, Hurlers Disease, sphingolipidoses, and metachromatic leukodystrophy).

Additionally or alternatively, the compositions and methods described herein can be used to treat a malignancy or proliferative disorder, such as a hematologic cancer, myeloproliferative disease, in particular the conjugates described herein. In the case of cancer treatment, the compositions and methods described herein may be administered to a patient so as to deplete a population of endogenous hematopoietic stem cells prior to hematopoietic stem cell transplantation therapy, in which case the transplanted cells can home to a niche created by the endogenous cell depletion step and establish productive hematopoiesis. This, in turn, can re-constitute a population of cells depleted during cancer cell eradication, such as during systemic chemotherapy. Exemplary hematological cancers that can be treated using the compositions and methods described herein include, without limitation, acute myeloid leukemia, acute lymphoid leukemia, chronic myeloid leukemia, chronic lymphoid leukemia, multiple myeloma, diffuse large B-cell lymphoma, and non-Hodgkin's lymphoma, as well as other cancerous conditions, including neuroblastoma.

Additional diseases that can be treated with the compositions and methods described herein include, without limitation, adenosine deaminase deficiency and severe combined immunodeficiency, hyper immunoglobulin M syndrome, Chediak-Higashi disease, hereditary lymphohistiocytosis, osteopetrosis, osteogenesis imperfecta, storage diseases, thalassemia major, systemic sclerosis, systemic lupus erythematosus, multiple sclerosis, and juvenile rheumatoid arthritis.

The antibodies, or antigen-binding fragments thereof, and conjugates described herein may be used to induce solid organ transplant tolerance. For instance, the compositions and methods described herein may be used to deplete or ablate a population of cells from a target tissue (e.g., to deplete hematopoietic stem cells from the bone marrow stem cell niche). Following such depletion of cells from the target tissues, a population of stem or progenitor cells from an organ donor (e.g., hematopoietic stem cells from the organ donor) may be administered to the transplant recipient, and following the engraftment of such stem or progenitor cells, a temporary or stable mixed chimerism may be achieved, thereby enabling long-term transplant organ tolerance without the need for further immunosuppressive agents. For example, the compositions and methods described herein may be used to induce transplant tolerance in a solid organ transplant recipient (e.g., a kidney transplant, lung transplant, liver transplant, and heart transplant, among others). The compositions and methods described herein are well-suited for use in connection the induction of solid organ transplant tolerance, for instance, because a low percentage temporary or stable donor engraftment is sufficient to induce long-term tolerance of the transplanted organ.

In addition, the compositions and methods described herein can be used to treat cancers directly, such as cancers characterized by cells that are CD117+. For instance, the compositions and methods described herein can be used to treat leukemia, particularly in patients that exhibit CD117+ leukemic cells. By depleting CD117+ cancerous cells, such as leukemic cells, the compositions and methods described herein can be used to treat various cancers directly. Exemplary cancers that may be treated in this fashion include hematological cancers, such as acute myeloid leukemia, acute lymphoid leukemia, chronic myeloid leukemia, chronic lymphoid leukemia, multiple myeloma, diffuse large B-cell lymphoma, and non-Hodgkin's lymphoma, In addition, the compositions and methods described herein can be used to treat autoimmune disorders. For instance, an antibody, or antigen-binding fragment thereof, can be administered to a subject, such as a human patient suffering from an autoimmune disorder, so as to kill a CD117+ immune cell. The CD117+ immune cell may be an autoreactive lymphocyte, such as a T-cell that expresses a T-cell receptor that specifically binds, and mounts an immune response against, a self-antigen. By depleting self-reactive, CD117+ cells, the compositions and methods described herein can be used to treat autoimmune pathologies, such as those described below. Additionally or alternatively, the compositions and methods described herein can be used to treat an autoimmune disease by depleting a population of endogenous hematopoietic stem cells prior to hematopoietic stem cell transplantation therapy, in which case the transplanted cells can home to a niche created by the endogenous cell depletion step and establish productive hematopoiesis. This, in turn, can re-constitute a population of cells depleted during autoimmune cell eradication.

Autoimmune diseases that can be treated using the compositions and methods described herein include, without limitation, psoriasis, psoriatic arthritis, Type 1 diabetes mellitus (Type 1 diabetes), rheumatoid arthritis (RA), human systemic lupus (SLE), multiple sclerosis (MS), inflammatory bowel disease (IBD), lymphocytic colitis, acute disseminated encephalomyelitis (ADEM), Addison's disease, alopecia universalis, ankylosing spondylitisis, antiphospholipid antibody syndrome (APS), aplastic anemia, autoimmune hemolytic anemia, autoimmune hepatitis, autoimmune inner ear disease (AIED), autoimmune lymphoproliferative syndrome (ALPS), autoimmune oophoritis, Balo disease, Behcet's disease, bullous pemphigoid, cardiomyopathy, Chagas' disease, chronic fatigue immune dysfunction syndrome (CFIDS), chronic inflammatory demyelinating polyneuropathy, Crohn's disease, cicatrical pemphigoid, coeliac sprue-dermatitis herpetiformis, cold agglutinin disease, CREST syndrome, Degos disease, discoid lupus, dysautonomia, endometriosis, essential mixed cryoglobulinemia, fibromyalgia-fibromyositis, Goodpasture's syndrome, Grave's disease, Guillain-Barre syndrome (GBS), Hashimoto's thyroiditis, Hidradenitis suppurativa, idiopathic and/or acute thrombocytopenic purpura, idiopathic pulmonary fibrosis, IgA neuropathy, interstitial cystitis, juvenile arthritis, Kawasaki's disease, lichen planus, Lyme disease, Meniere disease, mixed connective tissue disease (MCTD), myasthenia gravis, neuromyotonia, opsoclonus myoclonus syndrome (OMS), optic neuritis, Ord's thyroiditis, pemphigus vulgaris, pernicious anemia, polychondritis, polymyositis and dermatomyositis, primary biliary cirrhosis, polyarteritis nodosa, polyglandular syndromes, polymyalgia rheumatica, primary agammaglobulinemia, Raynaud phenomenon, Reiter's syndrome, rheumatic fever, sarcoidosis, scleroderma, Sjögren's syndrome, stiff person syndrome, Takayasu's arteritis, temporal arteritis (also known as "giant cell arteritis"), ulcerative colitis, collagenous colitis, uveitis, vasculitis, vitiligo, vulvodynia ("vulvar vestibulitis"), and Wegener's granulomatosis.

Routes of Administration and Dosing

Antibodies, or antigen-binding fragments thereof, described herein can be administered to a patient (e.g., a human patient suffering from cancer, an autoimmune disease, or in need of hematopoietic stem cell transplant therapy) in a variety of dosage forms. For instance, antibodies, or antigen-binding fragments thereof, described herein can be administered to a patient suffering from cancer, an autoimmune disease, or in need of hematopoietic stem cell transplant therapy in the form of an aqueous solution, such as an aqueous solution containing one or more pharmaceutically acceptable excipients. Pharmaceutically acceptable excipients for use with the compositions and methods described herein include viscosity-modifying agents. The aqueous solution may be sterilized using techniques known in the art.

Pharmaceutical formulations comprising anti-CD117 antibodies and ADCs as described herein are prepared by mixing such antibody or ADC with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

The antibodies, and antigen-binding fragments, described herein may be administered by a variety of routes, such as orally, transdermally, subcutaneously, intranasally, intravenously, intramuscularly, intraocularly, or parenterally. The most suitable route for administration in any given case will depend on the particular antibody, or antigen-binding fragment, administered, the patient, pharmaceutical formulation methods, administration methods (e.g., administration time and administration route), the patient's age, body weight, sex, severity of the diseases being treated, the patient's diet, and the patient's excretion rate.

The effective dose of an anti-CD117 conjugate, antibody, or antigen-binding fragment thereof, described herein can range, for example from about 0.001 to about 100 mg/kg of body weight per single (e.g., bolus) administration, multiple administrations, or continuous administration, or to achieve an optimal serum concentration (e.g., a serum concentration of 0.0001-5000 µg/mL) of the antibody, or antigen-binding fragment thereof. The dose may be administered one or more times (e.g., 2-10 times) per day, week, or month to a subject (e.g., a human) suffering from cancer, an autoimmune disease, or undergoing conditioning therapy in preparation for receipt of a hematopoietic stem cell transplant. In the case of a conditioning procedure prior to hematopoietic stem cell transplantation, the antibody, or antigen-binding fragment thereof can be administered to the patient at a time that optimally promotes engraftment of the exogenous hematopoietic stem cells, for instance, from 1 hour to 1 week (e.g., 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, or 7 days) or more prior to administration of the exogenous hematopoietic stem cell transplant.

Using the methods disclosed herein, a physician of skill in the art can administer to a human patient in need of hematopoietic stem cell transplant therapy an anti-CD117 ADC, an antibody or an antigen-binding fragment thereof capable of binding an antigen expressed by hematopoietic stem cells, such as an antibody or antigen-biding fragment thereof that binds CD117 (for example, an antibody or antigen-binding fragment thereof that binds GNNK+ CD117). In this fashion, a population of endogenous hematopoietic stem cells can be depleted prior to administration of an exogenous hematopoietic stem cell graft so as to promote engraftment of the hematopoietic stem cell graft.

As described above, the antibody may be covalently conjugated to a toxin, such as a cytotoxic molecule described herein or known in the art. For instance, an anti-CD117 antibody or antigen-binding fragment thereof (such as an anti-GNNK+ CD117 antibody or antigen-binding fragment thereof) can be covalently conjugated to a cytotoxin, such as *pseudomonas* exotoxin A, deBouganin, diphtheria toxin, an amatoxin, such as γ-amanitin, α-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, an indolinobenzodiazepine dimer, or a variant thereof. This conjugation can be performed using covalent bond-forming techniques described herein or known in the art. The antibody, antigen-binding fragment thereof, or drug-antibody conjugate can subsequently be administered to the patient, for example, by intravenous administration, prior to transplantation of exogenous hematopoietic stem cells (such as autologous, syngeneic, or allogeneic hematopoietic stem cells) to the patient.

The anti-CD117 (e.g., anti-GNNK+ CD117) antibody, antigen-binding fragment thereof, or drug-antibody conjugate can be administered in an amount sufficient to reduce the quantity of endogenous hematopoietic stem cells, for example, by 10%, 20%, 30%, 40%, 50%, 60%, 70%, 80%, 90%, 95%, or more prior to hematopoietic stem cell transplant therapy. The reduction in hematopoietic stem cell count can be monitored using conventional techniques known in the art, such as by FACS analysis of cells expressing characteristic hematopoietic stem cell surface antigens in a blood sample withdrawn from the patient at varying intervals during conditioning therapy. For instance, a physician of skill in the art can withdraw a blood sample from the patient at various time points during conditioning therapy and determine the extent of endogenous hematopoietic stem cell reduction by conducting a FACS analysis to elucidate the relative concentrations of hematopoietic stem cells in the sample using antibodies that bind to hematopoietic stem cell marker antigens. According to some embodiments, when the concentration of hematopoietic stem cells has reached a minimum value in response to conditioning therapy with an anti-CD117 (e.g., anti-GNNK+ CD117) antibody, antigen-binding fragment thereof, or drug-antibody conjugate, the physician may conclude the conditioning therapy, and may begin preparing the patient for hematopoietic stem cell transplant therapy.

The anti-CD117 (e.g., anti-GNNK+ CD117) antibody, antigen-binding fragment thereof, or drug-antibody conjugate can be administered to the patient in an aqueous solution containing one or more pharmaceutically acceptable excipients, such as a viscosity-modifying agent. The aqueous solution may be sterilized using techniques described herein or known in the art. The antibody, antigen-binding fragment thereof, or drug-antibody conjugate can be administered to the patient at a dosage of, for example, from 0.001 mg/kg to 100 mg/kg prior to administration of a hematopoietic stem cell graft to the patient. The antibody, antigen-binding fragment thereof, or drug-antibody conjugate can be administered to the patient at a time that optimally promotes engraftment of the exogenous hematopoietic stem cells, for instance, from 1 hour to 1 week (e.g., 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, or 7 days) or more prior to administration of the exogenous hematopoietic stem cell transplant.

Following the conclusion of conditioning therapy, the patient may then receive an infusion (e.g., an intravenous infusion) of exogenous hematopoietic stem cells, such as from the same physician that performed the conditioning therapy or from a different physician. The physician may administer the patient an infusion of autologous, syngeneic, or allogeneic hematopoietic stem cells, for instance, at a dosage of from $1 \times 10^3$ to $1 \times 10^9$ hematopoietic stem cells/kg. The physician may monitor the engraftment of the hematopoietic stem cell transplant, for example, by withdrawing a blood sample from the patient and determining the increase in concentration of hematopoietic stem cells or cells of the hematopoietic lineage (such as megakaryocytes, thrombocytes, platelets, erythrocytes, mast cells, myeloblasts, basophils, neutrophils, eosinophils, microglia, granulocytes, monocytes, osteoclasts, antigen-presenting cells, macrophages, dendritic cells, natural killer cells, T-lymphocytes, and B-lymphocytes) following administration of the transplant. This analysis may be conducted, for example, from 1 hour to 6 months, or more, following hematopoietic stem cell transplant therapy (e.g., 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, or more). A finding that the concentration of hematopoietic stem cells or cells of the hematopoietic lineage has increased (e.g., by 1%, 2%, 3%, 4%, 5%, 6%, 7%, 8%, 9%, 10%, 20%, 30%, 40%, 50%, 60%, 70%, 80%, 90%, 100%, 200%, 500%, or more) following the transplant therapy relative to the concentration of the corresponding cell type prior to transplant therapy provides one indication that treatment with the anti-CD117 (e.g., anti-GNNK+ CD117) antibody, antigen-binding fragment thereof, or drug-antibody conjugate has successfully promoted engraftment of the transplanted hematopoietic stem cell graft.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regard as their invention.

Example 1. Identification of Antagonist and Neutral Anti-CD117 Antibodies

Yeast Display

A yeast display library that displays antibodies (either natural or synthetic) was screened for binding to the ectodomain of human CD117. Yeast cells that encoded antibodies that bound to human CD117 were selected. Nucleic acid sequences representing the antibodies from the selected yeast cells were isolated according to techniques known in the art.

In particular, the screen was performed to identify antagonist anti-CD117 antibodies or neutral antibodies. Neutral antibodies provide the benefit of being inert on target. Antagonistic antibodies, e.g., an antagonistic anti-CD117 antibody, prevent the association of CD117 with SCF (stem cell factor). In the context of transplant, it is possible that a neutral antibody may be therapeutically more safe, because, for example, antagonistic activity may negatively impact a graft by delaying engraftment via engaging with a donor CD117-bearing cells. A neutral antibody (or neutral ADC) would circumvent this issue. The yeast display technique described below was utilized to identify such neutral antibodies in addition to antagonist antibodies. To specifically identify neutral antibodies, recombinant CD117 ectodomain was pre-complexed with the natural ligand Stem Cell Factor (SCF) and only antibodies capable of binding CD117 ectodomain in this complex were selected. Based on this selection method, isolated antibodies would not prevent the binding of SCF to CD117, classifying them as neutral. In addition to either CD117 neutral or CD117 antagonist antibodies, antibodies were also selected for their ability to internalize in a CD117 expressing cell, such as a hematopoietic stem cell (HSC), which is preferred for an antibody that will be used as an antibody drug conjugate (ADC).

Approximately 69 antibodies were initially obtained in the screening of a yeast library expressing recombinant fully human IgGs. From the 69 antibodies, 6 human IgG antibodies were selected for affinity maturation for further improvement by way of diversifying sequences in CDR1 and CDR2 in the heavy chain and selecting for improved affinity according to methods known in the art. 22 human IgG antibodies with improved affinity and variant sequences were subsequently identified following affinity maturation. From the overall screening process, 10 human IgG antibodies were selected based on desired binding properties, including 7 following affinity maturation and 3 antibodies identified prior to affinity maturation.

Thus, through multiple rounds of screening, selected anti-CD117 antibodies were expressed and the resulting antibodies were further screened to identify anti-CD117 antibodies having desired structure and/or functional activity (e.g., the screen selected for antagonistic (ligand blocking) antibodies with cell internalization properties or for neutral antibodies having cell internalization properties). Examples of methods and reagents particularly amenable for use in generating and screening antibody display libraries can be found in, for example, Boder E. T. and Wittrup K. D., Yeast surface display for directed evolution of protein expression, affinity, and stability, Methods Enzymol, 328: 430-44 (2000) and Boder E. T. and Wittrup K. D., Yeast surface display for screening combinatorial polypeptide libraries, Nat Biotechnol. 15(6):553-7 (June 1997).

The amino acid sequences of the variable regions and CDRs of the heavy and light chains of the 10 selected antibodies are provided in Table 10. The 10 antibodies include the following: antibody 54 (Ab54 having heavy chain (HC)-54 and light chain (LC)-54), Antibody 55 (Ab55 having HC-55 and LC-55), Antibody 56 (Ab56 having HC-56 and LC-56), Antibody 57 (Ab57 having HC-57 and LC-57), Antibody 58 (Ab58 having HC-58 and LC-58), Antibody 61 (Ab61 having HC-61 and LC-61), Antibody 66 (Ab66 having HC-66 and LC-66), Antibody 67 (Ab67 having HC-67 and LC-67), Antibody 68 (Ab68 having HC-68 and LC-68), and Antibody 69 (Ab69 having HC-69 and LC-69).

Example 2. In Vitro Binding Analysis of Anti-CD117 Antibodies

The antibodies described in Example 1 were studied to determine their binding characteristics with respect to human CD117 and their ability to cross react with rhesus CD117.

Figure 7A:
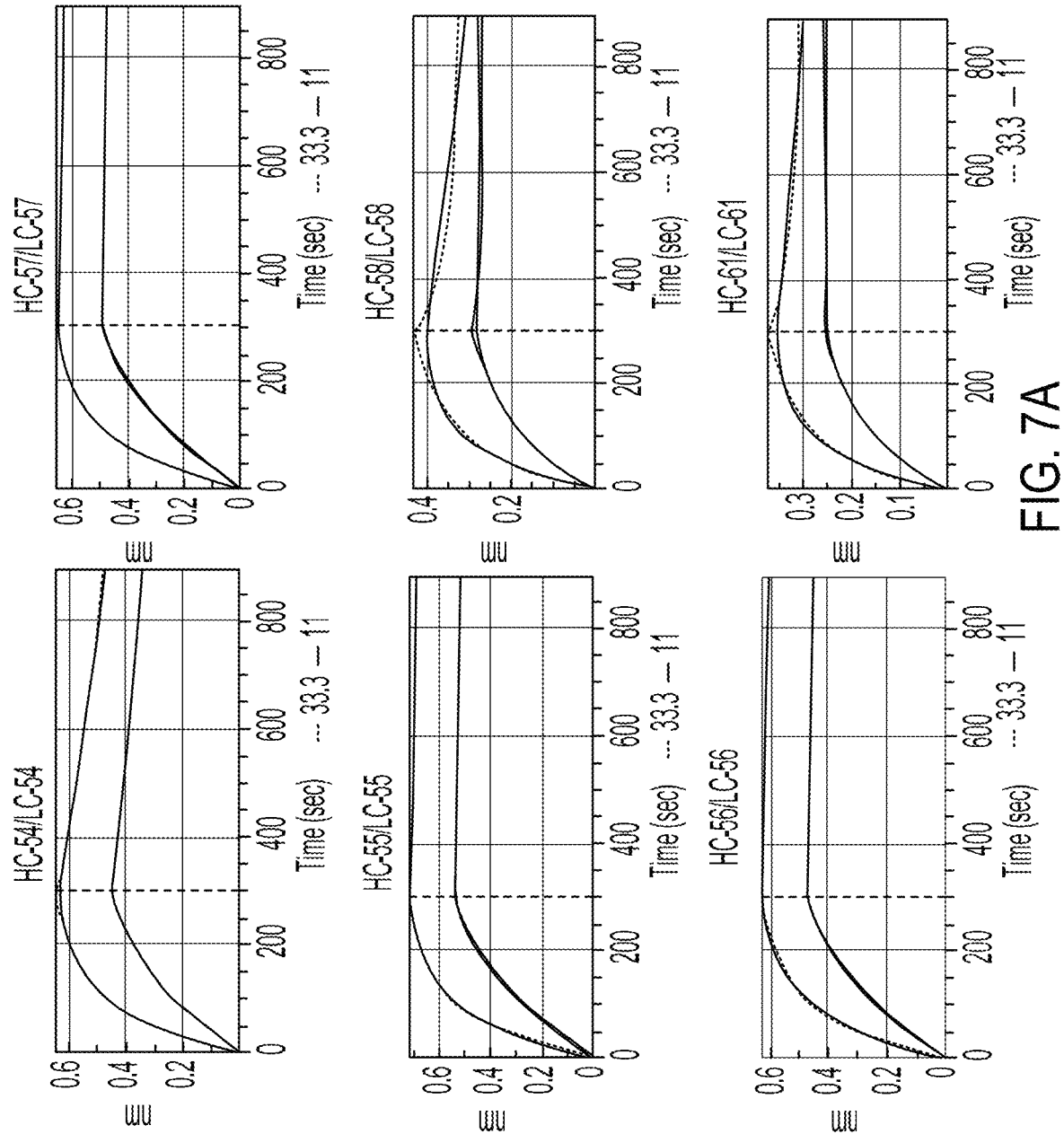
FIGS. 7A and 7B demonstrate the measurement of binding by Bio-Layer Interferometry (BLI) of the indicated purified IgG (sensor-associated) to purified human CD117 ectodomain (R&D Systems #332-SR) at concentrations of 33.3 nM and 11 nM as a function of time. The results for Ab54, Ab55, Ab56, Ab57, Ab68, and Ab61 are shown in FIG. 7A. The results for Ab66, Ab67, Ab68, and Ab69 are shown in FIG. 7B.
Figure 7B:
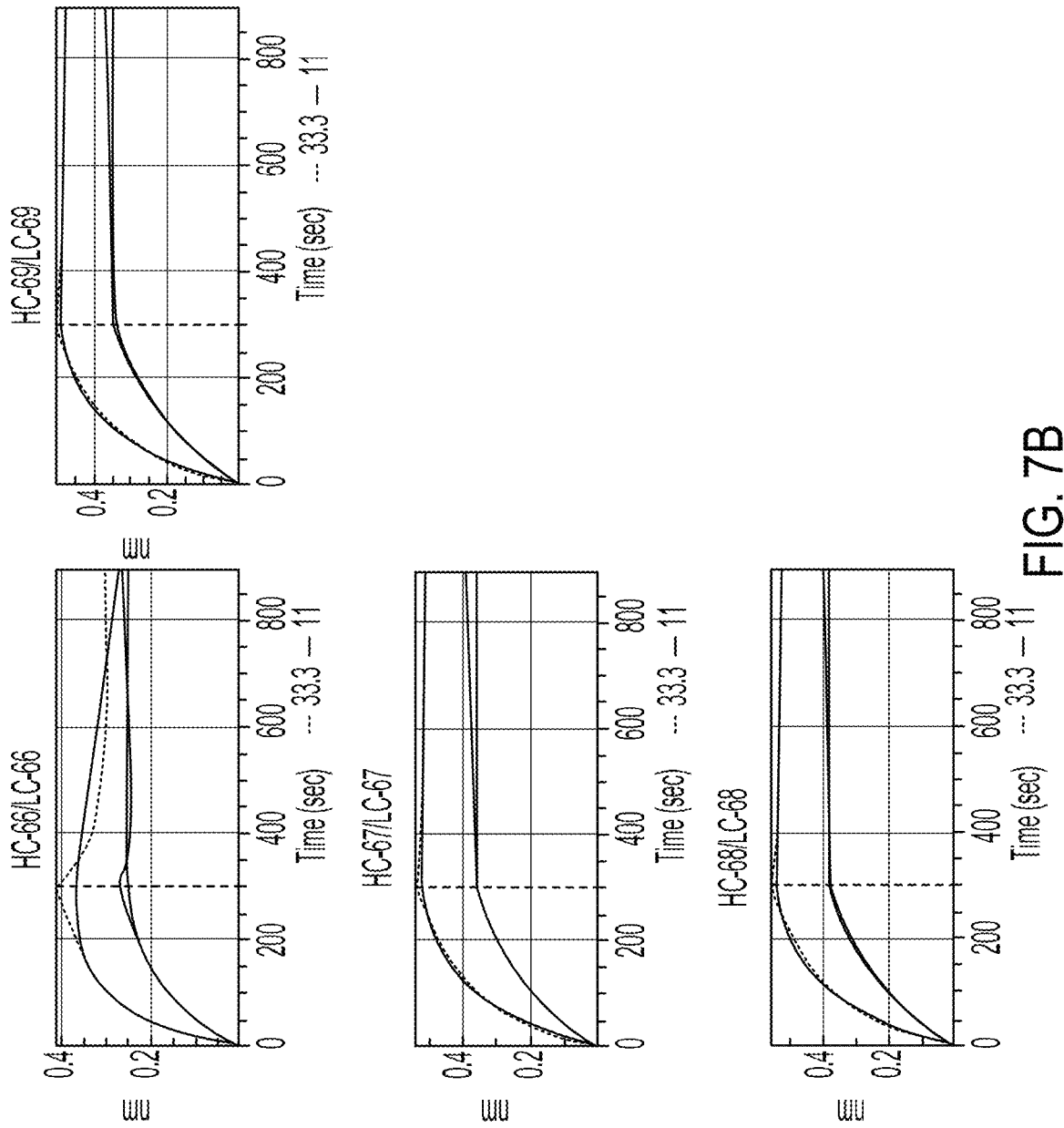

Antibody binding studies were performed at 25 degrees celsius in 1×PBS supplemented with 0.1% w/v bovine serum albumin with a Pall ForteBio Octet Red96 using biolayer interferometry (BLI). The indicated purified human antibody was immobilized onto anti-human Fc biosensors (AHC; Pall ForteBio 18-5063) and incubated with 33.3 nM and 11 nM of purified human CD117 ectodomain (R&D Systems #332-SR) or rhesus CD117 ectodomain. The resulting binding intervals to human CD117 ectodomain, which represent the association and dissociation curves are depicted in FIGS. 7A and 7B.

The apparent monovalent affinity ($K_D$), apparent association rate ($K_{ON}$), and apparent dissociation rate ($K_{OFF}$) were determined by local full fitting with a 1:1 binding model as calculated by ForteBio data analysis software version 10 of each IgG to purified human CD117 ectodomain (R&D Systems #332-SR) or rhesus CD117 ectodomain are shown in Table 1. Notably each of the selected antibodies was able to cross react with rhesus CD117 and human CD117, specifically, the CD117 ectodomain. The selected antibodies were also able to bind to both isoforms (1 and 2) of human CD117.

TABLE 1

Monovalent affinity ($K_D$), apparent association rate ($K_{ON}$), and apparent dissociation rate ($K_{OFF}$) of the indicated IgG to human CD117 ectodomain or rhesus CD117 ectodomain

| | Human CD117 | | | Rhesus CD117 | | |
|---|---|---|---|---|---|---|
| HC/LC | Monovalent $K_D$ (M) | $K_{ON}$ (1/MS) | $K_{OFF}$ (1/s) | Monovalent $K_D$ (M) | $K_{ON}$ (1/MS) | $K_{OFF}$ (1/s) |
| HC-54; LC-54 | 2.20E−09 | 2.74E+05 | 6.04E−04 | 2.60E−09 | 3.04E+05 | 7.93E−04 |
| HC-55; LC-55 | 2.59E−10 | 3.31E+05 | 8.57E−05 | 2.84E−10 | 3.15E+05 | 8.96E−05 |
| HC-56; LC-56 | 2.92E−10 | 2.94E+05 | 8.57E−05 | 2.80E−10 | 3.06E+05 | 8.57E−05 |
| HC-57; LC-57 | 2.96E−10 | 2.89E+05 | 8.57E−05 | 2.88E−10 | 2.98E+05 | 8.57E−05 |
| HC-58; LC-58 | 3.21E−08 | 2.10E+05 | 6.74E−03 | 3.03E−08 | 2.82E+05 | 8.55E−03 |
| HC-61; LC-61 | 2.49E−08 | 2.14E+05 | 5.33E−03 | 2.05E−08 | 2.30E+05 | 4.72E−03 |
| HC-66; LC-66 | 4.68E−08 | 2.43E+05 | 1.14E−02 | 6.60E−08 | 3.91E+05 | 2.58E−02 |
| HC-67; LC-67 | 3.94E−10 | 2.18E+05 | 8.57E−05 | 3.76E−10 | 2.28E+05 | 8.57E−05 |
| HC-68; LC-68 | 4.54E−10 | 2.33E+05 | 1.06E−04 | 3.74E−10 | 2.40E+05 | 8.98E−05 |
| HC-69; LC-69 | 5.88E−10 | 2.13E+05 | 1.25E−04 | 5.28E−10 | 2.40E+05 | 1.26E−04 |

Further characterization of the antibodies is provided in Examples 2 to 18.

Example 3. Characterization of Anti-CD117 Antibody 67 (Ab67)

Antibody 67 (Ab67) was identified in the above screen described in Example 1 in particular for being a neutral antibody. The heavy chain and light chain variable regions of Ab67 (including the CDR domains) are described below in Table 2.

TABLE 2

Variable and CDR amino acid sequences of anti-CD117 Ab67

| Antibody 67 | Backbone | Nucleic Acid Sequence | Amino acid sequence |
|---|---|---|---|
| HC-67 variable region | hIgG1 | GAGGTGCAGCTGGTGGAGTCTG GGGGAGGCTTGGTCCAGCCTG GAGGGTCCCTGAGACTCTCCTG TGCAGCCTCTGGATTCACCTTC AGTGACGCCGACATGGACTGGG TCCGCCAGGCTCCAGGGAAGG GGCTGGAGTGGGTTGGCCGTA CTAGAAACAAAGCAGGAAGTTA CACCACAGAATACGCCGCGTCT GTGAAAGGCAGATTCACCATCT CAAGAGATGATTCAAAGAACTCA CTGTATCTGCAAATGAACAGCCT GAAAACCGAGGACACGGCGGT GTACTACTGCGCCAGAGAGCCT AAATACTGGATCGACTTCGACCT ATGGGGGAGAGGTACCTTGGTC ACCGTCTCCTCA | EVQLVESGGGLVQP GGSLRLSCAASGFT FSDADMDWVRQAP GKGLEWVGRTRNK AGSYTTEYAASVKG RFTISRDDSKNSLYL QMNSLKTEDTAVYY CAREPKYWIDFDL WGRGTLVTVSS (SEQ ID NO: 9) |
| HC CDR1 | | | FTFSDADMD (SEQ ID NO: 11) |

TABLE 2-continued

Variable and CDR amino acid sequences of anti-CD117 Ab67

| Antibody 67 | Backbone | Nucleic Acid Sequence | Amino acid sequence |
|---|---|---|---|
| HC CDR2 | | | RTRNKAGSYTTEYA ASVKG (SEQ ID NO: 12) |
| HC CDR3 | | | AREPKYWIDFDL (SEQ ID NO: 13) |
| LC-67 variable region | hKappa | GACATCCAGATGACCCAGTCTC CATCCTCCCTGTCTGCATCTGTA GGAGACAGAGTCACCATCACTT GCCGGGCAAGTCAGAGCATTAG CAGCTATTTAAATTGGTATCAGC AGAAACCAGGGAAAGCCCCTAA GCTCCTGATCTATGCTGCATCC AGTTTGCAAAGTGGGGTCCCAT CAAGGTTCAGTGGCAGTGGATC TGGGACAGATTTCACTCTCACC ATCAGCAGTCTGCAACCTGAAG ATTTTGCAACTTACTACTGTCAG CAAAGCTACATCGCCCCTTACA CTTTTGGCGGAGGGACCAAGGT TGAGATCAAA | DIQMTQSPSSLSAS VGDRVTITCRASQSI SSYLNWYQQKPGK APKLLIYAASSLQSG VPSRFSGSGSGTDF TLTISSLQPEDFATY YCQQSYIAPYTFGG GTKVEIK (SEQ ID NO: 10) |
| LC CDR1 | | | RASQSISSYLN (SEQ ID NO: 14) |
| LC CDR2 | | | AASSLQS (SEQ ID NO: 15) |
| LC CDR3 | | | QQSYIAPYT (SEQ ID NO: 16) |

The heavy chain variable region (VH) amino acid sequence of Ab67 is described in SEQ ID NO: 9.

(SEQ ID NO: 9; CDR domains are in bold)
EVQLVESGGGLVQPGGSLRLSCAASGFTFSDADMDWVRQAPGKGLEWVGR

TRNKAGSYTTEYAASVKGRFTISRDDSKNSLYLQMNSLKTEDTAVYYCAR

EPKYWIDFDLWGRGTLVTVSS

The VH CDR amino acid sequences of Ab67 are as follows: FTFSDADMD (VH CDR1; SEQ ID NO: 11); RTRNKAGSYTTEYAASVKG (VH CDR2; SEQ ID NO: 12); and AREPKYWIDFDL (VH CDR3; SEQ ID NO: 13).

The light chain variable region (VL) amino acid sequence of Ab67 is provided below as SEQ ID NO 10.

(SEQ ID NO: 10; CDR domains in bold)
DIQMTQSPSSLSASVGDRVTITCRASQSISSYLNWYQQKPGKAPKLLIYA

ASSLQSGVPSRFSGSGSGTDFTLTISSLQPEDFATYYCQQSYIAPYTFGG

GTKVEIK

The VL CDR amino acid sequences of HC-67/LC-67 are underlined below and are as follows: RASQSISSYLN (VL CDR1; SEQ ID NO: 14); AASSLQS (VL CDR2; SEQ ID NO: 15); and QQSYIAPYT (VL CDR3; SEQ ID NO: 16).

The binding characteristics of Ab67 to bind human CD117 were studied using a standard biolayer interferometry binding assay. Antibody 67 (an IgG1) binding studies were performed at 25 degrees celsius in 1×PBS supplemented with 0.1% w/v bovine serum albumin with a Pall ForteBio Octet Red96 using biolayer interferometry (BLI). The indicated purified human antibody was immobilized onto anti-human Fc biosensors (AHC; Pall ForteBio 18-5063) and incubated with 33.3 nM and 11 nM CD117 ectodomain (R&D Systems #332-SR) The resulting binding intervals, which represented the association and dissociation curves, were depicted in FIG. 1. The apparent monovalent affinity (KD), apparent association rate (kon), and apparent dissociation rate (kOFF) were determined by local full fitting with a 1:1 binding model as calculated by Fortebio data analysis software version 10 of the indicated purified IgG (i.e., HC-67/LC-67) to purified human CD117 ectodomain (R&D Systems #332-SR) as shown in Table 3. The results demonstrate a purified IgG Ab 67 (i.e., HC-67/LC-67 (Ab67) IgG) binds with high affinity (i.e., $K_D$ greater than $1 \times 10^{-9}$ M) to the purified human CD117 ectodomain and is also characterized by a slow off rate, ($K_{OFF}$ (1/s) as determined by BLI.

TABLE 3

Binding characteristics of Ab67 as determined by BLI

| HC/LC | $K_D$ (M) | $K_{ON}$ (1/MS) | $K_{OFF}$ (1/S) |
|---|---|---|---|
| HC-67, LC-67 | $2.86 \times 10^{-10}$ | $4.16 \times 10^5$ | $1.19 \times 10^{-4}$ |

Example 4. In Vitro Analysis of Anti-CD117 Ab67

For in vitro cell proliferation assays using human CD34+ bone marrow cells, human CD34+ bone marrow cells were cultured for 5 days in the presence of stem-cell factor and the control antibody 3100 mAb (3100 corresponds to anti-CD117 antibody CK6; a known anti-CD117 antagonist antibody), the HC-67/LC-67 (Ab67) IgG (IgG1) or the isotype control (i.e., hIgG1). Full length IgG antibodies were tested. Live cell counts were determined for all cells or CD34+ CD90+ gated cells by flow cytometry.

Figure 2A:
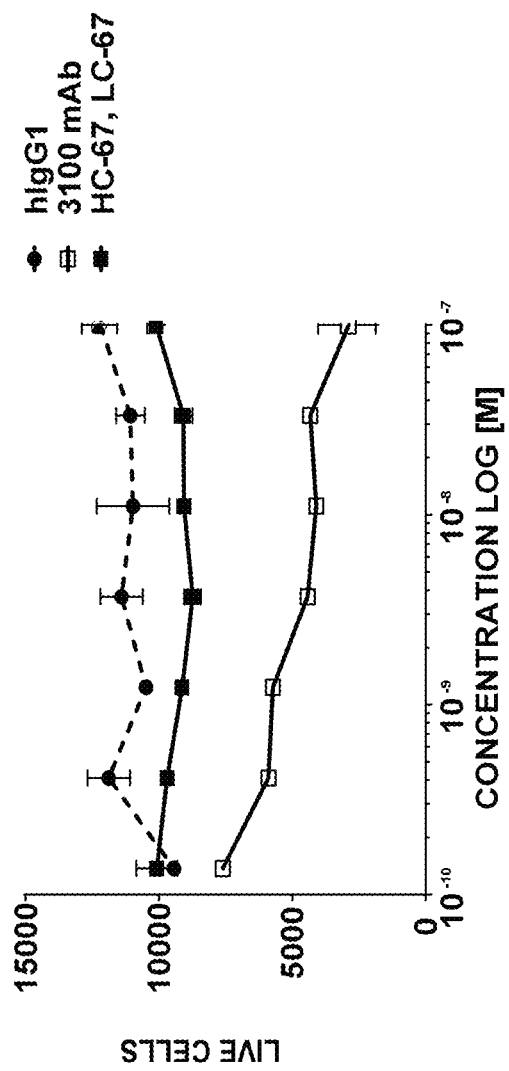
FIGS. 2A and 2B graphically depict the results of in vitro cell proliferation assays that show the dose-dependent effect of each indicated antibody on the Stem Cell Factor (SCF)-dependent proliferation of human CD34+ bone marrow cells. Total live cell counts (FIG. 2A) or viable CD34+ CD90+ cell counts as determined by flow cytometry (FIG. 2B) (y-axis) in the presence of the 3100 mAb, the HC-67/LC-67 (i.e., Ab67) IgG or control as a function of 3100 mAb, HC-67/LC-67 (i.e., Ab67) IgG or control concentration (x-axis) are depicted.
Figure 2B:
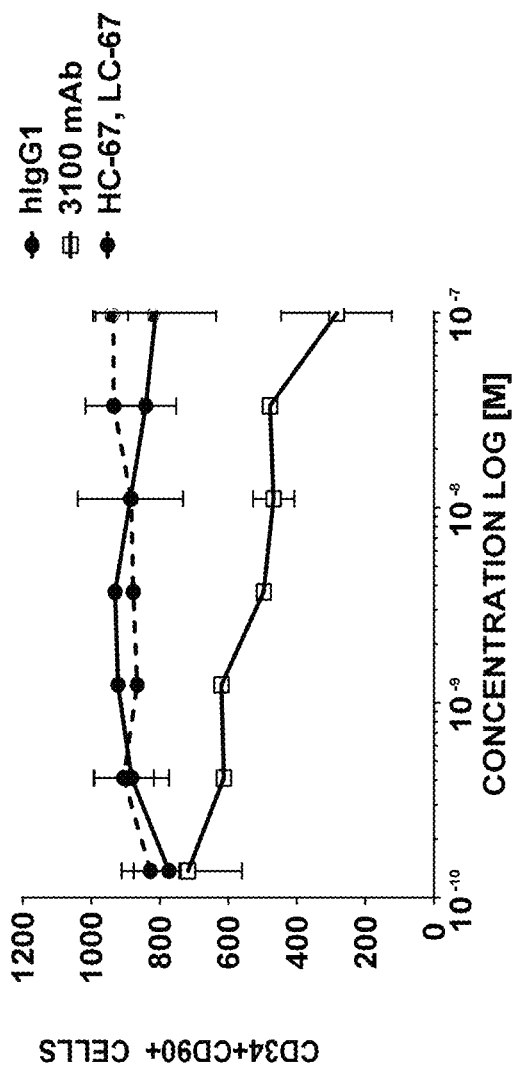

The results are described in FIGS. 2A and 2B and demonstrate the dose dependent effect of the 3100 mAb and the HC-67/LC-67 (Ab67) IgG in the SCF-dependent proliferation of human CD34+ cells as measured by flow cytometry. In particular, the results in FIGS. 2A and 2B (also shown in FIGS. 8A and 8B) demonstrate that HC-67/LC-67 is a neutral non-antagonist antibody that does not prohibit the SCF-dependent proliferation of primary human CD34+ bone marrow cells in culture, as the activity of Ab67 was similar to the isotype matched negative control. Note that the

Example 6. Characterization of Anti-CD117 Antibody 55 (Ab55)

Antibody 55

Antibody 55 (Ab55) was identified in the above yeast screen for having properties corresponding to a therapeutic human anti-CD117 antibody, particularly antagonistic characteristics, internalization, and an ability to cross react with rhesus CD117. The heavy chain and light chain variable regions of Ab55 (including the CDR domains) are described below in Table 4.

TABLE 4

Variable and CDR amino acid sequences of anti-CD117 antibody Ab55

| Antibody 55 | Backbone | Nucleic Acid Sequence | Amino acid sequence |
|---|---|---|---|
| HC-55 | hIgG1 | CAGGTGCAGCTGGTGCAGTCTG GGGCTGAGGTGAAGAAGCCTG GGTCCTCGGTGAAGGTCTCCTG CAAGGCTTCTGGAGGCACCTTC CGAATCTATGCTATCAGCTGGG TGCGACAGGCCCCTGGACAAG GGCTTGAGTGGATGGGAGGGAT CATCCCTGACTTCGGTGTAGCA AACTACGCACAGAAGTTCCAGG GCAGAGTCACGATTACCGCGGA CGAATCCACGAGCACAGCCTAC ATGGAGCTGAGCAGCCTGAGAT CTGAGGACACGGCGGTGTACTA CTGCGCCAGAGGTGGATTGGAC ACAGACGAGTTCGACCTATGGG GGAGAGGTACCTTGGTCACCGT CTCCTCA | QVQLVQSGAEVKKP GSSVKVSCKASGGT FRIYAISWVRQAPG QGLEWMGGIIPDFG VANYAQKFQGRVTI TADESTSTAYMELS SLRSEDTAVYYCAR GGLDTDEFDLWGR GTLVTVSS (SEQ ID NO: 19) |
| LC-55 | hKappa | GACATCCAGATGACCCAGTCTC CATCCTCCCTGTCTGCATCTGTA GGAGACAGAGTCACCATCACTT GCCGGGCAAGTCAGAGCATTAA CAGCTATTTAAATTGGTATCAGC AGAAACCAGGGAAAGCCCCTAA GCTCCTGATCTATGCTGCATCC AGTTTGCAAAGTGGGGTCCCAT CAAGGTTCAGTGGCAGTGGATC TGGGACAGATTTCACTCTCACC ATCAGCAGTCTGCAACCTGAAG ATTTTGCAACTTACTACTGTCAG CAAGGAGTCAGTGACATCACTT TTGGCGGAGGGACCAAGGTTGA GATCAAA | DIQMTQSPSSLSAS VGDRVTITCRASQSI NSYLNWYQQKPGK APKLLIYAASSLQSG VPSRFSGSGSGTDF TLTISSLQPEDFATY YCQQGVSDITFGGG TKVEIK (SEQ ID NO: 20) | protocol for the SCF cell proliferation assay used in this example is described in Example 11.

Example 5. In Vitro Analysis of an Anti-CD117-ADC (Ab67 ADC)

For in vitro cell killing assays using human CD34+ bone marrow cells, human CD34+ bone marrow cells were cultured for 5 days in the presence of the HC-67/LC-67 ADC (i.e., Ab67 ADC) or the isotype control (i.e., Ig-ADC). Ab67 (IgG1) was conjugated to an amatoxin via a cleavable peptide linker. Cell viability was measured using flow cytometry.

Figure 3A:
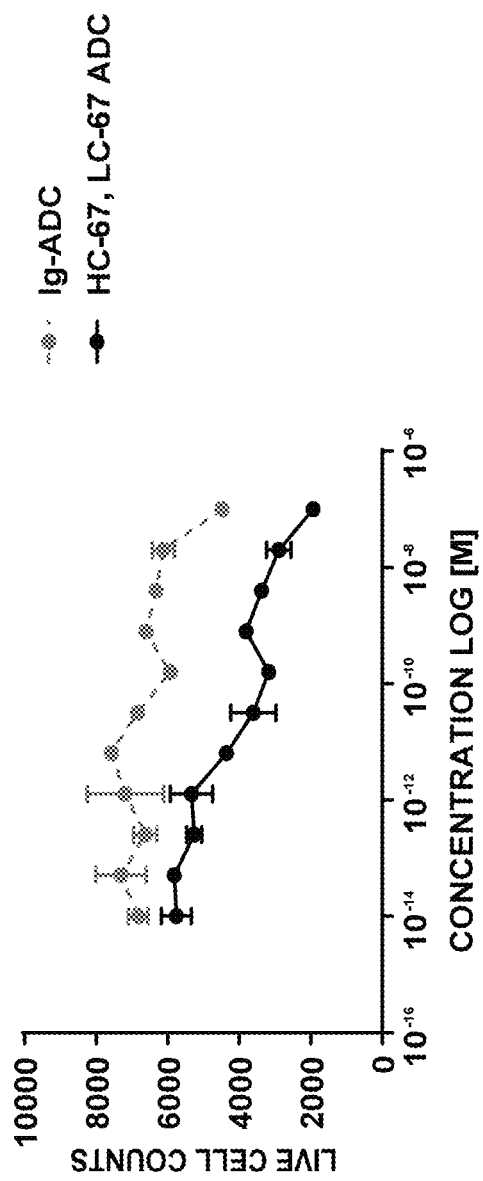
FIGS. 3A and 3B graphically depict the results of in vitro cell killing assays that show the dose-dependent effect of each indicated ADC on the viability of human CD34+ bone marrow cells. Total live cell counts (FIG. 3A) or viable CD34+CD90+ cell counts (FIG. 3B) (y-axis) in the presence of the HC-67/LC-67 ADC (i.e., the Ab67 ADC) or control as a function of HC-67/LC-67 ADC (i.e., the Ab67 ADC) or control concentration (x-axis) are depicted.
Figure 3B:
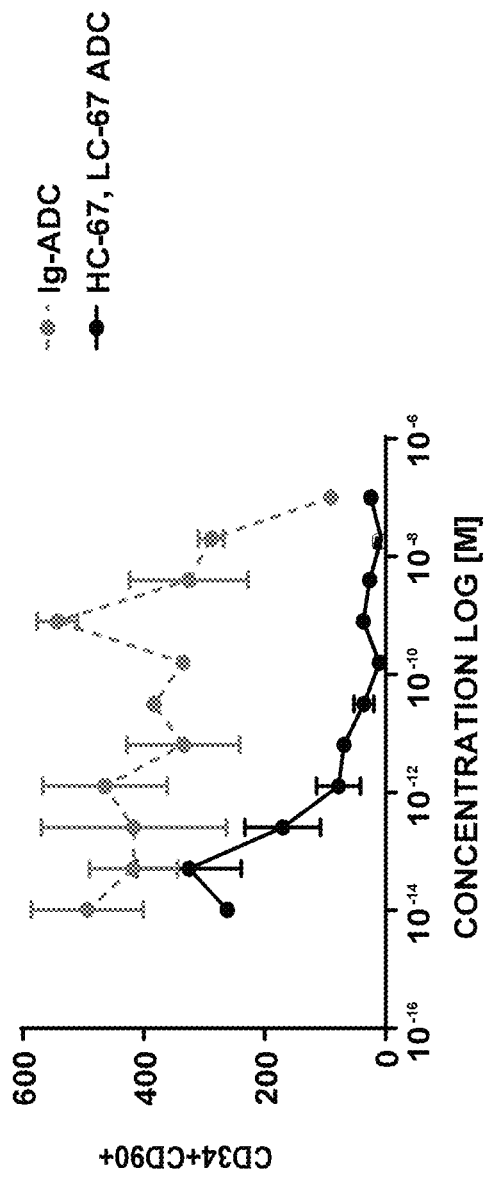

The results in FIGS. 3A and 3B indicate that the HC-67/LC-67 ADC was highly effective at killing primary human CD34+ CD90+ bone marrow cells in vitro. Thus, the HC-67/LC-67 ADC was highly effective at killing CD117 expressing cell lines and primary human CD34+CD90+ cells. Further, as described in FIG. 3B, the Ab67 ADC was particularly effective at killing bone marrow cells.

The heavy chain variable region (VH) amino acid sequence of Ab55 is described in SEQ ID NO: 19.

(SEQ ID NO: 19; CDR domains are in bold)
QVQLVQSGAEVKKPGSSVKVSCKASGGTFRIYAISWVRQAPGQGLEWMGG

IIPDFGVANYAQKFQGRVTITADESTSTAYMELSSLRSEDTAVYYCARGG

LDTDEFDLWGRGTLVTVSS

The VH CDR amino acid sequences of Ab55 are as follows: GTFRIYAIS (VH CDR1; SEQ ID NO: 21); GIIPDFGVANYAQKFQG (VH CDR2; SEQ ID NO: 22); and ARGGLDTDEFDL (VH CDR3; SEQ ID NO: 23).

The light chain variable region (VL) amino acid sequence of Ab55 is provided below as SEQ ID NO 20.

(SEQ ID NO: 20; CDR domains in bold)
DIQMTQSPSSLSASVGDRVTITCRASQSINSYLNWYQQKPGKAPKLLIYA

-continued

ASSLQSGVPSRFSGSGSGTDFTLTISSLQPEDFATYYCQQGVSDITFGGG
TKVEIK

The VL CDR amino acid sequences of HC-55/LC-55 are underlined below and are as follows: RASQSINSYLN (VL CDR1; SEQ ID NO: 24); AASSLQS (VL CDR2; SEQ ID NO: 25); and QQGVSDIT (VL CDR3; SEQ ID NO: 26).

Example 7. In Vitro Binding Studies of Ab55

Figure 4:
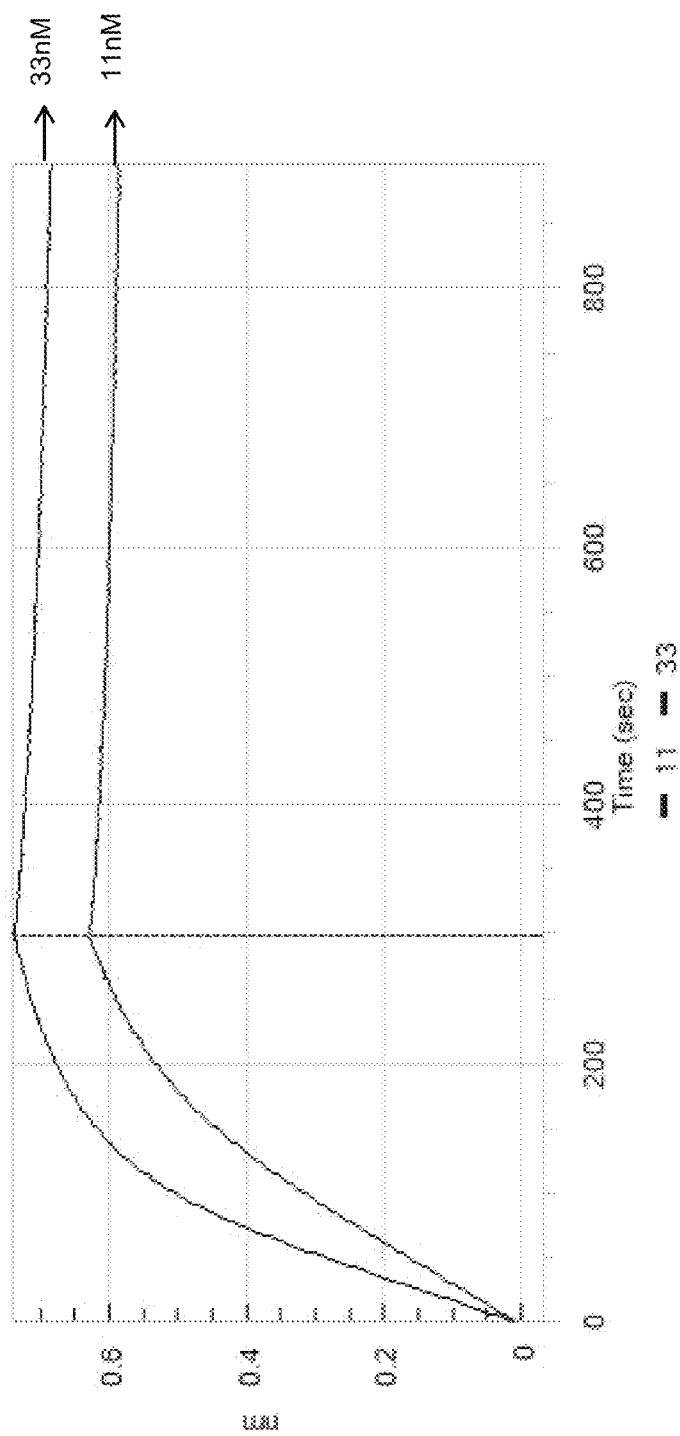
FIG. 4 demonstrates the measurement of binding by Bio-Layer Interferometry (BLI) of the indicated purified IgG (sensor-associated) to purified human CD117 ectodomain (R&D Systems #332-SR) at concentrations of 33.3 nM and 11 nM as a function of time.

Antibody binding studies were performed at 25 degrees celsius in 1×PBS supplemented with 0.1% w/v bovine serum albumin with a Pall ForteBio Octet Red96 using biolayer interferometry (BLI). The indicated purified human antibody was immobilized onto anti-human Fc biosensors (AHC; Pall ForteBio 18-5063) and incubated with 33.3 nM and 11 nM CD117 ectodomain (R&D Systems #332-SR). The resulting binding intervals, which represented the association and dissociation curves were depicted in FIG. 4. The apparent monovalent affinity (KD), apparent association rate (kon), and apparent dissociation rate (koff) are determined by local full fitting with a 1:1 binding model as calculated by ForteBio data analysis software version 10 of the indicated purified IgG (i.e., HC-55/LC-55) to purified human CD117 ectodomain (R&D Systems #332-SR) are shown in Table 5. The results demonstrate an Ab55 IgG (i.e., the HC-55/LC-55 IgG) binds with high affinity to the purified human CD117 ectodomain and was also characterized as having a slow koff (1/s) as determined by standard BLI.

TABLE 5

| HC/LC | $K_D$ (M) | $K_{ON}$ (1/MS) | $K_{OFF}$ (1/s) |
|---|---|---|---|
| Ab55 (HC-55/LC-55) | $2.88 \times 10^{-10}$ | $4.73 \times 10^5$ | $1.36 \times 10^{-4}$ |

Example 8. In Vitro Analysis of an Anti-CD117 Ab55

For in vitro cell proliferation assays using human CD34+ bone marrow cells, human CD34+ bone marrow cells were cultured for 5 days in the presence of stem-cell factor, the 3100 mAb, the HC-55/LC-55 IgG (Ab55 IgG1) or the control (i.e., hIgG1). Live cell counts were determined for all cells or CD34+ CD90+ gated cells by flow cytometry.

Figure 5A:
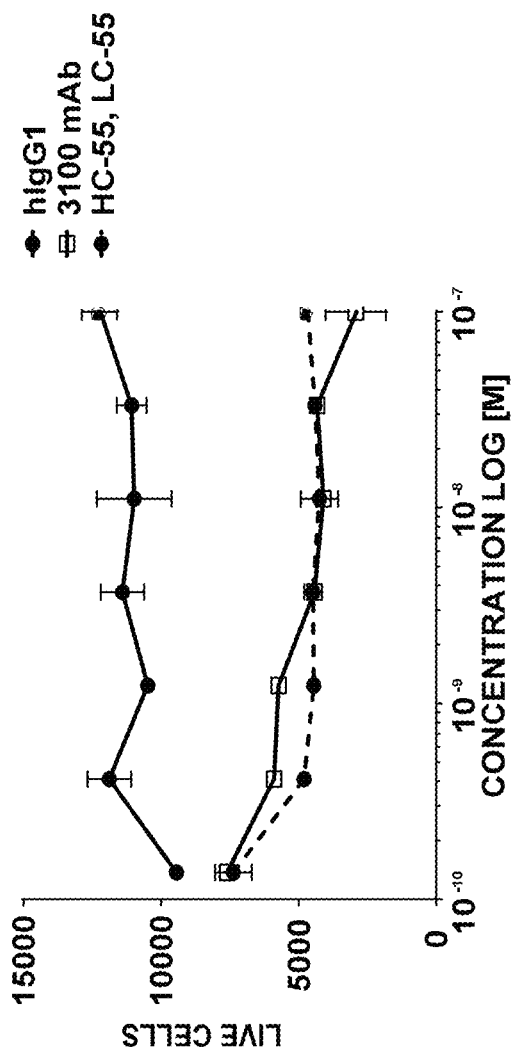
FIGS. 5A and 5B graphically depict the results of in vitro cell proliferation assays that show the dose-dependent effect of each indicated antibody on the Stem Cell Factor (SCF)-dependent proliferation of human CD34+ bone marrow cells. Total live cell counts (FIG. 5A) or viable CD34+ CD90+ cell counts as determined by flow cytometry (FIG. 5B) (y-axis) in the presence of the 3100 mAb, HC-55/LC-55 IgG (Ab55 IgG) or control as a function of 3100 mAb, HC-55/LC-55 IgG (Ab55 IgG) or control concentration (x-axis) are depicted.
Figure 5B:
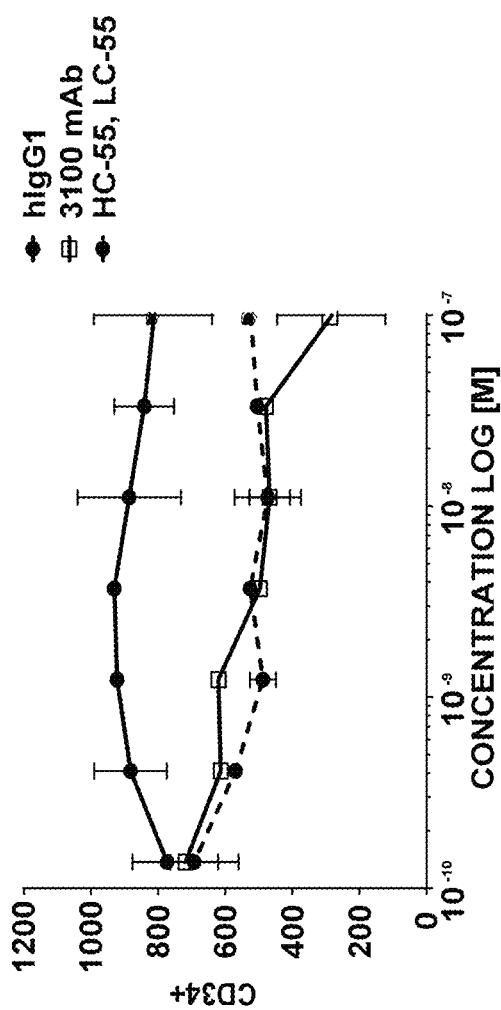

The results in FIGS. 5A and 5B demonstrate the dose dependent effect of the 3100 mAb (antagonist CD117 antibody CK6) and the HC-55/LC-55 IgG in the SCF-dependent proliferation of human CD34+ cells as measured by flow cytometry. This result demonstrates that HC-55/LC-55 is an antagonist antibody that prohibits the SCF-dependent proliferation of primary human CD34+ bone marrow cells in culture similar to the 3100 mAb.

Example 9. In Vitro Analysis of an Anti-CD117-ADC (Ab55 ADC)

The ability of Ab55 to act deplete cells, particularly CD34+ cells, when conjugated to a toxin was tested. Ab55 (IgG1) was conjugated to an amatoxin via a cleavable peptide linker. For in vitro cell killing assays using human CD34+ bone marrow cells, human CD34+ bone marrow cells were cultured for 5 days in the presence of the HC-55/LC-55 ADC (Ab55 ADC) or the control (i.e., Ig-ADC). Cell viability was measured using flow cytometry.

The results in FIGS. 6A and 6B indicate that the HC-55/LC-55 ADC is highly effective at killing primary human CD34+ bone marrow cells in vitro. Thus, the HC-55/LC-55 ADC was highly effective at killing CD117 expressing cell lines and primary human CD34+CD90+ cells.

Example 10. Analysis of Anti-CD117 Antibody Conjugates Using an In Vitro Cell Killing Assay Whole IgG of the 10 anti-CD117 human IgG1 antibodies selected in Example 1 were pre-incubated with an anti-human Fab conjugated to a toxin (saporin) to test the ability of the various antibodies to kill Kasumi-1 cells (ATCC No. CRL-2724) in vitro. Following the cell killing assay, the level of cytotoxicity was quantified.

For in vitro killing assays using Kasumi-1 cells, Kasumi-1 cells were grown according to ATCC guidelines. More specifically, Kasumi-1 cells were cultured for three days in the presence of CD117-ADC or the positive control antibody (CK6; a known antagonist antibody). Cell viability was measured by Celltiter Glo.

Figure 8A:
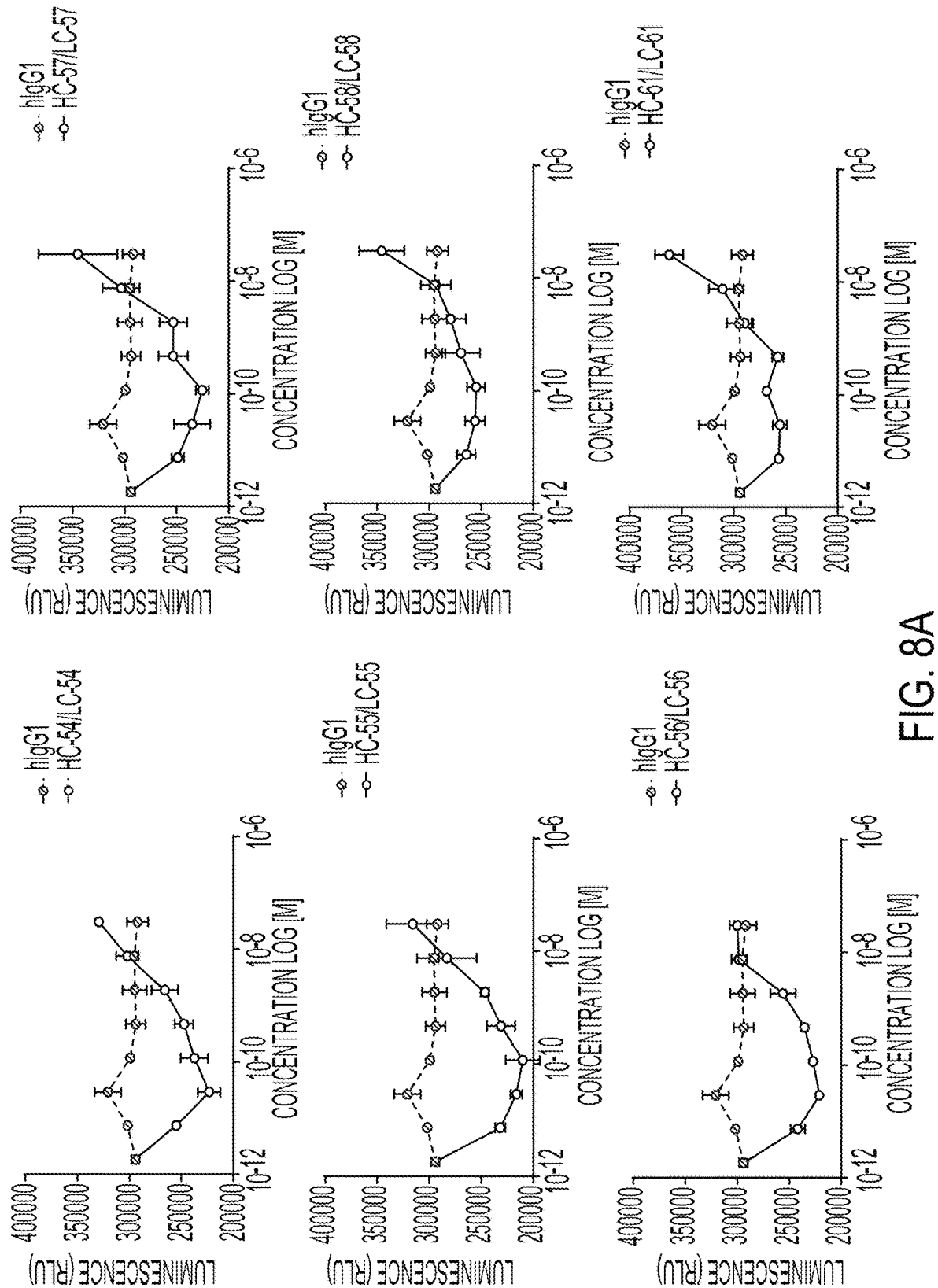
FIGS. 8A and 8B graphically depict the results of in vitro cell killing assays that show Kasumi-1 cell viability as measured in luminescence (RLU) by Celltiter Glo as a function of the indicated anti-CD117 ADC or control concentration. The results for Ab54, Ab55, Ab56, Ab57, Ab58, and Ab61 are shown in FIG. 8A. The results for Ab66, Ab67, Ab68, and Ab69 are shown in FIG. 8B.
Figure 8B:
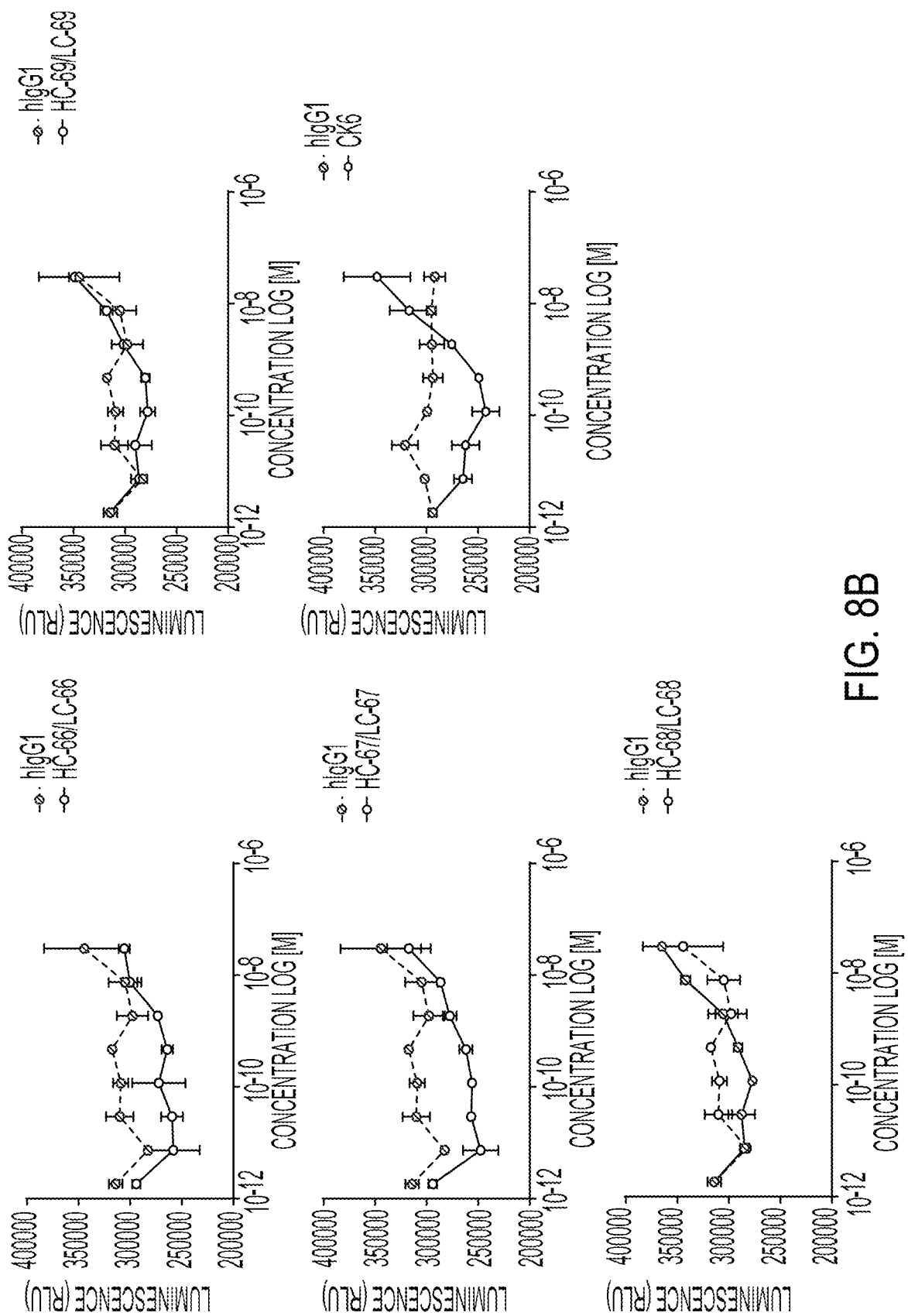
Figure 9:
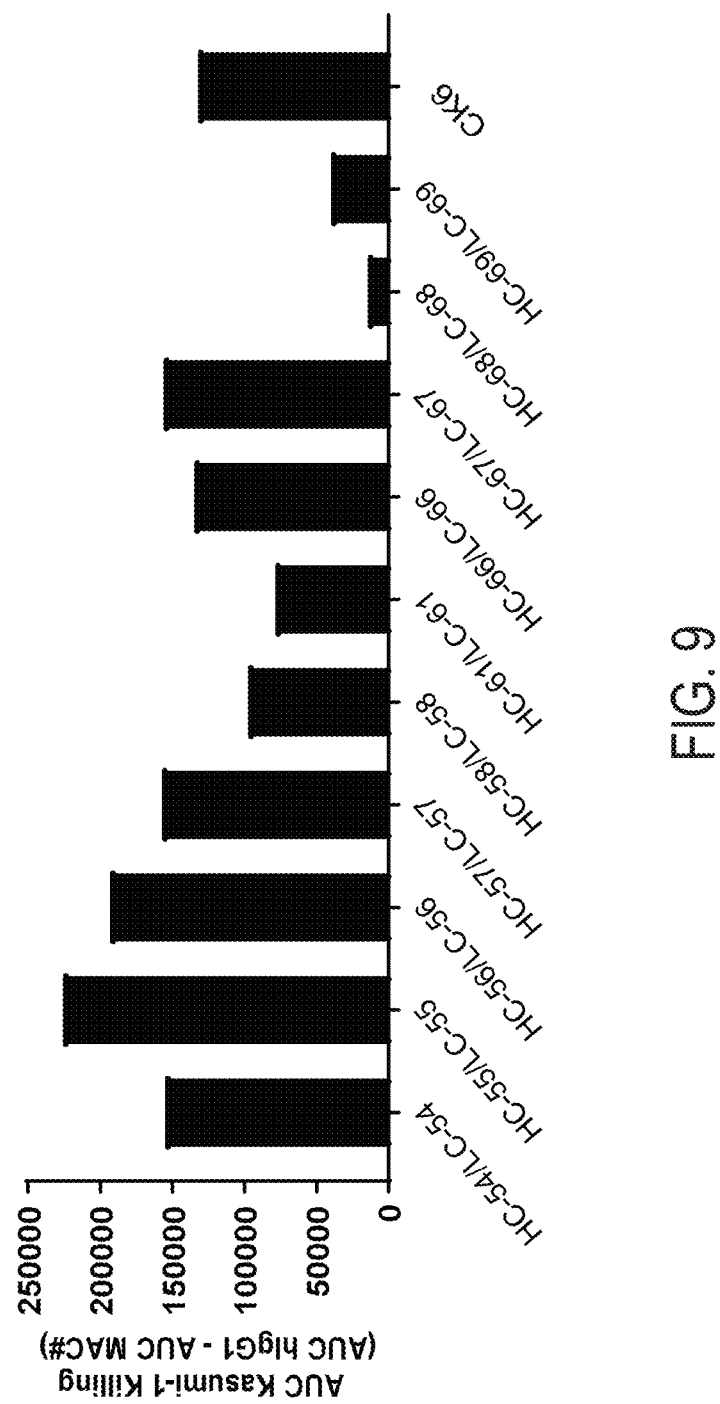
FIG. 9 graphically depicts a quantification of the area under the killing curve in the in vitro cell killing assays depicted in FIGS. 8A and 8B.

The results described in FIGS. 8A and 8B indicate that each of the various IgG:Fab-saporin complexes were effective at killing CD117 expressing cells (i.e., Kasumi-1 cells) in vitro and indicates that the complexes were internalized. FIG. 9 describes a quantification of the Kasumi-1 cell killing assay. Table 6 below provides additional data relating to this quantification of the Kasumi-1 cell killing assay. The Kasumi-1 cell killing assay was performed in the absence of SCF (as Kasumi-1 cells are not SCF dependent). As such, the antagonist/neutral characteristic of the tested antibodies was not apparent as in SCF-dependent cell killing assays (described in Example 11). Notably, the antibodies identified as antagonist in the SCF-dependent cell killing assay exhibited a higher level of killing in the Kasumi-1 assay, e.g., compare AUC value of Ab55 (antagonist) to Ab67 (neutral).

TABLE 6

Quantification of IgG:Fab-saporin complex cell killing

| HC/LC | AUC Kasumi-1 Killing (AUC hIgG1 − AUC MAC ID#) |
|---|---|
| HC-54; LC-54 | 154918 |
| HC-55; LC-55 | 225764 |
| HC-56; LC-56 | 193260 |
| HC-57; LC-57 | 157277 |
| HC-58; LC-58 | 97423 |
| HC-61; LC-61 | 78558 |
| HC-66; LC-66 | 134742 |
| HC-67; LC-67 | 155931 |
| HC-68; LC-68 | 14411 |
| HC-69; LC-69 | 39988 |
| CK6 | 132193 |

Example 11. Analysis of Anti-CD117 Antibodies Using an In Vitro SCF Dependent Cell Proliferation Assay To determine the degree of antibody antagonism, a number of identified antibodies were assessed in an in vitro stem cell factor (SCF) dependent proliferation assay using human CD34+ bone marrow cells. Death of cells in the presence of SCF upon the addition of an anti-CD117 antibody (IgG1) indicates that the antibody disrupts binding of SCF, therefore is considered an SCF antagonist. Anti-CD117.antibody CK6 was used as a positive control, as it is known to have antagonist activity (see U.S. Pat. No. 8,552,157), and an isotype non-CD117 binding antibody was used as a negative control. For this in vitro cell proliferation assay, human CD34+ bone marrow cells were cultured for 5 days in the presence of SCF and the indicated antibody. Live cell counts were determined for all cells or for CD34+ CD90+ gated cells by flow cytometry.

Figure 10A:
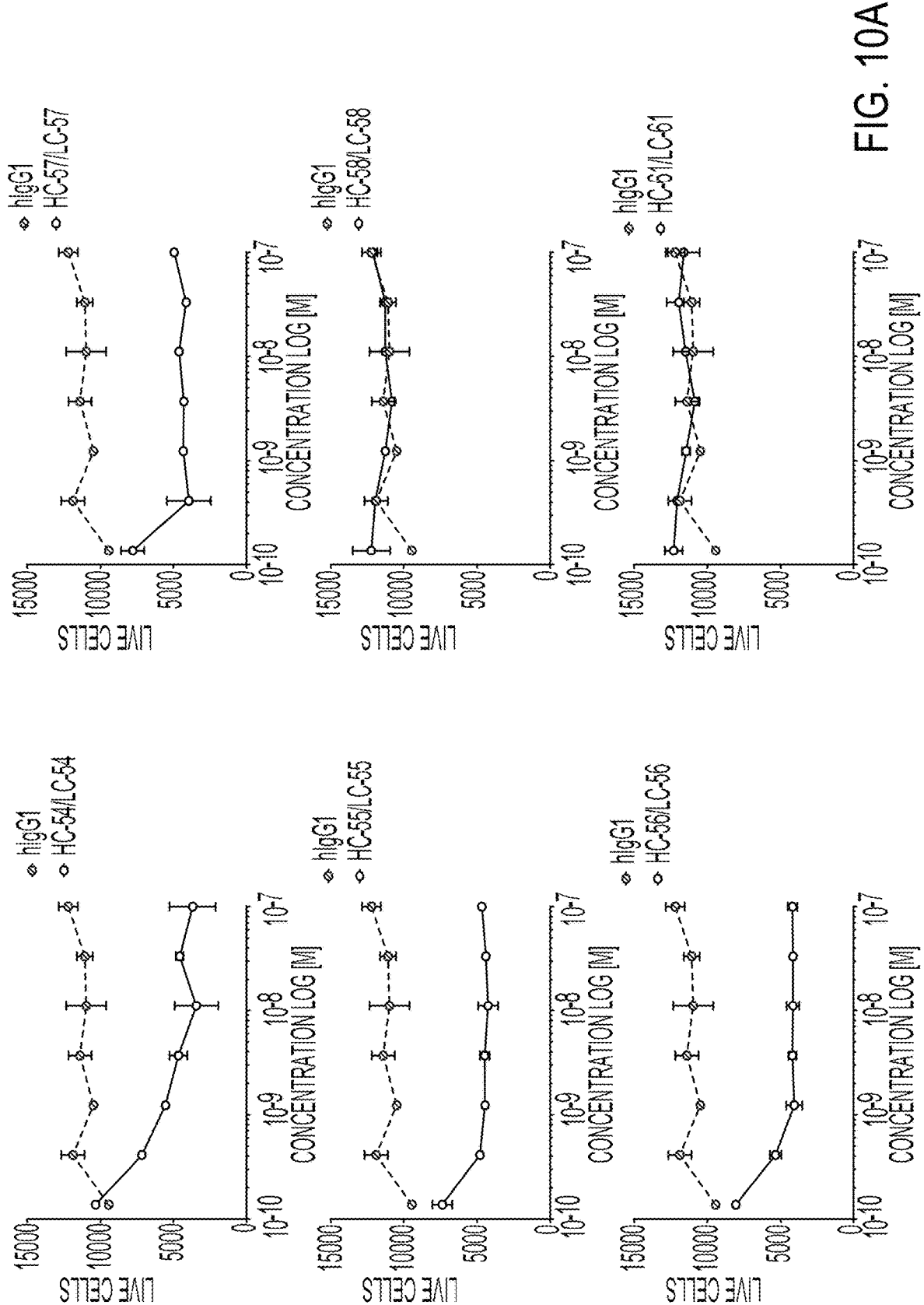
FIGS. 10A and 10B graphically depict the results of in vitro cell proliferation assays that show the effect of each indicated antibody on the Stem Cell Factor (SCF)-dependent proliferation of human CD34+ bone marrow cells. Total cell counts as determined by flow cytometry (y-axis) in the presence of the indicated antibody or control (CK6) as a function of antibody concentration (x-axis) are depicted. The results for Ab54, Ab55, Ab56, Ab57, Ab58, and Ab61 are shown in FIG. 10A. The results for Ab66, Ab67, Ab68, and Ab69 are shown in FIG. 10B.
Figure 10B:
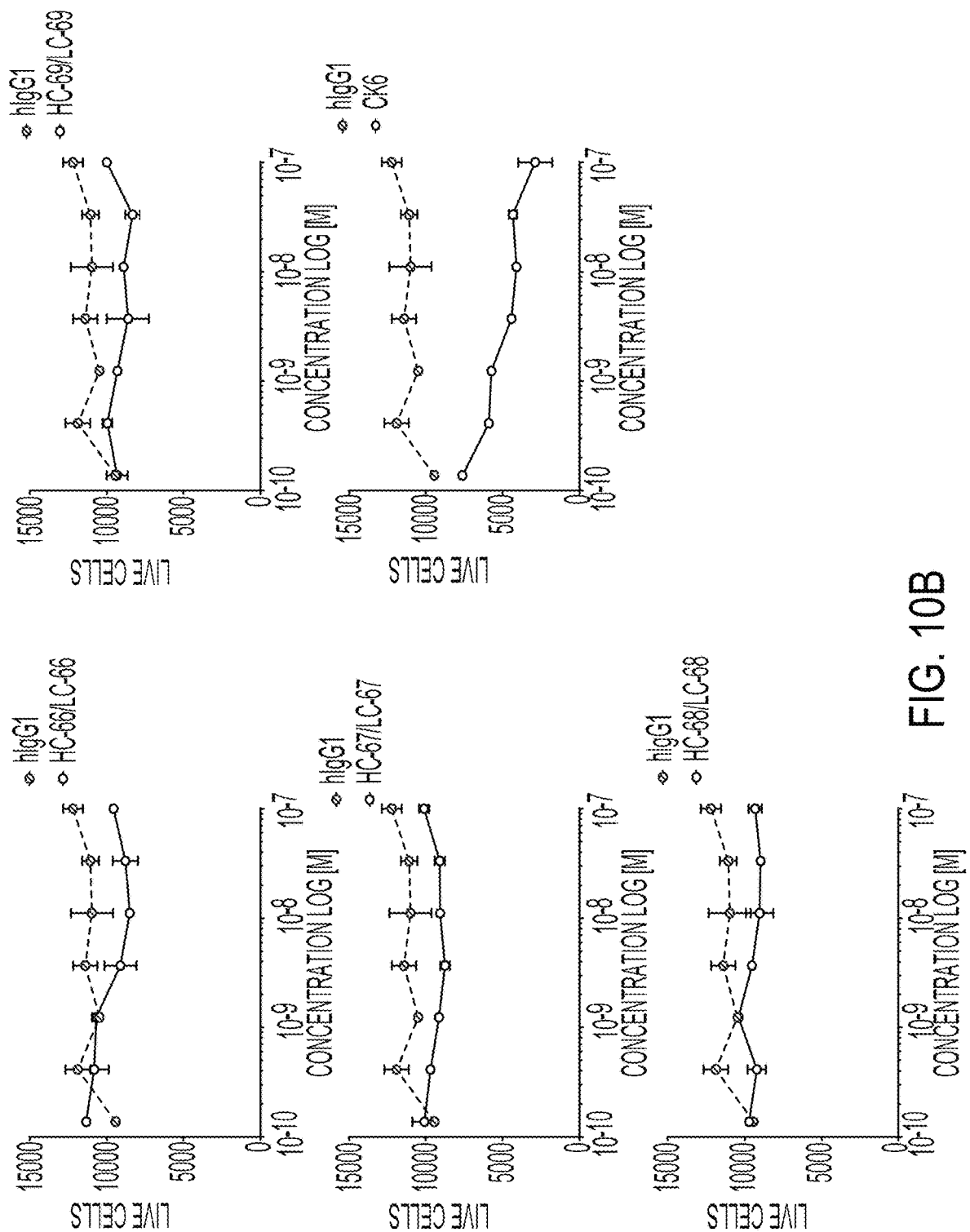
Figure 11A:
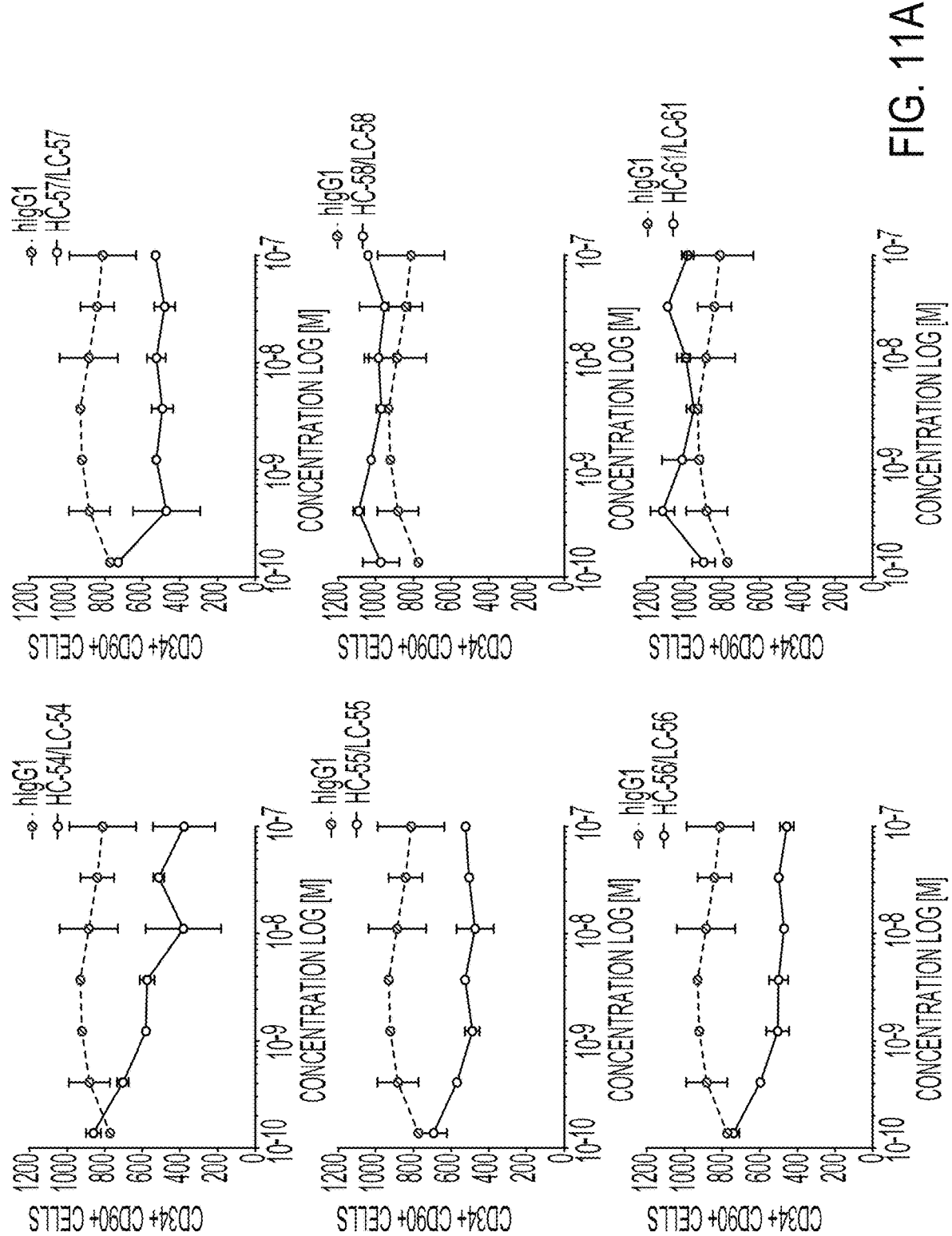
FIGS. 11A and 11B graphically depict the results of in vitro cell proliferation assays that show the effect of each indicated antibody on the Stem Cell Factor (SCF)-dependent proliferation of human CD34+ bone marrow cells. Viable CD34+ CD90+ cell counts as determined by flow cytometry (y-axis) in the presence of the indicated antibody or control (CK6) as a function of antibody concentration (x-axis) are depicted. The results for Ab54, Ab55, Ab56, Ab57, Ab58, and Ab61 are shown in FIG. 11A. The results for Ab66, Ab67, Ab68, and Ab69 are shown in FIG. 11B.
Figure 11B:
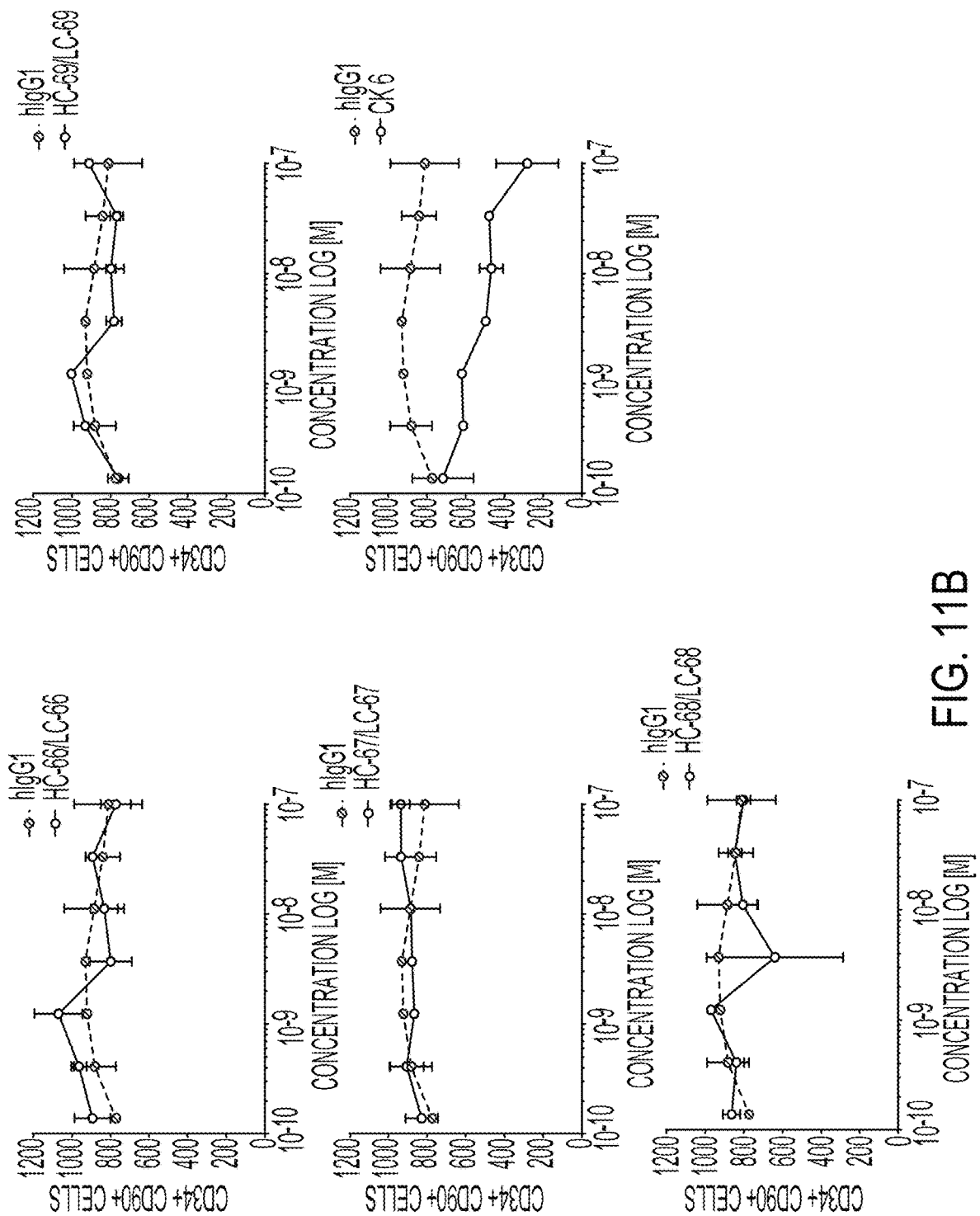

The results described in FIGS. 10A and 10B (live cells) and 11A and 11B (CD34+CD90+ cells) demonstrate whether the tested antibody limits cell proliferation through inhibition of SCF binding, and therefore would be considered an antagonist. As described in FIGS. 10A, 10B, 11A, and 11B, antibodies Ab54, Ab55, Ab56, and Ab57 are CD117 antagonistic as they were able to kill both live and CD34+ CD90 cells in an SCF dependent cell proliferation assay and prevent SCF-dependent proliferation. In contrast, Ab58, Ab61, Ab66, Ab67, Ab68, and Ab69 were determined to be neutral antibodies that do not inhibit the SCF-dependent proliferation of human CD34+ bone marrow cells in culture.

Example 12. Analysis of Anti-CD117 Antibodies Using a Cross-Blocking Assay

Ab67 and Ab55 were further assessed in a cross-blocking assay in the presence of CK6 (anti-CD117 antagonist antibody) or human SCF (the ligand to CD117). The cross-blocking assay was performed at 25 degrees celsius in 1×PBS supplemented with 0.1% w/v bovine serum albumin with a Pall ForteBio Octet Red96 using biolayer interferometry (BLI). The indicated purified human antibody was immobilized onto anti-human Fc biosensors (AHC; Pall ForteBio 18-5063) and incubated with 100 nM CD117 ectodomain (R&D Systems #332-SR). Following this, the indicated primary antibody in complex with CD117 ectodomain was incubated with either CK6 (a known antagonist) or recombinant human stem cell factor. A positive signal in the second binding event (the trace following the marked vertical line) suggests non-competitive binding or the absence of cross-blocking. No increase in signal in the second binding event suggests competitive binding or cross-blocking.

Figure 12:
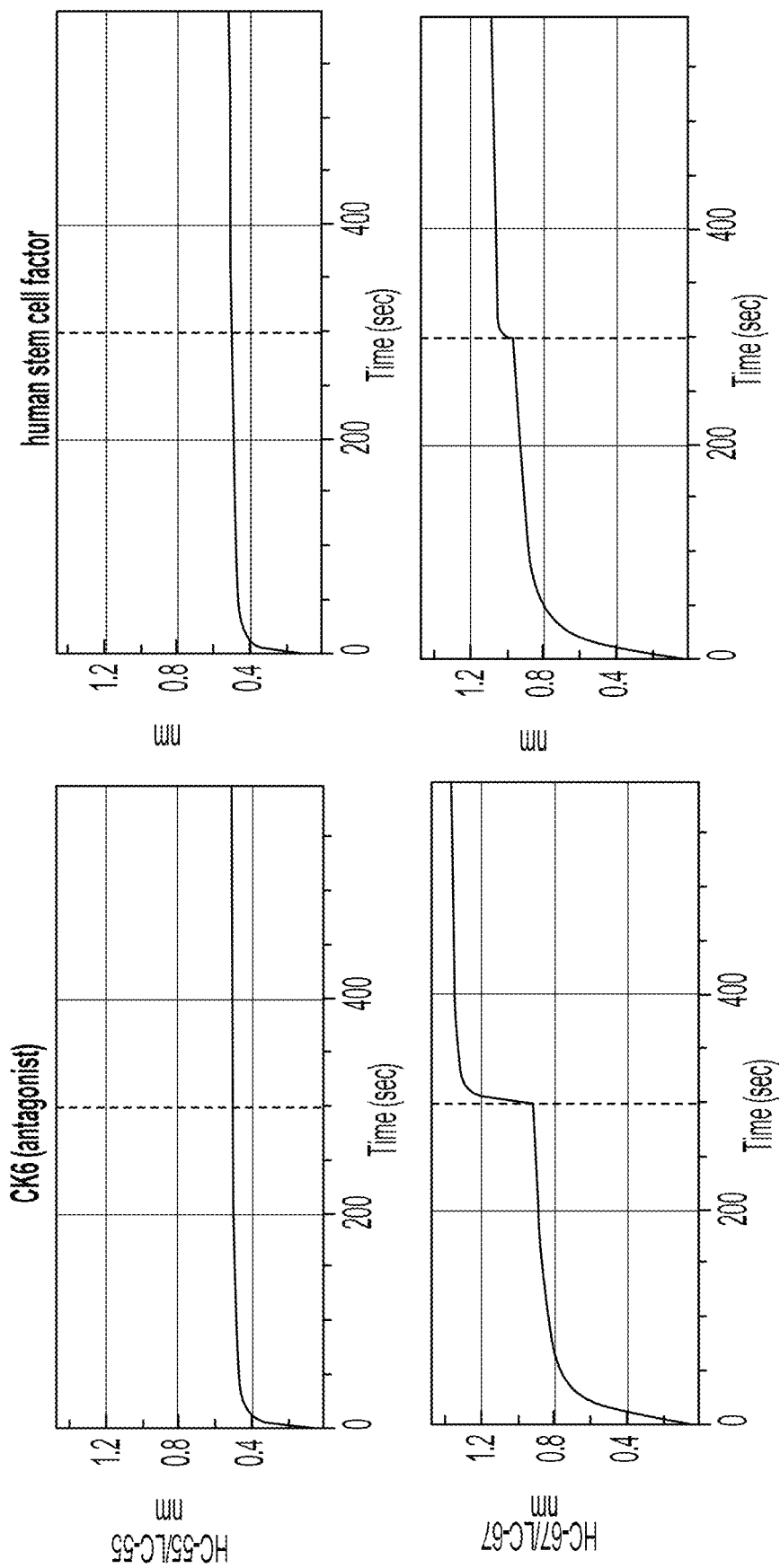
FIG. 12 graphically depicts the results of an in vitro cross-blocking assay in which the binding of CK6 or human SCF (y-axis) to Ab55 or Ab67 associated–CD117 was assessed as a function of time (x-axis).

As shown in FIG. 12, Ab55 was able to cross-block binding of both CK6 or SCF, indicating that Ab55 is an antagonistic antibody. In contrast, neutral Ab67 did not cross-block against CK6 or SCF. This experiment also suggests that CK6 and Ab67 do not have the same epitope (which is also suggested by their different properties).

Figure 13A:
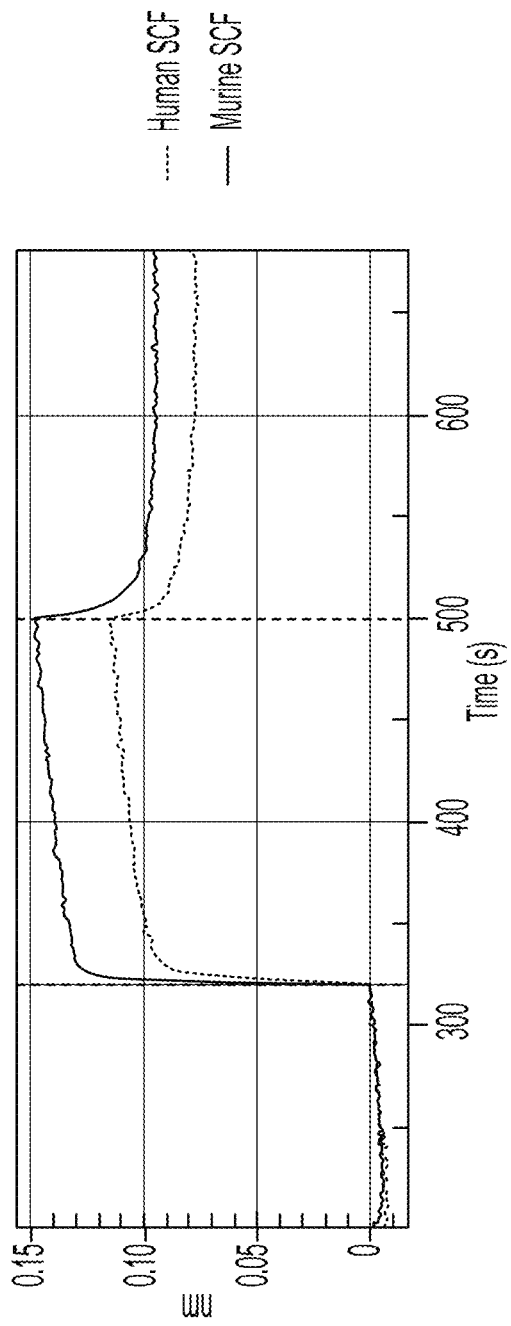
FIG. 13A demonstrates the binding of human or murine SCF to human CD117 ectodomain (y-axis) as a function of time (x-axis) as determined by BLI. Subsequently, as shown in FIG. 13B, an in vitro cross-blocking assay demonstrated the binding of human or murine SCF (y-axis) to Ab67 associated-CD117 as a function of time (x-axis).
Figure 13B:
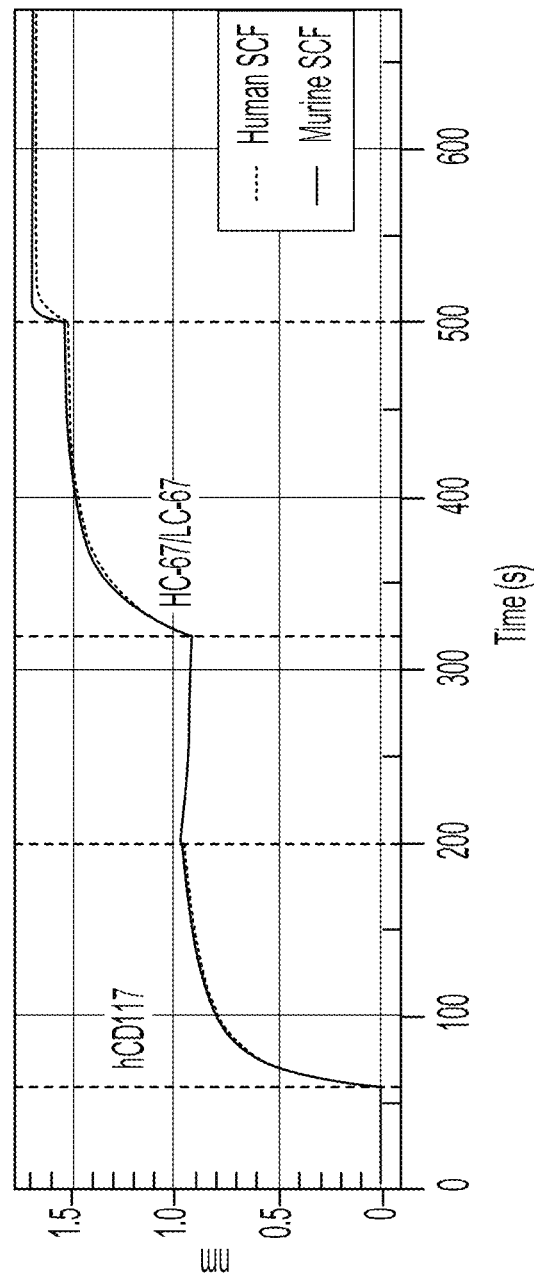

FIGS. 13A and 13B provides data from a second cross-blocking assay testing whether Ab67 could crossblock either human or mouse SCF from binding to huCD117. First, 25 nM of biotinylated recombinant CD117 ectodomain (R&D Systems #332-SR) was immobilized onto streptavidin biosensors (SA; Pall ForteBio 18-5019) and incubated with human (Thermo Fisher Scientific PHC2113) or mouse (R&D Systems #455-MC) stem cell factor. As described in FIG. 13, both human and murine stem cell factor are capable of binding to human recombinant CD117 ectodomain. To determine if Ab67 had neutral properties in regard to human and mouse SCF binding to CD117, a cross-blocking experiment was conducted. In brief, 25 nM of biotinylated recombinant CD117 ectodomain (R&D Systems #332-SR) was immobilized onto streptavidin biosensors (SA; Pall ForteBio 18-5019) and incubated with 100 nM of Ab67. Following this, the CD117 ectodomain in complex with Ab67 was incubated with human (ThermoFisher Scientific PHC2113) or mouse (R&D Systems #455-MC) stem cell factor. As described in FIG. 13B, Ab67 was not able to inhibit binding of either huSCF or mSCF to huCD117, thus further providing evidence of the neutral characteristic of Ab67.

Example 13. Analysis of Anti-CD117 Antibody Internalization

Figures 14A, 14B:
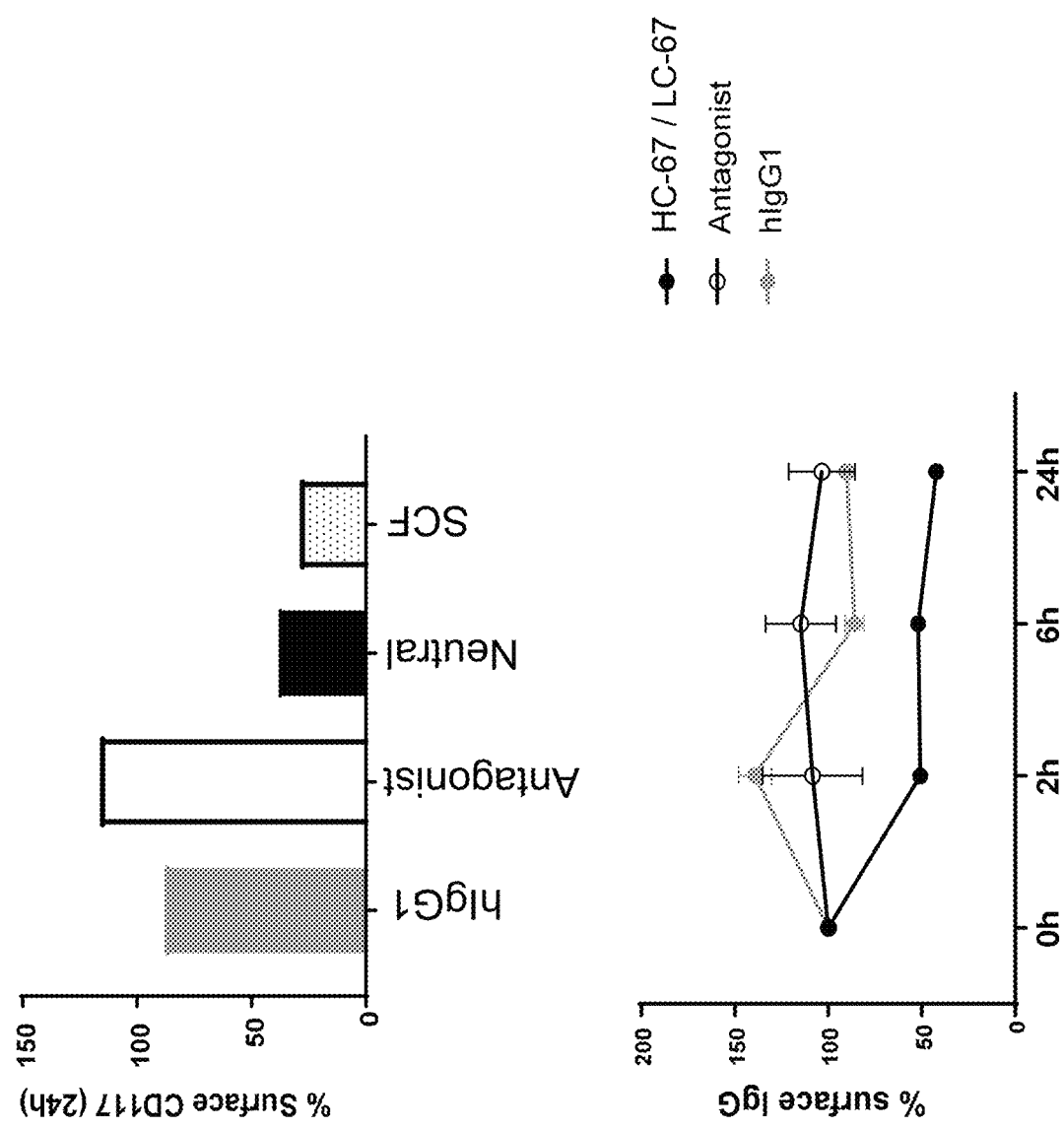
FIGS. 14A and 14B graphically depict the results of an in vitro internalization assay. The percent of surface CD117 was assessed on human bone marrow CD34+ cells following 24 hours of incubation with hIgG1, an antagonist antibody, a neutral antibody, or SCF (FIG. 14A). The corresponding percent of surface IgG was also assessed as a function of time (FIG. 14B).

The internalizing capacity of Ab67 versus an anti-CD117 antagonistic antibody was assessed in an in vitro antibody internalization assay. This assay was performed by incubating human bone marrow CD34+ cells with a saturating concentration of either a neutral, antagonistic, or control hIgG1 antibody over 24 hours. At the conclusion of the time course, a fluorophore-labeled anti-IgG molecule was used to assess remaining surface hIgG1 by flow cytometry. The percent of surface IgG was examined over time (FIG. 14B). Normalized CD117 surface expression (FIG. 14A) was calculated with a control condition incubated at 4 degrees C. where internalization would not be expected (not shown).

As described in FIG. 14A, the percent of CD117 on the surface of the cells was lower in the presence of neutral antibody Ab67 (IgG1) as compared to that observed following treatment with an antagonist anti-CD117 antibody or an isotype-matched hIgG1. Indeed, the level of internalization of CD117 was similar to that of SCF. Further, as described in FIG. 14B, the percent of neutral antibody Ab67 on the surface of the cells decreased over time relative to control antagonist or hIgG1 antibodies. This also suggests that the neutral anti-CD117 antibody, Ab67, internalized more rapidly than antagonist antibodies.

Example 14. Analysis of Anti-CD117 Ab67 and Ab55 ADCs Using an In Vitro Cell Killing Assay Ab67 and Ab55 were each conjugated to amatoxin with a cleavable linker to form Ab67-ADC and Ab55-ADC, each with an average approximate drug-to-antibody ratio (DAR) of about 3.7. The Ab67 and Ab55 ADCs were assessed in a cell killing assay in both Kasumi-1 cells (FIG. 15A) or primary human stem cells (FIGS. 15B and 15C).

For in vitro killing assays using Kasumi-1 cells, Kasumi-1 cells were grown according to ATCC guidelines. More specifically, Kasumi-1 cells were cultured for three days in the presence of CD117-ADC or the controls. Cell viability was measured by CellTiter-Glo. For in vitro killing assays using Human HSCs (i.e., isolated primary human CD34+ selected Bone Marrow Cells (BMCs)), human CD34+ BMCs were cultured for five days with CD117-ADC or the controls. Live cell counts were determined for all cells or CD34+ CD90+ gated cells by flow cytometry.

Figure 15A:
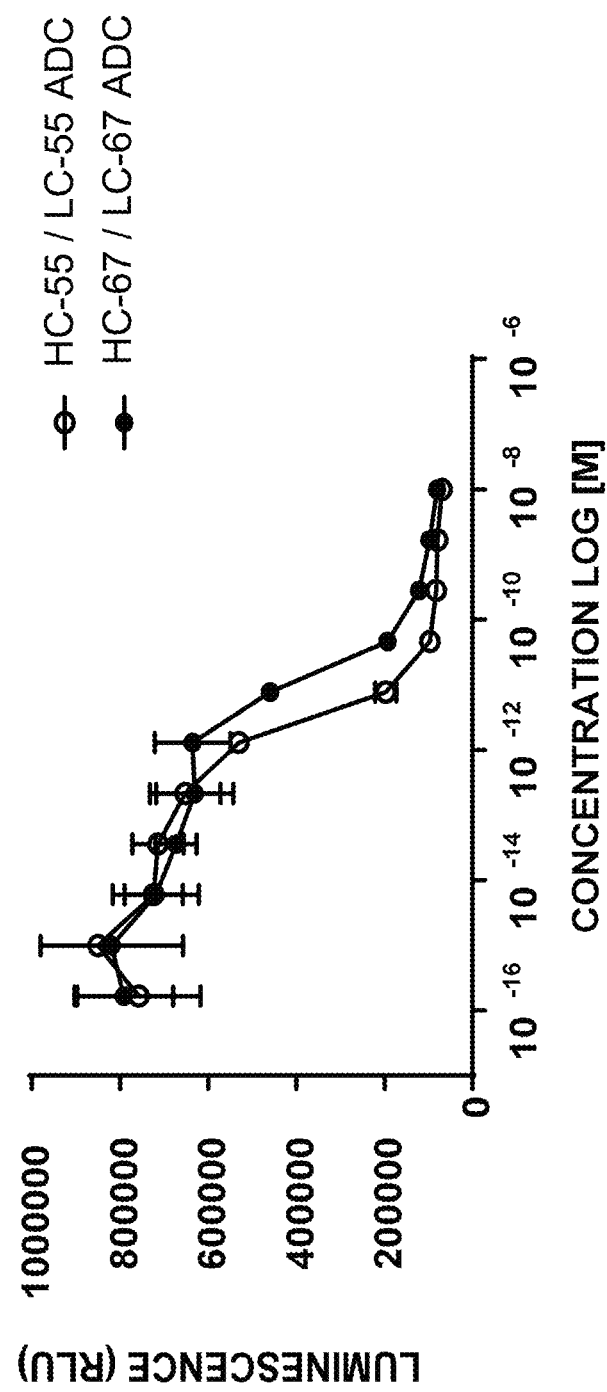
FIGS. 15A-15C graphically depict the results of in vitro cell killing assays in both Kasumi-1 cells (FIG. 15A) or primary human stem cells (FIGS. 15B and 15C) for Ab67 and Ab55 ADCs.
Figure 15B:
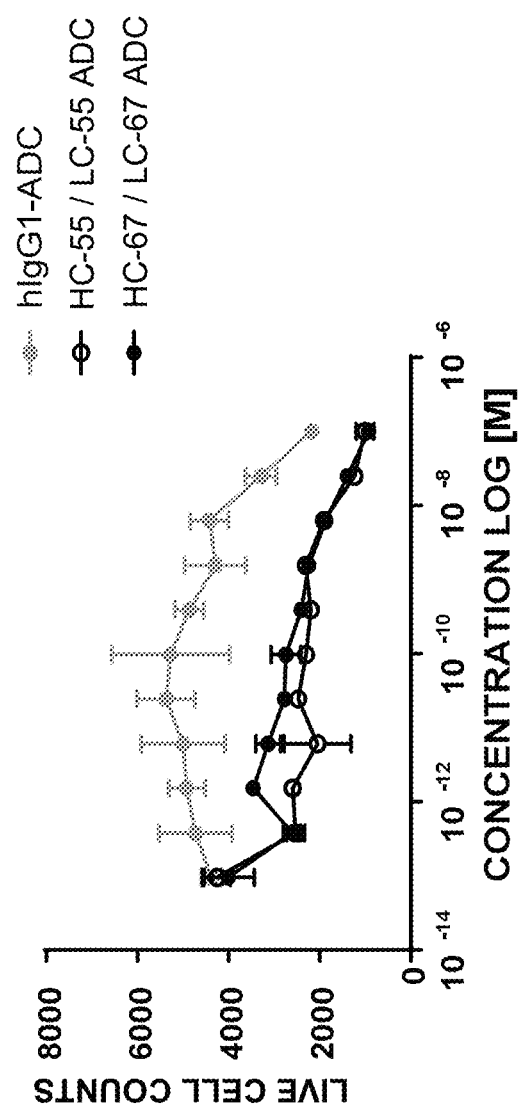
Figure 15C:
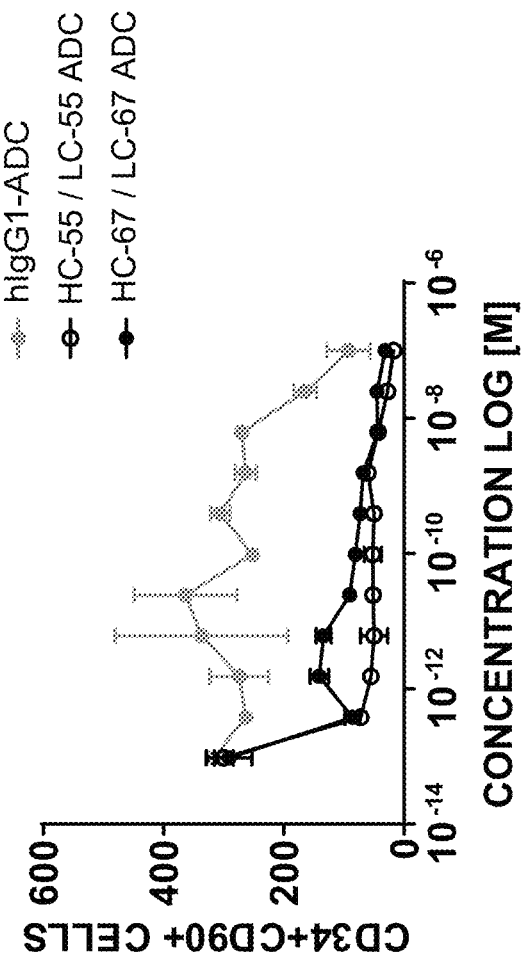

The results in FIGS. 15A-15C indicate that Ab55-ADC and Ab67-ADC are highly effective at killing CD117 expressing cell lines (e.g., Kasumi-1 cells) or primary human CD34+ cells in vitro, demonstrating potent killing of the leukemia cell line Kasumi-1 (FIG. 15A; Table 7; $IC_{50}$=2.1 pM), and equally effective killing of primary human CD34+ bone marrow cells during in vitro culture (FIGS. 15B and 15C; Table 7; $IC_{50}$=8.9 pM). Thus, Ab55-ADC and Ab67-ADC are highly effective at killing CD117 expressing cell lines and primary human CD34+ cells.

TABLE 7

| HC/LC | Antibody ID | DAR (average) | IC50 (M) |
|---|---|---|---|
| HC-55; LC-55 | Ab55 | 3.8 | $2.1 \times 10^{-12}$ |
| HC-67; LC-67 | Ab67 | 3.6 | $8.9 \times 10^{-12}$ |

Example 15. Characterization of Hydrophobicity of Anti-CD117 Antibodies

Figure 16A:
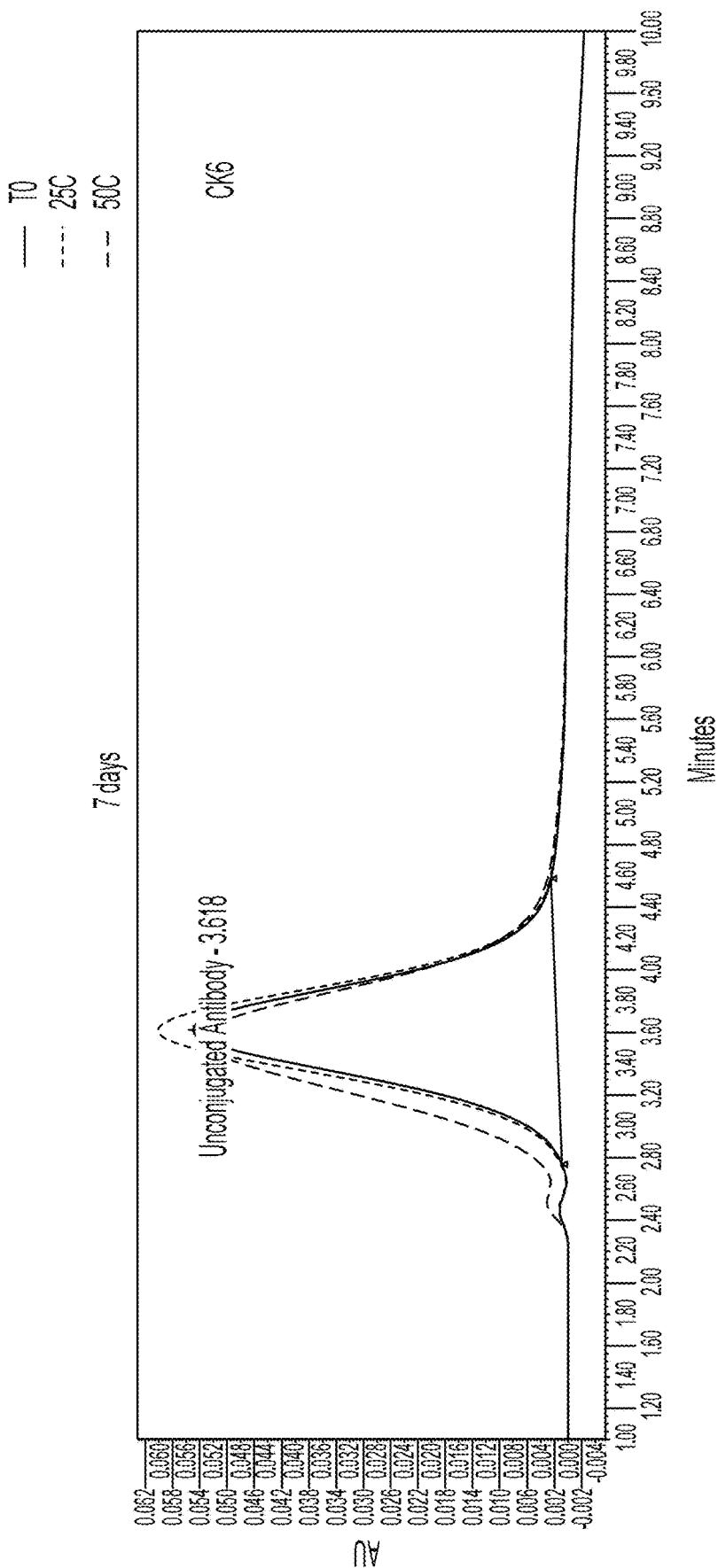
FIGS. 16A-16F depict chromatograms demonstrating the elution profile of the indicated antibody after 7 days (CK6 control (FIG. 16A), HC-55/LC-55 (Ab55.
Figure 16B:
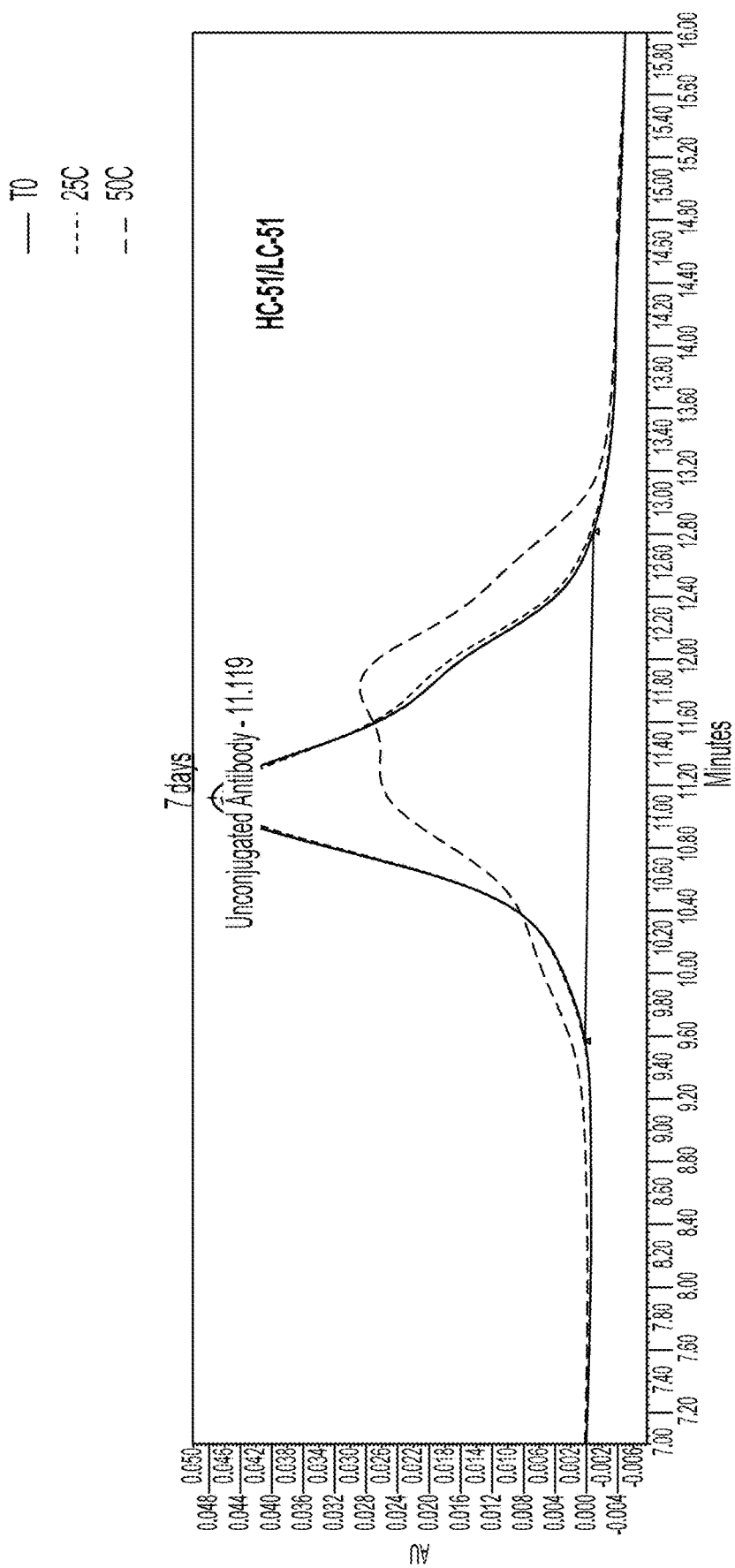
Figure 16C:
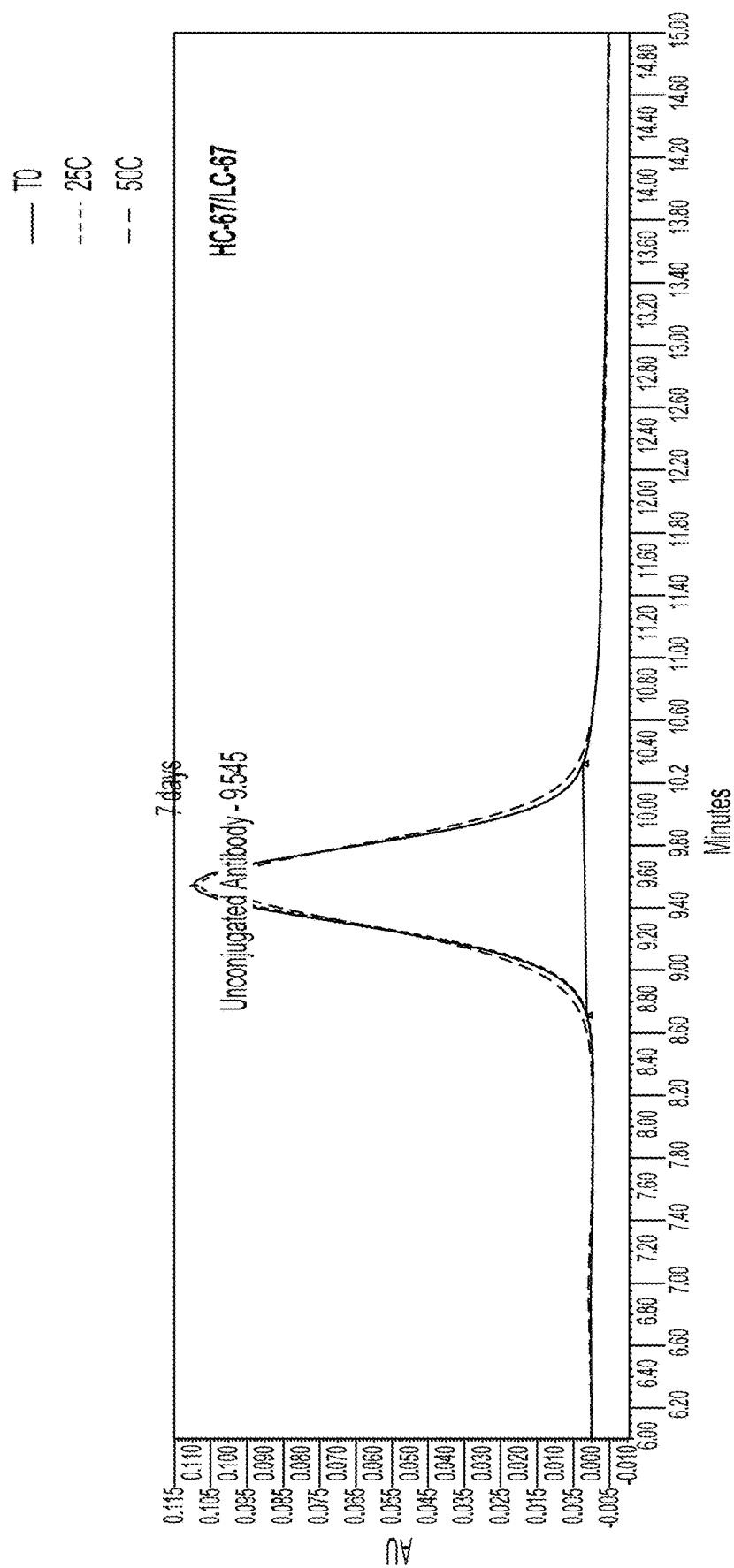
Figure 16D:
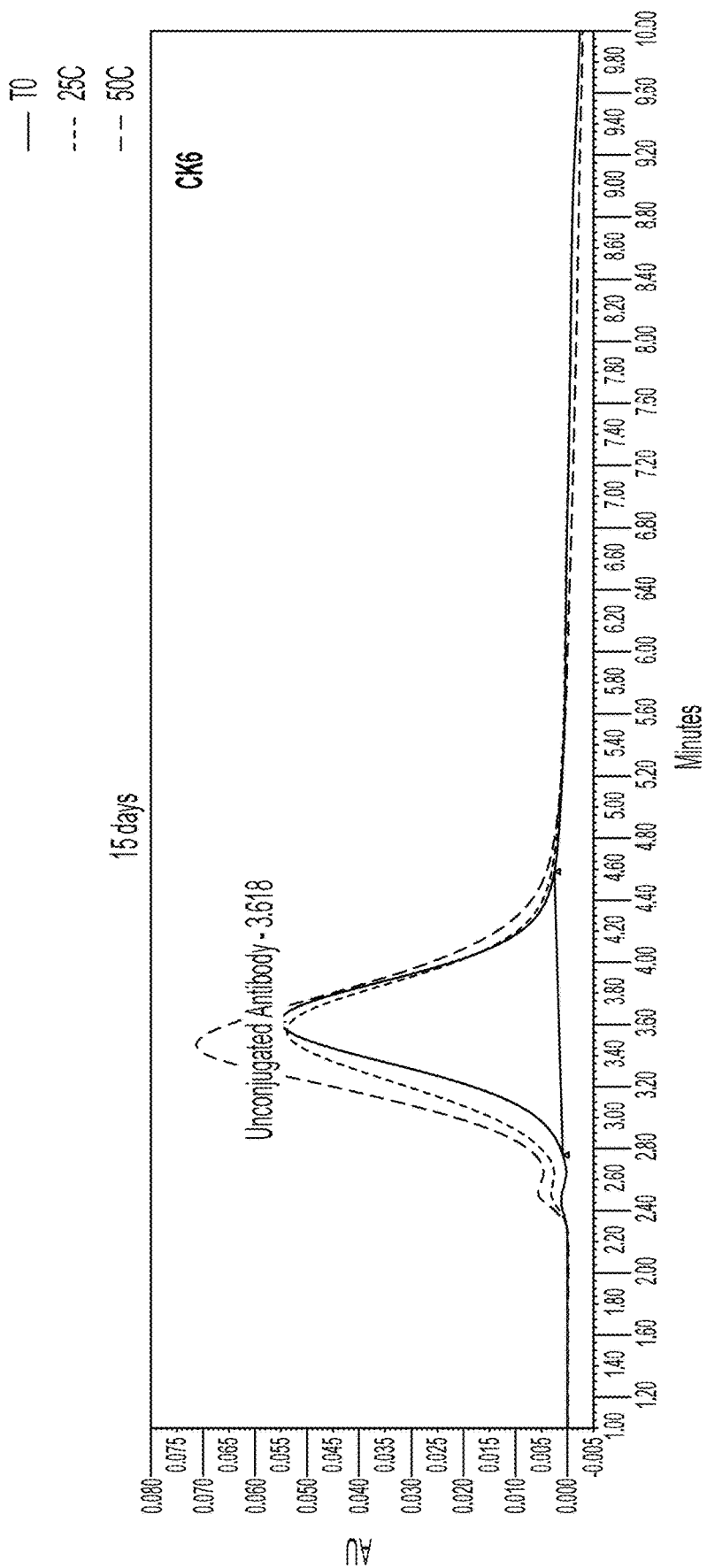
Figure 16E:
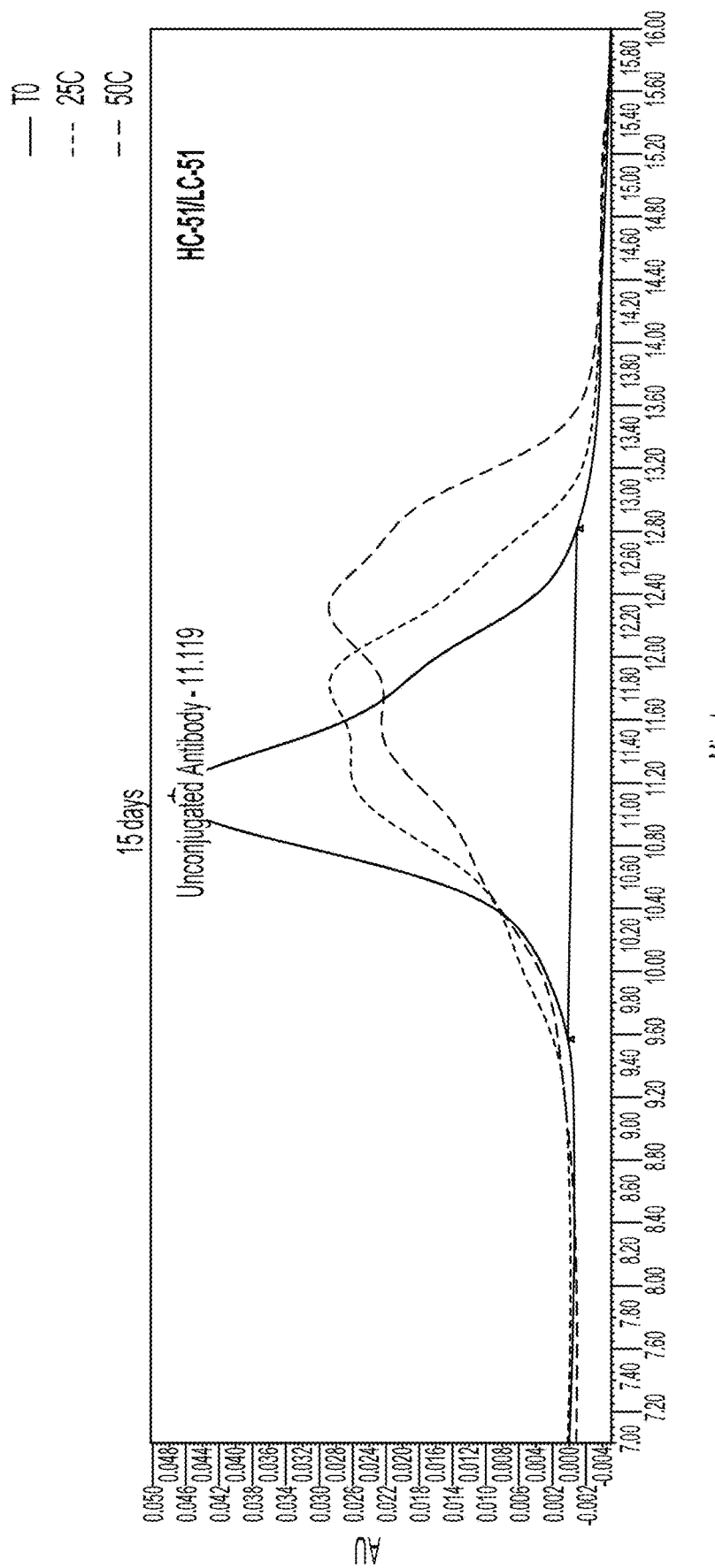
Figure 16F:
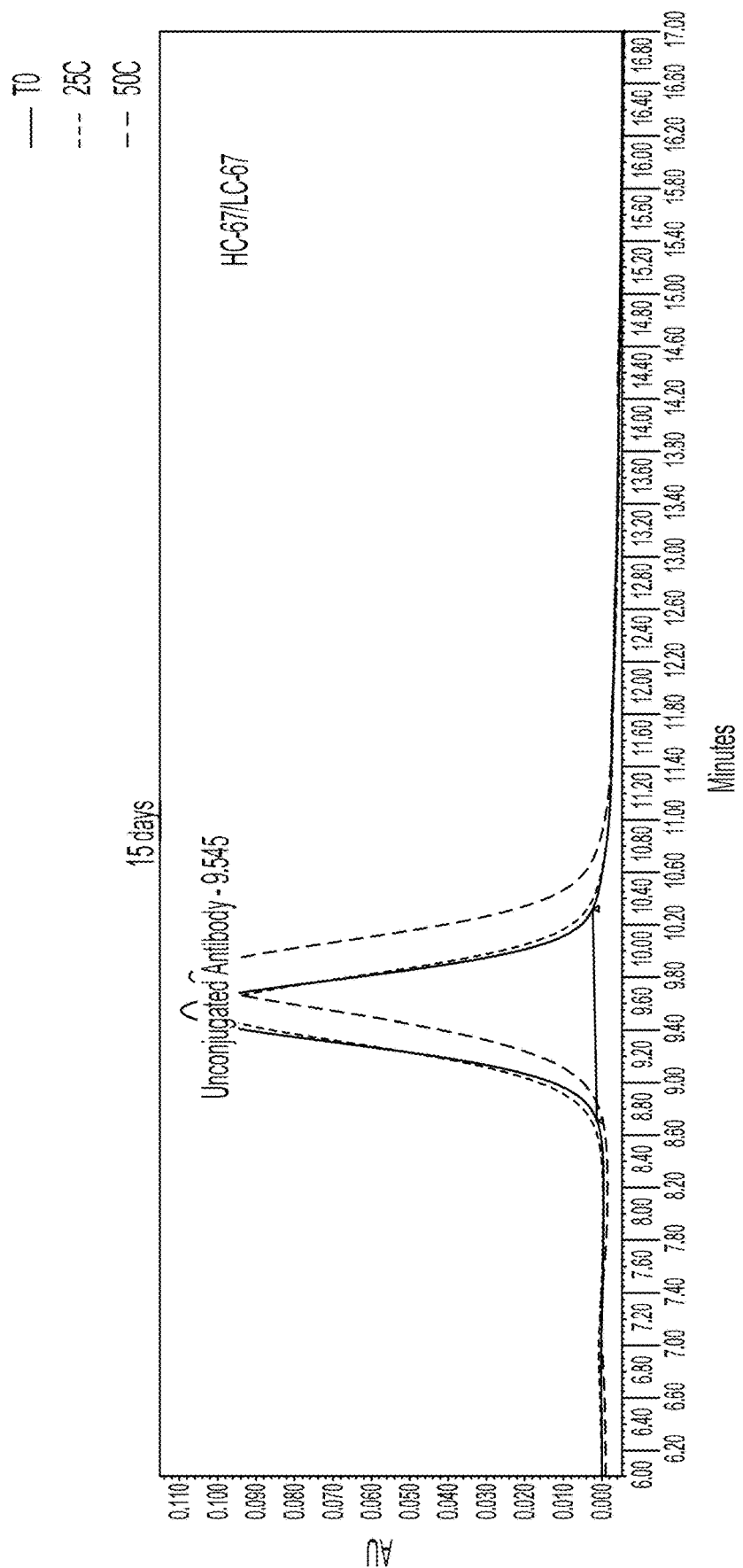

The hydrophobicity of each of Ab55 and AB67 was determined using hydrophobic interaction chromatography (HIC). Anti-CD117 antibody CK6 was used as a control for comparison. Antibodies Ab55 and Ab67 were evaluated after incubation at 25 or 50 degrees Celsius for 7 days or 15 days by hydrophobic interaction chromatography (HIC; FIGS. 16A-16F). Briefly, 50 micrograms of the indicated antibody were injected onto a Tosoh TSKgel Phenyl-5PW 7.5 mm ID×7.5 cm 10-micron column (Catalog #07573) on a Waters ARC HPLC/UPLC system. For CK6 (FIGS. 16A and 16D), peak broadening was observed after 15 days of incubation at 25 and 50 degrees Celsius. For Ab55 (FIGS. 16B and 16E), significant peak broadening was evident in the chromatograms for both mild (25 degrees Celsius) and severe (50 degrees Celsius) conditions after 7 days. Ab67 (FIGS. 16C and 16F) demonstrated minimal peak broadening (degradation) after incubation at 25 or 50 degrees Celsius after 15 days in comparison to either CK6 or Ab55, exhibiting the lowest change in hydrophobicity of the affinity improved anti-CD117 antibodies tested and compared to CK6 (FIGS. 16D-16F).

Example 16. Analysis of Fast Half-Life Anti-CD117 Antibody Using an In Vitro Cell Killing Assay An Ab67 variant with an engineered Fc region (i.e., an H435A Fc mutation (EU index Fc numbering)) was assessed in an in vitro cell killing assay. The H435A mutation resulted in a decrease in antibody half-life relative to the wild type Ab67 (i.e., WT Ab67 having H435 (EU index numbering)).

Ab67(WT) and Ab67(H435A) were each conjugated to amatoxin to form antibody drug conjugates (Ab67(WT)-ADC and Ab67(H435A)-ADC). These ADCs were further assessed in a cell killing assay using primary human stem cells. For in vitro killing assays using Human HSCs (i.e., isolated primary human CD34+ selected Bone Marrow Cells (BMCs)), human CD34+ BMCs were cultured for five days with CD117-ADC or the controls. Live cell counts were determined for CD34+ CD90+ gated cells by flow cytometry.

Figure 17A:
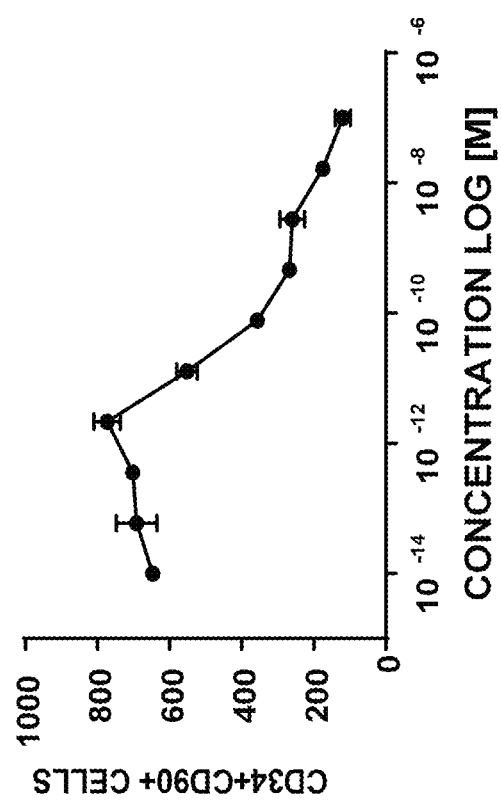
FIGS. 17A and 17B graphically depict the results of in vitro cell killing assays that show viable CD34+ CD90+ cell count as a function of Ab67(WT)-ADC (i.e., WT half-life) or Ab67(H435A)-ADC (i.e., fast half-life).
Figure 17B:
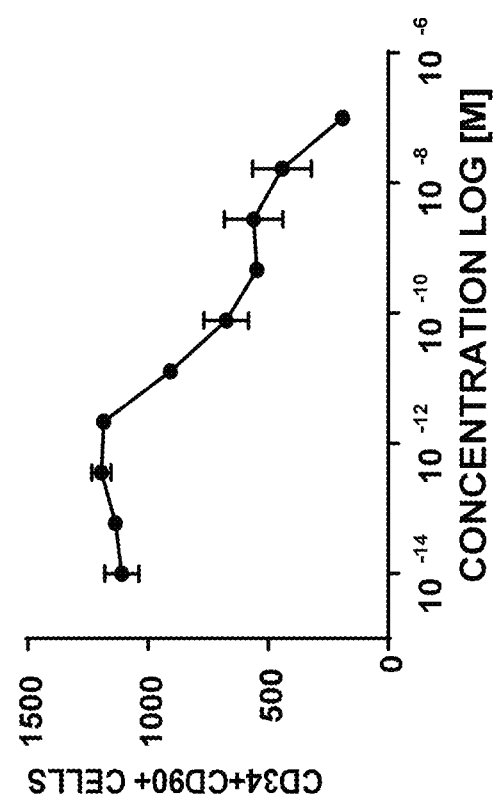

The results are described in FIGS. 17A and 17B and indicate that Ab67(WT)-ADC and Ab67(H435A)-ADC (i.e., fast half-life) were equally effective in the killing of primary human CD34+ bone marrow cells during in vitro culture ($IC_{50}$ Ab67(WT)=41 pM; $IC_{50}$ Ab67(H435A)=39.9 pM) (Tables 8 and 9).

TABLE 8

| HC/LC | Antibody ID | Half-life | DAR | IC50 (M) |
|---|---|---|---|---|
| HC-67; LC-67 | Ab67 | WT | 2 | $4.1 \times 10^{-11}$ |

TABLE 9

| HC/LC | Antibody ID | Half-life | DAR | IC50 (M) |
|---|---|---|---|---|
| HC-67 (H435A); LC-67 | Ab67(H435A) | Fast | 2 | $3.99 \times 10^{-11}$ |

Example 17. Characterization of Charge Variants of Anti-CD117 Antibodies

Figure 18:
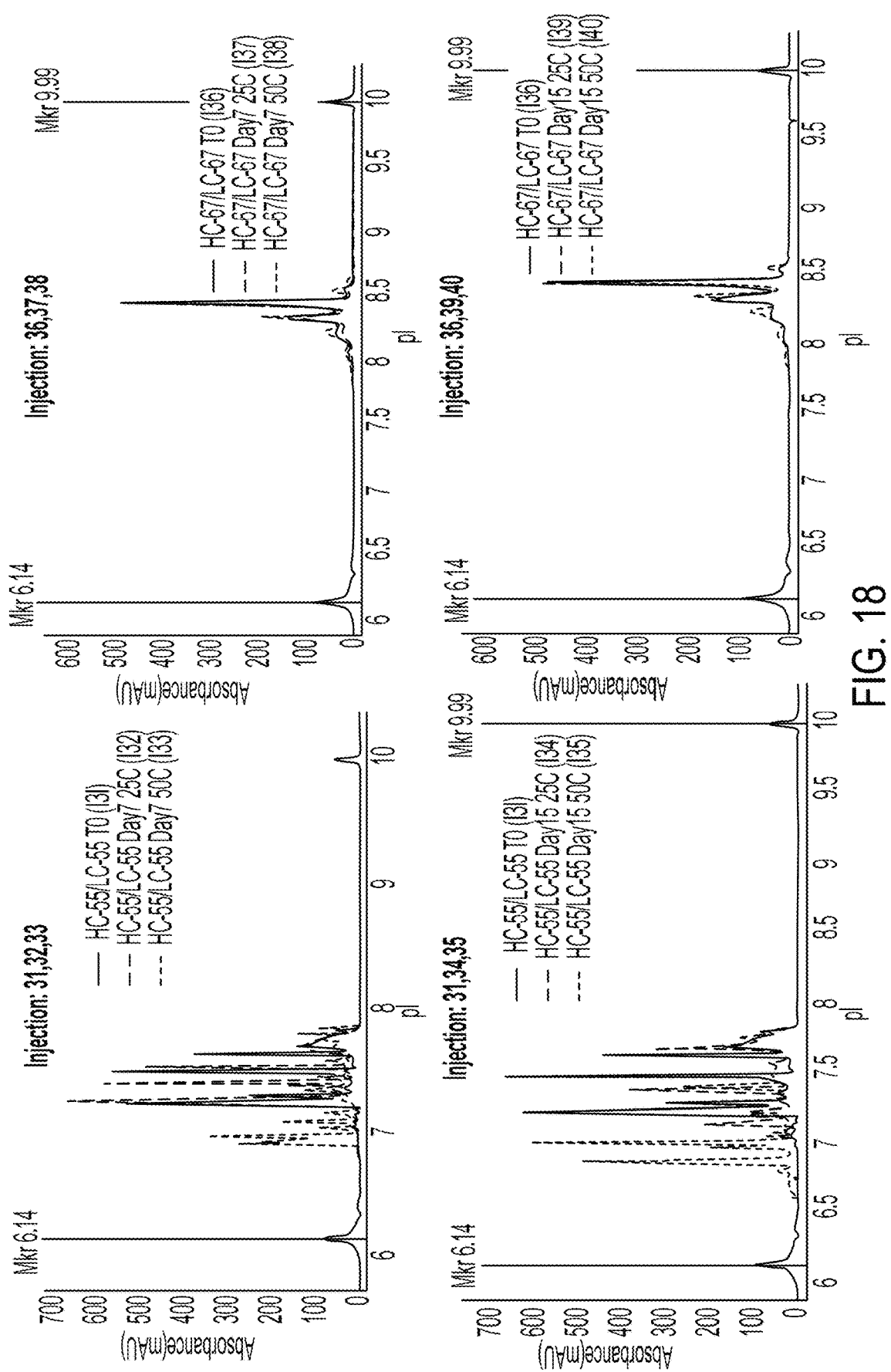
FIG. 18 graphically depicts electropherograms showing the charge heterogeneity profile of acidic variants present in the indicated antibody under the indicated incubation conditions (x-axis) as determined by capillary electrophoresis.

Capillary isoelectric focusing was performed on Ab55 and Ab67 antibodies to determine if sequence differentiation impacted the biophysical properties of the antibodies. Briefly, 10-40 micrograms of antibody were subjected to 7- and 15-days incubation at 25 or 50 degrees Celsius and analyzed through a capillary electrophoresis method using the Maurice instrument manufactured by Protein Simple according to standard manufacturer instruction. Antibody samples migrate to their electrically neutral pH. Acidic variants can be identified based on absorbance peaks detected below the isoelectric point relative to the total injected sample. The electropherograms in FIG. 18 demonstrate that Ab55 illustrated a complex charge heterogenereity profile compared to Ab67, which had less variants. Ab67 therefore had less accumulation of acidic species following stress conditions and was overall more stable than Ab55.

Example 18. In Vivo HSC Depletion Assay Using Anti-CD117 ADCs

Figures 19A, 19B:
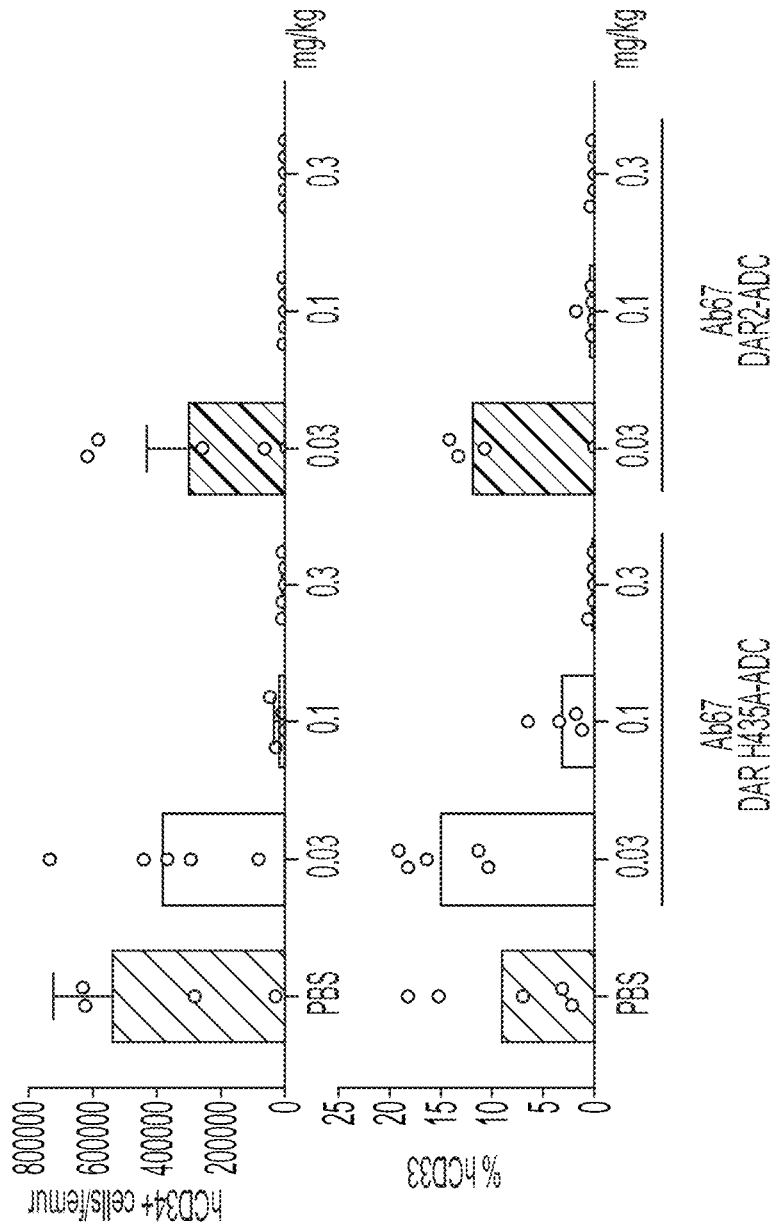
FIGS. 19A and 19B graphically depict the results of an in vivo cell depletion assay that shows a 0.1 mg/kg dose of Ab67(H435A)-ADC (i.e., fast half-life) or Ab67(WT)-ADC (i.e., WT half-life) selectively depletes human HSCs in humanized NSG mice. The absolute number of CD34+ cells in the bone marrow of Ab67(H435A)-ADC, Ab67(WT)-ADC, or control treated mice 21 days after a single administration of 0.03 mg/kg, 0.1 mg/kg, or 0.3 mg/kg of the ADC is shown in FIG. 19A. The percent of human myeloid cells present in the peripheral blood of Ab67(H435A)-ADC, Ab67(WT)-ADC, or control treated mice, expressed as a percent of that cell population prior to treatment (normalized to baseline) is also shown for each condition (FIG. 19B).

An in vivo experiment was performed to evaluate Ab67 with an engineered Fc (i.e., an H435A Fc mutation) to determine if the half life decrease impacted the ability of an anti-CD117 Ab67 ADC to kill CD117 expressing cells. In vivo HSC depletion assays were conducted using humanized NSG mice (Jackson Laboratories). The Ab67 antibody and the Ab67(H435A) antibody (i.e., characterized by a H435A Fc mutation (EU index)) were each conjugated to amatoxin to form an ADC and administered as a single injection of 0.3 mg/kg, 0.1 mg/kg, or 0.3 mg/kg to the humanized mouse model. Bone marrow was collected on day 21 and the absolute number of CD34+ cells was determined by flow cytometry (FIG. 19A). Blood was also collected on day 21 and examined by flow cytometry. The percentage of human CD33+ of treated or control treated mice relative to baseline are shown (FIG. 19B).

The results indicate that humanized NSG mice treated with the Ab67(H435A)-ADC showed significant depletion of human CD33+ myeloid cells relative to baseline following a single administration of the treatment regimen and indicate that the Ab67(H435A)-ADC and Ab(WT)-ADC depleted myeloid cells as a result of the depletion of early progenitor cells. In addition, humanized NSG mice treated with the Ab67-ADC showed significant depletion of human HSCs in the bone marrow, 21 days following a single administration of the ADC when compared to the control. Thus, the H435A mutation had no substantive impact on the ability of ADC comprising Ab67 to kill CD117 expressing cells.

Example 19: CD117-Amanitin Antibody Drug Conjugates Effectively Deplete Human and Non-Human Primate HSCs NHP HSC depletion was evaluated in male cynomolgus monkeys in single ascending or fractionated (Q3D×2) doses (3/group). HSC content in the bone marrow was monitored by flow cytometry. Hematology and clinical chemistries were evaluated throughout the study.

Figure 20:
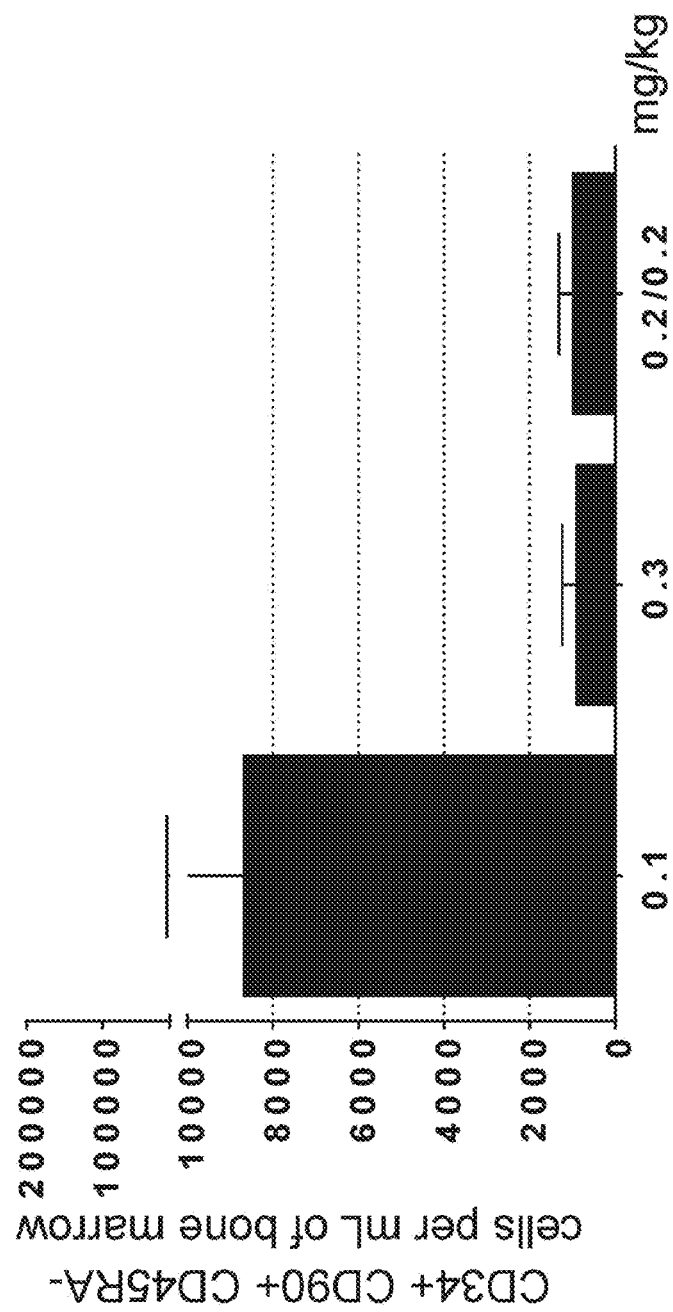
FIG. 20 graphically depicts the results of an in vivo cell depletion assay that shows a 0.3 mg/kg single dose or a fractionated dose of 0.2 mg/kg Q3D×2 of Ab67(H435A)-ADC (i.e. fast half-life) selectively depletes cynomolgus HSCs in cynomolgus monkeys. The absolute number of CD34+ CD90+ CD45RA− (phenotypic HSCs) isolated from the bone marrow of male cynomolgus monkeys dosed with the indicated dosing schema are shown (mean+/−SEM).

On-target, dose dependent decreases in phenotypic HSCs and CFUs were observed in the bone marrow at day 7 post anti-CD117 fast half-life conjugated to amatinin (Ab67; HC-67, LC-67) dosing with >95% HSC depletion observed with a single dose of 0.3 mg/kg (FIG. 20). The anti-CD117-amanitin induced depletion was on target and amanitin dependent as the unconjugated antibody and isotype-amanitin had no effect. Notably, white blood cell and lymphocyte counts were stable throughout the study, demonstrating that this strategy will spare the adaptive immune system. Platelet nadir occurred 4-8 days post infusion and was dose dependent transient and reversible. This also occurred with the isotype-amanitin suggesting the effect was off-target. Fractionated dosing (0.2/0.2 mg/kg Q3D×2) demonstrated similar potency on all cell parameters at 0.3 mg/kg and was well tolerated at the effective dose (FIG. 20). As expected, the fast half-life anti-CD117-amanitin was rapidly cleared with a half-life of 15-18 h. In conclusion, fast half-life Ab67 (H435A) conjugated to amanitin exhibits potent elimination of NHP HSCs and progenitors in vivo.

TABLE 10

SEQUENCE SUMMARY

| Sequence Identifier | Description | Sequence |
| --- | --- | --- |
| SEQ ID NO: 1 | CK6 CDR-H1 | SYWIG |
| SEQ ID NO: 2 | CK6 CDR-H2 | IIYPGDSDTRYSPSFQG |
| SEQ ID NO: 3 | CK6 CDR-H3 | HGRGYNGYEGAFDI |
| SEQ ID NO: 4 | CK6 CDR-L1 | RASQGISSALA |
| SEQ ID NO: 5 | CK6 CDR-L2 | DASSLES |
| SEQ ID NO: 6 | CK6 CDR-L3 | CQQFNSYPLT |
| SEQ ID NO: 7 | Consensus human Ab Heavy chain variable domain | EVQLVESGGGLVQPGGSLRLSCAASGFTFSDYA MSWVRQAPGKGLEWVAVISENGSDTYYADSVKG RFTISRDDSKNTLYLQMNSLRAEDTAVYYCARDR GGAVSYFDVWGQGTLVTVSS |
| SEQ ID NO: 8 | Consensus human Ab Light chain variable domain | DIQMTQSPSSLSASVGDRVTITCRASQDVSSYLA WYQQKPGKAPKLLIYAASSLESGVPSRFSGSGS GTDFTLTISSLQPEDFATYYCQQYNSLPYTFGQG TKVEIKRT |
| SEQ ID NO: 9 | Ab67 Heavy chain variable region (e.g., as found in HC-67) hIgG1 backbone (CDRs in bold) | EVQLVESGGGLVQPGGSLRLSCAASGFTFSDAD MDWVRQAPGKGLEWVGRTRNKAGSYTTEYAAS VKGRFTISRDDSKNSLYLQMNSLKTEDTAVYYCA REPKYWIDFDLWGRGTLVTVSS |
| SEQ ID NO: 10 | Ab67 Light chain variable region (e.g., as found in LC-67) hKappa backbone (CDRs in bold) | DIQMTQSPSSLSASVGDRVTITCRASQSISSYLN WYQQKPGKAPKLLIYAASSLQSGVPSRFSGSGS GTDFTLTISSLQPEDFATYYCQQSYIAPYTFGGGT KVEIK |
| SEQ ID NO: 11 | Ab67 CDR-H1 | FTFSDADMD |
| SEQ ID NO: 12 | Ab67 CDR-H2 | RTRNKAGSYTTEYAASVKG |
| SEQ ID NO: 13 | Ab67 CDR-H3 | AREPKYWIDFDL |
| SEQ ID NO: 14 | Ab67 CDR-L1 | RASQSISSYLN |
| SEQ ID NO: 15 | Ab67 CDR-L2 | AASSLQS |
| SEQ ID NO: 16 | Ab67 CDR-L3 | QQSYIAPYT |
| SEQ ID NO: 17 | Ab67 Heavy chain variable region (nucl) | GAGGTGCAGCTGGTGGAGTCTGGGGGAGGCTT GGTCCAGCCTGGAGGGTCCCTGAGACTCTCCT GTGCAGCCTCTGGATTCACCTTCAGTGACGCC GACATGGACTGGGTCCGCCAGGCTCCAGGGAA GGGGCTGGAGTGGGTTGGCCGTACTAGAAACA AAGCAGGAAGTTACACCACAGAATACGCCGCG TCTGTGAAAGGCAGATTCACCATCTCAAGAGAT GATTCAAAGAACTCACTGTATCTGCAAATGAAC AGCCTGAAAACCGAGGACACGGCGGTGTACTA CTGCGCCAGAGAGCCTAAATACTGGATCGACTT CGACCTATGGGGGAGAGGTACCTTGGTCACCG TCTCCTCA |
| SEQ ID NO: 18 | Ab67 Light chain variable region (nucl) | GACATCCAGATGACCCAGTCTCCATCCTCCCTG TCTGCATCTGTAGGAGACAGAGTCACCATCACT TGCCGGGCAAGTCAGAGCATTAGCAGCTATTTA AATTGGTATCAGCAGAAACCAGGGAAAGCCCCT AAGCTCCTGATCTATGCTGCATCCAGTTTGCAA |

TABLE 10-continued

SEQUENCE SUMMARY

| Sequence Identifier | Description | Sequence |
|---|---|---|
| | | AGTGGGGTCCCATCAAGGTTCAGTGGCAGTGG ATCTGGGACAGATTTCACTCTCACCATCAGCAG TCTGCAACCTGAAGATTTTGCAACTTACTACTGT CAGCAAAGCTACATCGCCCCTTACACTTTTGGC GGAGGGACCAAGGTTGAGATCAAA |
| SEQ ID NO: 19 | Ab55 Heavy chain variable region (e.g., as found in HC-55) hIgG1 backbone (CDRs in bold) | QVQLVQSGAEVKKPGSSVKVSCKASGGTFRIYAI SWVRQAPGQGLEWMGGIIPDFGVANYAQKFQG RVTITADESTSTAYMELSSLRSEDTAVYYCARGG LDTDEFDLWGRGTLVTVSS |
| SEQ ID NO: 20 | Ab55 Light chain variable region (e.g., as found in LC-55) hKappa backbone (CDRs in bold) | DIQMTQSPSSLSASVGDRVTITCRASQSINSYLN WYQQKPGKAPKLLIYAASSLQSGVPSRFSGSGS GTDFTLTISSLQPEDFATYYCQQGVSDITFGGGTK VEIK |
| SEQ ID NO: 21 | Ab55 CDR-H1 | GTFRIYAIS |
| SEQ ID NO: 22 | Ab55 CDR-H2 | GIIPDFGVANYAQKFQG |
| SEQ ID NO: 23 | Ab55 CDR-H3 | ARGGLDTDEFDL |
| SEQ ID NO: 24 | Ab55 CDR-L1 | RASQSINSYLN |
| SEQ ID NO: 25 | Ab55 CDR-L2 | AASSLQS |
| SEQ ID NO: 26 | Ab55 CDR-L3 | QQGVSDIT |
| SEQ ID NO: 27 | Ab55 Heavy chain variable region (nucl) | CAGGTGCAGCTGGTGCAGTCTGGGGCTGAGGT GAAGAAGCCTGGGTCCTCGGTGAAGGTCTCCT GCAAGGCTTCTGGAGGCACCTTCCGAATCTATG CTATCAGCTGGGTGCGACAGGCCCCTGGACAA GGGCTTGAGTGGATGGGAGGGATCATCCCTGA CTTCGGTGTAGCAAACTACGCACAGAAGTTCCA GGGCAGAGTCACGATTACCGCGGACGAATCCA CGAGCACAGCCTACATGGAGCTGAGCAGCCTG AGATCTGAGGACACGGCGGTGTACTACTGCGC CAGAGGTGGATTGGACACAGACGAGTTCGACC TATGGGGGAGAGGTACCTTGGTCACCGTCTCC TCA |
| SEQ ID NO: 28 | Ab55 Light chain variable region (nucl) | GACATCCAGATGACCCAGTCTCCATCCTCCCTG TCTGCATCTGTAGGAGACAGAGTCACCATCACT TGCCGGGCAAGTCAGAGCATTAACAGCTATTTA AATTGGTATCAGCAGAAACCAGGGAAAGCCCCT AAGCTCCTGATCTATGCTGCATCCAGTTTGCAA AGTGGGGTCCCATCAAGGTTCAGTGGCAGTGG ATCTGGGACAGATTTCACTCTCACCATCAGCAG TCTGCAACCTGAAGATTTTGCAACTTACTACTGT CAGCAAGGAGTCAGTGACATCACTTTTGGCGG AGGGACCAAGGTTGAGATCAAA |
| SEQ ID NO: 29 | Ab54 Heavy chain variable region (e.g., as found in HC-54) hIgG1 backbone (CDRs in bold) | QVQLVQSGAEVKKPGSSVKVSCKASGGTFSSYAI SWVRQAPGQGLEWMGGIIPIFGTANYAQKFQGR VTITADESTSTAYMELSSLRSEDTAVYYCARGGL DTDEFDLWGRGTLVTVSS |
| SEQ ID NO: 30 | Ab54 Light chain variable region (e.g., as found in LC-54) hKappa backbone (CDRs in bold) | DIQMTQSPSSLSASVGDRVTITCRASQSINSYLN WYQQKPGKAPKLLIYAASSLQSGVPSRFSGSGS GTDFTLTISSLQPEDFATYYCQQGVSDITFGGGTK VEIK |
| SEQ ID NO: 31 | Ab54 CDR-H1 | GTFSSYAIS |
| SEQ ID NO: 32 | Ab54 CDR-H2 | GIIPIFGTANYAQKFQG |
| SEQ ID NO: 33 | Ab54 CDR-H3 | ARGGLDTDEFDL |
| SEQ ID NO: 34 | Ab54 CDR-L1 | RASQSINSYLN |
| SEQ ID NO: 35 | Ab54 CDR-L2 | AASSLQS |

TABLE 10-continued

SEQUENCE SUMMARY

| Sequence Identifier | Description | Sequence |
|---|---|---|
| SEQ ID NO: 36 | Ab54 CDR-L3 | QQGVSDIT |
| SEQ ID NO: 37 | Ab54 Heavy chain variable region (nucl) | CAGGTGCAGCTGGTGCAGTCTGGGGCTGAGGT GAAGAAGCCTGGGTCCTCGGTGAAGGTCTCCT GCAAGGCTTCTGGAGGCACCTTCAGCAGCTAT GCTATCAGCTGGGTGCGACAGGCCCCTGGACA AGGGCTTGAGTGGATGGGAGGGATCATCCCTA TCTTTGGTACAGCAAACTACGCACAGAAGTTCC AGGGCAGAGTCACGATTACCGCGGACGAATCC ACGAGCACAGCCTACATGGAGCTGAGCAGCCT GAGATCTGAGGACACGGCGGTGTACTACTGCG CCAGAGGTGGATTGGACACAGACGAGTTCGAC CTATGGGGGAGAGGTACCTTGGTCACCGTCTC CTCA |
| SEQ ID NO: 38 | Ab54 Light chain variable region (nucl) | GACATCCAGATGACCCAGTCTCCATCCTCCCTG TCTGCATCTGTAGGAGACAGAGTCACCATCACT TGCCGGGCAAGTCAGAGCATTAACAGCTATTTA AATTGGTATCAGCAGAAACCAGGGAAAGCCCCT AAGCTCCTGATCTATGCTGCATCCAGTTTGCAA AGTGGGGTCCCATCAAGGTTCAGTGGCAGTGG ATCTGGGACAGATTTCACTCTCACCATCAGCAG TCTGCAACCTGAAGATTTTGCAACTTACTACTGT CAGCAAGGAGTCAGTGACATCACTTTTGGCGG AGGGACCAAGGTTGAGATCAAA |
| SEQ ID NO: 39 | Ab56 Heavy chain variable region (e.g., as found in HC-56) hIgG1 backbone (CDRs in bold) | QVQLVQSGAEVKKPGSSVKVSCKASGGTFSLYAI SWVRQAPGQGLEWMGGIIPAFGTANYAQKFQG RVTITADESTSTAYMELSSLRSEDTAVYYCARGG LDTDEFDLWGRGTLVTVSS |
| SEQ ID NO: 40 | Ab56 Light chain variable region (e.g., as found in LC-56) hKappa backbone (CDRs in bold) | DIQMTQSPSSLSASVGDRVTITCRASQSINSYLN WYQQKPGKAPKLLIYAASSLQSGVPSRFSGSGS GTDFTLTISSLQPEDFATYYCQQGVSDITFGGGTK VEIK |
| SEQ ID NO: 41 | Ab56 CDR-H1 | GTFSLYAIS |
| SEQ ID NO: 42 | Ab56 CDR-H2 | GIIPAFGTANYAQKFQG |
| SEQ ID NO: 43 | Ab56 CDR-H3 | ARGGLDTDEFDL |
| SEQ ID NO: 44 | Ab56 CDR-L1 | RASQSINSYLN |
| SEQ ID NO: 45 | Ab56 CDR-L2 | AASSLQS |
| SEQ ID NO: 46 | Ab56 CDR-L3 | QQGVSDIT |
| SEQ ID NO: 47 | Ab56 Heavy chain variable region (nucl) | CAGGTGCAGCTGGTGCAGTCTGGGGCTGAGGT GAAGAAGCCTGGGTCCTCGGTGAAGGTCTCCT GCAAGGCTTCTGGAGGCACCTTCAGCCTCTAT GCTATCTCCTGGGTGCGACAGGCCCCTGGACA AGGGCTTGAGTGGATGGGAGGGATCATCCCTG CCTTCGGTACCGCAAACTACGCACAGAAGTTCC AGGGCAGAGTCACGATTACCGCGGACGAATCC ACGAGCACAGCCTACATGGAGCTGAGCAGCCT GAGATCTGAGGACACGGCGGTGTACTACTGCG CCAGAGGTGGATTGGACACAGACGAGTTCGAC CTATGGGGGAGAGGTACCTTGGTCACCGTCTC CTCA |
| SEQ ID NO: 48 | Ab56 Light chain variable region (nucl) | GACATCCAGATGACCCAGTCTCCATCCTCCCTG TCTGCATCTGTAGGAGACAGAGTCACCATCACT TGCCGGGCAAGTCAGAGCATTAACAGCTATTTA AATTGGTATCAGCAGAAACCAGGGAAAGCCCCT AAGCTCCTGATCTATGCTGCATCCAGTTTGCAA AGTGGGGTCCCATCAAGGTTCAGTGGCAGTGG ATCTGGGACAGATTTCACTCTCACCATCAGCAG TCTGCAACCTGAAGATTTTGCAACTTACTACTGT CAGCAAGGAGTCAGTGACATCACTTTTGGCGG AGGGACCAAGGTTGAGATCAAA |

TABLE 10-continued

SEQUENCE SUMMARY

| Sequence Identifier | Description | Sequence |
|---|---|---|
| SEQ ID NO: 49 | Ab57 Heavy chain variable region (e.g., as found in HC-57) hIgG1 backbone (CDRs in bold) | QVQLVQSGAEVKKPGSSVKVSCKASGGTFSLYAI SWVRQAPGQGLEWMGGIIPHFGLANYAQKFQG RVTITADESTSTAYMELSSLRSEDTAVYYCARGG LDTDEFDLWGRGTLVTVSS |
| SEQ ID NO: 50 | Ab57 Light chain variable region (e.g., as found in LC-57) hKappa backbone (CDRs in bold) | DIQMTQSPSSLSASVGDRVTITCRASQSINSYLN WYQQKPGKAPKLLIYAASSLQSGVPSRFSGSGS GTDFTLTISSLQPEDFATYYCQQGVSDITFGGGTK VEIK |
| SEQ ID NO: 51 | Ab57 CDR-H1 | GTFSLYAIS |
| SEQ ID NO: 52 | Ab57 CDR-H2 | GIIPHFGLANYAQKFQG |
| SEQ ID NO: 53 | Ab57 CDR-H3 | ARGGLDTDEFDL |
| SEQ ID NO: 54 | Ab57 CDR-L1 | RASQSINSYLN |
| SEQ ID NO: 55 | Ab57 CDR-L2 | AASSLQS |
| SEQ ID NO: 56 | Ab57 CDR-L3 | QQGVSDIT |
| SEQ ID NO: 57 | Ab57 Heavy chain variable region (nucl) | CAGGTGCAGCTGGTGCAGTCTGGGGCTGAGGT GAAGAAGCCTGGGTCCTCGGTGAAGGTCTCCT GCAAGGCTTCTGGAGGCACCTTCTCCCTCTATG CTATCAGCTGGGTGCGACAGGCCCCTGGACAA GGGCTTGAGTGGATGGGAGGGATCATCCCTCA CTTCGGTCTCGCAAACTACGCACAGAAGTTCCA GGGCAGAGTCACGATTACCGCGGACGAATCCA CGAGCACAGCCTACATGGAGCTGAGCAGCCTG AGATCTGAGGACACGGCGGTGTACTACTGCGC CAGAGGTGGATTGGACACAGACGAGTTCGACC TATGGGGGAGAGGTACCTTGGTCACCGTCTCC TCA |
| SEQ ID NO: 58 | Ab57 Light chain variable region (nucl) | GACATCCAGATGACCCAGTCTCCATCCTCCCTG TCTGCATCTGTAGGAGACAGAGTCACCATCACT TGCCGGGCAAGTCAGAGCATTAACAGCTATTTA AATTGGTATCAGCAGAAACCAGGGAAAGCCCCT AAGCTCCTGATCTATGCTGCATCCAGTTTGCAA AGTGGGGTCCCATCAAGGTTCAGTGGCAGTGG ATCTGGGACAGATTTCACTCTCACCATCAGCAG TCTGCAACCTGAAGATTTTGCAACTTACTACTGT CAGCAAGGAGTCAGTGACATCACTTTTGGCGG AGGGACCAAGGTTGAGATCAAA |
| SEQ ID NO: 59 | Ab58 Heavy chain variable region (e.g., as found in HC-58) hIgG1 backbone (CDRs in bold) | EVQLLESGGGLVQPGGSLRLSCAASGFTFSNYA MSWVRQAPGKGLEWVSAISGSGGSTYYADSVK GRFTISRDNSKNTLYLQMNSLRAEDTAVYYCAKG PPTYHTNYYYMDVWGKGTTVTVSS |
| SEQ ID NO: 60 | Ab58 Light chain variable region (e.g., as found in LC-58) hKappa backbone (CDRs in bold) | DIQMTQSPSSVSASVGDRVTITCRASQGISSWLA WYQQKPGKAPKLLIYAASSLQSGVPSRFSGSGS GTDFTLTISSLQPEDFATYYCQQTNSFPYTFGGG TKVEIK |
| SEQ ID NO: 61 | Ab58 CDR-H1 | FTFSNYAMS |
| SEQ ID NO: 62 | Ab58 CDR-H2 | AISGSGGSTYYADSVKG |
| SEQ ID NO: 63 | Ab58 CDR-H3 | AKGPPTYHTNYYYMDV |
| SEQ ID NO: 64 | Ab58 CDR-L1 | RASQGISSWLA |
| SEQ ID NO: 65 | Ab58 CDR-L2 | AASSLQS |
| SEQ ID NO: 66 | Ab58 CDR-L3 | QQTNSFPYT |
| SEQ ID NO: 67 | Ab58 Heavy chain variable region (nucl) | GAGGTGCAGCTGTTGGAGTCTGGGGGAGGCTT GGTACAGCCTGGGGGGTCCCTGAGACTCTCCT GTGCAGCCTCTGGATTCACCTTTAGCAATTATG |

TABLE 10-continued

SEQUENCE SUMMARY

| Sequence Identifier | Description | Sequence |
|---|---|---|
| | | CCATGAGCTGGGTCCGCCAGGCTCCAGGGAAG GGGCTGGAGTGGGTCTCAGCTATTAGTGGTAG TGGTGGTAGCACATACTACGCAGACTCCGTGAA GGGCCGGTTCACCATCTCCAGAGACAATTCCAA GAACACGCTGTATCTGCAAATGAACAGCCTGAG AGCCGAGGACACGGCGGTGTACTACTGCGCCA AGGGCCCTCCTACATACCACACAAACTACTACT ACATGGACGTATGGGGCAAGGGTACAACTGTC ACCGTCTCCTCA |
| SEQ ID NO: 68 | Ab58 Light chain variable region (nucl) | GACATCCAGATGACCCAGTCTCCATCTTCCGTG TCTGCATCTGTAGGAGACAGAGTCACCATCACT TGTCGGGCGAGTCAGGGTATTAGCAGCTGGTT AGCCTGGTATCAGCAGAAACCAGGGAAAGCCC CTAAGCTCCTGATCTATGCTGCATCCAGTTTGC AAAGTGGGGTCCCATCAAGGTTCAGCGGCAGT GGATCTGGGACAGATTTCACTCTCACCATCAGC AGCCTGCAGCCTGAAGATTTTGCAACTTATTAC TGTCAGCAAACAAATAGTTTCCCTTACACTTTTG GCGGAGGGACCAAGGTTGAGATCAAA |
| SEQ ID NO: 69 | Ab61 Heavy chain variable region (e.g., as found in HC-61) hIgG1 backbone (CDRs in bold) | EVQLLESGGGLVQPGGSLRLSCAASGFTFSSYV MIWVRQAPGKGLEWVSSISGDSVTTYYADSVKG RFTISRDNSKNTLYLQMNSLRAEDTAVYYCAKGP PTYHTNYYYMDVWGKGTTVTVSS |
| SEQ ID NO: 70 | Ab61 Light chain variable region (e.g., as found in LC-61) hKappa backbone (CDRs in bold) | DIQMTQSPSSVSASVGDRVTITCRASQGISSWLA WYQQKPGKAPKLLIYAASSLQSGVPSRFSGSGS GTDFTLTISSLQPEDFATYYCQQTNSFPYTFGGG TKVEIK |
| SEQ ID NO: 71 | Ab61 CDR-H1 | FTFSSYVMI |
| SEQ ID NO: 72 | Ab61 CDR-H2 | SISGDSVTTYYADSVKG |
| SEQ ID NO: 73 | Ab61 CDR-H3 | AKGPPTYHTNYYYMDV |
| SEQ ID NO: 74 | Ab61 CDR-L1 | RASQGISSWLA |
| SEQ ID NO: 75 | Ab61 CDR-L2 | AASSLQS |
| SEQ ID NO: 76 | Ab61 CDR-L3 | QQTNSFPYT |
| SEQ ID NO: 77 | Ab61 Heavy chain variable region (nucl) | GAGGTGCAGCTGTTGGAGTCTGGGGGAGGCTT GGTACAGCCTGGGGGGTCCCTGAGACTCTCCT GTGCAGCCTCTGGATTCACCTTTAGCAGCTATG TCATGATCTGGGTCCGCCAGGCTCCAGGGAAG GGGCTGGAGTGGGTCTCAAGCATTAGTGGTGA CAGCGTAACAACATACTACGCAGACTCCGTGAA GGGCCGGTTCACCATCTCCAGAGACAATTCCAA GAACACGCTGTATCTGCAAATGAACAGCCTGAG AGCCGAGGACACGGCGGTGTACTACTGCGCCA AGGGCCCTCCTACATACCACACAAACTACTACT ACATGGACGTATGGGGCAAGGGTACAACTGTC ACCGTCTCCTCA |
| SEQ ID NO: 78 | Ab61 Light chain variable region (nucl) | GACATCCAGATGACCCAGTCTCCATCTTCCGTG TCTGCATCTGTAGGAGACAGAGTCACCATCACT TGTCGGGCGAGTCAGGGTATTAGCAGCTGGTT AGCCTGGTATCAGCAGAAACCAGGGAAAGCCC CTAAGCTCCTGATCTATGCTGCATCCAGTTTGC AAAGTGGGGTCCCATCAAGGTTCAGCGGCAGT GGATCTGGGACAGATTTCACTCTCACCATCAGC AGCCTGCAGCCTGAAGATTTTGCAACTTATTAC TGTCAGCAAACAAATAGTTTCCCTTACACTTTTG GCGGAGGGACCAAGGTTGAGATCAAA |
| SEQ ID NO: 79 | Ab66 Heavy chain variable region (e.g., as found in HC-66) hIgG1 backbone (CDRs in bold) | EVQLVESGGGLVQPGGSLRLSCAASGFTFSDHY MDWVRQAPGKGLEWVGRTRNKASSYTTEYAAS VKGRFTISRDDSKNSLYLQMNSLKTEDTAVYYCA REPKYWIDFDLWGRGTLVTVSS |

TABLE 10-continued

SEQUENCE SUMMARY

| Sequence Identifier | Description | Sequence |
|---|---|---|
| SEQ ID NO: 80 | Ab66 Light chain variable region (e.g., as found in LC-66) hKappa backbone (CDRs in bold) | DIQMTQSPSSLSASVGDRVTITCRASQSISSYLNWYQQKPGKAPKLLIYAASSLQSGVPSRFSGSGSGTDFTLTISSLQPEDFATYYCQQSYIAPYTFGGGTKVEIK |
| SEQ ID NO: 81 | Ab66 CDR-H1 | FTFSDHYMD |
| SEQ ID NO: 82 | Ab66 CDR-H2 | RTRNKASSYTTEYAASVKG |
| SEQ ID NO: 83 | Ab66 CDR-H3 | AREPKYWIDFDL |
| SEQ ID NO: 84 | Ab66 CDR-L1 | RASQSISSYLN |
| SEQ ID NO: 85 | Ab66 CDR-L2 | AASSLQS |
| SEQ ID NO: 86 | Ab66 CDR-L3 | QQSYIAPYT |
| SEQ ID NO: 87 | Ab66 Heavy chain variable region (nucl) | GAGGTGCAGCTGGTGGAGTCTGGGGGAGGCTTGGTCCAGCCTGGAGGGTCCCTGAGACTCTCCTGTGCAGCCTCTGGATTCACCTTCAGTGACCACTACATGGACTGGGTCCGCCAGGCTCCAGGGAAGGGGCTGGAGTGGGTTGGCCGTACTAGAAACAAAGCTAGTAGTTACACCACAGAATACGCCGCGTCTGTGAAAGGCAGATTCACCATCTCAAGAGATGATTCAAAGAACTCACTGTATCTGCAAATGAACAGCCTGAAAACCGAGGACACGGCGGTGTACTACTGCGCCAGAGAGCCTAAATACTGGATCGACTTCGACCTATGGGGGAGAGGTACCTTGGTCACCGTCTCCTCA |
| SEQ ID NO: 88 | Ab66 Light chain variable region (nucl) | GACATCCAGATGACCCAGTCTCCATCCTCCCTGTCTGCATCTGTAGGAGACAGAGTCACCATCACTTGCCGGGCAAGTCAGAGCATTAGCAGCTATTTAAATTGGTATCAGCAGAAACCAGGGAAAGCCCCTAAGCTCCTGATCTATGCTGCATCCAGTTTGCAAAGTGGGGTCCCATCAAGGTTCAGTGGCAGTGGATCTGGGACAGATTTCACTCTCACCATCAGCAGTCTGCAACCTGAAGATTTTGCAACTTACTACTGTCAGCAAAGCTACATCGCCCCTTACACTTTTGGCGGAGGGACCAAGGTTGAGATCAAA |
| SEQ ID NO 89 | Ab68 Heavy chain variable region (e.g., as found in HC-68) hIgG1 backbone (CDRs in bold) | EVQLVESGGGLVQPGRSLRLSCTASGFTFSDHDMNWVRQAPGKGLEWVGRTRNAAGSYTTEYAASVKGRFTISRDDSKNSLYLQMNSLKTEDTAVYYCAREPKYWIDFDLWGRGTLVTVSS |
| SEQ ID NO: 90 | Ab68 Light chain variable region (e.g., as found in LC-68) hKappa backbone (CDRs in bold) | DIQMTQSPSSLSASVGDRVTITCRASQSISSYLNWYQQKPGKAPKLLIYAASSLQSGVPSRFSGSGSGTDFTLTISSLQPEDFATYYCQQSYIAPYTFGGGTKVEIK |
| SEQ ID NO: 91 | Ab68 CDR-H1 | FTFSDHDMN |
| SEQ ID NO: 92 | Ab68 CDR-H2 | RTRNAAGSYTTEYAASVKG |
| SEQ ID NO: 93 | Ab68 CDR-H3 | AREPKYWIDFDL |
| SEQ ID NO: 94 | Ab68 CDR-L1 | RASQSISSYLN |
| SEQ ID NO: 95 | Ab68 CDR-L2 | AASSLQS |
| SEQ ID NO: 96 | Ab68 CDR-L3 | QQSYIAPYT |
| SEQ ID NO: 97 | Ab68 Heavy chain variable region (nucl) | GAGGTGCAGCTGGTGGAGTCTGGGGGAGGCTTGGTACAGCCAGGGCGGTCCCTGAGACTCTCCTGTACAGCTTCTGGATTCACCTTCAGTGACCACGACATGAACTGGGTCCGCCAGGCTCCAGGGAAGGGGCTGGAGTGGGTTGGCCGTACTAGAAACGCCGCTGGAAGTTACACCACAGAATACGCCGCGTCTGTGAAAGGCAGATTCACCATCTCAAGAGATGATTCAAAGAACTCACTGTATCTGCAAATGAACAGCCTGAAAACCGAGGACACGGCGGTGTACTAC |

TABLE 10-continued

SEQUENCE SUMMARY

| Sequence Identifier | Description | Sequence |
|---|---|---|
| | | TGCGCCAGAGAGCCTAAATACTGGATCGACTTC GACCTATGGGGAGAGGTACCTTGGTCACCGT CTCCTCA |
| SEQ ID NO: 98 | Ab68 Light chain variable region (nucl) | GACATCCAGATGACCCAGTCTCCATCCTCCCTG TCTGCATCTGTAGGAGACAGAGTCACCATCACT TGCCGGGCAAGTCAGAGCATTAGCAGCTATTTA AATTGGTATCAGCAGAAACCAGGGAAAGCCCCT AAGCTCCTGATCTATGCTGCATCCAGTTTGCAA AGTGGGGTCCCATCAAGGTTCAGTGGCAGTGG ATCTGGGACAGATTTCACTCTCACCATCAGCAG TCTGCAACCTGAAGATTTTGCAACTTACTACTGT CAGCAAAGCTACATCGCCCCTTACACTTTTGGC GGAGGGACCAAGGTTGAGATCAAA |
| SEQ ID NO: 99 | Ab69 Heavy chain variable region (e.g., as found in HC-69) hIgG1 backbone (CDRs in bold) | EVQLVESGGGLVQPGGSLRLSCAASGFTFVDHD MDWVRQAPGKGLEWVGRTRNKLGSYTTEYAAS VKGRFTISRDDSKNSLYLQMNSLKTEDTAVYYCA REPKYWIDFDLWGRGTLVTVSS |
| SEQ ID NO: 100 | Ab69 Light chain variable region (e.g., as found in LC-69) hKappa backbone (CDRs in bold) | DIQMTQSPSSLSASVGDRVTITCRASQSISSYLN WYQQKPGKAPKLLIYAASSLQSGVPSRFSGSGS GTDFTLTISSLQPEDFATYYCQQSYIAPYTFGGGT KVEIK |
| SEQ ID NO: 101 | Ab69 CDR-H1 | FTFVDHDMD |
| SEQ ID NO: 102 | Ab69 CDR-H2 | RTRNKLGSYTTEYAASVKG |
| SEQ ID NO: 103 | Ab69 CDR-H3 | AREPKYWIDFDL |
| SEQ ID NO: 104 | Ab69 CDR-L1 | RASQSISSYLN |
| SEQ ID NO: 105 | Ab69 CDR-L2 | AASSLQS |
| SEQ ID NO: 106 | Ab69 CDR-L3 | QQSYIAPYT |
| SEQ ID NO: 107 | Ab69 Heavy chain variable region (nucl) | GAGGTGCAGCTGGTGGAGTCTGGGGGAGGCTT GGTCCAGCCTGGAGGGTCCCTGAGACTCTCCT GTGCAGCCTCTGGATTCACCTTCGTAGACCACG ACATGGACTGGGTCCGCCAGGCTCCAGGGAAG GGGCTGGAGTGGGTTGGCCGTACTAGAAACAA ACTAGGAAGTTACACCACAGAATACGCCGCGTC TGTGAAAGGCAGATTCACCATCTCAAGAGATGA TTCAAAGAACTCACTGTATCTGCAAATGAACAG CCTGAAAACCGAGGACACGGCGGTGTACTACT GCGCCAGAGAGCCTAAATACTGGATCGACTTC GACCTATGGGGAGAGGTACCTTGGTCACCGT CTCCTCA |
| SEQ ID NO: 108 | Ab69 Light chain variable region (nucl) | GACATCCAGATGACCCAGTCTCCATCCTCCCTG TCTGCATCTGTAGGAGACAGAGTCACCATCACT TGCCGGGCAAGTCAGAGCATTAGCAGCTATTTA AATTGGTATCAGCAGAAACCAGGGAAAGCCCCT AAGCTCCTGATCTATGCTGCATCCAGTTTGCAA AGTGGGGTCCCATCAAGGTTCAGTGGCAGTGG ATCTGGGACAGATTTCACTCTCACCATCAGCAG TCTGCAACCTGAAGATTTTGCAACTTACTACTGT CAGCAAAGCTACATCGCCCCTTACACTTTTGGC GGAGGGACCAAGGTTGAGATCAAA |
| SEQ ID NO: 109 | Ab67 Light chain LC constant region underlined | DIQMTQSPSSLSASVGDRVTITCRASQSISSY LNWYQQKPGKAPKLLIYAASSLQSGVPSRFS GSGSGTDFTLTISSLQPEDFATYYCQQSYIAP YTFGGGTKVEIK<u>RTVAAPSVFIFPPSDEQLKS GTASVVCLLNNFYPREAKVQWKVDNALQSG</u> |

TABLE 10-continued

SEQUENCE SUMMARY

| Sequence Identifier | Description | Sequence |
|---|---|---|
| | | NSQESVTEQDSKDSTYSLSSTLTLSKADYEK HKVYACEVTHQGLSSPVTKSFNRGEC |
| SEQ ID NO: 110 | Ab67 Heavy chain HC constant region underlined | EVQLVESGGGLVQPGGSLRLSCAASGFTFS DADMDWVRQAPGKGLEWVGRTRNKAGSYT TEYAASVKGRFTISRDDSKNSLYLQMNSLKT EDTAVYYCAREPKYWIDFDLWGRGTLVTVSS ASTKGPSVFPLAPSSKSTSGGTAALGCLVKD YFPEPVTVSWNSGALTSGVHTFPAVLQSSGL YSLSSVVTVPSSSLGTQTYICNVNHKPSNTK VDKKVEPKSCDKTHTCPPCPAPELLGGPSVF LFPPKPKDTLMISRTPEVTCVVVDVSHEDPE VKFNWYVDGVEVHNAKTKPREEQYNSTYRV VSVLTVLHQDWLNGKEYKCKVSNKALPAPIE KTISKAKGQPREPQVYTLPPSRDELTKNQVS LTCLVKGFYPSDIAVEWESNGQPENNYKTTP PVLDSDGSFFLYSKLTVDKSRWQQGNVFSC SVMHEALHNHYTQKSLSLSPGK |
| SEQ ID NO: 111 | Ab67 Heavy chain (D265C)* HC constant region underlined | EVQLVESGGGLVQPGGSLRLSCAASGFTFS DADMDWVRQAPGKGLEWVGRTRNKAGSYT TEYAASVKGRFTISRDDSKNSLYLQMNSLKT EDTAVYYCAREPKYWIDFDLWGRGTLVTVSS ASTKGPSVFPLAPSSKSTSGGTAALGCLVKD YFPEPVTVSWNSGALTSGVHTFPAVLQSSGL YSLSSVVTVPSSSLGTQTYICNVNHKPSNTK VDKKVEPKSCDKTHTCPPCPAPELLGGPSVF LFPPKPKDTLMISRTPEVTCVVVCVSHEDPE VKFNWYVDGVEVHNAKTKPREEQYNSTYRV VSVLTVLHQDWLNGKEYKCKVSNKALPAPIE KTISKAKGQPREPQVYTLPPSRDELTKNQVS LTCLVKGFYPSDIAVEWESNGQPENNYKTTP PVLDSDGSFFLYSKLTVDKSRWQQGNVFSC SVMHEALHNHYTQKSLSLSPGK |
| SEQ ID NO: 112 | Ab67 Heavy chain (L234A/L235A/ D265C)* HC constant region underlined | EVQLVESGGGLVQPGGSLRLSCAASGFTFS DADMDWVRQAPGKGLEWVGRTRNKAGSYT TEYAASVKGRFTISRDDSKNSLYLQMNSLKT EDTAVYYCAREPKYWIDFDLWGRGTLVTVSS ASTKGPSVFPLAPSSKSTSGGTAALGCLVKD YFPEPVTVSWNSGALTSGVHTFPAVLQSSGL YSLSSVVTVPSSSLGTQTYICNVNHKPSNTK VDKKVEPKSCDKTHTCPPCPAPEAAGGPSV FLFPPKPKDTLMISRTPEVTCVVVCVSHEDP EVKFNWYVDGVEVHNAKTKPREEQYNSTYR VVSVLTVLHQDWLNGKEYKCKVSNKALPAPI EKTISKAKGQPREPQVYTLPPSRDELTKNQV SLTCLVKGFYPSDIAVEWESNGQPENNYKTT PPVLDSDGSFFLYSKLTVDKSRWQQGNVFS CSVMHEALHNHYTQKSLSLSPGK |
| SEQ ID NO: 113 | Ab67 Heavy chain (D265C/H435A)* HC constant region underlined | EVQLVESGGGLVQPGGSLRLSCAASGFTFS DADMDWVRQAPGKGLEWVGRTRNKAGSYT TEYAASVKGRFTISRDDSKNSLYLQMNSLKT EDTAVYYCAREPKYWIDFDLWGRGTLVTVSS ASTKGPSVFPLAPSSKSTSGGTAALGCLVKD YFPEPVTVSWNSGALTSGVHTFPAVLQSSGL YSLSSVVTVPSSSLGTQTYICNVNHKPSNTK VDKKVEPKSCDKTHTCPPCPAPELLGGPSVF LFPPKPKDTLMISRTPEVTCVVVCVSHEDPE VKFNWYVDGVEVHNAKTKPREEQYNSTYRV VSVLTVLHQDWLNGKEYKCKVSNKALPAPIE KTISKAKGQPREPQVYTLPPSRDELTKNQVS LTCLVKGFYPSDIAVEWESNGQPENNYKTTP PVLDSDGSFFLYSKLTVDKSRWQQGNVFSC SVMHEALHNAYTQKSLSLSPGK |
| SEQ ID NO: 114 | Ab67 Heavy chain (L234A/L235A/ D265C/H435A)* HC constant region underlined | EVQLVESGGGLVQPGGSLRLSCAASGFTFS DADMDWVRQAPGKGLEWVGRTRNKAGSYT TEYAASVKGRFTISRDDSKNSLYLQMNSLKT EDTAVYYCAREPKYWIDFDLWGRGTLVTVSS ASTKGPSVFPLAPSSKSTSGGTAALGCLVKD YFPEPVTVSWNSGALTSGVHTFPAVLQSSGL YSLSSVVTVPSSSLGTQTYICNVNHKPSNTK VDKKVEPKSCDKTHTCPPCPAPEAAGGPSV |

TABLE 10-continued

SEQUENCE SUMMARY

| Sequence Identifier | Description | Sequence |
|---|---|---|
| | | FLFPPKPKDTLMISRTPEVTCVVVCVSHEDP EVKFNWYVDGVEVHNAKTKPREEQYNSTYR VVSVLTVLHQDWLNGKEYKCKVSNKALPAPI EKTISKAKGQPREPQVYTLPPSRDELTKNQV SLTCLVKGFYPSDIAVEWESNGQPENNYKTT PPVLDSDGSFFLYSKLTVDKSRWQQGNVFS CSVMHEALHNAYTQKSLSLSPGK |
| SEQ ID NO: 115 | Ab55 Light chain LC constant region underlined | DIQMTQSPSSLSASVGDRVTITCRASQSINSYLNW YQQKPGKAPKLLIYAASSLQSGVPSRFSGSGSGT DFTLTISSLQPEDFATYYCQQGVSDITFGGGTKVE IKRTVAAPSVFIFPPSDEQLKSGTASVVCLLN NFYPREAKVQWKVDNALQSGNSQESVTEQD SKDSTYSLSSTLTLSKADYEKHKVYACEVTH QGLSSPVTKSFNRGEC |
| SEQ ID NO: 116 | Ab55 Heavy chain HC constant region underlined | QVQLVQSGAEVKKPGSSVKVSCKASGGTFRIYAI SWVRQAPGQGLEWMGGIIPDFGVANYAQKFQGR VTITADESTSTAYMELSSLRSEDTAVYYCARGGLD TDEFDLWGRGTLVTVSSASTKGPSVFPLAPSS KSTSGGTAALGCLVKDYFPEPVTVSWNSGA LTSGVHTFPAVLQSSGLYSLSSVVTVPSSSL GTQTYICNVNHKPSNTKVDKKVEPKSCDKTH TCPPCPAPELLGGPSVFLFPPKPKDTLMISRT PEVTCVVVDVSHEDPEVKFNWYVDGVEVHN AKTKPREEQYNSTYRVVSVLTVLHQDWLNG KEYKCKVSNKALPAPIEKTISKAKGQPREPQ VYTLPPSRDELTKNQVSLTCLVKGFYPSDIAV EWESNGQPENNYKTTPPVLDSDGSFFLYSK LTVDKSRWQQGNVFSCSVMHEALHNHYTQK SLSLSPGK |
| SEQ ID NO: 117 | Ab55 Heavy chain (D265C)* HC constant region underlined | QVQLVQSGAEVKKPGSSVKVSCKASGGTFRIYAI SWVRQAPGQGLEWMGGIIPDFGVANYAQKFQGR VTITADESTSTAYMELSSLRSEDTAVYYCARGGLD TDEFDLWGRGTLVTVSSASTKGPSVFPLAPSS KSTSGGTAALGCLVKDYFPEPVTVSWNSGA LTSGVHTFPAVLQSSGLYSLSSVVTVPSSSL GTQTYICNVNHKPSNTKVDKKVEPKSCDKTH TCPPCPAPELLGGPSVFLFPPKPKDTLMISRT PEVTCVVVCVSHEDPEVKFNWYVDGVEVHN AKTKPREEQYNSTYRVVSVLTVLHQDWLNG KEYKCKVSNKALPAPIEKTISKAKGQPREPQ VYTLPPSRDELTKNQVSLTCLVKGFYPSDIAV EWESNGQPENNYKTTPPVLDSDGSFFLYSK LTVDKSRWQQGNVFSCSVMHEALHNHYTQK SLSLSPGK |
| SEQ ID NO: 118 | Ab55 Heavy chain (L234A/L235A/ D265C)* HC constant region underlined | QVQLVQSGAEVKKPGSSVKVSCKASGGTFRIYAI SWVRQAPGQGLEWMGGIIPDFGVANYAQKFQGR VTITADESTSTAYMELSSLRSEDTAVYYCARGGLD TDEFDLWGRGTLVTVSSASTKGPSVFPLAPSS KSTSGGTAALGCLVKDYFPEPVTVSWNSGA LTSGVHTFPAVLQSSGLYSLSSVVTVPSSSL GTQTYICNVNHKPSNTKVDKKVEPKSCDKTH TCPPCPAPEAAGGPSVFLFPPKPKDTLMISR TPEVTCVVVCVSHEDPEVKFNWYVDGVEVH NAKTKPREEQYNSTYRVVSVLTVLHQDWLN GKEYKCKVSNKALPAPIEKTISKAKGQPREP QVYTLPPSRDELTKNQVSLTCLVKGFYPSDI AVEWESNGQPENNYKTTPPVLDSDGSFFLY SKLTVDKSRWQQGNVFSCSVMHEALHNHYT QKSLSLSPGK |
| SEQ ID NO: 119 | Ab55 Heavy chain (D265C/H435A)* HC constant region underlined | QVQLVQSGAEVKKPGSSVKVSCKASGGTFRIYAI SWVRQAPGQGLEWMGGIIPDFGVANYAQKFQGR VTITADESTSTAYMELSSLRSEDTAVYYCARGGLD TDEFDLWGRGTLVTVSSASTKGPSVFPLAPSS KSTSGGTAALGCLVKDYFPEPVTVSWNSGA LTSGVHTFPAVLQSSGLYSLSSVVTVPSSSL GTQTYICNVNHKPSNTKVDKKVEPKSCDKTH TCPPCPAPELLGGPSVFLFPPKPKDTLMISRT PEVTCVVVCVSHEDPEVKFNWYVDGVEVHN AKTKPREEQYNSTYRVVSVLTVLHQDWLNG KEYKCKVSNKALPAPIEKTISKAKGQPREPQ |

TABLE 10-continued

SEQUENCE SUMMARY

| Sequence Identifier | Description | Sequence |
|---|---|---|
| | | VYTLPPSRDELTKNQVSLTCLVKGFYPSDIAV EWESNGQPENNYKTTPPVLDSDGSFFLYSK LTVDKSRWQQGNVFSCSVMHEALHNAYTQK SLSLSPGK |
| SEQ ID NO: 120 | Ab55 Heavy chain (L234A/L235A/ D265C/H435A)* HC constant region underlined | QVQLVQSGAEVKKPGSSVKVSCKASGGTFRIYAI SWVRQAPGQGLEWMGGIIPDFGVANYAQKFQGR VTITADESTSTAYMELSSLRSEDTAVYYCARGGLD TDEFPDLWGRGTLVTVSS<u>ASTKGPSVFPLAPSS KSTSGGTAALGCLVKDYFPEPVTVSWNSGA LTSGVHTFPAVLQSSGLYSLSSVVTVPSSSL GTQTYICNVNHKPSNTKVDKKVEPKSCDKTH TCPPCPAPEAAGGPSVFLFPPKPKDTLMISR TPEVTCVVVCVSHEDPEVKFNWYVDGVEVH NAKTKPREEQYNSTYRVVSVLTVLHQDWLN GKEYKCKVSNKALPAPIEKTISKAKGQPREP QVYTLPPSRDELTKNQVSLTCLVKGFYPSDI AVEWESNGQPENNYKTTPPVLDSDGSFFLY SKLTVDKSRWQQGNVFSCSVMHEALHNAYT QKSLSLSPGK</u> |
| SEQ ID NO: 121 | Light chain constant region of LC-54, LC-55, LC-56, LC-57, LC-58, LC-61, LC-66, LC-67, LC-68, LC-69 | RTVAAPSVFIFPPSDEQLKSGTASVVCLLNNF YPREAKVQWKVDNALQSGNSQESVTEQDSK DSTYSLSSTLTLSKADYEKHKVYACEVTHQG LSSPVTKSFNRGEC |
| SEQ ID NO: 122 | Heavy chain constant region of WT | ASTKGPSVFPLAPSSKSTSGGTAALGCLVKD YFPEPVTVSWNSGALTSGVHTFPAVLQSSGL YSLSSVVTVPSSSLGTQTYICNVNHKPSNTK VDKKVEPKSCDKTHTCPPCPAPELLGGPSVF LFPPKPKDTLMISRTPEVTCVVVDVSHEDPE VKFNWYVDGVEVHNAKTKPREEQYNSTYRV VSVLTVLHQDWLNGKEYKCKVSNKALPAPIE KTISKAKGQPREPQVYTLPPSRDELTKNQVS LTCLVKGFYPSDIAVEWESNGQPENNYKTTP PVLDSDGSFFLYSKLTVDKSRWQQGNVFSC SVMHEALHNHYTQKSLSLSPGK |
| SEQ ID NO: 123 | Heavy chain constant region (D265C)* | ASTKGPSVFPLAPSSKSTSGGTAALGCLVKD YFPEPVTVSWNSGALTSGVHTFPAVLQSSGL YSLSSVVTVPSSSLGTQTYICNVNHKPSNTK VDKKVEPKSCDKTHTCPPCPAPELLGGPSVF LFPPKPKDTLMISRTPEVTCVVVCVSHEDPE VKFNWYVDGVEVHNAKTKPREEQYNSTYRV VSVLTVLHQDWLNGKEYKCKVSNKALPAPIE KTISKAKGQPREPQVYTLPPSRDELTKNQVS LTCLVKGFYPSDIAVEWESNGQPENNYKTTP PVLDSDGSFFLYSKLTVDKSRWQQGNVFSC SVMHEALHNHYTQKSLSLSPGK |
| SEQ ID NO: 124 | Heavy chain constant region (L234A/L235A/ D265C)* | ASTKGPSVFPLAPSSKSTSGGTAALGCLVKD YFPEPVTVSWNSGALTSGVHTFPAVLQSSGL YSLSSVVTVPSSSLGTQTYICNVNHKPSNTK VDKKVEPKSCDKTHTCPPCPAPEAAGGPSV FLFPPKPKDTLMISRTPEVTCVVVCVSHEDP EVKFNWYVDGVEVHNAKTKPREEQYNSTYR VVSVLTVLHQDWLNGKEYKCKVSNKALPAPI EKTISKAKGQPREPQVYTLPPSRDELTKNQV SLTCLVKGFYPSDIAVEWESNGQPENNYKTT PPVLDSDGSFFLYSKLTVDKSRWQQGNVFS CSVMHEALHNHYTQKSLSLSPGK |
| SEQ ID NO: 125 | Heavy chain constant region (H435A/D265C)* | ASTKGPSVFPLAPSSKSTSGGTAALGCLVKD YFPEPVTVSWNSGALTSGVHTFPAVLQSSGL YSLSSVVTVPSSSLGTQTYICNVNHKPSNTK VDKKVEPKSCDKTHTCPPCPAPELLGGPSVF LFPPKPKDTLMISRTPEVTCVVVCVSHEDPE VKFNWYVDGVEVHNAKTKPREEQYNSTYRV VSVLTVLHQDWLNGKEYKCKVSNKALPAPIE KTISKAKGQPREPQVYTLPPSRDELTKNQVS LTCLVKGFYPSDIAVEWESNGQPENNYKTTP PVLDSDGSFFLYSKLTVDKSRWQQGNVFSC SVMHEALHNAYTQKSLSLSPGK |

TABLE 10-continued

SEQUENCE SUMMARY

| Sequence Identifier | Description | Sequence |
|---|---|---|
| SEQ ID NO: 126 | Heavy chain constant region (L234A/L235A/ H435A/D265C)* | ASTKGPSVFPLAPSSKSTSGGTAALGCLVKD YFPEPVTVSWNSGALTSGVHTFPAVLQSSGL YSLSSVVTVPSSSLGTQTYICNVNHKPSNTK VDKKVEPKSCDKTHTCPPCPAPEAAGGPSV FLFPPKPKDTLMISRTPEVTCVVVCVSHEDP EVKFNWYVDGVEVHNAKTKPREEQYNSTYR VVSVLTVLHQDWLNGKEYKCKVSNKALPAPI EKTISKAKGQPREPQVYTLPPSRDELTKNQV SLTCLVKGFYPSDIAVEWESNGQPENNYKTT PPVLDSDGSFFLYSKLTVDKSRWQQGNVFS CSVMHEALHNAYTQKSLSLSPGK |
| SEQ ID NO: 127 | Consensus sequence of variable heavy chain CDR1 (Abs 54-57) | GTF(S/R)(S/I/L)YAIS |
| SEQ ID NO: 128 | Consensus sequence of variable heavy chain CDR2 (Abs 54-57) | GIIP(I/D/A/H)FG(T/V/L)ANYAQKFQG |
| SEQ ID NO: 129 | Variable heavy chain CDR3 (Abs 54-57) | ARGGLDTDEFDL |
| SEQ ID NO: 130 | Variable light chain CDR1 (Abs 54-57) | RASQSINSYLN |
| SEQ ID NO: 131 | Variable light chain CDR2 (Abs 54-57) | AASSLQS |
| SEQ ID NO: 132 | Variable light chain CDR3 (Abs 54-57) | QQGVSDIT |
| SEQ ID NO: 133 | Consensus sequence of variable heavy chain CDR1 (Abs 58, 61) | FTFS(N/S)Y(A/V)M(S/I) |
| SEQ ID NO: 134 | Consensus sequence of variable heavy chain CDR2 (Abs 58, 61) | (A/S)ISG(S/D)(G/S)(G/V)(S/T)TYYADSVKG |
| SEQ ID NO: 135 | Variable heavy chain CDR3 (Abs 58, 61) | AKGPPTYHTNYYYMDV |
| SEQ ID NO: 136 | Variable light chain CDR1 (Abs 58, 61) | RASQGISSWLA |
| SEQ ID NO: 137 | Variable light chain CDR2 (Abs 58, 61) | AASSLQS |
| SEQ ID NO: 138 | Variable light chain CDR3 (Abs 58, 61) | QQTNSFPYT |
| SEQ ID NO: 139 | Consensus sequence of variable heavy chain CDR1 (Abs 66-69) | FTF(S/V)D(H/A)(Y/D)M(D/N) |
| SEQ ID NO: 140 | Consensus sequence of variable heavy chain CDR2 (Abs 66-69) | RTRN(K/A)(A/L)(S/G)SYTTEYAASVKG |
| SEQ ID NO: 141 | Variable heavy chain CDR3 (Abs 66-69) | AREPKYWIDFDL |
| SEQ ID NO: 142 | Variable light chain CDR1 (Abs 66-69) | RASQSISSYLN |

TABLE 10-continued

SEQUENCE SUMMARY

| Sequence Identifier | Description | Sequence |
|---|---|---|
| SEQ ID NO: 143 | Variable light chain CDR2 (Abs 66-69) | AASSLQS |
| SEQ ID NO: 144 | Variable light chain CDR3 (Abs 66-69) | QQSYIAPYT |
| SEQ ID NO: 145 | Human CD117 (mast/stem cell growth factor receptor Kit isoform 1 precursor) Protein NCBI Reference Sequence: NP_000213.1 | MRGARGAWDFLCVLLLLLRVQTGSSQPSVS PGEPSPPSIHPGKSDLIVRVGDEIRLLCTDPG FVKWTFEILDETNENKQNEWITEKAEATNTG KYTCTNKHGLSNSIYVFVRDPAKLFLVDRSLY GKEDNDTLVRCPLTDPEVTNYSLKGCQGKPL PKDLRFIPDPKAGIMIKSVKRAYHRLCLHCSV DQEGKSVLSEKFILKVRPAFKAVPVVSVSKA SYLLREGEEFTVTCTIKDVSSSVYSTWKREN SQTKLQEKYNSWHHGDFNYERQATLTISSAR VNDSGVFMCYANNTFGSANVTTTLEVVDKG FINIFPMINTTVFVNDGENVDLIVEYEAFPKPE HQQWIYMNRTFTDKWEDYPKSENESNIRYV SELHLTRLKGTEGGTYTFLVSNSDVNAAIAFN VYVNTKPEILTYDRLVNGMLQCVAAGFPEPTI DWYFCPGTEQRCSASVLPVDVQTLNSSGPP FGKLVVQSSIDSSAFKHNGTVECKAYNDVGK TSAYFNFAFKGNNKEQIHPHILFTPLLIGFVIV AGMMCIIVMILTYKYLQKPMYEVQWKVVEEI NGNNYVYIDPTQLPYDHKWEFPRNRLSFGKT LGAGAFGKVVEATAYGLIKSDAAMTVAVKML KPSAHLTEREALMSELKVLSYLGNHMNIVNL LGACTIGGPTLVITEYCCYGDLLNFLRRKRDS FICSKQEDHAEAALYKNLLHSKESSCSDSTN EYMDMKPGVSYVVPTKADKRRSVRIGSYIER DVTPAIMEDDELALDLEDLLSFSYQVAKGMA FLASKNCIHRDLAARNILLTHGRITKICDFGLA RDIKNDSNYVVKGNARLPVKWMAPESIFNCV YTFESDVWSYGIFLWELFSLGSSPYPGMPVD SKFYKMIKEGFRMLSPEHAPAEMYDIMKTCW DADPLKRPTFKQIVQLIEKQISESTNHIYSNLA NCSPNRQKPVVDHSVRINSVGSTASSSQPLL VHDDV |
| SEQ ID NO: 146 | Human CD117 (mast/stem cell growth factor receptor Kit isoform 2 precursor) Protein NCBI Reference Sequence: NP_001087241.1 | MRGARGAWDFLCVLLLLLRVQTGSSQPSVS PGEPSPPSIHPGKSDLIVRVGDEIRLLCTDPG FVKWTFEILDETNENKQNEWITEKAEATNTG KYTCTNKHGLSNSIYVFVRDPAKLFLVDRSLY GKEDNDTLVRCPLTDPEVTNYSLKGCQGKPL PKDLRFIPDPKAGIMIKSVKRAYHRLCLHCSV DQEGKSVLSEKFILKVRPAFKAVPVVSVSKA SYLLREGEEFTVTCTIKDVSSSVYSTWKREN SQTKLQEKYNSWHHGDFNYERQATLTISSAR VNDSGVFMCYANNTFGSANVTTTLEVVDKG FINIFPMINTTVFVNDGENVDLIVEYEAFPKPE HQQWIYMNRTFTDKWEDYPKSENESNIRYV SELHLTRLKGTEGGTYTFLVSNSDVNAAIAFN VYVNTKPEILTYDRLVNGMLQCVAAGFPEPTI DWYFCPGTEQRCSASVLPVDVQTLNSSGPP FGKLVVQSSIDSSAFKHNGTVECKAYNDVGK TSAYFNFAFKEQIHPHTLFTPLLIGFVIVAGM MCIIVMILTYKYLQKPMYEVQWKVVEEINGNN YVYIDPTQLPYDHKWEFPRNRLSFGKTLGAG AFGKVVEATAYGLIKSDAAMTVAVKMLKPSA HLTEREALMSELKVLSYLGNHMNIVNLLGAC TIGGPTLVITEYCCYGDLLNFLRRKRDSFICS KQEDHAEAALYKNLLHSKESSCSDSTNEYM DMKPGVSYVVPTKADKRRSVRIGSYIERDVT PAIMEDDELALDLEDLLSFSYQVAKGMAFLA SKNCIHRDLAARNILLTHGRITKICDFGLARDI KNDSNYVVKGNARLPVKWMAPESIFNCVYTF ESDVWSYGIFLWELFSLGSSPYPGMPVDSKF YKMIKEGFRMLSPEHAPAEMYDIMKTCWDA DPLKRPTFKQIVQLIEKQISESTNHIYSNLANC SPNRQKPVVDHSVRINSVGSTASSSQPLLVH DDV |

*Fc residues are numbered according to the EU index in Kabat et al.

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

What is claimed is:

1. An isolated anti-CD117 antibody, or antigen-binding fragment thereof, comprising:
   (a) a heavy chain variable region comprising a CDR1 domain comprising the amino acid sequence as set forth in SEQ ID NO: 31, a CDR2 domain comprising the amino acid sequence as set forth in SEQ ID NO:32, and a CDR3 domain comprising the amino acid sequence as set forth in SEQ ID NO: 33; and a light chain variable region comprising a CDR1 domain comprising the amino acid sequence as set forth in SEQ ID NO: 34, a CDR2 domain comprising the amino acid sequence as set forth in SEQ ID NO:35, and a CDR3 domain comprising the amino acid sequence as set forth in SEQ ID NO: 36;
   (b) a heavy chain variable region comprising a CDR1 domain comprising the amino acid sequence as set forth in SEQ ID NO: 21, a CDR2 domain comprising the amino acid sequence as set forth in SEQ ID NO:22, and a CDR3 domain comprising the amino acid sequence as set forth in SEQ ID NO: 23; and a light chain variable region comprising a CDR1 domain comprising the amino acid sequence as set forth in SEQ ID NO: 24, a CDR2 domain comprising the amino acid sequence as set forth in SEQ ID NO:25, and a CDR3 domain comprising the amino acid sequence as set forth in SEQ ID NO: 26;
   (c) a heavy chain variable region comprising a CDR1 domain comprising the amino acid sequence as set forth in SEQ ID NO: 41, a CDR2 domain comprising the amino acid sequence as set forth in SEQ ID NO:42, and a CDR3 domain comprising the amino acid sequence as set forth in SEQ ID NO: 43; and a light chain variable region comprising a CDR1 domain comprising the amino acid sequence as set forth in SEQ ID NO: 44, a CDR2 domain comprising the amino acid sequence as set forth in SEQ ID NO:45, and a CDR3 domain comprising the amino acid sequence as set forth in SEQ ID NO: 46;
   (d) a heavy chain variable region comprising a CDR1 domain comprising the amino acid sequence as set forth in SEQ ID NO: 51, a CDR2 domain comprising the amino acid sequence as set forth in SEQ ID NO:52, and a CDR3 domain comprising the amino acid sequence as set forth in SEQ ID NO: 53; and a light chain variable region comprising a CDR1 domain comprising the amino acid sequence as set forth in SEQ ID NO: 54, a CDR2 domain comprising the amino acid sequence as set forth in SEQ ID NO:55, and a CDR3 domain comprising the amino acid sequence as set forth in SEQ ID NO: 56;
   (e) a heavy chain variable region comprising a CDR1 domain comprising the amino acid sequence as set forth in SEQ ID NO: 61, a CDR2 domain comprising the amino acid sequence as set forth in SEQ ID NO:62, and a CDR3 domain comprising the amino acid sequence as set forth in SEQ ID NO: 63; and a light chain variable region comprising a CDR1 domain comprising the amino acid sequence as set forth in SEQ ID NO: 64, a CDR2 domain comprising the amino acid sequence as set forth in SEQ ID NO:65, and a CDR3 domain comprising the amino acid sequence as set forth in SEQ ID NO: 66;
   (f) a heavy chain variable region comprising a CDR1 domain comprising the amino acid sequence as set forth in SEQ ID NO: 71, a CDR2 domain comprising the amino acid sequence as set forth in SEQ ID NO:72, and a CDR3 domain comprising the amino acid sequence as set forth in SEQ ID NO: 73; and a light chain variable region comprising a CDR1 domain comprising the amino acid sequence as set forth in SEQ ID NO: 74, a CDR2 domain comprising the amino acid sequence as set forth in SEQ ID NO:75, and a CDR3 domain comprising the amino acid sequence as set forth in SEQ ID NO: 76;
   (g) a heavy chain variable region comprising a CDR1 domain comprising the amino acid sequence as set forth in SEQ ID NO: 81, a CDR2 domain comprising the amino acid sequence as set forth in SEQ ID NO:82, and a CDR3 domain comprising the amino acid sequence as set forth in SEQ ID NO: 83; and a light chain variable region comprising a CDR1 domain comprising the amino acid sequence as set forth in SEQ ID NO: 84, a CDR2 domain comprising the amino acid sequence as set forth in SEQ ID NO:85, and a CDR3 domain comprising the amino acid sequence as set forth in SEQ ID NO: 86;
   (h) a heavy chain variable region comprising a CDR1 domain comprising the amino acid sequence as set forth in SEQ ID NO: 11, a CDR2 domain comprising the amino acid sequence as set forth in SEQ ID NO:12, and a CDR3 domain comprising the amino acid sequence as set forth in SEQ ID NO: 13; and a light chain variable region comprising a CDR1 domain comprising the amino acid sequence as set forth in SEQ ID NO: 14, a CDR2 domain comprising the amino acid sequence as set forth in SEQ ID NO:15, and a CDR3 domain comprising the amino acid sequence as set forth in SEQ ID NO: 16;
(i) a heavy chain variable region comprising a CDR1 domain comprising the amino acid sequence as set forth in SEQ ID NO: 91, a CDR2 domain comprising the amino acid sequence as set forth in SEQ ID NO:92, and a CDR3 domain comprising the amino acid sequence as set forth in SEQ ID NO: 93; and a light chain variable region comprising a CDR1 domain comprising the amino acid sequence as set forth in SEQ ID NO: 94, a CDR2 domain comprising the amino acid sequence as set forth in SEQ ID NO:95, and a CDR3 domain comprising the amino acid sequence as set forth in SEQ ID NO: 96; or
(j) a heavy chain variable region comprising a CDR1 domain comprising the amino acid sequence as set forth in SEQ ID NO: 101, a CDR2 domain comprising the amino acid sequence as set forth in SEQ ID NO:102, and a CDR3 domain comprising the amino acid sequence as set forth in SEQ ID NO: 103; and a light chain variable region comprising a CDR1 domain comprising the amino acid sequence as set forth in SEQ ID NO: 104, a CDR2 domain comprising the amino acid sequence as set forth in SEQ ID NO:105, and a CDR3 domain comprising the amino acid sequence as set forth in SEQ ID NO: 106.

2. The anti-CD117 antibody, or antigen-binding fragment thereof, of claim 1 further comprising:
(a) a heavy chain variable region comprising the amino acid sequence as set forth in SEQ ID NO: 29, and a light chain variable region comprising the amino acid sequence as set forth in SEQ ID NO: 30;
(b) a heavy chain variable region comprising the amino acid sequence as set forth in SEQ ID NO: 19, and a light chain variable region comprising the amino acid sequence as set forth in SEQ ID NO: 20;
(c) a heavy chain variable region comprising the amino acid sequence as set forth in SEQ ID NO: 39, and a light chain variable region comprising the amino acid sequence as set forth in SEQ ID NO: 40;
(d) a heavy chain variable region comprising the amino acid sequence as set forth in SEQ ID NO: 49, and a light chain variable region comprising the amino acid sequence as set forth in SEQ ID NO: 50;
(e) a heavy chain variable region comprising the amino acid sequence as set forth in SEQ ID NO: 59, and a light chain variable region comprising the amino acid sequence as set forth in SEQ ID NO: 60;
(f) a heavy chain variable region comprising the amino acid sequence as set forth in SEQ ID NO: 69, and a light chain variable region comprising the amino acid sequence as set forth in SEQ ID NO: 70;
(g) a heavy chain variable region comprising the amino acid sequence as set forth in SEQ ID NO: 79, and a light chain variable region comprising the amino acid sequence as set forth in SEQ ID NO: 80;
(h) a heavy chain variable region comprising the amino acid sequence as set forth in SEQ ID NO: 9, and a light chain variable region comprising the amino acid sequence as set forth in SEQ ID NO: 10;
(i) a heavy chain variable region comprising the amino acid sequence as set forth in SEQ ID NO: 89, and a light chain variable region comprising the amino acid sequence as set forth in SEQ ID NO: 90; or
(j) a heavy chain variable region comprising the amino acid sequence as set forth in SEQ ID NO: 99, and a light chain variable region comprising the amino acid sequence as set forth in SEQ ID NO: 100.

3. The anti-CD117 antibody, or antigen binding fragment thereof, of claim 1, wherein the antibody, or antigen-binding fragment thereof, binds CD117 with a $K_D$ of about 100 nM or less, about 90 nM or less, about 80 nM or less, about 70 nM or less, about 60 nM or less, about 50 nM or less, about 40 nM or less, about 30 nM or less, about 20 nM or less, about 10 nM or less, about 8 nM or less, about 6 nM or less, about 4 nM or less, about 2 nM or less, about 1 nM or less as determined by a Bio-Layer Interferometry (BLI) assay.

4. The anti-CD117 antibody, or antigen-binding fragment thereof, of claim 1, wherein the antibody, or antigen-binding fragment thereof, is human.

5. The anti-CD117 antibody of claim 1, wherein the antibody is an intact antibody.

6. The anti-CD117 antibody, or antigen-binding fragment thereof, of claim 1, wherein the antibody is an IgG.

7. The anti-CD117 antibody, or antigen-binding fragment thereof, of claim 6, wherein the IgG is an IgG1 or an IgG4.

8. The anti-CD117 antibody, or antigen-binding fragment thereof, of claim 1, wherein the antibody, or antigen-binding fragment thereof, is a monoclonal antibody.

9. A method of depleting a population of CD117+ cells in a human patient comprising administering the antibody, or antigen-binding fragment thereof, of claim 1 to the human patient.

10. A pharmaceutical composition comprising the antibody, or antigen-binding fragment thereof, of claim 1, and a pharmaceutically acceptable carrier.

11. A conjugate comprising an anti-CD117 antibody conjugated to a cytotoxin via a linker, wherein the antibody comprises the antibody, or antigen-binding fragment thereof, of claim 1.

12. The conjugate of claim 11, wherein the cytotoxin is selected from the group consisting of an amatoxin, a pseudomonas exotoxin A, deBouganin, a diphtheria toxin, saporin, a maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer.

13. The conjugate of claim 12, wherein the amatoxin is selected from the group consisting of α-amanitin, β-amanitin, γ-amanitin, ε-amanitin, amanin, amaninamide, amanullin, amanullinic acid, and proamanullin.

14. A conjugate represented by the formula Ab-Z-L-Am, wherein Ab is an antibody or antigen-binding fragment thereof, that binds CD117, L is a linker, Z is a chemical moiety, and Am is an amatoxin, wherein the antibody, or antigen-binding fragment thereof, comprises:
(a) a heavy chain variable region comprising a CDR1 domain comprising the amino acid sequence as set forth in SEQ ID NO: 31, a CDR2 domain comprising the amino acid sequence as set forth in SEQ ID NO:32, and a CDR3 domain comprising the amino acid sequence as set forth in SEQ ID NO: 33; and a light chain variable region comprising a CDR1 domain comprising the amino acid sequence as set forth in SEQ ID NO: 34, a CDR2 domain comprising the amino acid sequence as set forth in SEQ ID NO:35, and a CDR3 domain comprising the amino acid sequence as set forth in SEQ ID NO: 36;
(b) a heavy chain variable region comprising a CDR1 domain comprising the amino acid sequence as set forth in SEQ ID NO: 21, a CDR2 domain comprising the amino acid sequence as set forth in SEQ ID NO:22, and a CDR3 domain comprising the amino acid sequence as set forth in SEQ ID NO: 23; and a light chain variable region comprising a CDR1 domain comprising the amino acid sequence as set forth in SEQ ID NO: 24, a CDR2 domain comprising the amino acid sequence as set forth in SEQ ID NO:25, and a CDR3 domain comprising the amino acid sequence as set forth in SEQ ID NO: 26;

(c) a heavy chain variable region comprising a CDR1 domain comprising the amino acid sequence as set forth in SEQ ID NO: 41, a CDR2 domain comprising the amino acid sequence as set forth in SEQ ID NO:42, and a CDR3 domain comprising the amino acid sequence as set forth in SEQ ID NO: 43; and a light chain variable region comprising a CDR1 domain comprising the amino acid sequence as set forth in SEQ ID NO: 44, a CDR2 domain comprising the amino acid sequence as set forth in SEQ ID NO:45, and a CDR3 domain comprising the amino acid sequence as set forth in SEQ ID NO: 46;

(d) a heavy chain variable region comprising a CDR1 domain comprising the amino acid sequence as set forth in SEQ ID NO: 51, a CDR2 domain comprising the amino acid sequence as set forth in SEQ ID NO:52, and a CDR3 domain comprising the amino acid sequence as set forth in SEQ ID NO: 53; and a light chain variable region comprising a CDR1 domain comprising the amino acid sequence as set forth in SEQ ID NO: 54, a CDR2 domain comprising the amino acid sequence as set forth in SEQ ID NO:55, and a CDR3 domain comprising the amino acid sequence as set forth in SEQ ID NO: 56;

(e) a heavy chain variable region comprising a CDR1 domain comprising the amino acid sequence as set forth in SEQ ID NO: 61, a CDR2 domain comprising the amino acid sequence as set forth in SEQ ID NO:62, and a CDR3 domain comprising the amino acid sequence as set forth in SEQ ID NO: 63; and a light chain variable region comprising a CDR1 domain comprising the amino acid sequence as set forth in SEQ ID NO: 64, a CDR2 domain comprising the amino acid sequence as set forth in SEQ ID NO:65, and a CDR3 domain comprising the amino acid sequence as set forth in SEQ ID NO: 66;

(f) a heavy chain variable region comprising a CDR1 domain comprising the amino acid sequence as set forth in SEQ ID NO: 71, a CDR2 domain comprising the amino acid sequence as set forth in SEQ ID NO:72, and a CDR3 domain comprising the amino acid sequence as set forth in SEQ ID NO: 73; and a light chain variable region comprising a CDR1 domain comprising the amino acid sequence as set forth in SEQ ID NO: 74, a CDR2 domain comprising the amino acid sequence as set forth in SEQ ID NO:75, and a CDR3 domain comprising the amino acid sequence as set forth in SEQ ID NO: 76;

(g) a heavy chain variable region comprising a CDR1 domain comprising the amino acid sequence as set forth in SEQ ID NO: 81, a CDR2 domain comprising the amino acid sequence as set forth in SEQ ID NO:82, and a CDR3 domain comprising the amino acid sequence as set forth in SEQ ID NO: 83; and a light chain variable region comprising a CDR1 domain comprising the amino acid sequence as set forth in SEQ ID NO: 84, a CDR2 domain comprising the amino acid sequence as set forth in SEQ ID NO:85, and a CDR3 domain comprising the amino acid sequence as set forth in SEQ ID NO: 86;

(h) a heavy chain variable region comprising a CDR1 domain comprising the amino acid sequence as set forth in SEQ ID NO: 11, a CDR2 domain comprising the amino acid sequence as set forth in SEQ ID NO:12, and a CDR3 domain comprising the amino acid sequence as set forth in SEQ ID NO: 13; and a light chain variable region comprising a CDR1 domain comprising the amino acid sequence as set forth in SEQ ID NO: 14, a CDR2 domain comprising the amino acid sequence as set forth in SEQ ID NO:15, and a CDR3 domain comprising the amino acid sequence as set forth in SEQ ID NO: 16;

(i) a heavy chain variable region comprising a CDR1 domain comprising the amino acid sequence as set forth in SEQ ID NO: 91, a CDR2 domain comprising the amino acid sequence as set forth in SEQ ID NO:92, and a CDR3 domain comprising the amino acid sequence as set forth in SEQ ID NO: 93; and a light chain variable region comprising a CDR1 domain comprising the amino acid sequence as set forth in SEQ ID NO: 94, a CDR2 domain comprising the amino acid sequence as set forth in SEQ ID NO:95, and a CDR3 domain comprising the amino acid sequence as set forth in SEQ ID NO: 96; or (j) a heavy chain variable region comprising a CDR1 domain comprising the amino acid sequence as set forth in SEQ ID NO: 101, a CDR2 domain comprising the amino acid sequence as set forth in SEQ ID NO:102, and a CDR3 domain comprising the amino acid sequence as set forth in SEQ ID NO: 103; and a light chain variable region comprising a CDR1 domain comprising the amino acid sequence as set forth in SEQ ID NO: 104, a CDR2 domain comprising the amino acid sequence as set forth in SEQ ID NO:105, and a CDR3 domain comprising the amino acid sequence as set forth in SEQ ID NO: 106.

15. The conjugate of claim 14, wherein the antibody, or antigen-binding fragment thereof, further comprises:

(a) a heavy chain variable region comprising the amino acid sequence as set forth in SEQ ID NO: 29, and a light chain variable region comprising the amino acid sequence as set forth in SEQ ID NO: 30;

(b) a heavy chain variable region comprising the amino acid sequence as set forth in SEQ ID NO: 19, and a light chain variable region comprising the amino acid sequence as set forth in SEQ ID NO: 20;

(c) a heavy chain variable region comprising the amino acid sequence as set forth in SEQ ID NO: 39, and a light chain variable region comprising the amino acid sequence as set forth in SEQ ID NO: 40;

(d) a heavy chain variable region comprising the amino acid sequence as set forth in SEQ ID NO: 49, and a light chain variable region comprising the amino acid sequence as set forth in SEQ ID NO: 50;

(e) a heavy chain variable region comprising the amino acid sequence as set forth in SEQ ID NO: 59, and a light chain variable region comprising the amino acid sequence as set forth in SEQ ID NO: 60;

(f) a heavy chain variable region comprising the amino acid sequence as set forth in SEQ ID NO: 69, and a light chain variable region comprising the amino acid sequence as set forth in SEQ ID NO: 70;

(g) a heavy chain variable region comprising the amino acid sequence as set forth in SEQ ID NO: 79, and a light chain variable region comprising the amino acid sequence as set forth in SEQ ID NO: 80;

(h) a heavy chain variable region comprising the amino acid sequence as set forth in SEQ ID NO: 9, and a light chain variable region comprising the amino acid sequence as set forth in SEQ ID NO: 10;

(i) a heavy chain variable region comprising the amino acid sequence as set forth in SEQ ID NO: 89, and a light chain variable region comprising the amino acid sequence as set forth in SEQ ID NO: 90; or (j) a heavy chain variable region comprising the amino acid sequence as set forth in SEQ ID NO: 99, and a light chain variable region comprising the amino acid sequence as set forth in SEQ ID NO: 100.

16. The conjugate of claim 14, wherein Z-L-Am is represented by formula (I)

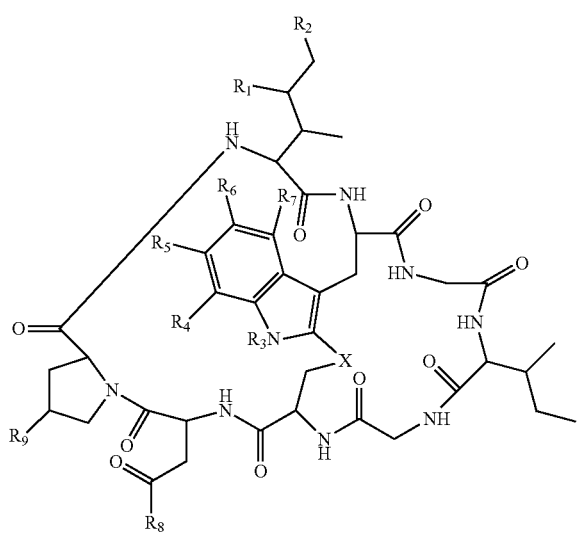

(I)

wherein $R_1$ is H, OH, $OR_A$, or $OR_C$;

$R_2$ is H, OH, $OR_B$, or $OR_C$;

$R_A$ and $R_B$, when present, together with the oxygen atoms to which they are bound, combine to form an optionally substituted 5-membered heterocycloalkyl group;

$R_3$ is H, $R_C$, or $R_D$;

$R_4$, $R_5$, $R_6$, and $R_7$ are each independently H, OH, $OR_C$, $OR_D$, $R_C$, or $R_D$;

$R_8$ is OH, $NH_2$, $OR_C$, $OR_D$, $NHR_C$, or $NR_CR_D$;

$R_9$ is H, OH, $OR_C$, or $OR_D$;

X is —S—, —S(O)—, or —SO$_2$—;

$R_C$ is -L-Z;

$R_D$ is optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ heteroalkenyl, optionally substituted $C_2$-$C_6$ alkynyl, optionally substituted $C_2$-$C_6$ heteroalkynyl, optionally substituted cycloalkyl, optionally substituted heterocycloalkyl, optionally substituted aryl, or optionally substituted heteroaryl;

L is optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ heteroalkenylene, optionally substituted $C_2$-$C_6$ alkynylene, optionally substituted $C_2$-$C_6$ heteroalkynylene, optionally substituted cycloalkylene, optionally substituted heterocycloalkylene, optionally substituted arylene, optionally substituted heteroarylene, a peptide, a dipeptide, —(C=O)—, or a combination thereof; and Z is a chemical moiety formed from a coupling reaction between a reactive substituent present on L and a reactive substituent present within the antibody or antigen-binding fragment thereof, wherein Am comprises exactly one $R_C$ substituent.

17. The conjugate of claim 14, wherein the antibody, or antigen-binding fragment thereof, is conjugated to the amatoxin by way of a cysteine residue in the Fc domain of the antibody, or antigen-binding fragment thereof.

18. The conjugate of claim 17, wherein the cysteine residue is Cys239 or Cys265 (according to numbering EU index).

19. The conjugate of claim 14, wherein the conjugate is either

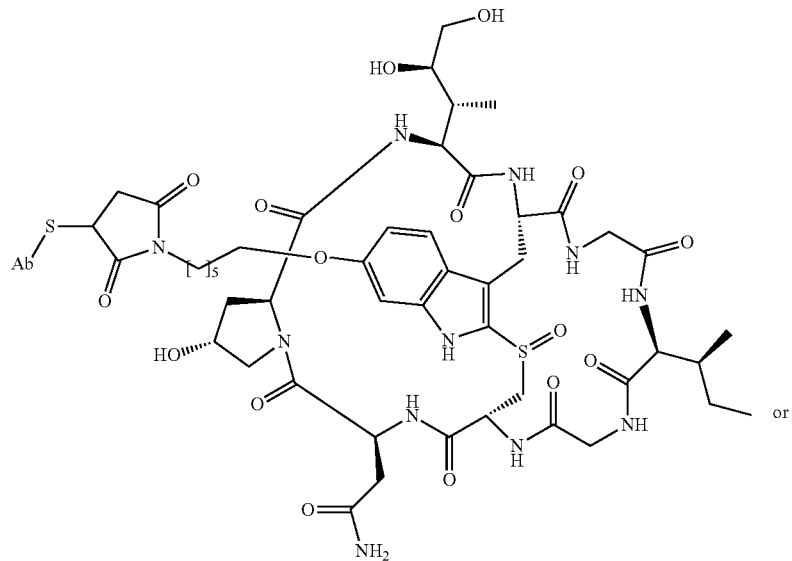

or

-continued

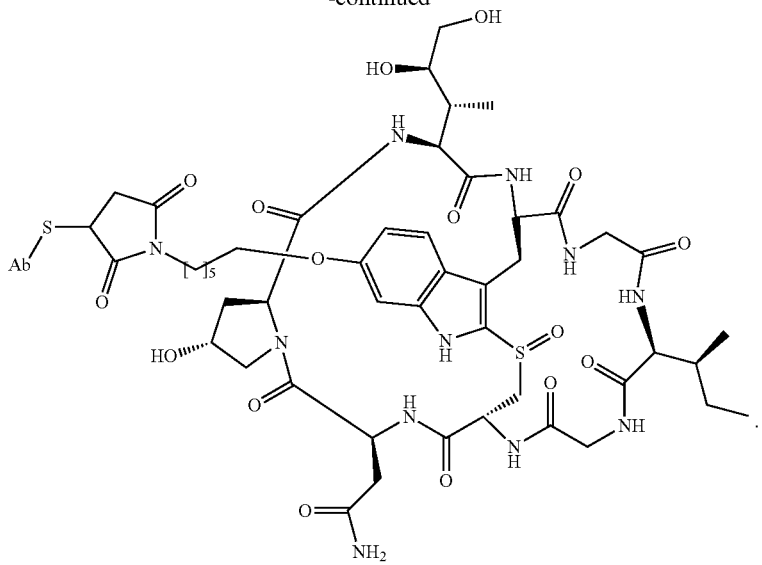

20. The conjugate of claim 14, wherein the antibody, or antigen-binding fragment thereof, comprises a heavy chain constant region having an amino acid sequence as set forth as SEQ ID NO: 122 and/or a light chain constant region comprising an amino acid sequence as set forth in SEQ ID NO: 121.

21. The conjugate of claim 14, wherein the antibody, or antigen-binding fragment thereof, comprises an Fc region comprising at least one amino acid substitution selected from the group consisting of D265C, H435A, L234A, and L235A (numbering according to the EU index).

22. The conjugate of claim 14, wherein the antibody, or antigen-binding fragment thereof, comprises an Fc region, wherein the Fc region comprises D265C, L234A, and L235A (numbering according to the EU index).

23. A method of depleting a population of CD117+ cells in a human patient, the method comprising administering to the patient an effective amount of the conjugate of claim 14.

24. A method of depleting a population of CD117+ cells in a human patient in need of a hematopoietic stem cell transplant, the method comprising administering to the patient an effective amount of the conjugate of claim 14 prior to the patient receiving a transplant comprising hematopoietic stem cells.

25. A method comprising:
   a. administering to a human patient the conjugate of claim 14, in an amount sufficient to deplete a population of CD117+ cells in the patient; and
   b. subsequently administering to the patient a transplant comprising hematopoietic stem cells.

26. The method of claim 23, wherein the conjugate is internalized by a cancer cell, an autoimmune cell, or a hematopoietic stem cell following administration to the patient.

27. The method of claim 23, wherein the patient is suffering from a disorder selected from the group consisting of a stem cell disorder, a hemoglobinopathy disorder, a myelodysplastic disorder, an immunodeficiency disorder, a metabolic disorder, adenosine deaminase deficiency and severe combined immunodeficiency, hyper immunoglobulin M syndrome, Chediak-Higashi disease, hereditary lymphohistiocytosis, osteopetrosis, osteogenesis imperfecta, storage diseases, thalassemia major, systemic sclerosis, systemic lupus erythematosus, multiple sclerosis, juvenile rheumatoid arthritis and cancer.

* * * * *